United States Patent
Jefferis et al.

(10) Patent No.: US 11,291,265 B2
(45) Date of Patent: *Apr. 5, 2022

(54) SURGICAL GARMENT

(71) Applicant: Stryker Corporation, Kalamazoo, MI (US)

(72) Inventors: Ryan Jefferis, Seattle, WA (US); Beau Kidman, Kalamazoo, MI (US); Stephen Isham, Mattawan, MI (US)

(73) Assignee: Stryker Corporation, Kalamazoo, MI (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/462,926

(22) Filed: Aug. 31, 2021

(65) Prior Publication Data
US 2021/0392988 A1     Dec. 23, 2021

Related U.S. Application Data

(63) Continuation of application No. 16/528,018, filed on Jul. 31, 2019, which is a continuation-in-part of
(Continued)

(51) Int. Cl.
*A42B 3/20* (2006.01)
*A42B 3/04* (2006.01)
(Continued)

(52) U.S. Cl.
CPC ............ *A42B 3/20* (2013.01); *A41D 13/1153* (2013.01); *A42B 3/0406* (2013.01); *A42B 3/28* (2013.01);
(Continued)

(58) Field of Classification Search
CPC ........... A42B 3/20; A42B 3/28; A42B 3/0406; A42B 3/225; A41D 13/1153;
(Continued)

(56) References Cited

U.S. PATENT DOCUMENTS 5,095,552 A * 3/1992 Parkinson ................ A42B 3/20
                                                        2/424
5,301,372 A    4/1994 Matoba
(Continued)

FOREIGN PATENT DOCUMENTS

CA       2852110     * 12/2014 ............. A62B 17/04
DE   202007002857 U1    6/2007
(Continued)

OTHER PUBLICATIONS

Bio-Medical Devices Intl, "MaxAir Systems 2270-01 Pre-Filter DLC Hood Instructions for Use", Available on or before Apr. 2017, 3 pages.
(Continued)

*Primary Examiner* — Katherine M Moran
(74) *Attorney, Agent, or Firm* — Howard & Howard Attorneys PLLC

(57) ABSTRACT

A surgical garment for use with a helmet, wherein the garment comprises a shell, a transparent face shield, and an attachment element coupled to the transparent face shield. The garment may be configured to define a barrier between the wearer and the environment. The attachment element configured to removably couple with a coupling member of the helmet, wherein the attachment element and coupling member comprise complementary coupling surfaces. The attachment element comprises a head having a distal surface and a proximal surface, and defining a coupling recess, the coupling recess is defined in the proximal surface of the head. The garment may comprise a first and second attachment element, with the first attachment element being coupled to upper portion of the transparent face shield and the second attachment element being coupled to lower portion of the transparent face shield.

21 Claims, 62 Drawing Sheets

Related U.S. Application Data application No. 16/257,668, filed on Jan. 25, 2019, now Pat. No. 10,420,386.

(51) Int. Cl.
| | |
|---|---|
| *A42B 3/28* | (2006.01) |
| *A42B 3/22* | (2006.01) |
| *A41D 13/11* | (2006.01) |
| *A41D 13/12* | (2006.01) |
| *A61B 90/00* | (2016.01) |
| *A61B 90/50* | (2016.01) |

(52) U.S. Cl.
CPC .......... *A41D 13/1218* (2013.01); *A42B 3/225* (2013.01); *A61B 90/05* (2016.02); *A61B 2090/502* (2016.02)

(58) Field of Classification Search
CPC .. A41D 13/1218; A61B 90/05; A61B 90/502; A62B 17/04
See application file for complete search history.

(56) References Cited

U.S. PATENT DOCUMENTS

| | | | |
|---|---|---|---|
| 5,362,186 A | 11/1994 | Peroni | |
| 5,630,412 A | 5/1997 | Dubruille et al. | |
| 5,711,033 A | 1/1998 | Green et al. | |
| 6,102,033 A * | 8/2000 | Baribeau | A62B 18/08 128/201.24 |
| 6,170,084 B1 | 1/2001 | Gordon et al. | |
| 6,481,019 B2 | 11/2002 | Diaz et al. | |
| 6,622,311 B2 | 9/2003 | Diaz et al. | |
| 6,792,944 B1 | 9/2004 | Green et al. | |
| 6,918,141 B2 | 7/2005 | Green et al. | |
| 6,928,662 B2 | 8/2005 | Fournier | |
| 6,954,968 B1 | 10/2005 | Sitbon | |
| 6,973,677 B2 | 12/2005 | Diaz et al. | |
| 7,093,302 B1 | 8/2006 | Burns | |
| 7,200,873 B2 * | 4/2007 | Klotz | A41D 13/1153 2/171.3 |
| 7,225,471 B2 | 6/2007 | Sutter et al. | |
| 7,735,156 B2 | 6/2010 | VanDerWoude et al. | |
| 7,752,682 B2 | 7/2010 | VanDerWoude et al. | |
| 7,937,775 B2 | 5/2011 | Manzella, Jr. et al. | |
| 8,196,224 B2 | 6/2012 | Manzella, Jr. et al. | |
| 8,225,421 B1 * | 7/2012 | Froissard | A42B 3/225 2/9 |
| 8,234,722 B2 | 8/2012 | VanDerWoude et al. | |
| 8,261,375 B1 | 9/2012 | Reaux | |
| 8,282,234 B2 | 10/2012 | VanDerWoude et al. | |
| 8,302,599 B2 | 11/2012 | Green | |
| 8,407,818 B2 | 4/2013 | VanDerWoude et al. | |
| 8,453,262 B2 | 6/2013 | Green | |
| 8,621,664 B2 | 1/2014 | Peebles | |
| 8,745,763 B2 | 6/2014 | Cho | |
| 8,819,869 B2 | 9/2014 | VanDerWoude et al. | |
| 8,955,168 B2 | 2/2015 | Manzella, Jr. et al. | |
| 9,173,437 B2 | 11/2015 | VanDerWoude et al. | |
| 9,833,032 B2 | 12/2017 | Jacobsen | |
| 10,384,084 B2 | 8/2019 | Isham et al. | |
| 10,420,386 B1 | 9/2019 | Jefferis et al. | |
| 10,574,006 B2 | 2/2020 | Storione et al. | |
| 10,750,800 B2 * | 8/2020 | Jefferis | A41D 13/11 |
| 2001/0032348 A1 | 10/2001 | Diaz et al. | |
| 2005/0010992 A1 | 1/2005 | Klotz et al. | |
| 2007/0050898 A1 | 3/2007 | Larson et al. | |
| 2007/0060011 A1 | 3/2007 | Daftari et al. | |
| 2009/0151054 A1 | 6/2009 | VanDerWoude et al. | |
| 2013/0283508 A1 | 10/2013 | Durham et al. | |
| 2015/0090254 A1 | 4/2015 | Pavalarajan et al. | |
| 2015/0375019 A1 | 12/2015 | VanDerWoude et al. | |
| 2016/0366968 A1 | 12/2016 | Kass et al. | |
| 2018/0084848 A1 | 3/2018 | Pavalarajan et al. | |
| 2018/0263326 A1 | 9/2018 | Ulmer et al. | |
| 2018/0323556 A1 | 11/2018 | Storione et al. | |
| 2018/0368505 A1 | 12/2018 | Kidman et al. | |
| 2020/0275724 A1 | 9/2020 | Jefferis et al. | |
| 2020/0359718 A1 | 11/2020 | Jefferis et al. | |

FOREIGN PATENT DOCUMENTS

| | | | |
|---|---|---|---|
| WO | 0152675 A2 | 7/2001 | |
| WO | 2007011646 A3 | 4/2007 | |
| WO | 2009079292 A1 | 6/2009 | |
| WO | 2017053232 A1 | 3/2017 | |
| WO | 2017072620 A1 | 5/2017 | |
| WO | 2017112485 A1 | 6/2017 | |
| WO | 2017184479 A2 | 10/2017 | |
| WO | 2017184479 A8 | 3/2018 | |

OTHER PUBLICATIONS

English language abstract and machine-assisted English translation for DE 20 2007 002 857 extracted from espacenet.com database on Nov. 30, 2020, 5 pages.
International Search Report for Application No. PCT/US2019/015128 dated Jun. 21, 2019, 5 pages.
Non-Final Office Action for U.S. Appl. No. 16/223,523, dated Jul. 11, 2019, 14 pages.
Partial International Search Report for Application No. PCT/US2020/044216 dated Oct. 21, 2020, 2 pages.
U.S. Appl. No. 16/257,668, filed Jan. 25, 2019.
English language abstract for WO 2017/072620 A1 extracted from espacenet.com database on Sep. 8, 2021, 2 pages.
Fischer Connectors SA, "Breakthrough Low-Profile Fischer LP360 Connectivity Technology Webpage", https://www.fischerconnectors.com/us/en/new-lp360-wearable-connectivity-technology, 2021, 9 pages.
Hanselman, MD., Andrew E. et al., "Contamination Relative to the Activation Timing of Filtered-Exhaust Helmets", J. Arthroplasty, vol. 31, No. 4, Apr. 2016, pp. 776-780.
International Search Report for Application No. PCT/US2017/027857 dated Oct. 18, 2017, 2 pages.
International Search Report for Application No. PCT/US2020/044216 dated Dec. 17, 2020, 3 pages.
Non-Final Office Action for U.S. Appl. No. 16/257,668, dated Mar. 18, 2019, 8 pages.

* cited by examiner

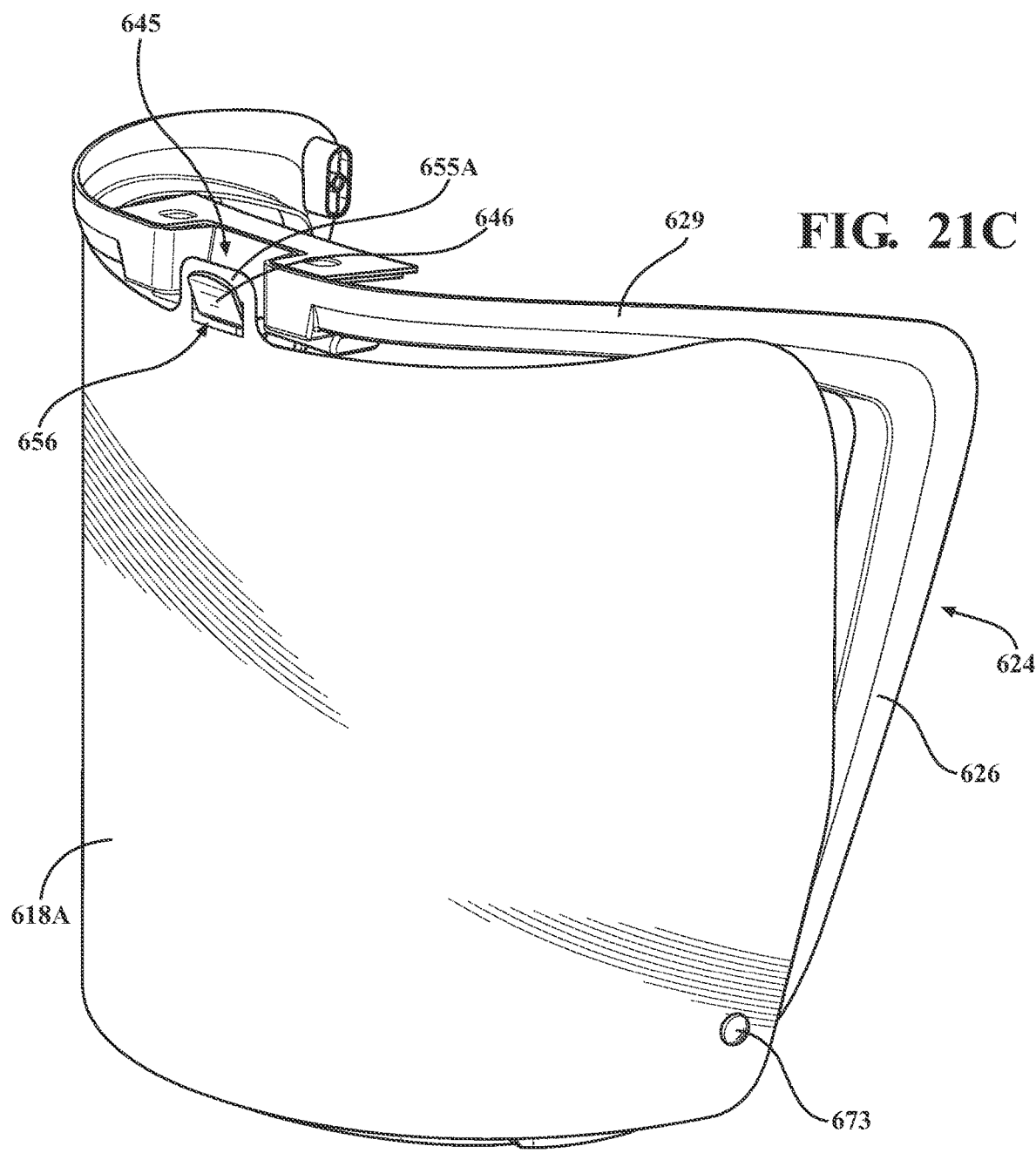

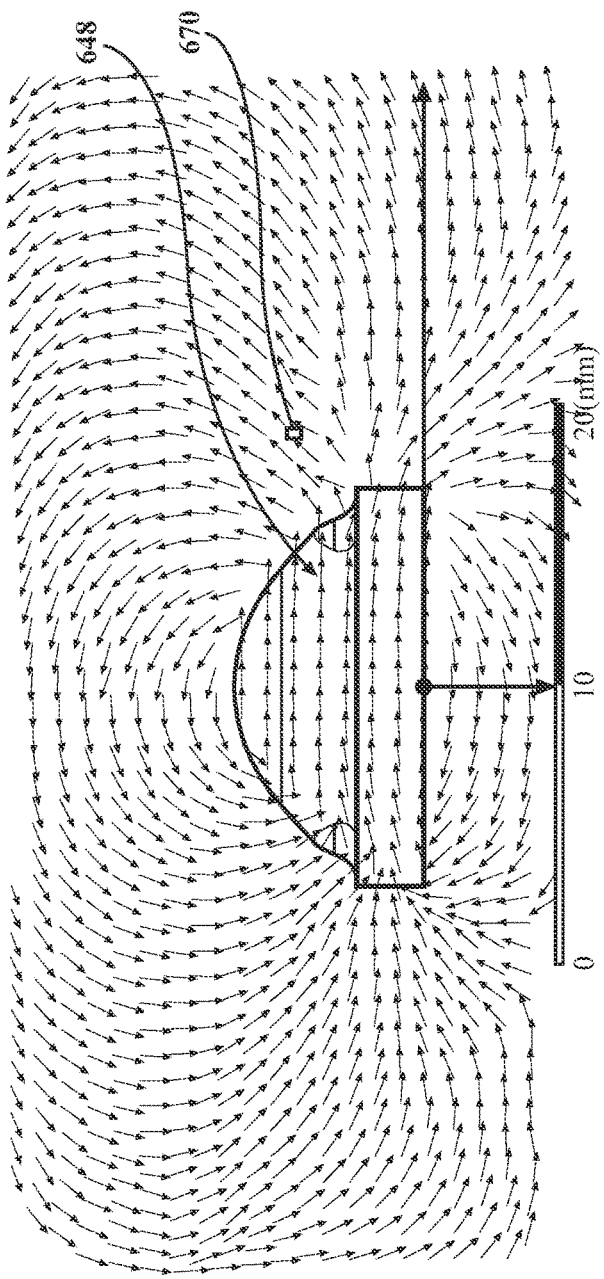
FIG. 22C
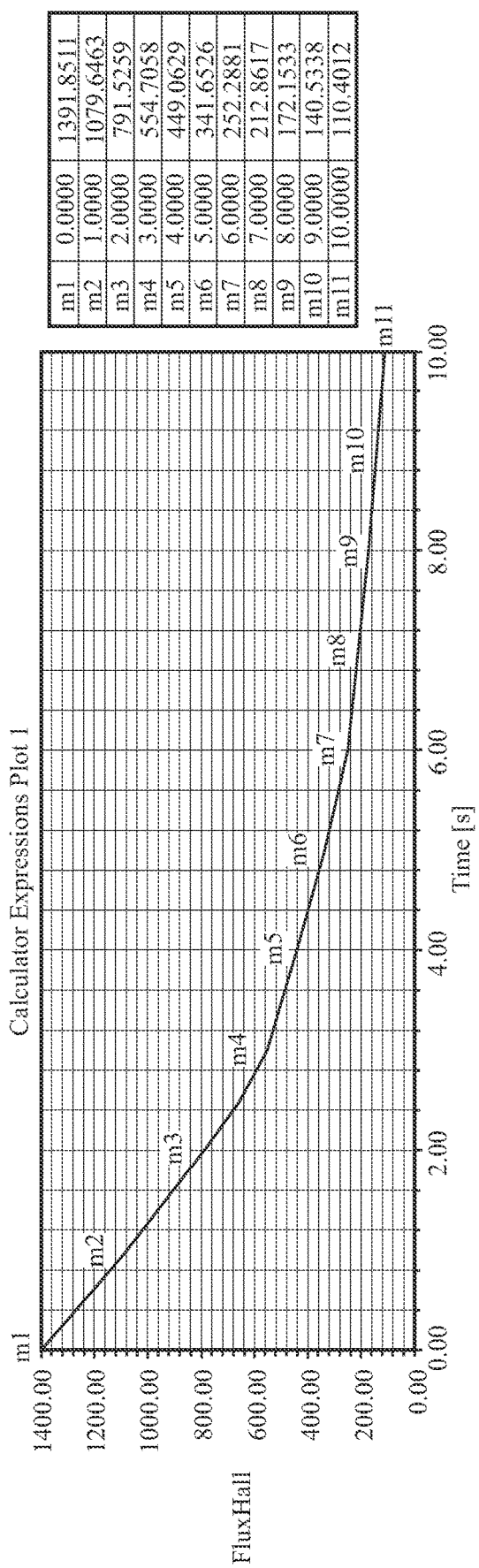

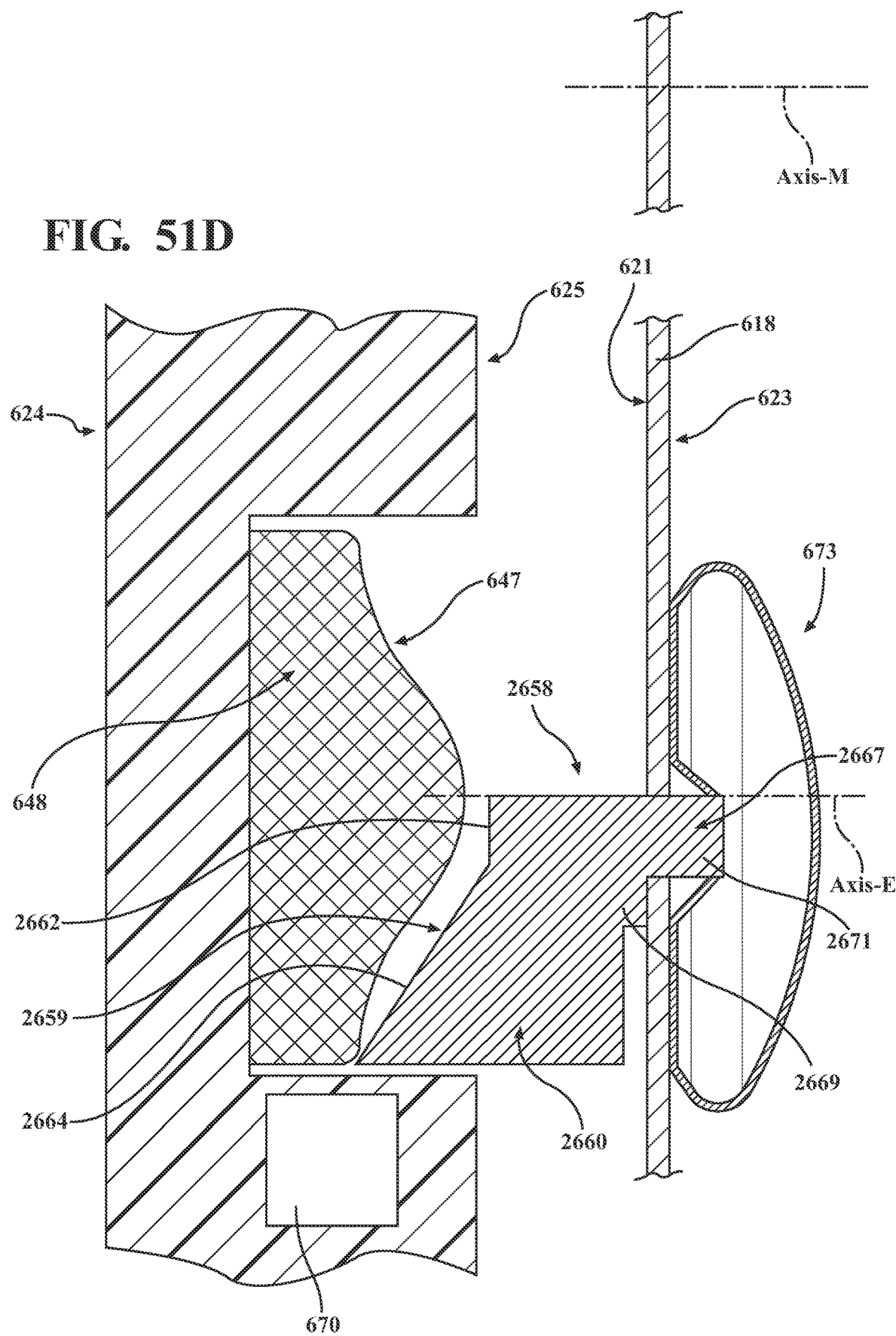

SURGICAL GARMENT

RELATED APPLICATIONS

This application is a continuation of U.S. application Ser. No. 16/528,018, filed on Jul. 31, 2019, which is a continuation-in-part of U.S. application Ser. No. 16/257,668, filed on Jan. 25, 2019, each of which is hereby incorporated herein by reference in its entirety.

BACKGROUND

Personal protection systems are used in surgical procedures to provide a sterile barrier between the surgical personnel and the patient. Specifically, the traditional system includes a helmet that supports a toga or a hood. This system is worn by medical/surgical personnel that want to establish the sterile barrier. The toga or the hood may include a transparent face shield. The helmet includes a ventilation unit that includes a fan. The ventilation unit draws air through the toga/hood so the air is circulated around the wearer. This reduces both the amount of heat that is trapped within the toga/hood and the amount of $CO_2$ that builds up in this space. It is further known to mount a light to the helmet, which may be directed to illuminate the surgical site.

Conventional togas or hoods have been configured to be removably coupled to the helmet. This allows the toga/hood to be removed from the helmet following a surgical procedure and to be disposed of. Prior designs of the togas and hoods have included hooks and/or generic fasteners for coupling the toga/hood to the helmet. Therefore, a medical garment including an improved fastener for coupling the medical garment to a helmet could improve the performance of the personal protection system.

SUMMARY

The present disclosure relates generally to a medical garment. The medical garment comprises an assembly including a shield that may be configured for attachment to a surgical helmet, wherein the medical garment including a shield can be employed to provide a barrier between an individual wearing the system and the surrounding environment.

An exemplary configuration provides a medical garment comprising a shell configured for attachment to the surgical helmet, wherein the shell includes an attachment member that may be integral with the shell and configured to removably couple the shell to the surgical helmet. The attachment member may be configured to removably couple to the surgical helmet on a wearer side of a microbial barrier created by the shell. The surgical helmet may comprise a helmet coupler assembly configured to matingly engage the attachment member to removably couple the shell to the surgical helmet. The helmet coupler assembly may further comprise a moveable member configured to selectively engage a detector based, at least in part, on the position of the shell relative to the surgical helmet. The switch may be communicatively connected to a controller configured to control an operational characteristic of a peripheral device of the surgical helmet.

In another exemplary configuration, a medical garment may comprise a shell configured to provide a microbial barrier between a medical environment and a wearer. The shell may be configured to be disposed over a surgical helmet including a hook at least partially disposed within an alignment channel, and a chin bar. The chin bar may include at least two magnetic coupling members. The shell may comprise a first material configured to be at least partially disposed over the surgical helmet. The first material may comprise an opening, said opening configured to be positioned in front of the wearer's face when disposed over the surgical helmet. The shell may further comprise a transparent face shield disposed within said opening of the first material. The transparent face shield may comprise a first surface and an opposing second surface, an upper portion and a lower portion, and a first aperture in the transparent face shield configured to removably engage the protrusion of the surgical helmet to align the first material relative to the surgical helmet. The shell may further comprise a first attachment element and a second attachment element, wherein the first and second attachment elements may be secured to the lower portion of the transparent face shield on opposing lateral sides of the first aperture. Each of the first and second attachment elements may comprise a retention feature configured to secure the first and second attachment elements to the transparent face shield. At least one of the first and second attachment elements may comprise a ferromagnetic material, wherein at least one of the first and second attachment elements define a recess on the wearer side of the microbial barrier, and are each configured to removably engage one of the magnetic coupling members on the surgical helmet.

In yet another exemplary configuration, a medical garment may comprise a shell configured to provide a microbial barrier between a medical environment and a wearer. The shell may be configured to be disposed over a surgical helmet including at least two magnetic coupling members. The shell may comprise a first material configured to be at least partially disposed over the surgical helmet. The first material may comprise an opening. The shell may further comprise a transparent face shield disposed within the opening of the first material. The transparent face shield may comprise a first surface and an opposing second surface, an upper portion and a lower portion, and a first coupler disposed on wearer side of said first material to removably engage the surgical helmet. The shell may also comprise a first attachment element and a second attachment element. The first and second attachment elements may be secured to the lower portion of the transparent face shield. Each of the first and second attachment elements may also comprise a retention feature configured to secure the first and second attachment elements to the transparent face shield. At least one of the first and second attachment elements may comprise a ferromagnetic material and define a recess on said wearer side of said microbial barrier. The recess may be configured to removably engage the magnetic coupling member(s) on the surgical helmet.

In yet another exemplary configuration, a medical garment may comprise a shell configured to provide a microbial barrier between a medical environment and a wearer. The shell may be configured to be disposed over a surgical helmet including at least two magnetic coupling members. The shell may comprise a first material configured to be at least partially disposed over the surgical helmet. The first material may comprise an opening. The shell may further comprise a transparent face shield disposed within the opening of the first material. The transparent face shield may comprise an upper portion and a lower portion. The shell may further comprise a first coupler disposed on wearer side of said first material configured to removably engage the surgical helmet. The shell may also comprise a first attachment element and/or a second attachment element. The first and second attachment elements may be secured to the lower portion of the transparent face shield. Each of the first and second attachment elements may comprise a head including a distal surface and a proximal surface. Each of the first and second attachment elements may also comprise a post extending from said distal surface of the head. The post may comprise a distal portion and a proximal portion, wherein the proximal portion is configured to abut the distal surface of the head. The proximal portion may comprise a first dimension and the distal portion may comprise a second dimension, wherein the first dimension is greater than said second dimension. The head of each of the first and second attachment elements may further comprise a ferromagnetic material and said proximal surface of each head may be configured to removably engage one of the magnetic coupling members on the surgical helmet.

In yet another exemplary configuration, a protective apparel system configured for use with a helmet may provide a barrier between an environment and a wearer. The helmet may include a protrusion at least partially disposed within an alignment channel, and a chin bar. The chin bar may include at least two magnetic coupling members. The protective apparel system may further comprise a medical garment including a shell configured to be at least partially disposed over the helmet. The shell may comprise an opening configured to be positioned forward of the wearer's face when at least partially disposed over the helmet. The medical garment may also comprise a transparent face shield disposed within the opening of the shell. The transparent face shield may comprise an upper portion and a lower portion. The medical garment may further comprise a tab on the wearer side of the shell, wherein the tab comprises outer edges for aligning the shell relative to the helmet via the alignment channel of the helmet. The tab may comprise a first aperture configured to removably engage the protrusion of the helmet to align said shell relative to the helmet. The medical garment may further comprise a first attachment element and a second attachment element, the first and second attachment elements being secured to the lower portion of the transparent face shield on opposing lateral sides of the first aperture. At least one of the first and second attachment elements comprise a ferromagnetic material, and define a coupling recess on said wearer side of said barrier. The first and second attachment elements and/or the coupling recess are configured to removably engage the magnetic coupling members on the helmet.

In yet another exemplary configuration, a protective apparel system configured for use with a helmet may provide a barrier between an environment and a wearer. The helmet may include a protrusion at least partially disposed within an alignment channel, and a chin bar. The chin bar may include at least two magnetic coupling members. The protective apparel system may comprise a medical garment including a shell configured to be at least partially disposed over the helmet. The shell may comprise an opening configured to be positioned forward of the wearer's face when at least partially disposed over the helmet. The protective apparel system may further comprise a transparent face shield disposed within the opening of the shell. The transparent face shield may comprise a first surface and an opposing second surface, and an upper portion and a lower portion. The protective apparel system may further comprise a tab on the wearer side of said shell, the tab having outer edges for aligning the shell relative to the helmet via the alignment channel of the helmet. The protective apparel system may further comprise a first aperture at least partially formed in said tab and configured to removably engage the protrusion of the helmet to align the shell relative to the helmet. The protective apparel system may further comprise a first attachment element and a second attachment element, the first and second attachment elements being secured to said lower portion of said transparent face shield on opposing lateral sides of said first aperture of the tab. Each of the first and second attachment elements may comprise a retention feature, the retention feature being positioned closer to the second surface of the transparent face shield than the first surface. The first and second attachment elements may comprise a ferromagnetic material and define a respective coupling recess on said wearer side of said barrier. First and second attachment elements and/or the coupling recess are configured to removably engage the magnetic coupling members on the helmet.

In yet another exemplary configuration, a surgical garment assembly may be configured for use with a surgical helmet comprising a magnetic coupling member disposed in a recess and a detector spaced from the coupling member. The surgical garment assembly may be configured to be at least partially disposed over the surgical helmet to provide a microbial barrier between the user and a medical environment. The surgical garment assembly may comprise a surgical fabric defining an opening and a transparent face shield disposed within the opening. The transparent face shield may comprise an upper portion, a lower portion, a first surface and an opposing second surface. The surgical garment assembly may also comprise a first attachment element coupled to the lower portion of the transparent face shield. The first attachment element may comprise a ferromagnetic material. The first attachment element may define a proximal surface facing away from the transparent face shield, wherein the proximal surface may include a first point that lies on a longitudinal axis of the first attachment element and may define a first distance from the first surface of the transparent face shield. The proximal surface may also include a second point that may define a second distance from the first surface of the transparent face shield. The second point on the proximal surface may be spaced apart from the first point on the proximal surface, wherein the proximal surface is shaped such that the first distance is less than the second distance. The first attachment element may be configured to removably engage the coupling member on the surgical helmet and trigger the detector when the first attachment element is coupled to the coupling member.

In yet another exemplary configuration, a surgical garment assembly may be configured for use with a surgical helmet comprising a coupling member disposed in a recess and a hall-effect sensor spaced apart from the coupling member. The surgical garment assembly may be configured to be at least partially disposed over the surgical helmet and configured to provide a microbial barrier between the user and a medical environment. The surgical garment assembly may comprise a surgical fabric defining an opening and a transparent face shield disposed within the opening. The transparent face shield may comprise an upper portion, a lower portion, a first surface and an opposing second surface. The surgical garment assembly may also comprise a first attachment element coupled to the lower portion of the transparent face shield. The first attachment element may define a proximal surface facing away from the transparent face shield. A first axis of the first attachment element may intersect the proximal surface. The proximal surface may be shaped such that a first point on the proximal surface that lies on the first axis defines a first distance from the first surface of the transparent face shield. A second point on the proximal surface may define a second distance from the first surface of the transparent face shield, wherein the second point on the proximal surface is spaced apart from the first point on the proximal surface, and the first distance is less than the second distance. The first attachment element may comprise a ferromagnetic material, wherein the first attachment element is configured to removably engage the coupling member on the surgical helmet.

In yet another exemplary configuration, a surgical garment assembly may be configured for use with a surgical helmet comprising a coupling member disposed in a recess and a hall-effect sensor spaced apart from the coupling member. The surgical garment assembly may be configured to be at least partially disposed over the surgical helmet and to provide a microbial barrier between the user and a medical environment. The surgical garment assembly may comprise a surgical fabric defining an opening and a transparent face shield disposed within the opening. The transparent face shield may comprise an upper portion, a lower portion, a first surface and an opposing second surface. The surgical garment assembly may also comprise a first attachment element coupled to said lower portion of the transparent face shield. The first attachment element may define a proximal surface facing away from the transparent face shield. The proximal surface may be shaped such that a first point on the proximal surface may define a first distance from the first surface of the transparent face shield. A second point on the proximal surface may define a second distance from the first surface of the transparent face shield. The proximal surface may be shaped such that the second point on the proximal surface may be spaced apart from the first point on the proximal surface, and the first distance is less than the second distance. The first attachment element may comprise a ferromagnetic material and may be configured to removably engage the coupling member on the surgical helmet.

In yet another exemplary configuration, a surgical garment assembly may be configured for use with a surgical helmet comprising a coupling member disposed in a recess and a detector spaced from the coupling member. The surgical garment assembly may be configured to be at least partially disposed over the surgical helmet and to provide a microbial barrier between the user and a medical environment. The surgical garment assembly may comprise a surgical fabric defining an opening and a transparent face shield disposed within the opening. The transparent face shield may comprise an upper portion, a lower portion, a first surface and an opposing second surface. The surgical garment assembly may also comprise a first attachment element comprising a head, the head comprising a ferromagnetic material and defining a proximal surface facing away from the transparent face shield. The proximal surface may be shaped such that a first portion of the proximal surface extends a first distance from the first surface of the transparent face shield, and a second portion of the proximal surface defines a second distance from the first surface of the transparent face shield. The proximal surface may be shaped such that the first distance is less than said second distance. The first attachment element may be configured to removably engage the coupling member on the surgical helmet.

In yet another exemplary configuration, a surgical garment assembly may be configured for use with a surgical helmet comprising a coupling member disposed in a recess and a detector spaced from the coupling member. The surgical garment assembly may be configured to be at least partially disposed over the surgical helmet and to provide a microbial barrier between the user and a medical environment. The surgical garment assembly may comprise a surgical fabric defining an opening and a transparent face shield disposed within the opening. The transparent face shield may comprise a first surface and an opposing second surface, and may be bisected by a midline. The surgical garment assembly may also comprise a first attachment element coupled to the transparent face shield. The first attachment element may comprise a head defining a proximal surface. A first point on the proximal surface that lies on an axis of the first attachment element may define a first distance from the first surface of the transparent face shield. A second point on the proximal surface may define a second distance from the first surface of the transparent face shield. The second point on said proximal surface may be spaced apart from the first point on the proximal surface, and the proximal surface may be shaped such that the first distance is less than the second distance. The first attachment element may be oriented relative to the transparent face shield such that the second point on the proximal surface is positioned farther away from the midline of the transparent face shield than the first point on the proximal surface.

In yet another exemplary configuration, a surgical garment assembly may be configured for use with a surgical helmet comprising a coupling member disposed in a recess and a detector spaced from the coupling member. The surgical garment assembly may be configured to be at least partially disposed over the surgical helmet and configured to provide a microbial barrier between the user and a medical environment. The surgical garment assembly may comprise a surgical fabric defining an opening and a transparent face shield disposed within the opening. The transparent face shield may comprise a first surface and an opposing second surface, and may be bisected by a midline. A first attachment element may be coupled to the transparent face shield. The first attachment element may comprise a head defining a proximal surface and an opposing distal surface. A first point on the proximal surface that lies on an axis of the first attachment element may define a first distance from the first surface of the transparent face shield. A second point on the proximal surface may define a second distance from the first surface of the transparent face shield. The second point on said proximal surface may be spaced apart from the first point on the proximal surface, and the proximal surface may be shaped such that the first distance is less than the second distance. The transparent face shield and said first attachment element may also comprise complementary features configured to prevent said first attachment element from rotating relative to the transparent face shield. The first attachment element may be oriented such that the second point on the proximal surface is positioned farther away from the midline of the transparent face shield than the first point on the proximal surface.

The surgical garment assembly may be configured such that the complementary features of the transparent face shield and the first attachment element may comprise an aperture in a lower portion of the transparent face shield and a post extending from the distal surface of the head. The aperture may have a first shape that extends between the first surface and the second surface. The post may comprise a complementary shape to the first shape and may be configured to prevent the post from rotating within the aperture.

In yet another exemplary configuration, a surgical garment assembly may be configured for use with a surgical helmet comprising a coupling member disposed in a recess and a detector spaced from the coupling member. The surgical garment assembly may be configured to be at least partially disposed over the surgical helmet and to provide a microbial barrier between the user and a medical environment. The surgical garment assembly may comprise a surgical fabric defining an opening and a transparent face shield disposed within the opening. The transparent face shield may comprise a first surface and an opposing second surface, and may be bisected by a midline. A first attachment element may be coupled to the transparent face shield. The first attachment element may comprise a head defining a proximal surface and an opposing distal surface. The surgical garment assembly may also comprise a means to prevent the rotation of the first attachment element relative to the transparent face shield. A first point on the proximal surface that lies on an axis of the first attachment element may define a first distance from the first surface of the transparent face shield. A second point on the proximal surface may define a second distance from the first surface of the transparent face shield. The second point on the proximal surface may be spaced apart from the first point on the proximal surface, and the proximal surface may be shaped such that the first distance is less than the second distance. The first attachment element may be oriented such that the second point on the proximal surface is positioned farther away from the midline of the transparent face shield than the first point on the proximal surface.

The surgical garment assembly may be configured such that means to prevent the rotation of the first attachment element relative to the transparent face shield may comprise an aperture that extends between said first surface and said second surface, and a post extending distally from said distal surface of said head. The post may be at least partially disposed within the aperture, and the post and the aperture may comprise complementary features that prevent the rotation of the post within the aperture.

In yet another exemplary configuration, a method of making a surgical garment assembly for use with a surgical helmet may comprise providing a fabric suitable to provide a microbial barrier, the fabric defining an opening, and the fabric shaped to encompass at least a portion of a wearer's head, the fabric defining an environment side and a wearer side. The method may also comprise providing a transparent face shield including an upper portion and an opposing lower portion. The method may further comprise forming a recess in a proximal surface of a head of a ferromagnetic attachment element. The method may also comprise attaching the ferromagnetic attachment element to the transparent face shield. The method may also comprise coupling the transparent face shield to the fabric such that the proximal surface of the ferromagnetic attachment element is positioned on the wearer side of the fabric.

In yet another exemplary configuration, a method of reusing a feature of a surgical garment may comprise obtaining a surgical garment that has been used, the surgical garment including a surgical fabric defining an opening and a transparent face shield disposed within the opening. The transparent face shield may comprise an upper portion, a lower portion, a first surface and an opposing second surface. The method may further comprise a first attachment element secured to said lower portion of said transparent face shield, wherein the first attachment element may comprise a ferromagnetic material and may define a coupling recess on the wearer side of said surgical garment. The first attachment element may be configured to removably engage the magnetic coupling member on the helmet. The first attachment element may further comprise a head comprising a distal surface and a proximal surface, and a post extending distally from the distal surface of the head. The coupling recess may be formed in said proximal surface of the head. The method may also comprise disengaging the first attachment element from the transparent face shield. The method may further comprise discarding the surgical garment and the transparent face shield. The method may also comprise cleaning and/or sterilizing the first attachment element. The method may also comprise coupling the cleaned or sterilized first attachment element to a new surgical garment having a new face shield such that, in subsequent use of the new surgical garment, the cleaned or sterilized first attachment element may be utilized to couple the new surgical garment to a helmet.

In yet another exemplary configuration, a surgical garment assembly may be configured for use with a surgical helmet comprising at least one coupling member. The surgical garment assembly may comprise a surgical fabric defining an opening and a transparent face shield disposed within the opening. The transparent face shield may comprise a first surface and an opposing second surface. A first attachment element may be coupled to the transparent face shield, the first attachment element comprising a proximal surface. An adapter member may be configured to removably couple with the first attachment element. The adapter member may comprise a proximal surface and an opposing distal surface. The adapter member may comprise a first point on the proximal surface of the adapter member and a second point on the proximal surface of the adapter member. The second point on the proximal surface of the adapter member may be spaced apart from the first point on the proximal surface on the adapter member. The distal surface of said adapter member may be configured to removably engage the proximal surface of the first attachment element. The first point on the proximal surface of the adapter member may define a first distance from the first surface of the transparent face shield when the adapter member is coupled to the first attachment element. The second point on the proximal surface of the adapter member may define a second distance from the first surface of the transparent face shield when the adapter member is coupled to the first attachment element. The proximal surface of the adapter member may be shaped such that the first distance is less than the second distance from the first surface of the transparent face shield.

In yet another exemplary configuration, a method of coupling a surgical garment including a first attachment element to a surgical helmet including a first coupling member may comprise providing an adapter member. The adapter member may comprise a proximal surface and an opposing distal surface. The adapter member may also comprise a first point on the proximal surface of the adapter member and a second point on the proximal surface of the adapter member. The second point on the proximal surface of the adapter member may be spaced apart from the first point on the proximal surface of the adapter member. The first point on the proximal surface of the adapter member may define a first distance from the first surface of the transparent face shield when the adapter member is coupled to the first attachment element. The second point on the proximal surface of the adapter member may define a second distance from the first surface of the transparent face shield when the adapter member is coupled to the first attachment element. The method may also comprise removably coupling the adapter member to the first coupling member of the surgical helmet. The method may further comprise removably coupling the adapter member to the first attachment element of the surgical garment.

In yet another exemplary configuration, a surgical garment assembly may be configured for use with a surgical helmet comprising a magnetic coupling member disposed in a recess and a hall-effect sensor spaced from the coupling member. The surgical garment assembly may be configured to be at least partially disposed over the surgical helmet to provide a microbial barrier between the user and a medical environment. The surgical garment assembly may comprise a surgical fabric defining an opening and a transparent face shield disposed within the opening. The transparent face shield may comprise an upper portion, a lower portion, a first surface and an opposing second surface. A first attachment element may be coupled to the lower portion of the transparent face shield. The first attachment element may comprise a cylindrical head including a distal end and an opposing proximal end. The proximal end may define a proximal surface facing away from the transparent face shield. The proximal surface may include a first portion angularly extending in a proximal direction from a medial plane of the cylindrical head to a first edge. A second portion may angularly extend in the proximal direction from the medial plane of the cylindrical head to a second edge. The cylindrical head comprises a ferromagnetic material, and the first attachment element may be configured to removably engage the coupling member on the surgical helmet and trigger the hall-effect sensor when the first attachment element is coupled to the coupling member.

In yet another exemplary configuration, a surgical garment assembly may be configured for use with a surgical helmet comprising a magnetic coupling member disposed in a recess and a hall-effect sensor spaced from the coupling member. The surgical garment assembly may be configured to be at least partially disposed over the surgical helmet to provide a microbial barrier between the user and a medical environment. The surgical garment assembly may comprise a surgical fabric defining an opening and a transparent face shield disposed within the opening. The transparent face shield may comprise an upper portion, a lower portion, a first surface and an opposing second surface. A first attachment element may be coupled to said lower portion of said transparent face shield. The first attachment element may comprise a cylindrical head including a distal end and an opposing proximal end. The proximal end may define a proximal surface facing away from the transparent face shield. The proximal surface may include a planar surface (portion) with a first side and a second side. A first face (portion) may angularly extend in a proximal direction from the first side of the planar surface to a first edge. A second face (portion) may angularly extend in the proximal direction from the second side of the planar surface to a second edge. The planar surface may be perpendicular to a longitudinal axis. The cylindrical head may comprise a ferromagnetic material, and the first attachment element may be configured to removably engage the coupling member on the surgical helmet and trigger the hall-effect sensor when the first attachment element is coupled to the coupling member.

In yet another exemplary configuration, a surgical garment assembly may be configured for use with a surgical helmet comprising a magnetic coupling member disposed in a recess and a hall-effect sensor spaced from the coupling member. The surgical garment assembly may be configured to be at least partially disposed over the surgical helmet to provide a microbial barrier between the user and a medical environment. The surgical garment assembly may comprise a surgical fabric defining an opening and a transparent face shield disposed within the opening. The transparent face shield may comprise an upper portion, a lower portion, a first surface and an opposing second surface. A first attachment element may be coupled to said lower portion of said transparent face shield. The first attachment element may comprise a cylindrical head including a distal end with a distal surface and a proximal end with a proximal surface. The proximal surface may angularly extend in a proximal direction from a first edge of the cylindrical head to a second edge of the cylindrical head. The first attachment element may be configured to removably engage the coupling member on the surgical helmet and trigger the hall-effect sensor when said first attachment element is coupled to the coupling member.

In yet another exemplary configuration, a surgical garment assembly may be configured for use with a surgical helmet comprising a magnetic coupling member disposed in a recess and a hall-effect sensor spaced from the coupling member. The surgical garment assembly may be configured to be at least partially disposed over the surgical helmet to provide a microbial barrier between the user and a medical environment. The surgical garment assembly may comprise a surgical fabric defining an opening and a transparent face shield disposed within the opening. The transparent face shield may comprise an upper portion, a lower portion, a first surface and an opposing second surface. A first attachment element may be coupled to said lower portion of said transparent face shield. The first attachment element may comprise a cylindrical head including a bore, the bore extending along a longitudinal axis between a distal end and a proximal end. The cylindrical head may comprise a ferromagnetic material, and the first attachment element may be configured to removably engage the coupling member on the surgical helmet and trigger the hall-effect sensor when the first attachment element is coupled to the coupling member.

In yet another exemplary configuration, a surgical garment assembly may be configured for use with a surgical helmet comprising a magnetic coupling member disposed in a recess and a hall-effect sensor spaced from the coupling member. The surgical garment assembly may be configured to be at least partially disposed over the surgical helmet to provide a microbial barrier between the user and a medical environment. The surgical garment assembly may comprise a surgical fabric defining an opening and a transparent face shield disposed within the opening. The transparent face shield may comprise an upper portion, a lower portion, a first surface and an opposing second surface. A first attachment element may be coupled to said lower portion of said transparent face shield. The first attachment element may comprise a cylindrical head including a bore, the bore extending along a longitudinal axis between a closed distal end and an open proximal end. The bore may include a mouth, and the mouth may taper circumferentially from the open proximal end towards a center of the bore. The cylindrical head may comprise a ferromagnetic material, and may be configured to removably engage the coupling member on the surgical helmet and trigger the hall-effect sensor when the first attachment element is coupled to the coupling member.

These and other configurations, features, and advantages of the present disclosure will be apparent to those skilled in the art. The present disclosure is not intended to be limited to or by these configurations, embodiments, features, and/or advantages.

BRIEF DESCRIPTION OF THE DRAWINGS

Referring now to the drawings, exemplary illustrations are shown in detail. Although the drawings represent schematic embodiments and/or exemplary configurations, the drawings are not necessarily to scale and certain features may be exaggerated to better illustrate and explain an innovative aspect of an exemplary configuration. Furthermore, the exemplary illustrations described herein are not intended to be exhaustive or otherwise limiting or restricting to the precise form and configuration shown in the drawings and disclosed in the following detailed description.

Advantages of the present disclosure will be readily appreciated as the same becomes better understood by reference to the following detailed description when considered in connection with the accompanying drawings.

FIG. 21C is a perspective view of the face shield of the surgical apparel system of FIG. 13A coupled to the surgical helmet.

FIG. 22C is a schematic view of the magnetic field surrounding a coupling member of a surgical helmet relative to a detector in the absence of an attachment element.

FIG. 51D is a partial sectional view of the twenty-fourth configuration of the attachment element of FIGS. 51A-51C coupled to the coupling member of the surgical helmet of FIG. 37.

DETAILED DESCRIPTION

Maintaining a reliable barrier between a healthcare provider and a patient to prevent the exchange and/or transfer of particles or foreign material during a medical procedure or examination is of the utmost importance. During medical and surgical procedures, a healthcare provider may wear an assembly known as a surgical apparel system, such as the surgical apparel system 10 illustrated in FIG. 1.

Accordingly, the surgical apparel system 10 may comprise a surgical garment assembly comprising a surgical garment 12, which may also be referred to as a medical garment, configured for attachment to a surgical helmet 20. The surgical garment 12 is configured to provide a barrier, such as a microbial barrier, between the wearer and the surrounding environment. The barrier created by the surgical garment 12 may benefit both the wearer and the patient. The barrier provided by the surgical garment 12 may substantially eliminate the likelihood that the wearer may come into contact with fluid or solid particles of matter from the patient that may be generated during the course of a surgical procedure. The barrier may substantially prevent the transfer of any foreign particles emitted by the wearer from being transferred to the patient during the surgical procedure.

Figure 1:
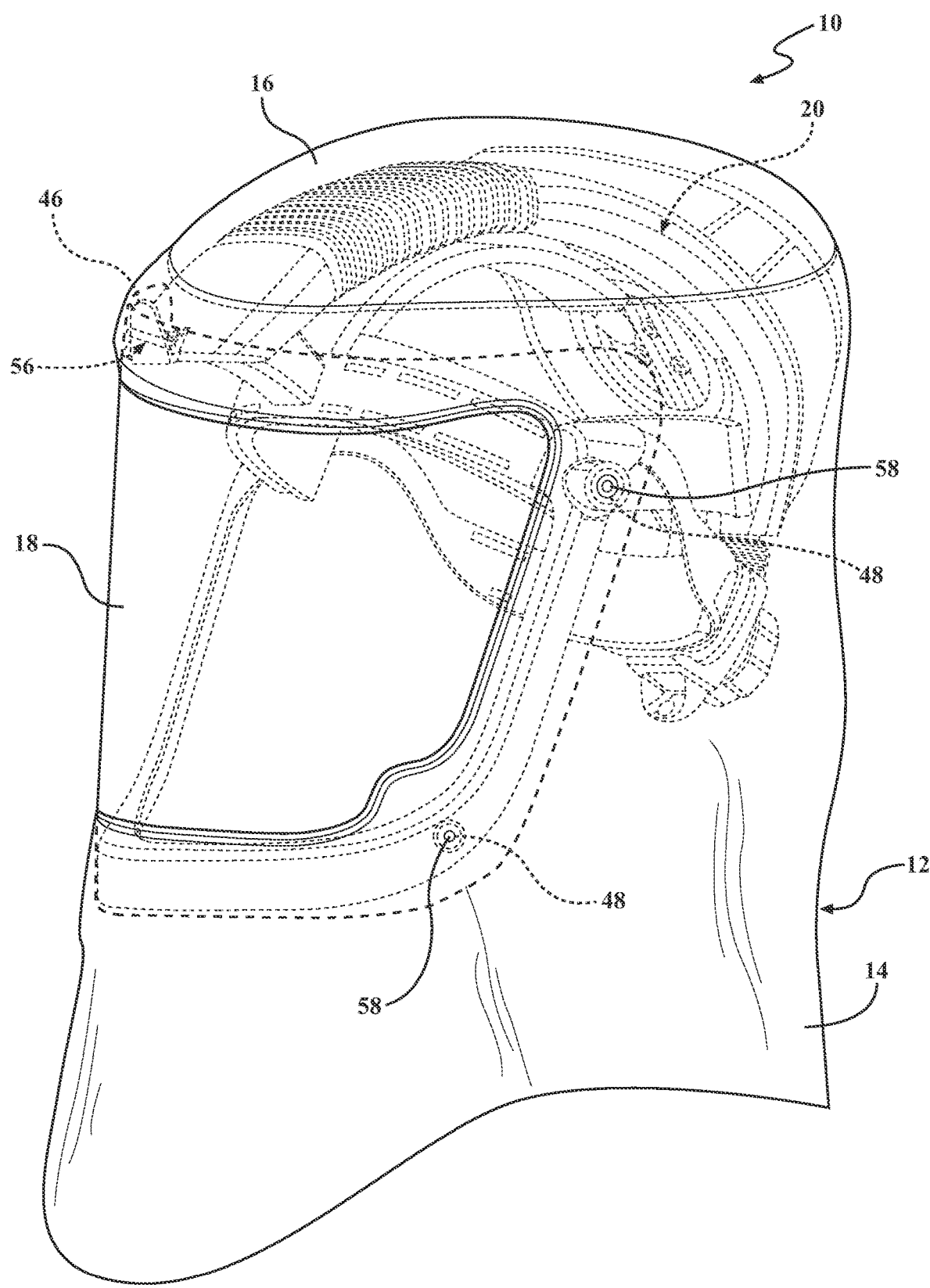
FIG. 1 is a perspective view of a first configuration of a surgical apparel system that includes a medical garment and a surgical helmet, with the surgical helmet shown in phantom.

Referring to FIG. 1, the surgical garment 12 may include a surgical fabric 14, which may also be referred to as a shell, configured to cover the surgical helmet 20 and at least a portion of the head of the wearer. The surgical garment 12 may be configured as a hood, as illustrated in FIG. 1. It will be understood that a hood refers to a surgical garment 12 that covers the head and likely only extends a short distance below the neck when worn by the wearer. However, while not illustrated in the figures, it is further contemplated that the surgical garment 12 may be configured as a toga, a shirt, or a jacket. It will be understood that a toga 12 refers to a surgical garment 12 that covers the head in the same manner as a hood and extends to at least the waist when worn by the wearer.

The surgical garment 12 may be manufactured from any suitable surgical fabric 14 or combinations of fabrics to help repel and/or absorb water, debris and other contaminants. The surgical fabric 14 may include multiple layers. One such layer may be a microporous film that allows gas to pass through the fabric while still maintaining the microbial barrier. In certain configurations, the surgical fabric 14 is one that satisfies the ASTM F1670-98 standard for blood penetration resistance and/or the ASTM F1671-97B standard for viral penetration resistance. In one non-limiting example of the surgical fabric 14, the surgical fabric 14 of the surgical garment 12 has a pore size in the approximate range of 0.05 to 0.20 microns. However, other pore sizes for the surgical fabric 14 are also contemplated.

It is further contemplated that the surgical garment 12 may be constructed of multiple different fabrics coupled to one another to define the barrier. For example, the surgical garment 12 may be primarily constructed from a barrier surgical fabric 14 and a filter fabric 16. The filter fabric 16 may be more permeable, and hence more breathable, than the barrier surgical fabric 14 described above. The filter fabric 16 may be located in an area with a reduced risk of having a microbial particle cross the barrier, such as above the wearer's head or proximate to the crown of the wearer's head, and configured to aid in the circulation of air through the barrier. The barrier surgical fabric 14 may be attached to the filter fabric 16 using any suitable means, such as adhesive, sewing, welding, or a combination thereof.

As illustrated in FIG. 1, the surgical garment 12 may further comprise a face shield 18. The face shield 18 portion of the surgical garment 12 allows the wearer to see through the barrier provided by the surgical garment 12. The face shield 18 is generally a sheet-like structure and may have a thickness of approximately 1 mm or less. The face shield 18 may be mounted and/or attached to an opening or cut-out formed in the surgical fabric 14 of the surgical garment 12. The surgical fabric 14 may be attached around the periphery or edge of the face shield 18 by sewing, snaps, hook and loop, adhesive, welding, or combinations thereof. The face shield 18 may be constructed from a transparent material, such as a polycarbonate. One such polycarbonate is sold under the trademark LEXAN™ by Sabic. The face shield 18 of the surgical garment 12 may also be tinted to protect the wearer's eyes from heightened exposure to bright lights. Furthermore, the face shield 18 may be flexible such that the face shield 18 may be curved to accommodate different head sizes as will be described below.

The face shield 18 may further comprise an opening 56 proximate to the top portion of the face shield 18. The opening 56 may be generally rectangular shaped. While not illustrated in the figures, it is further contemplated that the opening 56 may be configured in the shape of a circle, oval, square, or any similar polygonal shape. The opening 56 may also be generally centered between the opposing ends of the face shield 18, and serve as an alignment element and/or centering feature. Furthermore, the opening 56 may be positioned on the face shield 18 above the point of attachment for the surgical fabric 14 to the face shield 18, so as to ensure the surgical fabric 14 covers the opening 56 to maintain the barrier provided by the surgical garment 12 between the wearer and the environment. For example, as illustrated in FIG. 1, the surgical fabric 14 of the surgical garment 12 is attached to the top of the face shield 18 at a location below the opening 56 of the face shield 18.

The surgical garment 12 may also include one or more attachment elements 58 positioned about the surgical garment 12. The attachment elements 58 may also be referred to as a garment fastener or a second member. The attachment elements 58 are configured to releasably secure the surgical garment 12 to the surgical helmet 20. The attachment elements 58 may take any suitable form, and may comprise metal tacks, rivets, buttons, magnets, hook and loop, snaps, or similar types of fasteners, alone or in combination. As illustrated in FIG. 1, the attachment elements 58 may be mounted to the face shield 18 of the surgical garment 12 so as to extend inwardly from the wearer side of the face shield 18. While not illustrated in the figures, it is also contemplated that the attachment elements 58 may be positioned at any other position or location about the surgical garment 12, including being mounted to the barrier surgical fabric 14 and/or the filtration fabric 16. The attachment elements 58 may be mounted to the face shield 18 and/or fabric(s) 14/16 via an adhesive, rivet, snap, similar mounting device, or combination thereof.

Referring again to FIGS. 1 and 2, an example configuration of the surgical apparel system 10 is described in detail. The system may include a surgical garment 12 and a surgical helmet 20. The surgical garment 12 may be configured as a hood or a toga to be placed over the surgical helmet 20. In the hood configuration illustrated in FIG. 1, the surgical garment 12 may be positioned over the surgical helmet 20 and configured to encompass the surgical helmet 20 and, correspondingly, the head of the person wearing the surgical apparel system 10, thereby covering the wearer's face and back of the head. Alternatively, if the surgical garment 12 were configured as a toga, the toga may be positioned over the surgical helmet 20 and configured to encompass the surgical helmet 20 and, correspondingly, the head, arms, shoulders, and torso of the person wearing the surgical apparel system 10. To place the surgical garment 12 over the surgical helmet 20, the surgical garment 12 will typically be turned inside out as the face shield 18 is aligned and affixed to the surgical helmet 20 in the manner described below. Once the face shield 18 is positioned relative to the surgical helmet 20, the remainder of the surgical fabric 14 will typically be pulled over the wearer's head to cover the exposed components of the surgical helmet 20 and the wearer's head.

Figure 2:
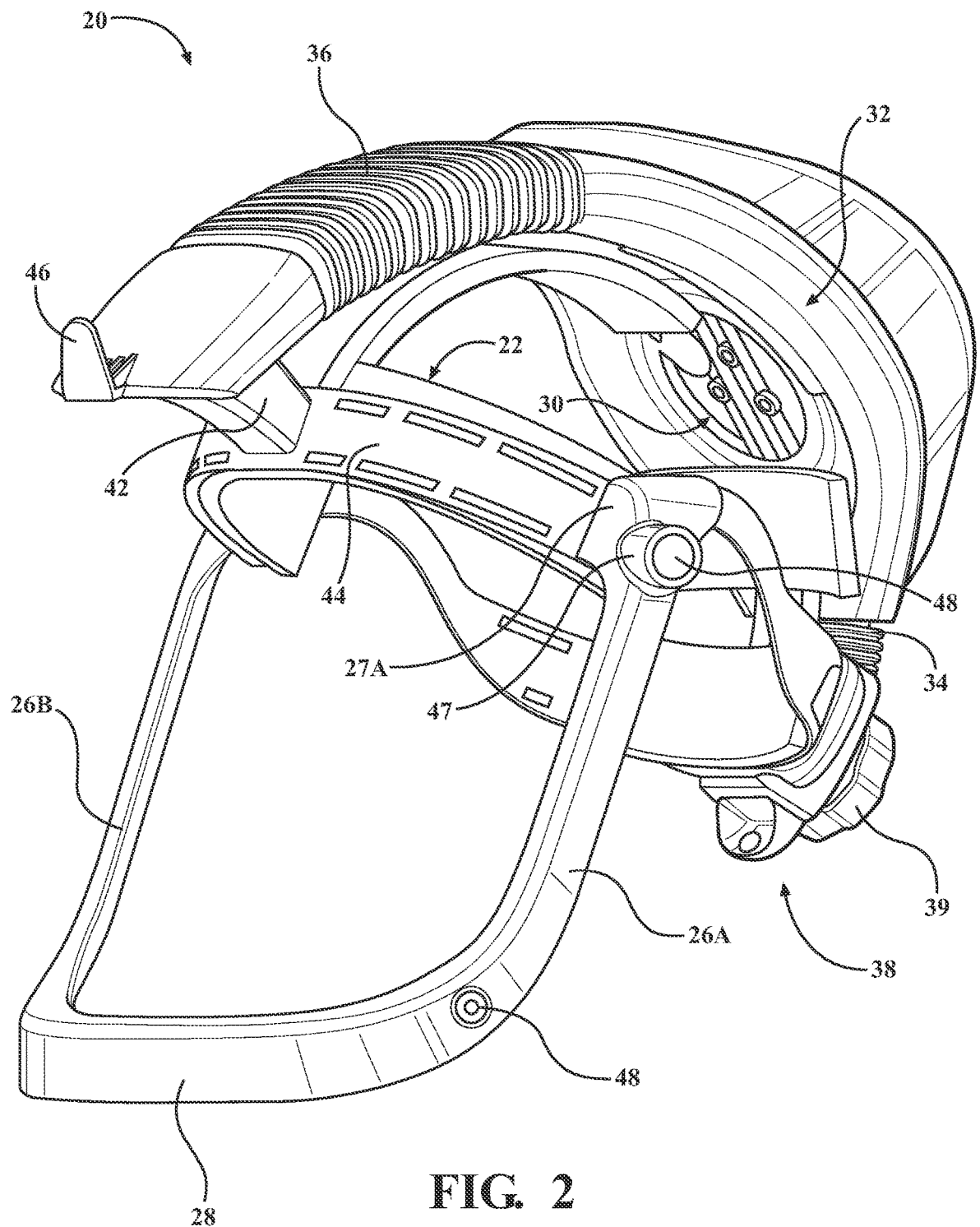
FIG. 2 is a perspective view of the surgical helmet of the surgical apparel system of FIG. 1.

Referring to FIG. 2, an example configuration of the surgical helmet 20 that may be utilized as part of the surgical apparel system 10 is illustrated. The surgical helmet 20 in FIG. 2 includes a headband 22. The headband 22 may be configured to encircle the wearer's head and support the surgical helmet 20. The headband 22 may be constructed from a generally flexible or pliable material, allowing the headband 22 to conform to general shape of the wearer's head. The headband 22 may comprise a headband control assembly 38 configured to adjust the size/shape of the headband 22. The headband control assembly 38 may comprise a control member 39 that is manipulatable by the wearer to adjust the size of the headband 22. For example, as illustrated in FIG. 2, the control member 39 may comprise a rotatable knob or lever. When the wearer rotates the control member 39 in one direction, the headband control assembly 38 may be configured to reduce the size, i.e., the circumference, of the headband 22. Alternatively, when the wearer rotates the control member 39 in the opposite direction, the headband control assembly 38 may be configured to increase the size, i.e., the circumference, of the headband 22. This allows for the headband 22 of the surgical helmet 20 to be adjusted and/or customized to securely fit on a particular individual's head irrespective of the individual's head size and/or shape.

The surgical helmet 20 further includes a housing 32 that is supported by and located above the headband 22. The housing 32 may be configured in an arcuate shape to fit over the head of the individual wearing the personal protection system 10. Other helmet designs are contemplated. Many portions of the housing 32 may be formed to define voids, or open interior spaces. For example, the housing 32 may comprise a center void. The center void may be located toward the rear of the housing 32. There may be an intake opening or aperture in the top portion of the housing 32 to provide access to the center void. The housing 32 may also include additional voids, such as a front void proximate to the front of the housing 32 and a rear void proximate to the rear of the housing 32. The additional voids may be configured to form duct-like structures or passageways within the housing 32. The additional voids may even be interconnected to the center void.

The surgical helmet 20 may include one or more electrically-powered peripheral devices 30, including but not limited to, a ventilation assembly, a light, a camera, microphone or other communication device, cooling device, or combinations thereof. These devices may be mounted to and/or attached at various locations and orientations relative to the surgical helmet 20. Each of the peripheral devices 30 may be configured to receive commands that affect the operating state of the corresponding peripheral device. For example, each of the peripheral devices 30 can receive on/off commands. Alternatively, the peripheral devices 30 may receive commands that change one or more settings of the peripheral devices 30. Such configurations allow the wearer of the surgical helmet 20 to control the operating state of the various peripheral devices 30 during the surgical procedure. In one specific example, when the peripheral device is a ventilation assembly 30, the ventilation assembly 30 may be configured to receive various commands to control the actuation and/or adjust the speed of the fan in the ventilation assembly 30. Alternatively, when the peripheral device is a cooling device 30, the cooling device 30 may be configured to receive commands to control the intensity of the cooling output provided by the cooling strip. When the peripheral device is a microphone 30, the microphone 30 may be configured to receive commands to control the volume of the audible signal produced by the microphone. When the peripheral device is a light 30, the light 30 may be configured to receive commands to control the direction and/or intensity of light emitted. The peripheral devices 30 may of course be configured to be responsive to other types of commands that control the operation of the peripheral device 30.

Wearing the surgical apparel system 10, including the surgical garment 12, over a wearer's head can inevitably result in the buildup of carbon dioxide and increased temperatures within the surgical garment 12 as a result of the wearer's normal breathing. An increase in temperature underneath the surgical garment 12 can also result in the buildup of water vapor on the wearer and/or the face shield 18, resulting in the wearer's view being obstructed. In order to prevent these undesirable effects, the surgical helmet 20 of the surgical apparel system 10 may be configured for the attachment and/or inclusion of one or more peripheral devices 30 described above, such as the ventilation assembly, the cooling device, etc. Certain features of the surgical helmet 20, the peripheral devices 20, and the surgical garments 12 may be found in one or more of the following U.S. patents, which are hereby incorporated by reference: U.S. Pat. Nos. 6,481,019; 6,622,311; 6,973,677; 7,735,156; 7,752,682; 8,234,722; 8,282,234; 8,407,818; 8,819,869; and 9,173,437.

The ventilation assembly 30 illustrated in FIG. 2 is one example of a peripheral device 30 that may be incorporated into the surgical helmet 20 of the surgical apparel system 10. While the ventilation assembly 30 is shown as an integral component of the surgical helmet 20, it should be appreciated that each of the other peripheral devices 30 described above may be either an integral component of the surgical helmet 20, or may be removably coupled to the surgical helmet 20. The surgical helmet 20 illustrated in FIG. 2 comprises the ventilation assembly 30 positioned within the center void of the housing 32. The ventilation assembly 30 may include a fan blade, impeller, propeller, fan wheel, or similar blade mechanism configured to induce air movement. The blade may be coupled to a motor configured to rotate the blade when energized by a power source. When the blade is actuated, the ventilation assembly 30 is configured to draw air into the center void of the housing 32 through the intake opening in the top of the housing 32. The additional voids of the housing 32 may be connected to the center void and serve as ducts for dispersing the air drawn into the center void.

The exemplary ventilation assembly 30 may include a front bellows 36 that extends forward from the front void in the front of the housing 32 and connects to a front nozzle 40. The front nozzle 40 may be mounted to the front of the headband 22. The ventilation assembly 30 may further include a rear bellows 34 that extends from the rear void in the rear of the housing 32 to a rear nozzle (not shown in figures). The rear nozzle may be mounted to the back of the headband 22. When the ventilation assembly 30 of the surgical helmet 20 is actuated, the fan draws air in through the surgical garment 12 into the opening in the top of the housing 32 and disperses the air outward through the additional voids. For example, the ventilation assembly 30 may be configured to draw air through the filter fabric 16 of the surgical garment 12. The air is then discharged through front bellows 36 and rear bellows 34, respectively. The air that flows through the front bellows 36 is discharged through the front nozzle 40 in front of the face of the wearer. The air discharged through the front nozzle 40 may be discharged against the face shield 18 and/or on the face of the wearer. The air that flows through the rear bellows 34 is discharged through the rear nozzle. The rear nozzle is positioned so as to open below the headband 22. The air discharged from the rear nozzle can be discharged against the back of the neck of the wearer.

The front nozzle 40 of the surgical helmet 20 may include a block 42. The block 42 is the portion of the front nozzle 40 that is mounted to the headband 22 or a component of the surgical helmet 20 integral with the headband 22. In the illustrated version of the system 10, the block 42 is mounted to a strap 44 that is part of the headband 22.

The front nozzle 40 may further be configured to include a protrusion 46. The protrusion 46 protrudes upwardly from the front edge of the front nozzle 40. As seen in FIG. 2, the protrusion 46 protrudes outwardly from the top surface of the front nozzle 40. As will be described in detail below, the protrusion 46 may be utilized to attach and/or secure the surgical garment 12 to the surgical helmet 20. In other configurations, the protrusion 46 may extend other portions of the surgical helmet 20, such as the top beam 29 of the face frame, or the housing 32 of the surgical helmet 20.

The surgical helmet 20 may include a chin bar 24 that extends downwardly from the front of the headband 22. The chin bar 24 may comprise a first post 26A and a second post 26B. Each of the first post 26A and second post 26B may comprise a first end 27A, 27B that is coupled to opposing sides of the strap 44 of the headband 22. The first and second posts 26A, 26B may be configured to be coupled to the headband 22 via the first ends 27A, 27B and to extend from opposing sides of the headband 22. The chin bar 24 may be constructed from a generally flexible or pliable material.

A beam 28 extends between the opposed free ends of the posts 26A, 26B. The chin bar 24 is formed so that a beam 28 is located below and slightly forward of the chin of the person wearing the surgical helmet 20. The beam 28 may be bowed outwardly from the free ends of posts 26A, 26B. The chin bar 24 may extend outwardly from the headband 22 such that the chin bar 24 is positioned forward of and generally encircles the face of the wearer when the surgical helmet 20 is secured to the wearer's head.

A plurality of coupling members 48, such as magnets, hook and loop, metal rivets, snaps, or similar type fasteners, may be mounted to the chin bar 24 and configured to align and/or attach to the face shield 18 of the surgical garment 12. Each coupling member 48 may be positioned on the chin bar 24 proximate to the opposed free ends of the posts 26A, 26B and/or adjacent opposing ends of beam 28. Alternatively, the coupling members 48 of the surgical helmet 20 could be arranged or otherwise configured in any suitable way to cooperate with the complementary attachment elements 58 of the face shield 18, as described above, to releasably secure the surgical garment 12 to the surgical helmet 20. For example, the protrusion 46 extending from the front nozzle 40 may be replaced with a coupling member 48 configured to cooperate with a complementary attachment element 58 on the surgical garment 12.

As described above, referring now to both FIGS. 1 and 2, in one configuration of the system 10, the face shield 18 may comprise an opening 56 proximate the top edge of the face shield 18. The opening 56 in the face shield 18 may be configured to receive the protrusion 46 protruding from the front nozzle 40 of the surgical helmet 20 or from another portion of the surgical helmet. The opening 56 and the protrusion 46 may be configured to releasably secure the face shield 18 and/or surgical garment 12 to the surgical helmet 20. Furthermore, the opening 56 and the protrusion 46 may serve as an alignment feature configured to align the face shield 18 with the surgical helmet 20, such that the face shield 18 will be positioned in front of the wearer's face when the system 10 is worn. While not shown in the figures, it should be understood that it has been contemplated that the face shield 18 may include additional openings 56, and the surgical helmet 20 may be configured to include additional protrusions 46 correspondingly arranged relative to the openings 56 of the face shield 18. For example, a plurality of protrusions 46 may extend from the headband 22 and/or front nozzle 40, and the face shield 18 may be configured to include complementary openings 56 that releasably engage the plurality of protrusions 46 when attaching the surgical garment 12 to the surgical helmet 20.

Figure 3:
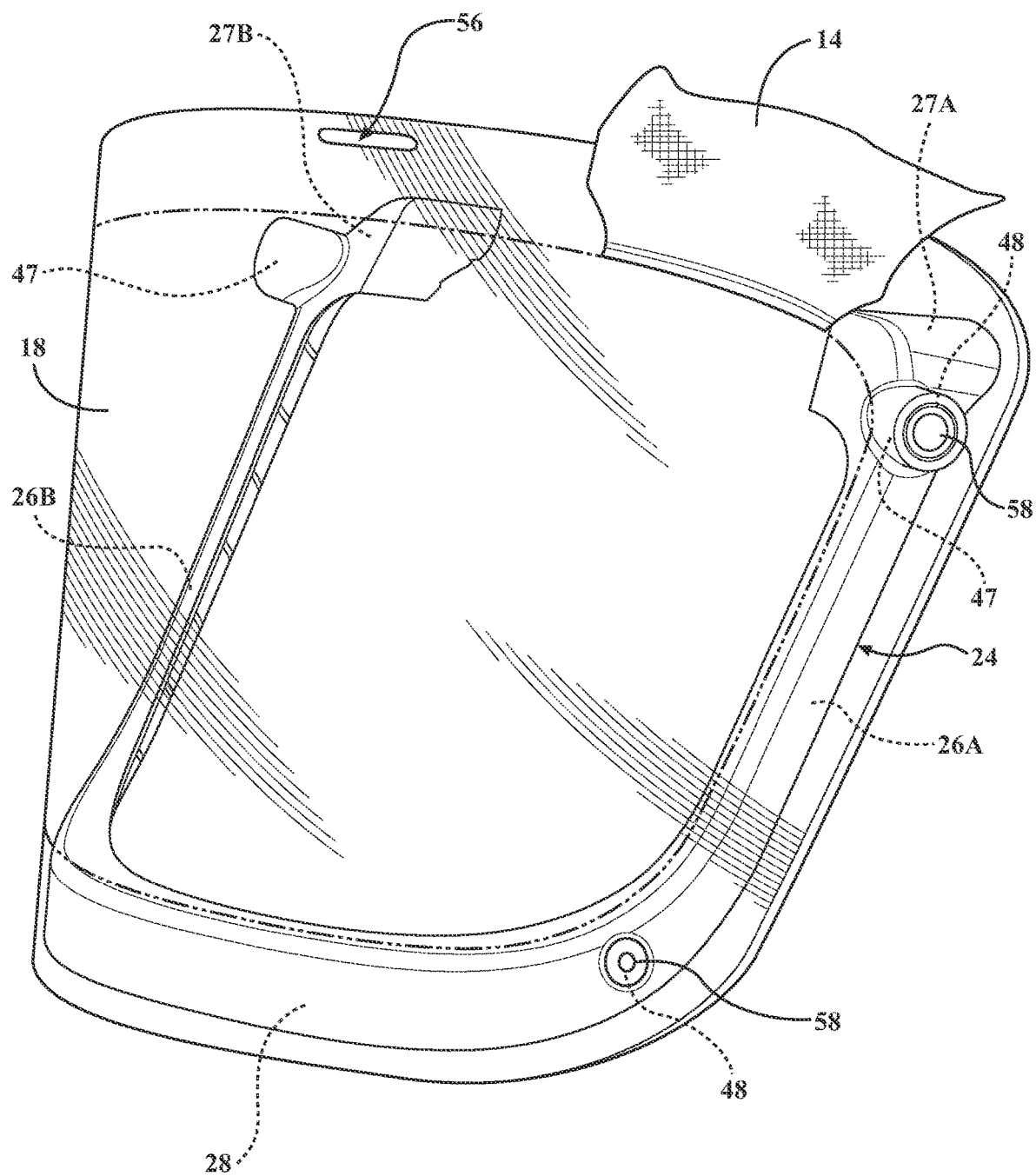
FIG. 3 is a partial perspective view of the medical garment coupled to a chin bar of the surgical helmet shown in FIG. 1.

Furthermore, as described above, the face shield 18 and/or surgical fabric 14 may comprise a plurality of attachment elements 58 arranged about the surgical garment 12. In the example configuration of the surgical garment 12 that is illustrated in FIGS. 1 and 3, the attachment elements 58 of the surgical garment 12 may be arranged and/or positioned on the face shield 18 so that, when the protrusion 46 of the surgical helmet 20 is seated in the opening 56 of the face shield 18, and the face shield 18 is flexed around the chin bar 24 and the strap 44 of the headband 22, each of the garment attachment elements 58 will abut and latch to a complementary magnet or other suitable coupling member 48 on the surgical helmet 20. Referring to the example configuration of the system 10 illustrated in FIG. 1 and the sectional view of the face shield 18 and chin bar 24 of FIG. 3, the surgical garment 12 comprises the opening 56 proximate to the top portion of the face shield 18 and a plurality of attachment elements 58 are positioned about the periphery of the face shield 18. The attachment elements 58 may be spaced about the periphery of the face shield 18 to matingly engage complementary magnets 48 on the chin bar 24 of the surgical helmet 20. While the surgical garment 12 illustrated in the figures comprises the opening 56, it is also contemplated that the opening 56 is not required in certain configurations. Alternatively, the attachment elements 58 may also be configured to couple and/or align the face shield 18 with the surgical helmet 20.

In operation, once the opening 56 in the face shield 18 is seated on the protrusion 46 of the surgical helmet 20, the face shield 18 may then be flexed around the surgical helmet 20 and/or chin bar 24 to matingly engage the attachment elements 58 spaced about the periphery of the face shield 18 with the complementary coupling members 48 on the chin bar 24 of the surgical helmet 20. The size of the face shield 18, as well as the spacing and/or position of the attachment elements 58 on the surgical garment 12 may be changed to alter the curvature and/or shape of the face shield 18 when attached to the surgical helmet 20. For example, the attachment elements 58 on the surgical garment 12 may be spaced closer together to reduce the curvature of the face shield 18 when it is attached to the surgical helmet 20. Alternatively, the attachment elements 58 on the surgical garment 12 may be spaced farther apart to increase the curvature of the face shield 18 when it is attached to the surgical helmet 20. Furthermore, as illustrated in FIG. 3, the coupling member 48 of the chin bar 24 may be part of a protrusion 47 configured to space the face shield 18 a defined distance from the chin bar 24 and/or surgical helmet 20. The size of the protrusion 47 may be similarly adapted to manipulate the curvature or arc of the face shield 18. Altering the curvature of the face shield 18 may help to reduce glare or provide an expanded/reduced peripheral view through the face shield 18. While not illustrated in the figures, it should be understood that alternative configurations for securing the surgical garment 12 and/or face shield 18 to the surgical helmet 20 are also contemplated. For example, in one alternative configuration, the face shield 18 may not include a rectangular opening 56, but instead comprise only a plurality of attachment elements 58, such as rivets or magnets, spaced about the face shield 18 and/or surgical garment 12 and configured to couple to complementary magnets or similar coupling members 48 spaced about the surgical helmet 20. For example, the complementary magnets or similar coupling members 48 may be secured to the housing 32, headband 22, and/or chin bar 24. The surgical garment 12 and the surgical helmet 20 of the surgical apparel system 10 described above are typically removably coupled to allow for disposal of the surgical garment 12 and reuse of the surgical helmet 20 following a procedure or exam.

Figure 4A:
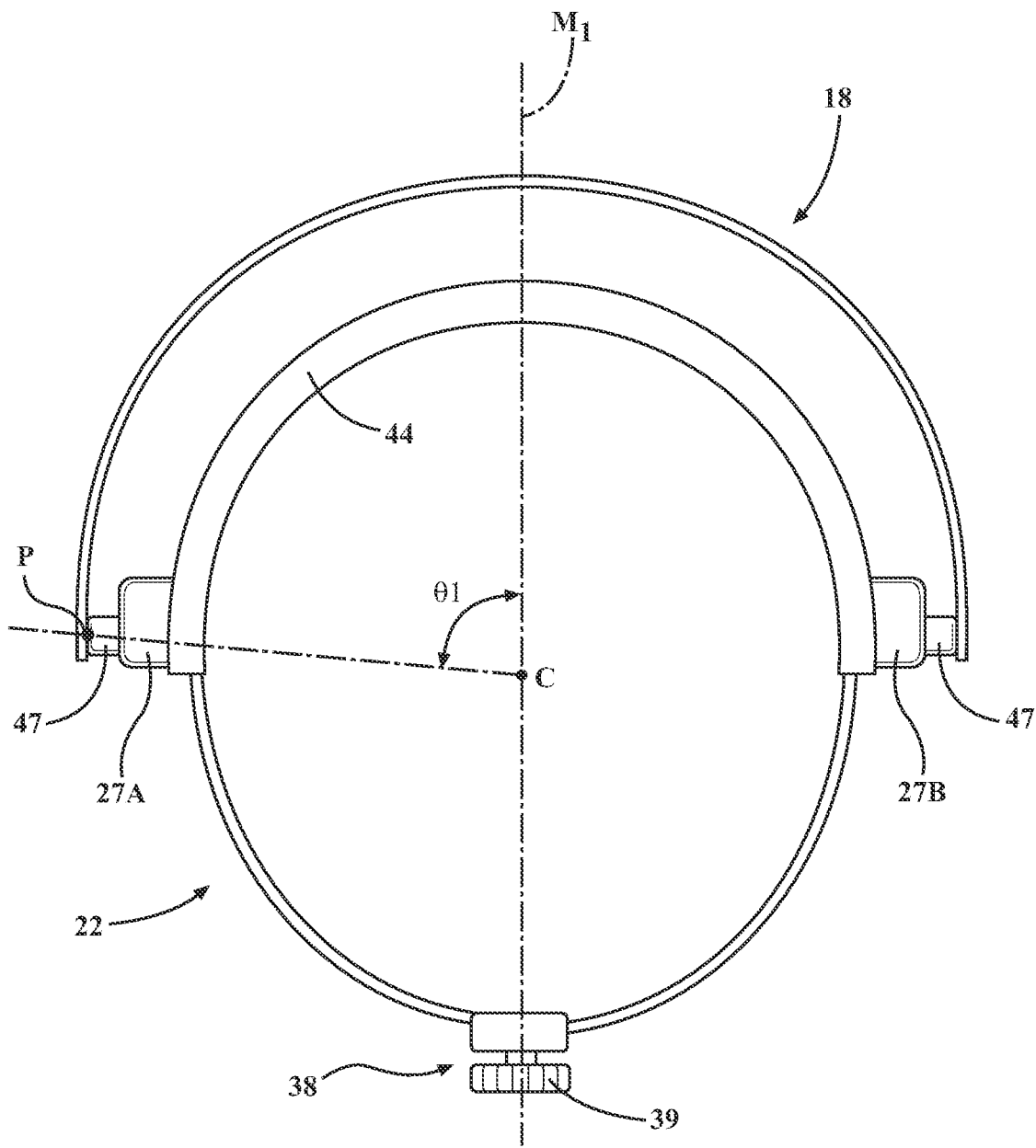
FIG. 4A is a partial schematic top view of a first configuration of a headband of the surgical apparel system of FIG. 1, with the medical garment coupled to the surgical helmet.
Figure 4B:
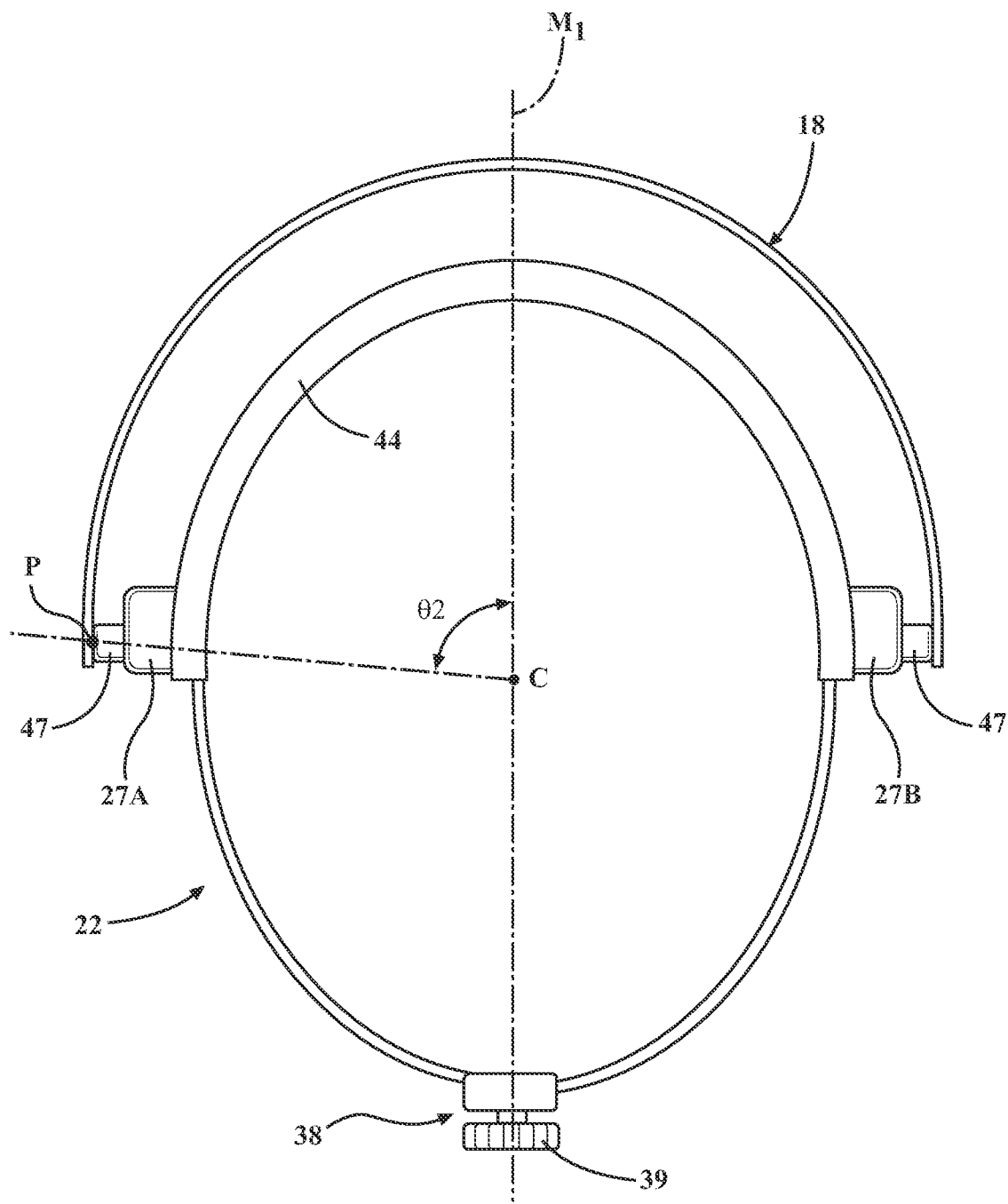
FIG. 4B is a partial schematic top view of a second configuration of the headband of the surgical apparel system of FIG. 1, with the medical garment coupled to the surgical helmet.

Referring to FIGS. 4A and 4B, an example configuration of the system 10 comprising differing face shield 18 curvatures is illustrated. FIGS. 4A and 4B each illustrate a top sectional view of a portion of the surgical helmet 20 including the headband 22, strap 44, headband control assembly 38, headband control member 39, first ends 27A, 27B of the posts 26A, 26B of the chin bar 24, and the protrusions 47 extending from the first ends 27A, 27B. Coupled to the headband 22 at the first ends 27A, 27B of the posts 26A, 26B is the face shield 18. Because the posts 26A, 26B are coupled to the headband 22 as opposed to the housing 32, and because the headband 22 can have various shapes and sizes, the contour and/or curvature of the face shield 18 on the hood may change as the headband 22 is adjusted. This 'dynamic' adjustment may improve the usability of the face shield 18. For example, it may allow the contour and/or curvature of the face shield 18 to be adapted to be more optimally positioned relative to the wearer's face. While not illustrated in the figures, it is also contemplated that the shield may comprise an array of attachment elements 58 extending across the top of the face shield 18 that are configured to couple the face shield 18 to the headband 22 and/or the strap 44. In this configuration, the headband 22 and/or strap may comprise an array of fasteners or coupling members configured to couple with the array of attachment elements 58 on the face shield 18. This configuration would similarly allow the contour of the shield 18 to change as the headband 22 is adjusted.

The diagrams of FIGS. 4A and 4B may illustrate the concept of a dynamic curvature shield in a useful manner, but shall not be construed as limiting in any fashion, i.e., the headband 22 and face shield 18 may be understood to operate in different fashions other than the manner described below. A medial axis M1 that bisects the headband 22 of the surgical helmet 20 and the face shield 18 is illustrated in FIGS. 4A and 4B. A center point C is positioned along the medial axis M1 proximate the center of the generally circular or oval shaped headband 22. A second line may be configured to extend between the center point C and an intersection point P that is positioned proximate the intersection of the face shield 18 and the protrusion 47 of the first ends 27A, 27B of the chin bar 24.

Referring to FIG. 4A, the headband control member 39 of the headband control assembly 38 may be set to a first position to define a first circumference and/or shape of the headband 22, and the second line extending between the center point C and the intersection point P intersects with the medial axis M1 at a first angle $\theta_1$. Referring to FIG. 4B, the control member 39 of the headband control assembly 38 may be set to a second position to define a second circumference and/or shape of the headband 22 that is larger or smaller than the first circumference and/or shape. The second line extending between the center point C and the intersection point P intersects with the medial axis M1 at a second angle $\theta_2$. Assuming the length of the face shield 18 is generally unchanged, by manipulating the control member 39 of the headband control assembly 38 to increase or reduce the size, i.e., the circumference, of the headband 22 to fit a particular wearer's head, the arc and/or curvature of the face shield 18 will be manipulated by the change in the size and/or shape of the headband 22. For example, if the size and/or circumference of the headband 22 is reduced, the intersection angle $\theta$ will likely increase, which is likely to reduce the radius of the arc of the face shield 18 and/or generally increase the bend and/or the curvature of the face shield 18. Alternatively, if the circumference of the headband 22 is increased, the intersection angle θ will likely decrease, which, in some cases, is likely to increase the radius of the arc of the face shield 18 and/or generally flatten the curvature of the face shield 18. The arc and/or curvature of the face shield 18 is therefore dynamic and at least partially defined by the size and/or shape of the headband 22. As described above, the chin bar 24 may be generally constructed from a flexible and/or pliable material to allow for the components of the chin bar 24 to flex, bend, twist, and/or rotate as needed in response to the changes in the size and/or shape of the headband 22.

The curvature and/or arc of the face shield 18 may also be modified or adapted by the size and/or shape of the attachment element(s) 58 of the face shield 18 and/or the corresponding coupling member(s) 48 of the surgical helmet 20.

Figure 5:
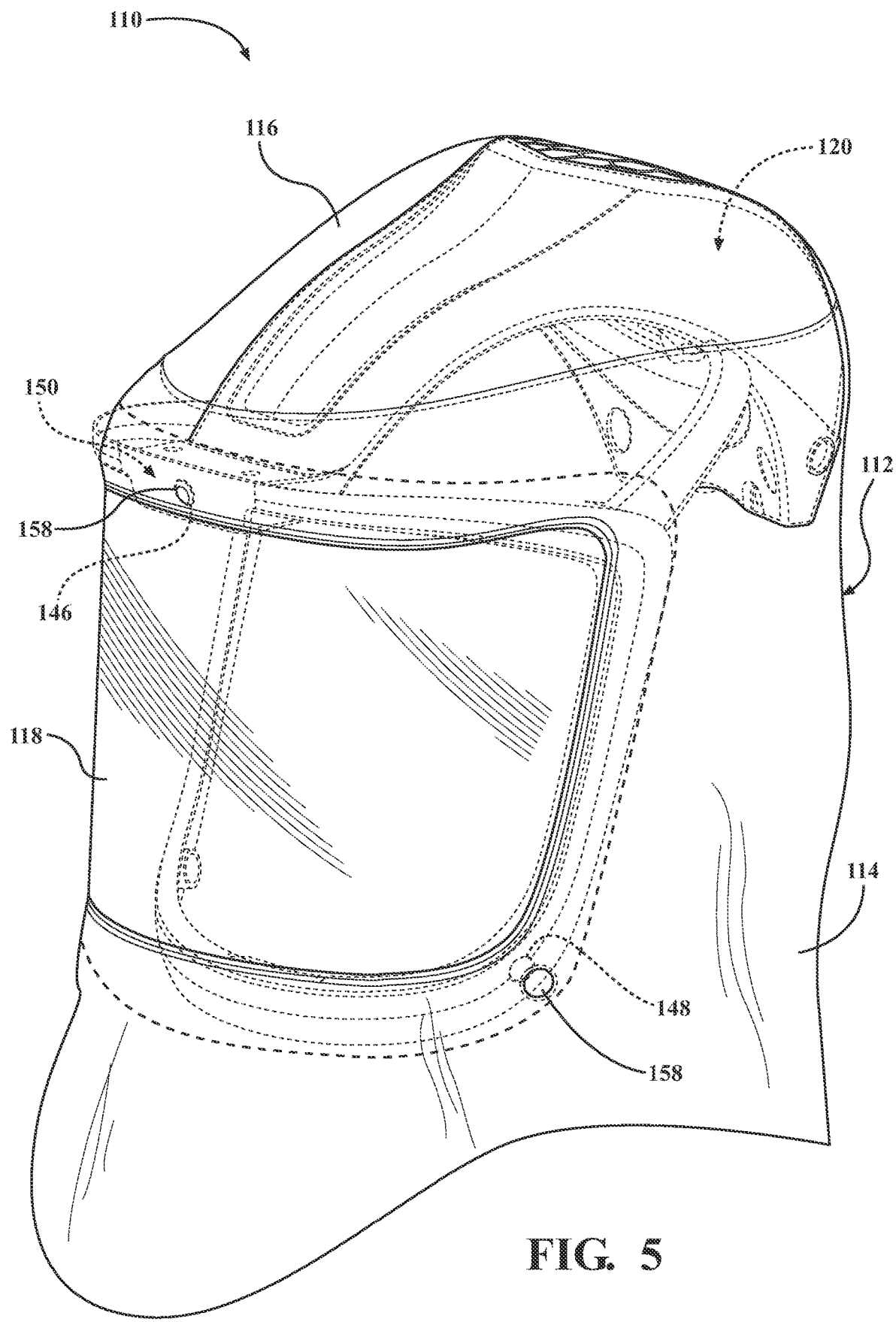
FIG. 5 is a perspective view of a second configuration of a surgical apparel system that includes a medical garment and a surgical helmet, with the surgical helmet shown in phantom.

Referring to FIG. 5, an alternative configuration of a surgical apparel system 110 is illustrated. It should be appreciated that the various configurations of the surgical apparel system 110 may include similar elements that may be identified by reference numerals that are incremented by 100. It should be understood that those elements including reference numerals which are incremented by 100 can have the same features as described above. The surgical apparel system 110 may comprise a surgical garment assembly comprising a surgical garment 112, which may also be referred to as a medical garment, configured for attachment to a surgical helmet 120. As described above, the surgical garment 112 may be configured to provide a barrier, such as a microbial barrier, between the wearer and the surrounding environment. The barrier created by the surgical garment 112 may benefit both the wearer and the patient. The barrier provided by the surgical garment 112 may substantially eliminate the likelihood that the wearer may come into contact with fluid or solid particles of matter from the patient that may be generated during the course of a surgical procedure. The barrier may substantially prevent the transfer of any foreign particles emitted by the wearer from being transferred to the patient during the surgical procedure.

Referring to FIG. 5, the surgical garment 112 may include a fabric 114, which may also be referred to as a shell, configured to cover the surgical helmet 120 and at least a portion of the head of the wearer. The surgical garment 112 may be configured as a hood, toga, or other similar medical garment, as described above with regard to the first configuration of the surgical apparel system 10. The surgical garment 112 may further comprise a face shield 118 and one or more attachment elements 158 positioned about the surgical garment 112. The attachment elements 158 may also be referred to as a second member. The attachment elements 158 may be configured to serve as an alignment element and/or centering feature. Furthermore, the attachment elements 158 may be positioned on the face shield 118 above the point of attachment for the fabric 114 to the face shield 118, so as to ensure the fabric 114 covers the attachment elements 158 to maintain the barrier provided by the surgical garment 112 between the wearer and the environment. The attachment elements 158 may be configured to be constructed of one of a ferromagnetic material or a magnetic material. It should be appreciated that the surgical garment 112, and all components thereof, may be configured similarly and/or have the features described above with respect to the surgical garment 12 described above.

Referring again to FIGS. 5 and 6, an example configuration of the surgical apparel system 110 is described in detail. The system 110 may include a surgical garment 112 and surgical helmet 120. Similar to the system 10 described above, the configuration of the system 110 illustrated in FIGS. 5 and 6 may comprise one or more peripheral devices, such as a ventilation assembly.

Figure 6:
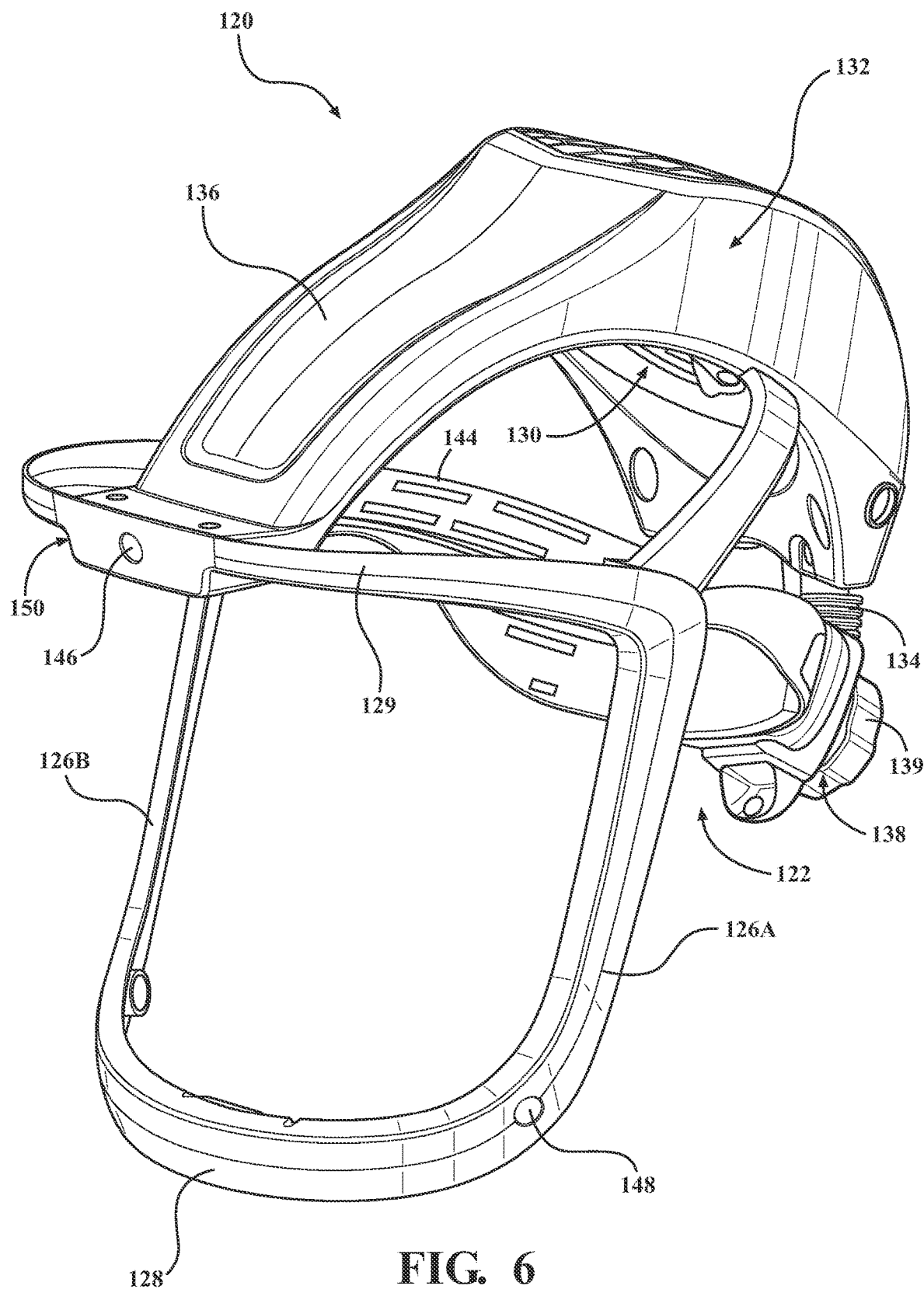
FIG. 6 is a perspective view of the surgical helmet of the surgical apparel system of FIG. 5.

The ventilation assembly 130 illustrated in FIG. 6, is one example of a peripheral device 130 that may be incorporated into the surgical helmet 120 of the surgical apparel system 110. While the ventilation assembly 130 is shown as an integral component of the surgical helmet 120, it should be appreciated that each of the other peripheral devices 130 described above may be either an integral component of the surgical helmet 120, or may be removably coupled to the surgical helmet 120. The surgical helmet 120 illustrated in FIG. 6 comprises the ventilation assembly 130 positioned within the center void of the housing 132. The ventilation assembly 130 may include a fan blade, impeller, propeller, fan wheel, or similar blade mechanism configured to induce air movement. The blade may be coupled to a motor configured to rotate the blade when energized by a power source. When the blade is actuated, the ventilation assembly 130 is configured to draw air into the center void of the housing 132 through the intake opening in the top of the housing 132. The additional voids of the housing 132 may be connected to the center void and serve as ducts for dispersing the air drawn into the center void.

The exemplary ventilation assembly 130 may include a front bellows 136 that extends forward from the front void in the front of the housing 132 and connects to a front nozzle (not shown in figures). The front nozzle may be mounted to the front of the headband 122. The ventilation assembly 130 may further include a rear bellows 134 that extends from the rear void in the rear of the housing 132 to a rear nozzle (not shown in figures). The rear nozzle may be mounted to the back of the headband 122. When the ventilation assembly 130 of the surgical helmet 120 is actuated, the fan draws air in through the surgical garment 112 into the opening in the top of the housing 132 and disperses the air outward through the additional voids. For example, the ventilation assembly 130 may be configured to draw air through the filter fabric 116 of the surgical garment 112. The air is then discharged through front bellows 136 and rear bellows 134, respectively.

The surgical helmet 120 may further comprise a control housing 150, which may be located on the front face of the helmet 20 and, as illustrated, be coupled to the front bellows 136 opposite the ventilation assembly 130. It is also contemplated that the control housing 150 may be positioned on or within the chin bar 124. For example, the control housing 150 may be positioned within the chin bar 124 relative to one or more of the coupling members 148. The control housing 150 may comprise a coupling feature 146 configured to engage with at least one of the attachment elements 158. The coupling feature 146 may also be referred to as a helmet coupler, as the coupling feature 146 may generally be configured to couple and/or attach an item, such as the surgical garment 112, to the surgical helmet 120. The control housing 150 may be coupled to a top beam 129 extending across the front of the surgical helmet 120 from opposing sides of the control housing 150.

The surgical helmet 120 may include a chin bar 124 that extends downwardly from the front portion of the surgical helmet 120. The chin bar 124 may comprise a first post 126A and a second post 126B. Each of the first post 126A and second post 126B may comprise a first end 127A, 127B that is coupled to opposing sides of the surgical helmet 120. The first and second posts 126A, 126B may be configured to be coupled to the top beam 129 extending from the control housing 150 via the first ends 127A, 127B and to extend from opposed sides of the surgical helmet 120. For example, as illustrated in FIG. 6, the first ends 127A, 127B may be connected to opposing ends of the top beam 129 extending from the control housing 150. The chin bar 124 may be constructed from a generally flexible or pliable material.

A bottom beam 128 may extend between the opposed free ends of the posts 126A, 126B of the chin bar 124. The chin bar 124 may be formed so that the bottom beam 128 is located below and slightly forward of the chin of the person wearing the surgical helmet 120. The bottom beam 128 may be bowed outwardly from the free ends of posts 126A, 126B. The chin bar 124 may extend outwardly from the top beam 129 such that the chin bar 124 is positioned forward of and generally encircles the face of the wearer when the surgical helmet 120 is secured to the wearer's head.

A plurality of coupling members 148, such as magnets, hook and loop, metal rivets, snaps, or similar type fasteners, may be mounted to the chin bar 124 and configured to align and/or attach to the face shield 118 of the surgical garment 112. Each coupling member 148 may be positioned on the chin bar 124 proximate to the opposed free ends of the posts 126A, 126B and/or adjacent opposing ends of the bottom beam 128. Alternatively, the coupling members 148 of the surgical helmet 120 could be arranged or otherwise configured in any suitable way to cooperate with the complementary attachment elements 158 of the face shield 118, as described above, to releasably secure the surgical garment 112 to the surgical helmet 120.

Figure 7:
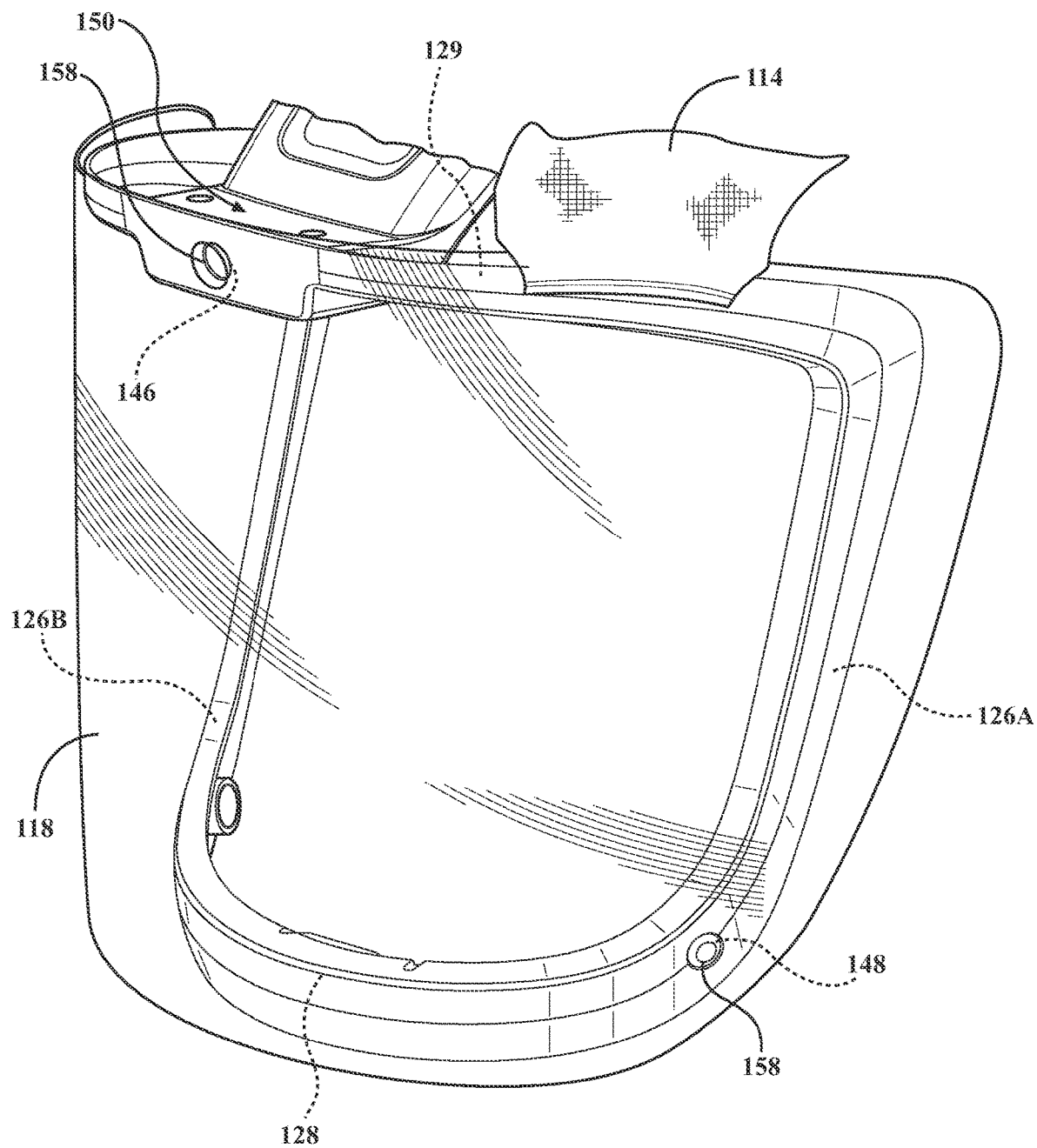
FIG. 7 is a partial perspective view of the medical garment coupled to a chin bar of the surgical helmet shown in FIG. 5.

Referring to FIG. 7, a partial perspective view of the surgical garment 112 coupled to the chin bar 124 and the control housing 150 of the surgical helmet 120 is illustrated. The surgical garment 112 comprises a plurality of attachment elements 158 positioned about the periphery of the face shield 118. For example, as illustrated in FIG. 7, the face shield 118 comprises a pair of attachment elements 158 positioned on opposing ends of the lower portion of the face shield 118, and each is configured to couple with a corresponding coupling member 148 on the chin bar 124. The face shield 118 further comprises an attachment element 158 positioned near the center of the top portion of the face shield 118 and configured to couple with the coupling feature 146 of the control housing 150.

Figure 8:
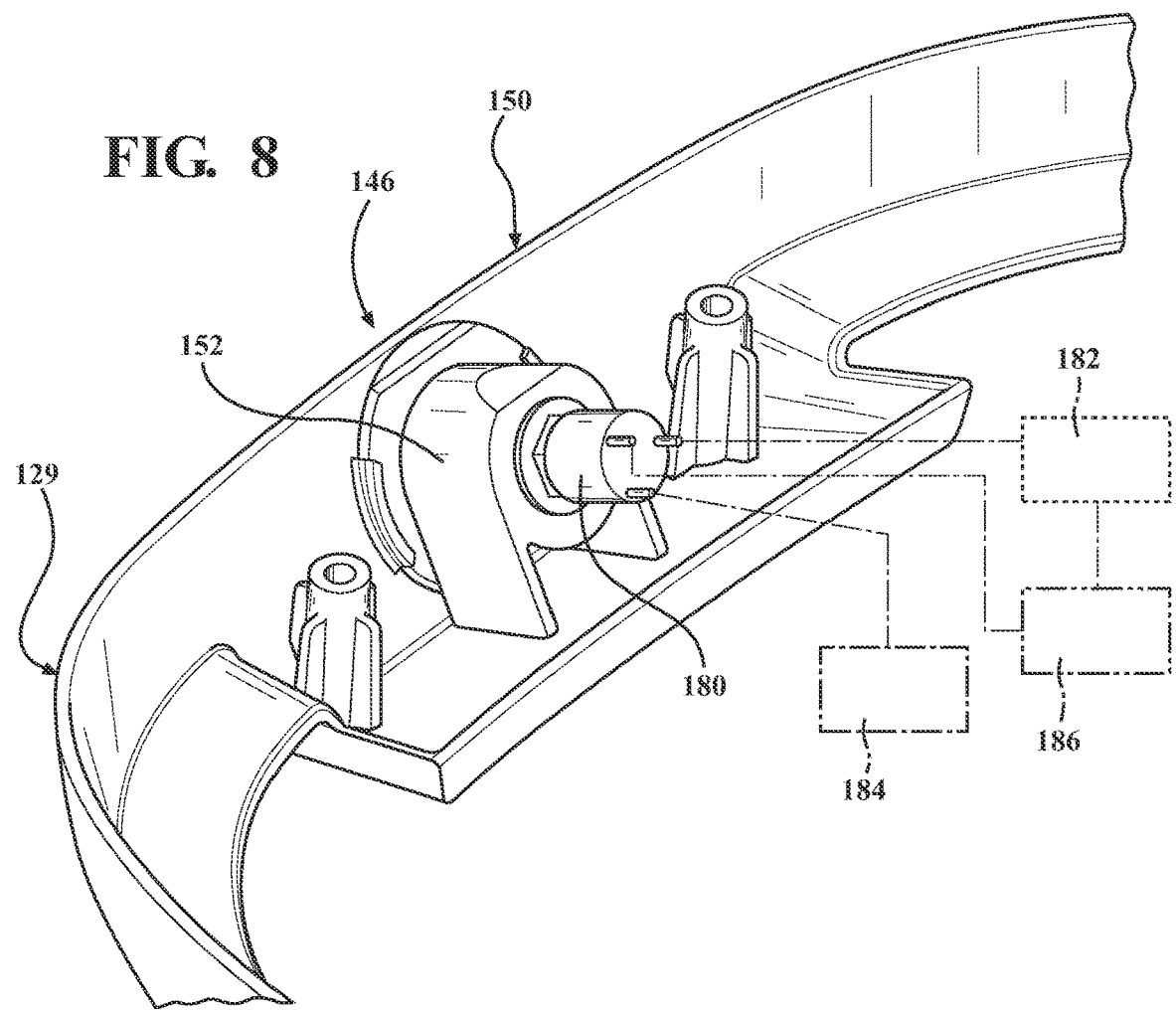
FIG. 8 is a partial perspective view of an interior portion of a control housing of the surgical apparel system of FIG. 5 including a first configuration of a coupling feature.

Referring to FIG. 8, a partial perspective view of an interior portion of the control housing 150 of the surgical apparel system 110 of FIGS. 5 and 6 is illustrated. At least partially disposed within the control housing 150 is a portion of the coupling feature 146 of the surgical helmet 120. While not illustrated in FIG. 8, additional components of the surgical helmet 120 and peripheral devices 130 may be at least partially disposed within or mounted to the control housing 150. For example, a light may be mounted to an outer surface of the control housing 150 or another portion of the surgical helmet 120. A memory device, circuit board or other electrical component utilized in operation of the surgical helmet 120 and/or peripheral device 130 may also be at least partially disposed within the control housing 150.

Figure 9A:
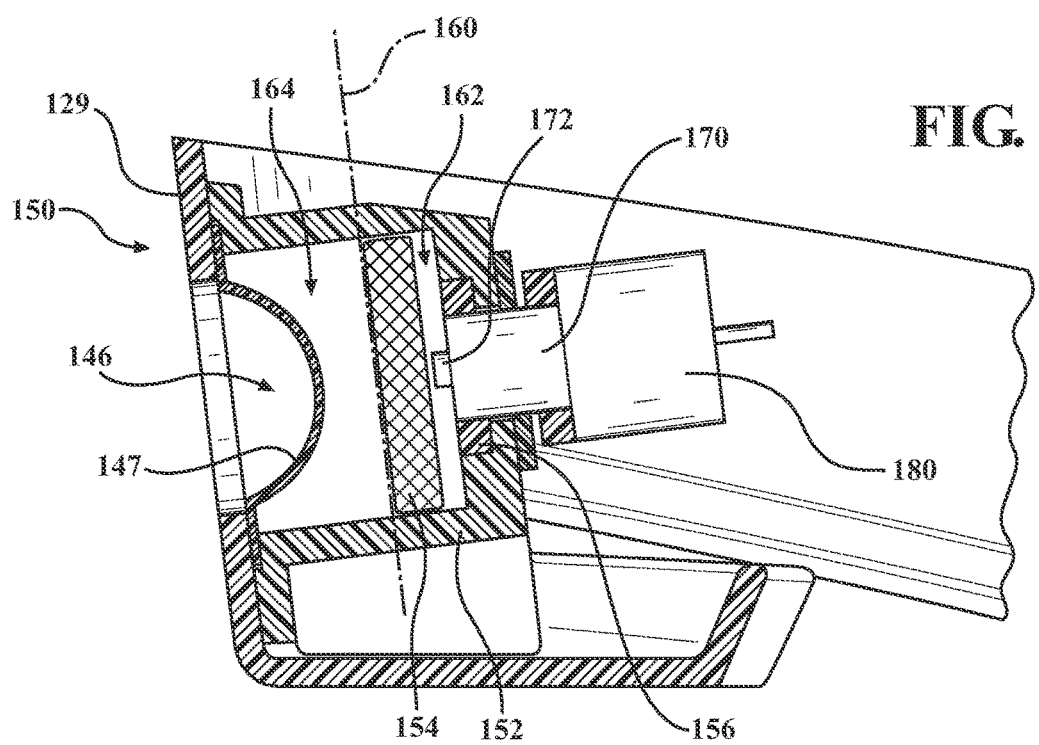
FIG. 9A is a close-up cross-sectional view of a first state of the first configuration of the coupling feature of FIG. 8.
Figure 9B:
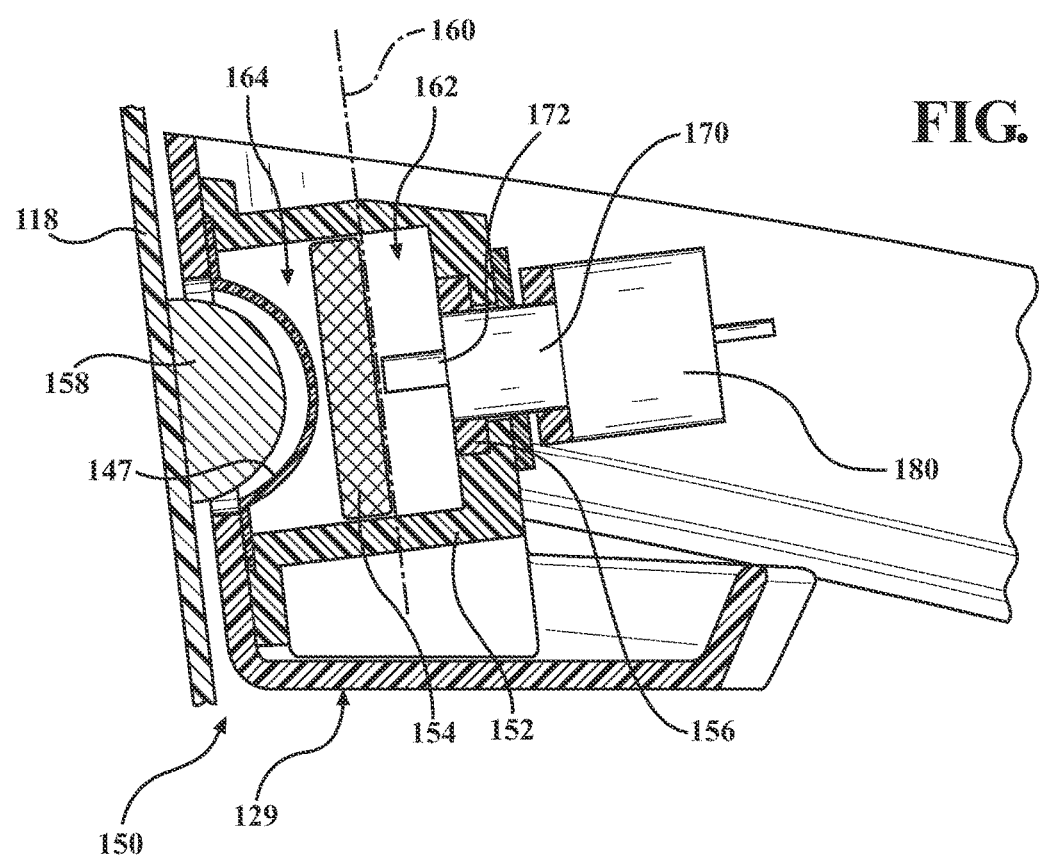
FIG. 9B is a close-up cross-sectional view of a second state of the first configuration of the coupling feature of FIG. 8, wherein the medical garment is coupled to the surgical helmet.

Illustrated in each of FIGS. 9A and 9B is a close-up sectional view of a first configuration of the coupling feature 146. More specifically, FIG. 9A illustrates a sectional view of the first configuration of the coupling feature in a first state, i.e., when the attachment element 158 of the surgical garment 112 is not coupled to the coupling feature 146 of the surgical helmet 120. Alternatively, FIG. 9B illustrates a sectional view of the first configuration of the coupling feature in a second state, i.e., when the surgical garment 112 is coupled to the coupling feature 146.

The first configuration of the coupling feature 146 may comprise a distal surface 147 configured to removably engage an attachment element 158 of the surgical garment 112. The distal surface 147 may be configured in any number of shapes configured to at least partially engage the corresponding attachment element 158 of the surgical garment 112. For example, the distal surface 147 may be configured as a generally flat surface configured to engage an attachment element 158 of the surgical garment 112 comprising a flat rivet. Alternatively, the distal surface 147 may be curved, arched, rounded, and/or hemispherically shaped and configured to matingly engage a complementarily-shaped attachment element 158. While the distal surface 147 as illustrated in FIGS. 9A and 9B is generally formed in a concave or inwardly directed hemispherical shape, it is also contemplated that the distal surface 147 may be formed in a convex or outwardly projected hemispherical shape, a half-cylinder shape or other similar shapes. For example, the distal surface 147 may be curved, arched, or rounded in a manner that projects outwardly from an outer surface of the control housing 150 to create a convex shaped distal surface 147. The corresponding attachment element 158 of the surgical garment 112 may comprise a concave surface configured to matingly engage the convex shaped distal surface 147 of the coupling feature 146.

The helmet may comprise an enclosure 152 configured to define a void space. The enclosure 152 may be generally configured in a cylindrical or tubular shape. Alternatively, the enclosure 152 may be generally configured in a rectangular or similar polygonal shape. As illustrated in FIGS. 9A and 9B, the enclosure 152 is generally configured in a cylindrical shape, wherein the distal surface 147 forms a portion of the distal end of the enclosure 152.

The void space defined by the enclosure 152 may be divided into one or more regions. For example, as illustrated in FIGS. 9A and 9B, the enclosure 152 may be divided by a first line 160 to define a first region 162 and a second region 164 of the void space. The first region 162 may be positioned on the side of the first line 160 such that the first region 162 is generally proximal to the surgical helmet 120 and away from the distal surface 147. By contrast, the second region 164 may be positioned on the side of the first line 160 such that the second region 164 is generally distal to the surgical helmet 120 and proximal from the distal surface 147.

The coupling feature 146 at least partially disposed within the control housing 150 of the surgical helmet 120 may further comprise a first member 154 movably disposed within the enclosure 152. The first member 154 may be configured to move within the void space defined by the enclosure 152. For example, the first member 154 and the enclosure 152 may be configured wherein the first member 154 is movable between the first region 162 and the second region 164 of the void space defined by the enclosure 152. The first member 154 may be constructed of one of a ferromagnetic material or a magnetic material, and the attachment element 158 may be constructed from the other of the ferromagnetic material or the magnetic material. For example, the first member 154 may comprise a magnetic material and the attachment element 158 may comprise a ferromagnetic material. Alternatively, the first member 154 may comprise a ferromagnetic material and the attachment element 158 may comprise a magnetic material. In either configuration, the first member 154 and the attachment element 158 may be configured such that when the attachment element 158 is positioned proximate to the distal surface 147, the attachment element 158 and the first member 154 may be magnetically attracted to one another. For example, when the attachment element 158 is positioned proximate to the distal surface 147 of the coupling feature 146, the magnetic force between the first member 154 and the attachment element 158 may serve to attach and/or couple the surgical garment 112 to the surgical helmet 120.

The first member 154 and the enclosure 152 may be sized and/or shaped to allow the first member to slidably move within the enclosure 152. For example, as illustrated in FIGS. 9A and 9B, the first member 154 may be shaped like a circular or polygonal shaped disc configured to match the shape defined by the lateral surfaces of the enclosure 152. The first member 154 may further comprise opposing forward and rearward facing surfaces. For example, as illustrated in FIGS. 9A and 9B, the opposing forward and rearward facing surfaces are flat. Alternatively, while not illustrated in the figures, the opposing forward and rearward facing surfaces of the first member 154 may correspond to the distal surface 147 of the enclosure 152. For example, the forward facing surface of the first member 154 may be concave or hemispherically shaped to correspond with the shape of the distal surface 147. The rearward facing surface of the first member 154 may be flat. Alternatively, if the distal surface 147 were convex shaped, the forward facing surface of the first member 154 may be convex or hemispherically shaped to correspond with the shape of the distal surface 147. The rearward facing surface of the first member 154 may be flat.

The coupling feature 146 may further comprise a detector 170, such as a mechanical switch, at least partially disposed within the void space defined by the enclosure 152, and positioned proximate to the first region 162. Alternatively, the detector 170 may be positioned proximate to the second region 164. It is further contemplated that the detector 170 may be positioned adjacent and/or external to the perimeter defined by the enclosure 152. The detector 170 may further comprise a toggle member 172 that is moveable between a first position and a second position. As illustrated in FIGS. 9A and 9B, the toggle member 172 is configured to extend through a surface of the enclosure 152 that is opposite the distal surface 147. In this configuration, the toggle member 172 may be configured to move proximally and distally relative to the distal surface 147 and generally parallel to a longitudinal axis defined by the toggle member 172. While not illustrated in the figures, it is contemplated that the detector 170 may be positioned adjacent to a lateral surface of the enclosure 152. In this configuration, the toggle member 172 may be configured to extend through the lateral surface of the enclosure 152 so that the toggle member 172 is at least partially disposed within the enclosure 152, while the detector 170 may be located outside the perimeter defined by the enclosure 152. The detector 170 may be positioned adjacent to the lateral surface such that the toggle member 172 is at least partially disposed within the first region 162 or the second region 164 of the void space defined by the enclosure 152. In this configuration, the toggle member 172 may be configured to move proximally and distally relative to the distal surface 147 and generally perpendicular to the longitudinal axis defined by the toggle member 172. The detector 170 may further comprise a biasing member, such as a spring, that is configured to move and/or hold the toggle member 172 in the second position absent an additional force being applied to the toggle member 172. The detector 170 may be configured to detect the position of the toggle member 172 and output a signal based, at least in part, on the position of the toggle member 172.

In operation, the first member 154 may be configured to operatively and/or slidingly engage the toggle member 172 of the detector 170 to move the toggle member 172 between the first position and the second position. For example, as illustrated in FIG. 9A, when the first member 154 is in the first region 162 of the void space, the first member 154 may be configured to engage the toggle member 172 and overcome the force of the biasing member to move and/or hold the toggle member 172 in the first position. Alternatively, as illustrated in FIG. 9B, when the first member 154 is in the second region 164 of the void space, the first member 154 may be configured to be disengaged from the toggle member 172 allowing the biasing member of the toggle member 172 to move and/or hold the toggle member 172 in the second position. As described above, the detector 170 may be configured to detect the position of the toggle member 172 and output a signal based on said toggle member 172 being in either the first position and/or the second position. In other words, the detector 170 is configured to determine whether the toggle member 172 is in the first position or the second position, which corresponds to whether or not the surgical garment 112 is coupled to the surgical helmet 120.

The coupling feature 146 may also comprise a third member 156 positioned proximate to the detector 170 and/or the toggle member 172. The third member 156 may be configured as a disk positioned on a distal tip of the toggle member 172 or a ring configured to encircle at least a portion of the toggle member 172. As illustrated in FIGS. 9A and 9B, the third member 156 may be configured as a loop, ring, or similar circular shape positioned adjacent a wall or surface of the enclosure 152 opposite the distal surface 147. The third member 156 may encircle at least a portion of the toggle member 172 and/or the detector 170, or may be adjacent to the toggle member 172 or the detector 170. While the third member 156 illustrated in FIGS. 9A and 9B is illustrated as being at least partially disposed within the enclosure 152, it is also contemplated that the third member 156 may be positioned outside the enclosure 152. Furthermore, the surface of the enclosure 152 opposite the distal surface 147 may be configured as the third member 156. For example, the surface of the enclosure 152 opposite the distal surface 147 may be integrally formed with the third member 156. The third member 156 may be constructed of the other of the ferromagnetic material or the magnetic material, such that the third member 156 and the first member 154 may be magnetically attracted to one another. The magnetic attraction force between the first member 154 and the third member 156 should provide sufficient force to overcome the biasing member of the toggle member 172. For example, the magnetic attraction force between the first member 154 and the third member 156, absent the application of any additional forces to the first member 154, should be sufficient to allow the first member 154 to move and/or hold the toggle member 172 in the first position, as illustrated in FIG. 9A.

In addition, the magnetic attraction force between the attachment element 158 and the first member 154 should be sufficient to overcome the magnetic attraction force between the first member 154 and the third member 156. When the attachment element 158 and the third member 156 each comprise a ferromagnetic material, the attachment element 158 and the third member 156 may be configured to comprise differing magnetic masses. For example, in order to have the magnetic attraction force between the first member 154 and the attachment element 158 be greater than the magnetic attraction force between the first member 154 and the third member 156, the attachment element 158 may be configured to comprise a greater magnetic mass than the third member 156. Alternatively, when the attachment element 158 and third member 156 each comprise a magnetic material, the attachment element 158 and the third member 156 may be configured to comprise differing strength magnetic fields. For example, in order to have the magnetic attraction force between the first member 154 and the attachment element 158 be greater than the magnetic attraction force between the first member 154 and the third member 156, the attachment element 158 may exploit a stronger magnetic field than the third member 156 so that the attachment element 158 may pull the first member 154 away from the third member 156.

In operation, as illustrated in FIG. 9B, when the attachment element 158 is positioned adjacent to the distal surface 147 of the coupling feature 146, the magnetic attraction force generated between the first member 154 and the attachment element 158 should be sufficient to overcome the magnetic attraction force between the first member 154 and the third member 156. The magnetic attraction force between the first member 154 and the attachment element 158 should overcome the magnetic attraction force between the first member 154 and the third member 156, moving the first member 154 from the first region 162 to the second region 164 of the void space. This should allow the toggle member 172 to move from the second position to the first position, i.e., move the first member 154 and the toggle member 172 from the configuration illustrated in FIG. 9A to the configuration illustrated in FIG. 9B. This change in position is detected by the detector 170. The detector 170 can be in communication with a controller 180 on the surgical helmet 120 that is in communication with the peripheral device(s) 130. The operation of the controller 180 will be described in detail below.

Figure 10A:
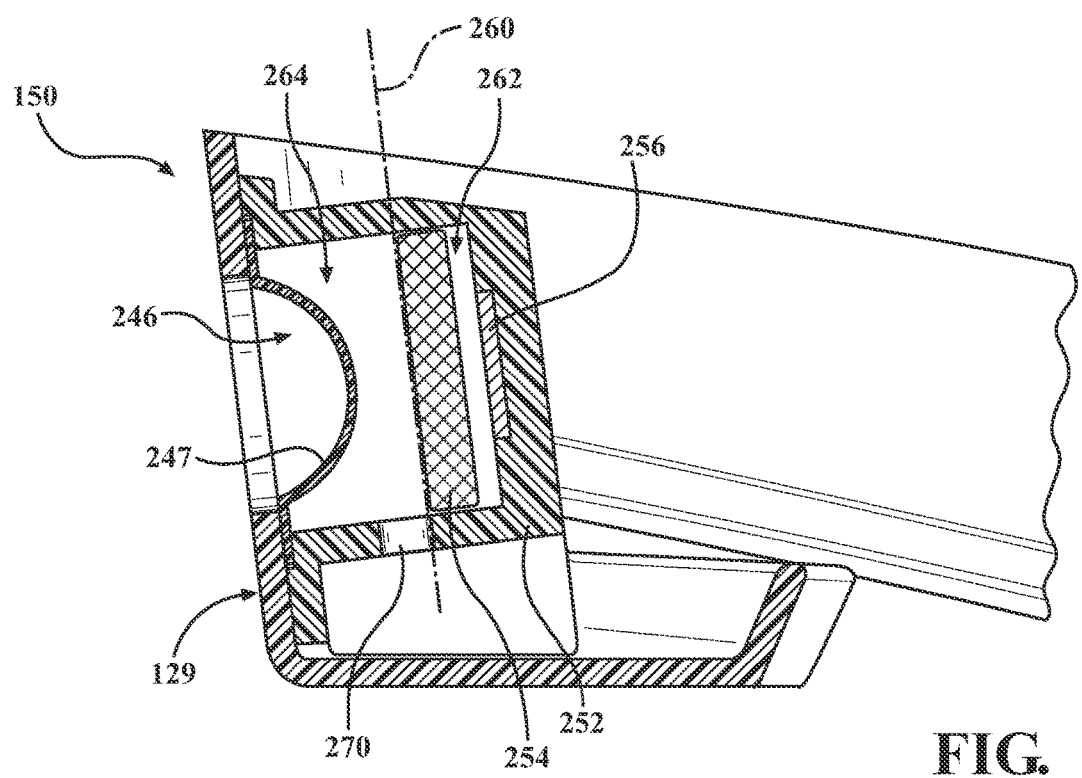
FIG. 10A is a close-up cross-sectional view of a first state of a second configuration of the coupling feature of FIG. 8.
Figure 10B:
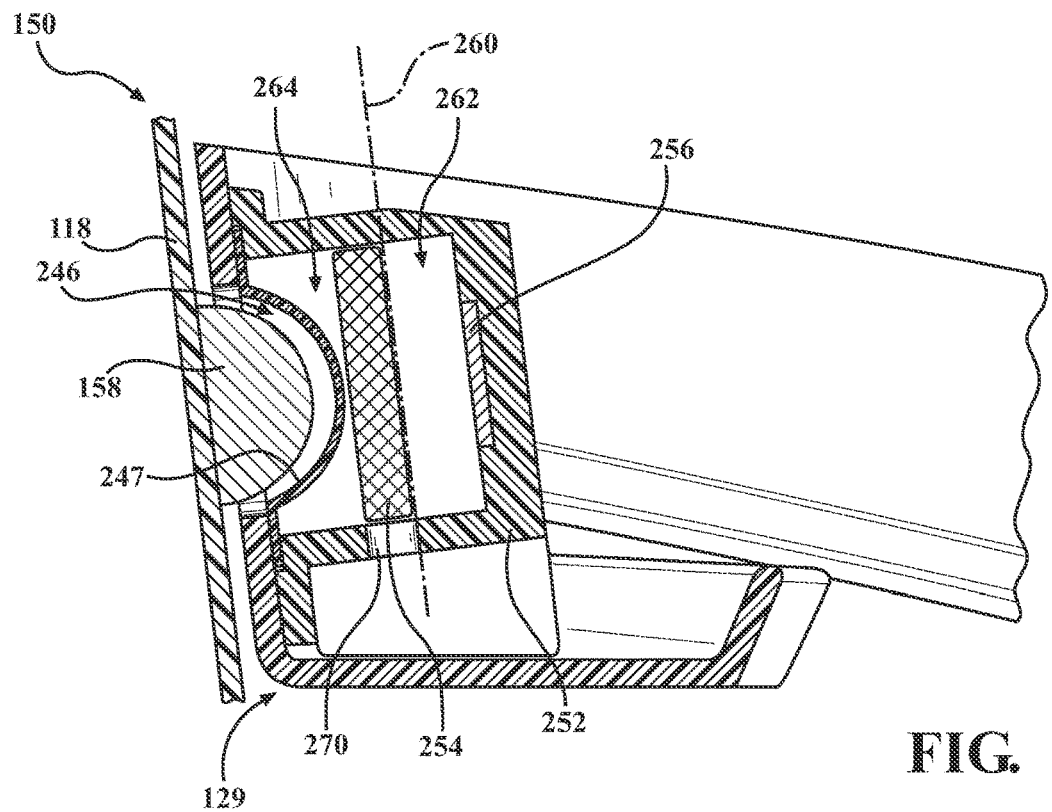
FIG. 10B is a close-up cross-sectional view of a second state of the second configuration of the coupling feature of FIG. 8.

Illustrated in each of FIGS. 10A and 10B is a close-up sectional view of a second configuration of the coupling feature 246. More specifically, FIG. 10A illustrates a sectional view of the second configuration of the coupling feature 246 in a first state, i.e., when the surgical garment 112 is not coupled to the coupling feature 246. Alternatively, FIG. 10B illustrates a sectional view of a second configuration of the coupling feature 246 in a second configuration, i.e., when the surgical garment 112 is coupled to the coupling feature 246.

The second configuration of the coupling feature 246 may comprise a distal surface 247 configured to removably engage an attachment element 158. The distal surface 247 may be configured in any number of shapes configured to engage the corresponding attachment element 158 of the surgical garment 112. For example, the distal surface 247 may be configured as a generally flat surface configured to engage an attachment element 158 comprising a flat rivet of the surgical garment 112. Alternatively, the distal surface 247 may be curved, arched, rounded, and/or hemispherically-shaped and configured to matingly engage a reciprocally-shaped attachment element 158. While the distal surface 247 as illustrated in FIGS. 10A and 10B is generally formed in a concave hemispherical shape, it is also contemplated that the distal surface 247 may be formed in a convex hemispherical shape or other similar shapes.

The coupling feature 246 further comprises an enclosure 252 configured to define a void space. The distal surface 247 may comprise all or a portion of at least one surface of the enclosure 252. The enclosure 252 may be generally configured in a cylindrical or tubular shape. Alternatively, the enclosure 252 may be generally configured in a rectangular or similar polygonal shape. As illustrated in FIGS. 10A and 10B, the enclosure 252 is generally configured in a cylindrical shape wherein the distal surface 247 forms a portion of the distal end of the enclosure 252.

The void space defined by the enclosure 252 may be divided into one or more regions. For example, as illustrated in FIGS. 10A and 10B, the enclosure 252 may be divided by a first line 260 to define a first region 262 and a second region 264 of the void space. The first region 262 may be positioned on the side of the first line 260 such that the first region 262 is generally proximal to the surgical helmet 120 and away from the distal surface 247. By contrast, the second region 264 may be positioned on the side of the first line 260 such that the second region 264 is generally distal to the surgical helmet 120 and proximate from the distal surface 247.

The coupling feature 246 positioned within the control housing 150 of the surgical helmet 120 may further comprise a first member 254 movably disposed within the enclosure 252. The first member 254 may be configured to move within the void space defined by the enclosure 252. For example, the first member 254 and the enclosure 252 may be configured wherein the first member 254 is movable between the first region 262 and the second region 264 of the void space defined by the enclosure 252. The first member 254 may be constructed of one of a ferromagnetic material or a magnetic material, and the attachment element 158 may be constructed from the other of the ferromagnetic material or the magnetic material. For example, the first member 254 may comprise a magnetic material and the attachment element 158 may comprise a ferromagnetic material. Alternatively, the first member 254 may comprise a ferromagnetic material and the attachment element 158 may comprise a magnetic material. In either configuration, the first member 254 and the attachment element 158 may be configured such that when the attachment element 158 is positioned proximate to the distal surface 247, the attachment element 158 and the first member 254 may be magnetically attracted to one another. For example, when the attachment element 158 is positioned proximate to the distal surface 247 of the coupling feature 246, the magnetic force between the first member 254 and the attachment element 158 may serve to attach and/or couple the surgical garment 112 to the surgical helmet 120. The first member 254 may be sized and/or shaped similar to as described above with regard to first member 154.

The coupling feature 246 may also comprise a third member 256 positioned proximate to the surface of the enclosure 252 opposite the distal surface 247. For example, the surface of the enclosure 252 opposite the distal surface 247 may be integrally formed with the third member 256. While the third member 256 illustrated in FIGS. 10A and 10B is illustrated as being at least partially disposed within the enclosure 252, it is also contemplated that the third member 256 may be positioned outside the enclosure 252. The third member 256 may be constructed of the other of ferromagnetic material or the magnetic material, such that the third member 256 and the first member 254 may be magnetically attracted to one another. The magnetic attraction force between the first member 254 and the third member 256 should provide sufficient force to move and/or hold the first member 254 in the first region 262 of the void space in the absence of an additional force being applied to the first member 254. For example, in the absence of the application of an additional force to the first member 254, the attraction force between the first member 254 and the third member 256 should hold the first member 254 in the first region 262 of the void space, as illustrated in FIG. 10A.

Alternatively, the magnetic attraction force between the attachment element 158 and the first member 254 should be sufficient to overcome the magnetic attraction force between the first member 254 and the third member 256. When the attachment element 158 and third member 256 each comprise a ferromagnetic material, the attachment element 158 and the third member 256 may be configured to comprise differing magnetic masses. For example, in order to have the magnetic attraction force between the first member 254 and the attachment element 158 be greater than the magnetic attraction force between the first member 254 and the third member 256, the attachment element 158 may be configured to comprise a greater magnetic mass than the third member 256. Alternatively, when the attachment element 158 and third member 256 each comprise a magnetic material, the attachment element 158 and the third member 256 may be configured to comprise differing magnetic fields. For example, in order to have the magnetic attraction force between the first member 254 and the attachment element 158 be greater than the magnetic attraction force between the first member 254 and the third member 256, the attachment element 158 may exhibit a stronger magnetic field than the third member 256.

In operation, as illustrated in FIG. 10B, when the attachment element 158 is positioned adjacent to the distal surface 247 of the coupling feature 246, the magnetic attraction force generated between the first member 254 and the attachment element 158 should be sufficient to overcome the magnetic attraction force between the first member 254 and the third member 256. The magnetic attraction force between the first member 254 and the attachment element 158, when positioned adjacent to the distal surface 247, should overcome the magnetic attraction force between the first member 254 and the third member 256, moving the first member 254 from the first region 262 to the second region 264 of the void space.

The coupling feature 246 may further comprise a detector 270 positioned adjacent to the enclosure 252 and configured to detect the position of the first member 254. For example, the detector 270 may comprise a near field detector, radar, optical sensor, Hall Effect sensor, or similar sensor. The detector 270 may be positioned near or adjacent the enclosure 252. The detector may be located within the enclosure 252 or external to the perimeter defined by the enclosure 252. For example, as illustrated in FIGS. 10A and 10B, the detector 270 may be positioned adjacent to a lateral surface of the enclosure 252 and proximate to the second region 264 of the void space. Alternatively, the detector 270 may be positioned adjacent to the lateral surface of the enclosure 252 and proximate to the first region 262 of the void space. It is further contemplated that it is not required that the detector 270 be attached or coupled to the enclosure 252. For example, the detector 270 may be radially spaced from the lateral surface of the enclosure 252. When the detector 270 is configured as a near field detector, such as a Hall Effect sensor, it is contemplated that the detector 270 may be positioned anywhere within and/or proximate the control housing 150, which will allow the detector 270 to detect and/or identify movement and/or the position of the first member 254 within the enclosure 252. While not illustrated in the figures, it is also contemplated that the detector 270 may be positioned adjacent to the surface of the enclosure 252 opposite the distal surface 247 and/or proximate the third member 256.

However, depending on the type of sensor that is utilized, the positioning of the detector 270 may provide operation advantages. For example, if the detector 270 is configured as a Hall-Effect sensor configured to determine whether the first member 254 is positioned in the first region 262 or the second region 264 of the void space, positioning the Hall Effect sensor adjacent to the lateral surface of the enclosure 252 may allow the Hall Effect sensor to more accurately detect whether the first member 254 is positioned in the first region 262 or the second region 264. In an example configuration of the coupling feature 246 wherein the first member 254 comprises a magnetic material, a magnetic field will be created surrounding the outer surfaces of the first member 254. The coupling feature 246 is configured such that at least one outer surface of the first member 254 slidably travels adjacent to a lateral surface of the enclosure 252. By positioning the detector 270, i.e., the Hall Effect sensor, adjacent to the lateral surface of the enclosure 252, the Hall Effect sensor may more accurately detect subtle changes in the magnetic field surrounding the first member 254 that are created when the first member 254 is in the first region 262 or the second region 264. For example, the Hall Effect sensor may be positioned adjacent to the lateral surface of the enclosure 252 proximate the first region 262. In this configuration, the Hall Effect sensor is likely to detect the magnetic field created by the first member 254 when the first member 254 is in the first region 262. Alternatively, the Hall Effect sensor is likely to detect the absence of a magnetic field when the first member 254 is in the second region 264. Based on the presence or absence of the magnetic field, the detector may be configured to generate a signal indicative of the position of the first member 254. In another example, the Hall Effect sensor may be positioned adjacent the lateral surface of the enclosure 252 proximate the second region 264. In this configuration, the Hall Effect sensor is likely to detect the magnetic field created by the first member 254 when the first member 254 is in the second region 264. Alternatively, the Hall Effect sensor is likely to detect the absence of a magnetic field when the first member 254 is in the first region 262. Based on the presence or absence of the magnetic field, the detector 270, i.e., the Hall Effect sensor, again may be configured to generate a signal indicative of the position of the first member 254.

In yet another configuration, as described above, the detector 270, i.e., the Hall Effect sensor, may be positioned on or proximate to the surface of the enclosure 252 opposite the distal surface 247. In this configuration, wherein the first member 254 comprises a magnetic material, the Hall Effect sensor is likely to detect the magnetic field created by the first member 254 when the first member 254 is in the first region 262. Alternatively, the Hall Effect sensor is likely to detect the absence of a magnetic field when the first member 254 is in the second region 264. Based on the presence or absence of the magnetic field, the detector 270 may be configured to generate a signal indicative of the position of the first member 254. In the configuration described above, wherein the first member 254 comprises a ferromagnetic material and the third member 256 comprises a magnetic material, the Hall Effect sensor is likely to detect the magnetic field created by the third member 256. In this configuration, the magnetic field created by the third member 256 is likely to change based on the position of the first member 254 relative to the third member 256. For example, when the first member 254 is positioned in the first region 262 and is proximate the third member 256, the third member is likely to create a first magnetic field. Alternatively, when the first member 254 is positioned in the second region 264 and is distant from the third member 256, the third member is likely to create a second magnetic field. The detector 270 may be configured to detect whether the first magnetic field or the second magnetic field surrounds the third member 256.

In operation, the first member 254 may be configured to operatively and/or slidingly move between the first region 262 and the second region 264 of the void space. For example, as illustrated in FIG. 10A, the first member 254 may be positioned in the first region 262 of the void space. Alternatively, as illustrated in FIG. 10B, the first member 254 may be positioned in the second region 264 of the void space. In the examples described above, the detector 270 may be configured as a near field sensor, such as a Hall Effect sensor. As the first member 254 moves between the first region 262 and the second region 264, there may be changes in the characteristics of the magnetic field surrounding the first member 254, and the detector 270 may be configured to detect or identify the position of the first member 254 based, at least in part, on the magnetic field that is detected.

Alternatively, the detector 270 may be configured as an optical sensor, wherein the lateral surface of the enclosure 252 comprises an aperture and/or transparent window. The aperture and/or transparent window may be positioned in the lateral surface of the enclosure 252 proximate the first region 262 or the second region 264 of the void space. The optical sensor may be positioned adjacent to the enclosure 252 so as to align the optical sensor with the aperture and/or transparent window, allowing the optical sensor to see at least a portion of the void space within the enclosure 252. For example, if the aperture or window in the enclosure 252 is positioned to allow the optical sensor to view a portion of the second region 264 of the void space, the optical sensor may be configured to detect the presence or absence of the first member 254 in the second region 264. The optical sensor may then be configured to output a signal identifying whether the first member 254 is present or absent in the second region 264. An emitter may need to be positioned opposite the optical sensor in certain configurations. In this configuration, the emitter may produce a signal to be received and/or detected by the optical sensor. The emitter and optical sensor may be positioned relative to one another such that the first member 254 may be configured to inhibit and/or block the signal from the emitter to the optical sensor when the first member 254 is positioned in the first region 262 or the second region 264. The optical sensor may then be configured to produce a signal based on the receipt of or failure to receive the signal from the emitter which is indicative of whether the first member 254 is positioned in the first region 262 or the second region 264. For example, the emitter and optical sensor may be positioned relative to one another such that the first member 254 may inhibit and/or block the signal from the emitter to the optical sensor when the first member 254 is positioned in the first region 262. In this configuration, the optical sensor may be configured to produce a signal indicating the first member 254 is in the first region 262 when the optical sensor fails to receive the signal from the emitter. Alternatively, the optical sensor may produce a signal indicating the first member 254 is in the second region 262 when the optical sensor receives the signal from the emitter. The optical sensor and emitter may be similarly configured to identify the position of the first member 254 if the optical sensor and emitter are positioned such that the first member 254 may inhibit and/or block the signal from the emitter to the optical sensor when the first member 254 is positioned in the second region 264.

As described above with regard to the various configurations of the detector 270 of the coupling feature 246, the detector 270 may be configured to detect the movement and/or position of the first member 254. The detector 270 can be in communication with a controller 180 on the helmet 120 that is in communication with the peripheral device(s) 130. The detector 270 may be further configured to communicate a signal to the controller 180 based, at least in part, on the position and/or movement of the first member 254. The operation of the controller 180 will be described in detail below.

Figure 11:
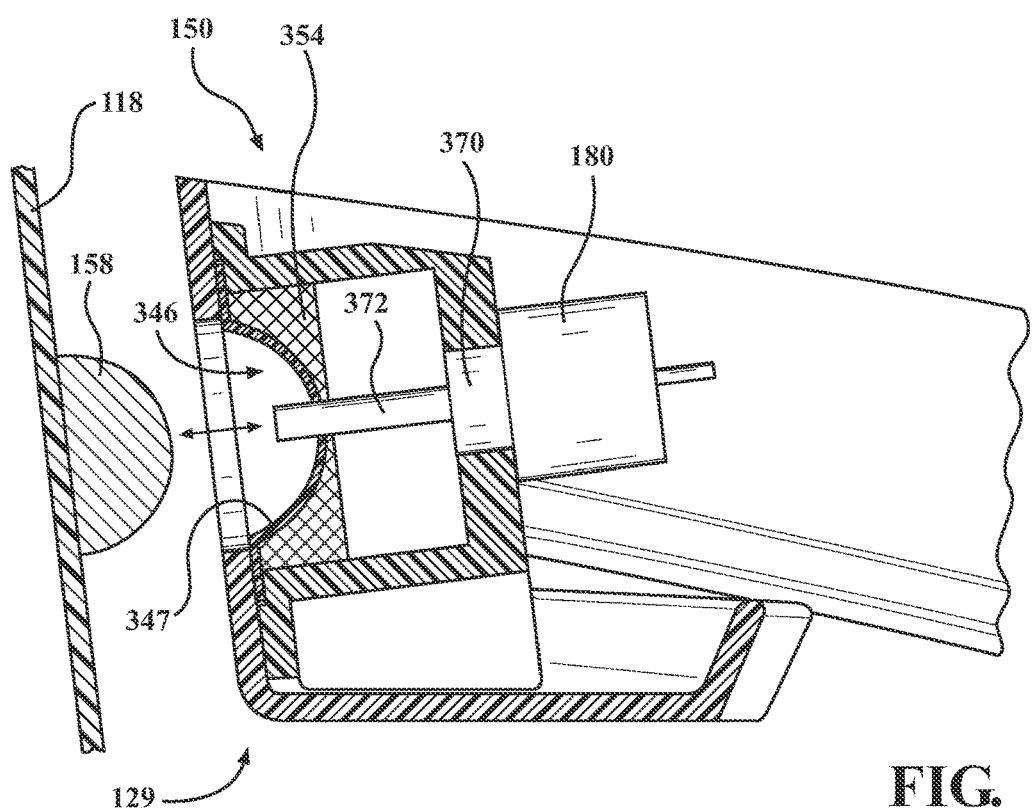
FIG. 11 is a close-up cross-sectional view of a third configuration of a coupling feature of FIG. 8.

Illustrated in FIG. 11 is a close-up sectional view of a third configuration of a coupling feature 346. The coupling feature 346 may be at least partially disposed within the control housing 150 of the surgical helmet 120. The third configuration of the coupling feature 346 may comprise a first member 354 comprising a distal surface 347 configured to removably couple with one of the attachment elements 158 of the surgical garment 112. The distal surface 347 of the first member 354 may be at least partially recessed within the control housing 150 of the surgical helmet 120. For example, as illustrated in FIG. 11, the distal surface 347 may be generally formed in a concave hemispherical shape. It is also contemplated that the distal surface 347 may be formed in a convex hemispherical shape or other similar curved shape configured to receive a complementary shaped attachment elements 158 of the surgical garment 112. While the distal surface 347 as illustrated in FIG. 11 is generally formed in a concave or inwardly directed hemispherical shape, it is also contemplated that the distal surface 347 may be formed in a convex or outwardly projected hemispherical-shape, a half-cylinder shape or other similar shapes. For example, the distal surface 347 may be curved, arched, or rounded in a manner that projects outwardly from an outer surface of the control housing 150 to create a convex-shaped distal surface 347. The corresponding attachment element 158 of the surgical garment 112 may comprise a concave surface configured to matingly engage the convex shaped distal surface 347 of the coupling feature 346. The distal surface 347 of the first member 354 may also be configured in a generally flat and circular shape.

The first member 354, and by extension the distal surface 347, of the coupling feature 346 may be constructed of the other of the ferromagnetic material or the magnetic material. For example, the first member 354 may comprise a magnetic material and the attachment element 158 may comprise a ferromagnetic material. Alternatively, the first member 354 may comprise a ferromagnetic material and the attachment element 158 may comprise a magnetic material. In either configuration, the first member 354 and the corresponding attachment element 158 may be configured such that the first member 354 and the attachment element 158 may be magnetically attracted to one another. The magnetic attraction force between the first member 354 and the attachment element 158 should provide sufficient force to removably couple the surgical garment 112 to the surgical helmet 120. The distal surface 347 of the first member 354 may be configured in a hemispherical or similar curved shape, as described above, to improve the retaining force between the first member 354 and the attachment element 158 when coupled.

The coupling feature 346 may further comprise a detector 370, such as a mechanical switch, at least partially disposed within the control housing 150. The detector 370 may be positioned adjacent to the first member 354 and proximate to the distal surface 347. The detector 370 may further comprise a toggle member 372 that is moveable between a first position and a second position. The toggle member 372 may comprise a biasing member, such as a spring, that is configured to move and/or hold the toggle member 372 in the second position absent an additional force being applied to the toggle member 372. The detector 370 may be configured to detect the position of the toggle member 372 and output a signal based, at least in part, on the position of the toggle member 372.

In operation, the attachment element 158 of the surgical garment 112 may be configured to operatively engage the toggle member 372 of the detector 370 to move the toggle member 372 between the first position and the second position. For example, when the attachment element 158 is positioned adjacent to the distal surface 347 of the first member 354, the attachment element 158 may be configured to engage the toggle member 372. The attraction force between the first member 354 and the attachment element 158 may be sufficient to overcome the force of the biasing member to move and/or hold the toggle member 372 in the first position while the attachment element 158 is coupled to the coupling feature 364. Alternatively, when the attachment element 158 is not positioned adjacent to the distal surface 347 of the first member 354, the biasing member of the toggle member 372 may move and/or hold the toggle member 372 in the second position. As described above, the detector 370 may be configured to detect the position of the toggle member 372. The detector 370 can be in communication with a controller 180 on the helmet 120 that is in communication with the peripheral device(s) 130. The operation of the controller 180 will be described in detail below. The detector 370 may be configured to communicate a signal to the controller 180 based, at least in part, on said toggle member 372 being in either the first position and/or the second position.

Figure 12A:
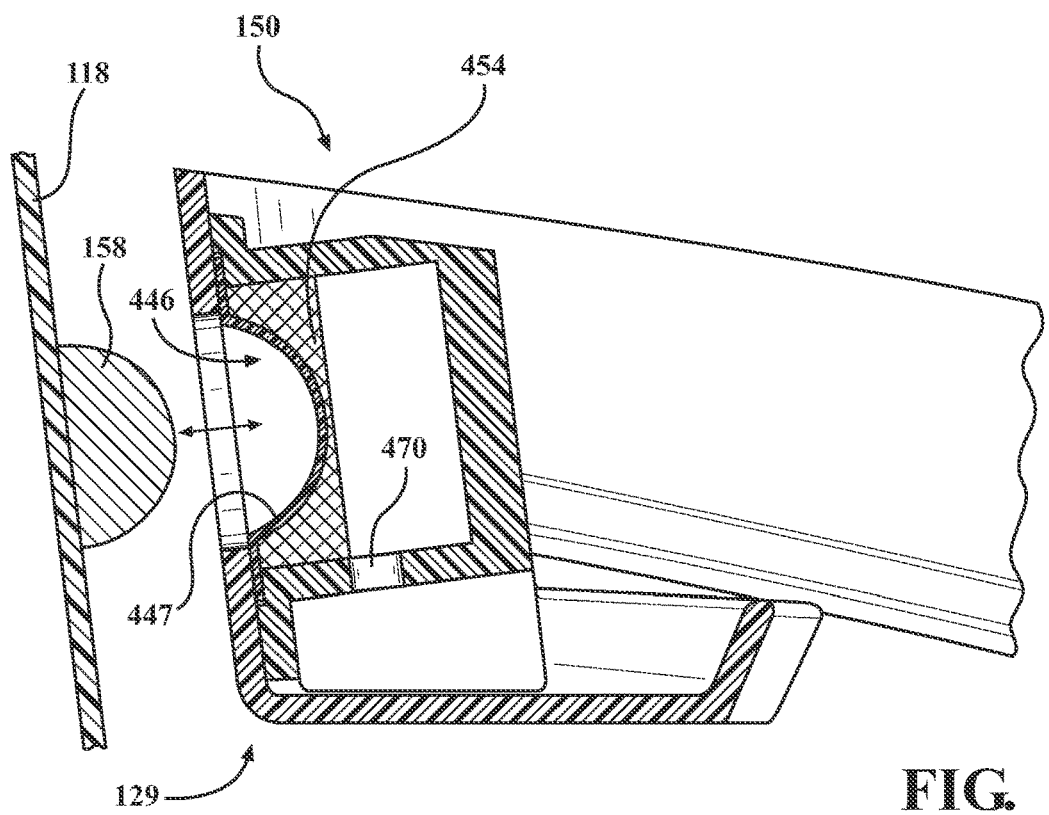
FIG. 12A is a close-up cross-sectional view of a fourth configuration of the coupling feature of FIG. 8.

Illustrated in FIG. 12A is a close-up sectional view of a fourth configuration of the coupling feature 446. The coupling feature 446 may be at least partially disposed within the control housing 150 of the surgical helmet 120. The fourth configuration of the coupling feature 446 may comprise a first member 454 comprising a distal surface 447 configured to removably couple with one of the attachment elements 158 of the surgical garment 112. The distal surface 447 of the coupling feature 446 may be at least partially recessed within the control housing 150 of the surgical helmet 120. For example, as illustrated in FIG. 12A, the distal surface 447 may be generally formed in a concave hemispherical shape. It is also contemplated that the distal surface 447 may be formed in a convex hemispherical shape or other similar curved shape configured to receive a complementary attachment element 158 of the surgical garment 112. While the distal surface 447 as illustrated in FIG. 12A is generally formed in a concave or inwardly directed hemispherical shape, it is also contemplated that the distal surface 447 may be formed in a convex or outwardly projected hemispherical shape, a half-cylinder shape or other similar shapes. For example, the distal surface 447 may be curved, arched, or rounded in a manner that projects outwardly from an outer surface of the control housing 150 to create a convex-shaped distal surface 447. The corresponding attachment element 158 of the surgical garment 112 may comprise a concave surface configured to matingly engage the convex-shaped distal surface 447 of the coupling feature 146. The distal surface 447 of the first member 454 may also be configured in a generally flat and circular shape.

The first member 454, and by extension the distal surface 447, of the coupling feature 446 may be constructed of the other of the ferromagnetic material or the magnetic material. For example, the first member 454 may comprise a magnetic material and the attachment element 158 may comprise a ferromagnetic material. Alternatively, the first member 454 may comprise a ferromagnetic material and the attachment element 158 may comprise a magnetic material. In either configuration, the first member 454 and the attachment element 158 may be configured such that the first member 454 and the attachment element 158 may be magnetically attracted to one another. The magnetic attraction force between the first member 454 and the attachment element 158 should provide sufficient force to removably couple the surgical garment 112 to the surgical helmet 120. The distal surface 447 of the first member 454 may be configured in a hemispherical or similar curved shape, as described above, in part to improve the retaining force between the first member 454 and the attachment element 158 when coupled together. The hemispherical or similarly curved shape distal surface 447 of the first member 454 may also serve to align the attachment element 158 with the center of the first member 454.

Figure 12B:
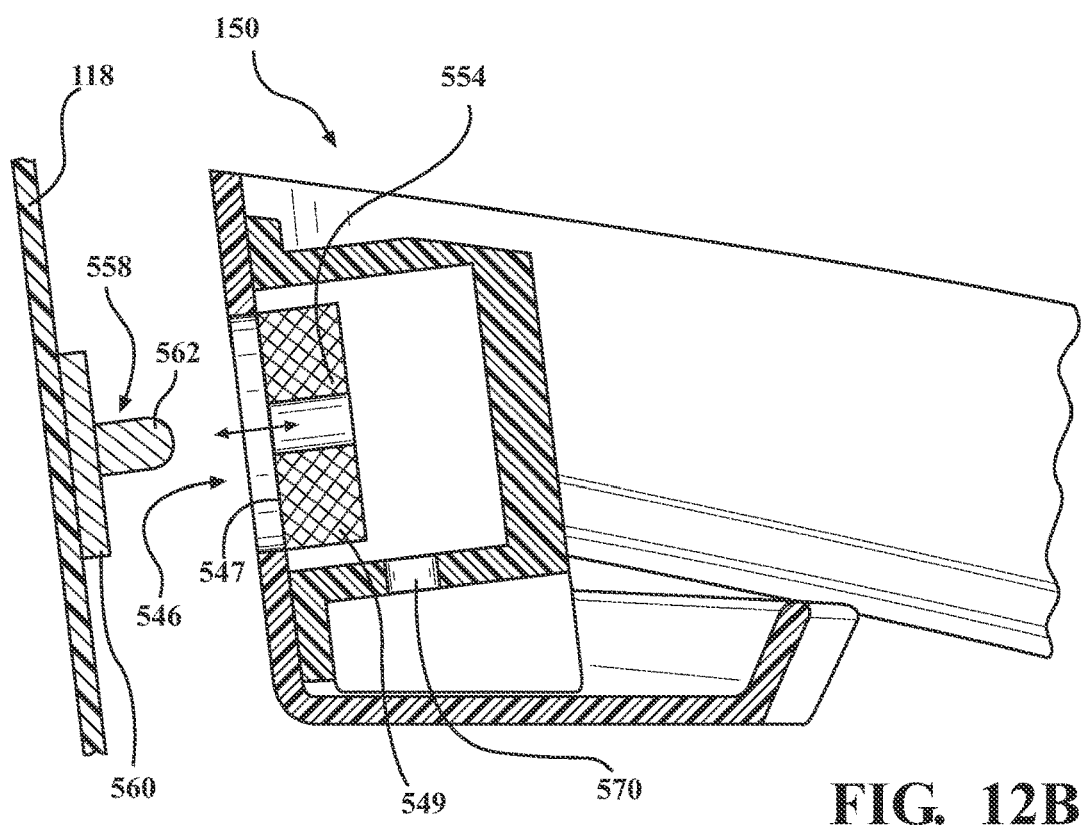
FIG. 12B is a close-up cross-sectional view of a fifth configuration of the coupling feature of FIG. 8.

Alternatively, referring to FIG. 12B, a close-up sectional view of a fifth configuration of the coupling feature 546 is illustrated. The distal surface 547 of the first member 554 may define an aperture. The first member 554 may comprise a distal surface 547. The first member 554, and by extension, the distal surface 547, of the coupling feature 546 may be constructed of one of the ferromagnetic material or the magnetic material. By contrast, at least a portion of the attachment element 558 of the face shield 118 may comprise the other of the ferromagnetic material or the magnetic material. For example, the first member 554 may comprise a magnetic material and the attachment element 558 may comprise a ferromagnetic material. Alternatively, the first member 554 may comprise a ferromagnetic material and the attachment element 558 may comprise a magnetic material. In either configuration, the first member 554 and the attachment element 558 may be configured such that the first member 554 and the attachment element 558 may be magnetically attracted to one another.

The distal surface 547 may further define an aperture positioned proximate to the center of the generally flat distal surface 547 resulting in the first member 554 having a ring-shape. The aperture may define an aperture axis relative to the first member 554. The first member 554 may further comprise a lateral axis that is generally perpendicular to the aperture axis. The first member 554 may also comprise a lateral surface 549 oriented to be generally parallel to the lateral axis of the first member 554. In this configuration of the coupling feature 546, the attachment element 558 may be configured to comprise a protrusion 562 extending from a base 560. The protrusion 562 may be constructed from the other of the ferromagnetic material or the magnetic material. Alternatively, the protrusion 562 may be constructed from a plastic or polymeric material or other non-magnetic material. For example, the protrusion 562 may be constructed from a polymeric material, and the base 560 of the attachment element 558 may be constructed of a magnetic material and configured to create a magnetic attraction with the first member 554 of the coupling feature 546. In yet another configuration, the protrusion 562 may be constructed from a combination of a magnetic and a non-magnetic material. For example, an interior portion of the protrusion 562 may be constructed from a magnetic material, and an outer surface of the magnetic material may be coated with a non-magnetic material, such as a plastic polymer. The interior portion of the protrusion 562 comprising the magnetic material may be magnetically attracted to the first member 554 of the coupling feature 546.

The protrusion 562 of the attachment element 558 may be configured to matingly engage the aperture of the distal surface 547 of the first member 554, wherein the aperture of the distal surface 547 may be configured to receive the protrusion 562 of the attachment element 558. The aperture may further be configured to align and/or position the attachment element 558 relative to the coupling feature 546 and/or with the center of the first member 554.

In both the fourth and fifth configurations of the coupling feature 446, 546 described above, the coupling features 446, 546 may further comprise a detector 470, 570, such as a near field sensor or Hall Effect sensor, that is at least partially disposed within the control housing 150. The detector 470, 570 may be positioned adjacent to the lateral surface of the respective first member 454, 554 and proximate to the distal surface 447, 547. The detector 470, 570 may be configured to detect changes in the magnetic field surrounding the first member 454, 554 created by the presence or absence of the attachment element 158, 558 of the surgical garment 112 being adjacent the distal surface 447, 547. For example, if the detector 470, 570 is configured as a Hall Effect sensor, the detector 470, 570 may be configured to determine whether the attachment element 158, 558 is positioned adjacent the distal surface 447, 547 of the first member 454, 554 based on the magnetic field surrounding the first member 454, 554. By placing the Hall Effect sensor adjacent to the lateral surface of the first member 454, 554 and incorporating an alignment feature into the distal surface 447, 547 to align the center of the attachment element 158, 558 with the center of the first member 454, 554, the Hall Effect sensor may be able to more accurately detect subtle changes in the magnetic field surrounding the first member 454, 554 created by the presence or absence of the attachment element 158, 558 being positioned adjacent to the distal surface 447, 547. Furthermore, when the detector 470, 570 is configured as a near field detector, such as a Hall Effect sensor, it is contemplated that the detector 470, 570 may be positioned anywhere within and/or proximate the control housing 150, which will allow the detector 470, 570 to detect and/or identify a change in the magnetic field surrounding the first member 454, 554. While not illustrated in the figures, it is also contemplated that the detector 470, 570 may be positioned adjacent to the distal surface 447, 547 and/or proximate the first member 454, 554.

In operation, the attachment element 158, 558 of the surgical garment 112 may be configured to removably couple with the first member 454, 554, such that the attachment element 158, 558 may be positioned adjacent the distal surface 447, 547 when the surgical garment 112 is coupled to the surgical helmet 120. For example, when the attachment element 158, 558 is positioned adjacent the distal surface 447, 547 of the first member 454, 554, a third magnetic field may surround the first member 454, 554. The detector 470, 570 may be configured to detect the third magnetic field. Alternatively, when the attachment element 158, 558 is not positioned adjacent to the distal surface 447, 547 of the first member 454, 554, a fourth magnetic field may surround the first member 454, 554. The detector 470, 570 may similarly be configured to detect the fourth magnetic field. As described above, the detector 470, 570 can be in communication with a controller 180 on the surgical helmet 120 that is in communication with the peripheral device(s) 130. The detector 470, 570 may be configured to communicate a signal to the controller 180 indicating the presence or absence of the surgical garment 112 based on whether the detector 470, 570 detects the third magnetic field or the fourth magnetic field. The operation of the controller 180 will be described in detail below.

Each of the various configurations of the surgical apparel system 110 described above may further comprise an energy source 182. As each of the various configurations of the system 10, 110 described above may comprise the energy source 182, a generic schematic representation of the energy source 182 in communication with the controller 180 is illustrated in phantom in FIG. 8. The energy source 182 may be configured to be connected or interconnected with the system 10, 110 and/or the surgical helmet 20, 120. The energy source 182, such as a battery, may be configured to be portable. The energy source 182 may be rechargeable and/or replaceable, such that the energy source 182 of the system 10, 110 may be exchanged or replaced.

Each of the various configurations of the surgical apparel system 110 described above may also comprise an energy sensor 186 in communication with the controller 180 and/or the energy source 182. As each of the various configurations of the system 10, 110 described above may comprise the energy sensor 186, a schematic representation of the energy sensor 186 in communication with the controller 180 and the energy source 182 is illustrated in phantom in FIG. 8. The energy sensor 186 may be configured to detect a characteristic of the energy source 182. The characteristic of the energy source detected by the energy sensor 186 may comprise (but is not limited to) the remaining power level or electrical charge, state of charge, voltage, capacity, health, current draw or similar characteristic related to the energy source 182. The energy sensor 186 may be further configured to generate or produce an energy signal based on the detected characteristic. The energy sensor 186 may also be configured to communicate the energy signal to the controller 180. The energy sensor 186 may be configured to communicate the energy signal to the controller 180 based on a default or user defined threshold value. For example, the energy sensor 186 may be configured to detect the remaining electrical charge of the energy source 182 where the threshold value is defined as fifteen percent (15%) of remaining electrical charge. In this configuration, the energy sensor 186 may be configured to communicate the energy signal to the controller 180 when the remaining electrical charge reaches and/or drops below fifteen percent (15%) of remaining electrical charge. The energy sensor 186 may also be configured to generate the energy signal at a plurality of different threshold values. For example, in the configuration described above, the energy sensor 186 may also be configured to generate a plurality of energy signals based on the remaining electric charge of the energy source 182. In operation, the energy sensor 186 may be configured to generate a first energy signal when the energy source 182 reaches and/or drops below 50% remaining electric charge, a second energy signal when the energy source 182 reaches and/or drops below 25% remaining electric charge, and/or a third energy signal when the energy source 182 reaches and/or drops below 10% remaining electric charge. In this configuration, the first, second, and/or third energy signal generated by the energy sensor 186 and communicated to the controller 180 may be indicative of the remaining electrical charge of the energy source 182.

The controller 180 may be configured to produce a signal that may be communicated to a user display, such as a LCD screen, digital display, or plurality of lights, wherein the user display is configured to display indicia indicative of the remaining electric charge. For example, when the user display comprises an LCD screen, the LCD screen may be configured to display "50%", "25%", etc. indicating the remaining electric charge. Alternatively, when the user display comprises a plurality of lights, each of the lights may comprise a different color, wherein each color light represents a different level of remaining electric charge of the energy source 182. For example, the user display may comprise a yellow light, an orange light, and a red light, and the controller 180 may be configured to communicate a signal to the user display to illuminate the yellow light when the remaining electric charge reaches and/or drops below 50%. The controller 180 may be configured to communicate a signal to the user display to illuminate the orange light when the remaining electric charge reaches and/or drops below 25%. The controller 180 may be configured to communicate a signal to the user display to illuminate the red light when the remaining electric charge reaches and/or drops below 10%. Based on which light is illuminated, the user may determine the approximate remaining electric charge of the energy source 182. The remaining electric charge may also be conveyed with a speaker.

Each of the various configurations of the coupling feature 146, 246, 346, 446, 546 described above comprises a detector 170, 270, 370, 470, 570 configured to detect a characteristic of the coupling feature 146, 246, 346, 446, 546 that may be utilized to identify whether the surgical garment 112 is coupled to the surgical helmet 120. The detector 170, 270, 370, 470, 570 may be further configured to output a signal based on the detected characteristic to indicate the presence or absence of the surgical garment 112 being coupled to the surgical helmet 120. For example, the detector 170, 270, 370, 470, 570 may be configured to detect and/or determine when the surgical garment 112 is coupled to the surgical helmet 120 and output the signal indicative of the surgical garment 112 being coupled to or absent from the surgical helmet 120. In one exemplary configuration, the detector 170, 270, 370, 470, 570 may be configured to output the signal when the surgical garment 112 is coupled to the surgical helmet 120. In another exemplary configuration, the detector 170, 270, 370, 470, 570 may be configured to output the signal when the surgical garment 112 is absent or de-coupled from the surgical helmet 120. In yet another exemplary configuration, the detector 170, 270, 370, 470, 570 may be configured to output a first signal when the surgical garment 112 is coupled to the surgical helmet 120 and output a second signal when the surgical garment 112 is absent or de-coupled from the surgical helmet 120.

In each embodiment and/or configuration of the coupling feature 146, 246, 346, 446, 546 described above, the detector 170, 270, 370, 470, 570 may be in communication with a controller 180. The controller 180 may further be in communication with one or more of the peripheral devices 130 of the surgical helmet 120 that are described above. It should be understood that the controller 180 may be positioned anywhere on the surgical helmet 120. For example, the controller 180 may be positioned within the control housing 150 and adjacent to the detector 170, 270, 370, 470, 570. Alternatively, the controller 180 may be positioned within the void in the housing 132 of the surgical helmet 120.

The controller 180 may be configured to communicate operational commands to the detector 170, 270, 370, 470, 570, as well as be configured to receive a signal from the detector 170, 270, 370, 470, 570 related to a characteristic of the signal detected by the detector 170, 270, 370, 470, 570. The controller 180 may also be connected to the one or more peripheral devices 130 of the surgical helmet 120, such as the ventilation assembly 130, wherein the controller 180 is configured to communicate operational commands to and from the ventilation assembly 130, or other peripheral device 130 based on the signal received from the detector 170, 270, 370, 470, 570. For example, the controller 180 may be configured to adjust the amount of power transmitted to the ventilation system 130 to control the speed of the fan blade. It is further contemplated that two separate controllers may also be utilized.

Regardless of the configuration of the coupling feature 146, 246, 346, 446, 546 configuration, the detector 170, 270, 370, 470, 570 may be configured to communicate a signal to the controller 180 based on the presence of, absence of, and/or changes in the characteristic to be detected by the detector 170, 270, 370, 470, 570. For example, the detector 170, 370 of the first configuration of the coupling feature 146 and/or the third configuration of the coupling feature 346 may be configured to detect the presence or absence of the surgical garment 112 based on the position of the toggle member 172, 372. Alternatively, the detector 270, 470, 570 of the second configuration of the coupling feature 246 and/or the fourth configuration of the coupling feature 446 and/or the fifth configuration of the coupling feature 546 may be configured to detect the presence or absence of the surgical garment 112 based on changes in the magnetic field surrounding the first member 254, 454, 554 of the coupling feature 246, 446, 546. The controller 180 may be configured to communicate a command or regulate an operational characteristic of the peripheral device 130 based on the signal received from the detector 170, 270, 370, 470, 570.

In one configuration, the controller 180 may be configured to interpret the signal(s) received from the detector 170, 270, 370, 470, 570 and control the transmission of energy from the energy source to the peripheral device 130. For example, if the controller 180 determines that, based on the signal received from detector 170, 270, 370, 470, 570 or the absence of a signal from the detector 170, 270, 370, 470, 570, the surgical garment 112 is absent from the surgical helmet 120, the controller 180 may be configured to prevent the transmission of energy from the energy source to the peripheral device 130. One disadvantage of operating the system 110 that is eliminated by this feature is the generation of unnecessary noise that may be produced by the peripheral device(s) 130 when the peripheral device(s) 130 is not serving a useful purpose. A second disadvantage that may be eliminated by preventing the actuation of a peripheral device 130 prior to mounting the surgical garment 112 to the surgical helmet 120 is the drawing down of the charge in the energy source 182 when actuation of the peripheral device 130 is not needed. Alternatively, if the controller 180 determines that, based on the signal received from detector 170, 270, 370, 470, 570 or the absence of a signal from the detector 170, 270, 370, 470, 570, the surgical garment 112 is coupled to the surgical helmet 120, the controller 180 may be configured to allow the transmission of energy to the peripheral device 130. Alternatively still, the controller 180 may control operation of the peripheral device 130 based on the signal received from the detector 170, 270, 370, 470, 570.

The surgical apparel system 110 may further comprise a memory device 184 coupled to the surgical helmet 120 and in communication with the controller 180. The memory device 184 may be positioned within or on any portion of the surgical helmet 120. For example, the memory device 184 may be positioned within the control housing 150. Alternatively, the memory device 184 may be positioned within the housing 132 of the surgical helmet 120. The memory device 184 may be configured to store data related to the operation of the peripheral device(s) 130. For example, the memory device 184 may store operating conditions related to each peripheral device 130, such as operating conditions based on the various types of surgical garments 112 that may be attached to the surgical helmet 120. The operating conditions stored on the memory device 184 may include a maximum and/or minimum operating speed for peripheral device(s) 130 of the surgical helmet 120 for each type of surgical garment 112. For example, the memory device 184 may store different operating fan speeds for a toga and a hood. The memory device 184 may also be configured to store operating instructions or programming steps configured to be executed by the controller 180. The memory device 184 may also store individual user settings or preferences for operating one or more of the peripheral device(s) 130. For example, the user settings stored on the memory device 184 may comprise the most recent fan speed of the ventilation assembly selected by the individual user wearing the surgical helmet 120.

In each of the various embodiments and/or configurations of the surgical apparel system 110 and the coupling feature 146, 246, 346, 446, 546 described above, the system 110 may comprise additional features and/or components configured to work in communication with the controller 180 to prevent operation of the surgical helmet 120 and/or any peripheral devices 130 of the surgical helmet 120 based on a defined characteristic. For example, the controller 180 may be configured to prevent operation of the peripheral device(s) 130 until after the surgical garment 112 has been mounted on the surgical helmet 120. Alternatively, the controller 180 may be configured to prevent operation of the peripheral device(s) 130 if a previously used or incompatible surgical garment 112 is coupled to the surgical helmet 120.

Figure 13A:
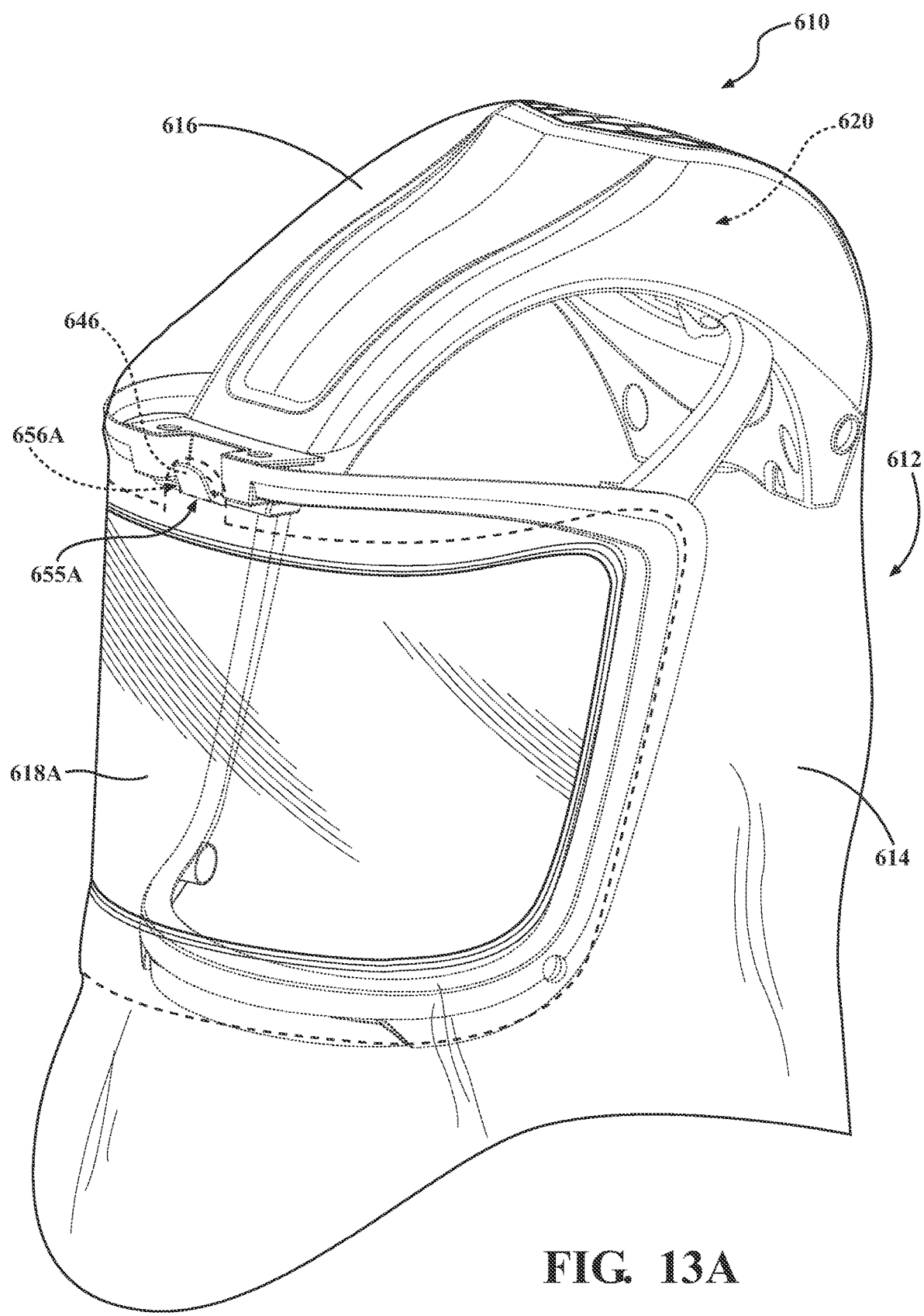
FIG. 13A is a perspective view of a third configuration of a surgical apparel system that includes a medical garment with a first configuration of tab extending from the transparent face shield, with the surgical helmet shown in phantom.
Figure 13B:
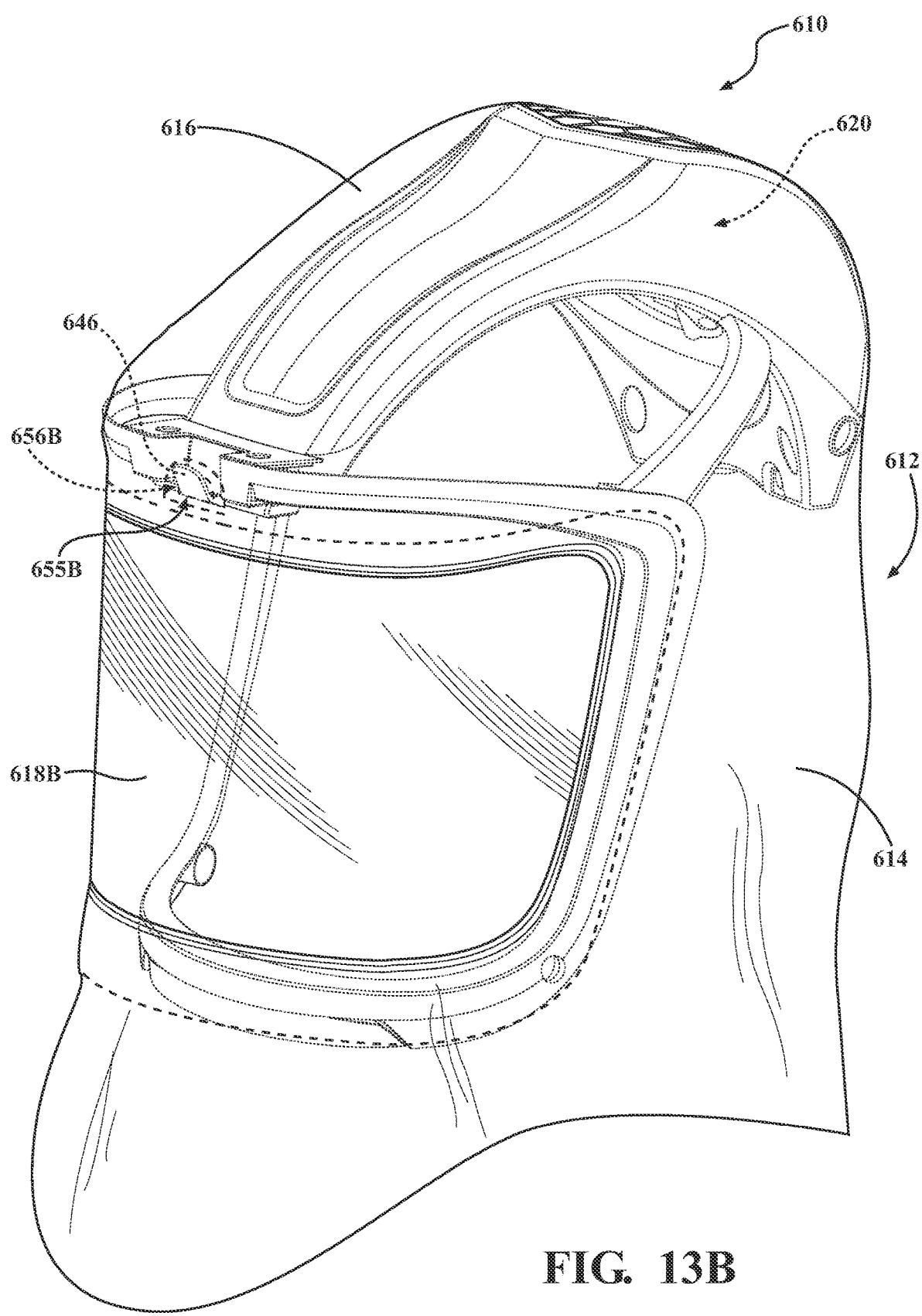
FIG. 13B is a perspective view of the third configuration of a surgical apparel system that includes an alternative configuration of a medical garment with a second configuration of tab that is separate from the transparent face shield, with the surgical helmet shown in phantom.

Referring to FIGS. 13A and 13B, an alternative configuration of the surgical apparel system 610 is illustrated. It should be appreciated that the various configurations of the surgical apparel system 610 may include similar elements to the systems described above and identified by reference numerals that are incremented by 100. It should be understood that those elements including reference numerals which are incremented by 100 can have the same and/or similar features to those described above.

The third configuration of the surgical apparel system 610 may comprise a surgical garment assembly comprising a surgical garment 612 configured for attachment to a surgical helmet 620. As described above, the surgical garment 612 may provide a barrier, such as a microbial barrier, between the wearer and the surrounding environment. The barrier created by the surgical garment 612 may benefit both the wearer and the patient. The barrier provided by the surgical garment 612 may substantially eliminate the likelihood that the wearer may come into contact with fluid or solid particles of matter from the patient that may be generated during the course of a surgical procedure. The barrier may substantially prevent the transfer of any foreign particles emitted by the wearer from being transferred to the patient during the surgical procedure.

Figure 14:
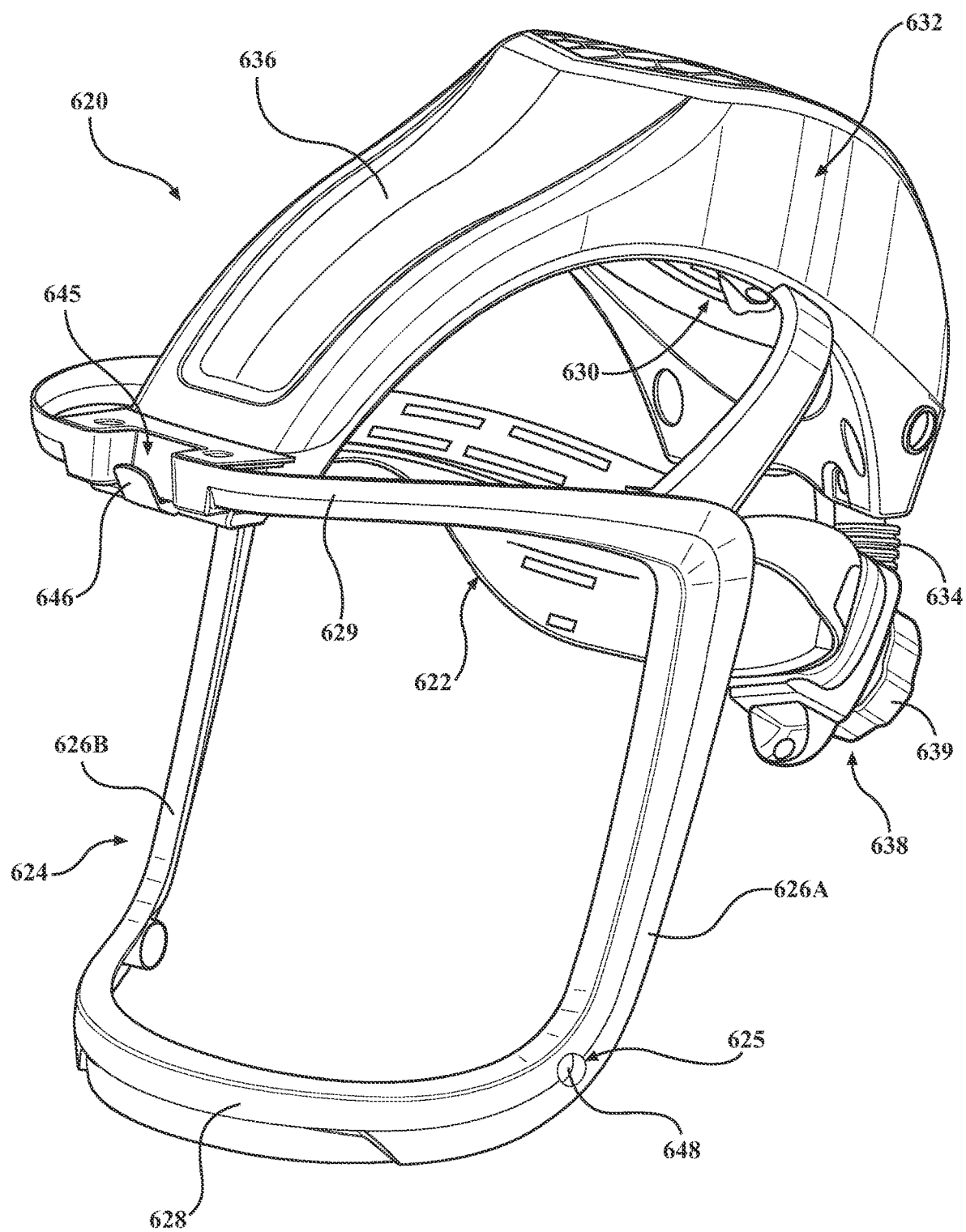
FIG. 14 is a perspective view of the surgical helmet of FIGS. 13A and 13B, the helmet including an alignment channel and coupling members in the chin bar.

Referring to FIGS. 13A, 13B, and 14, the surgical garment 612 may include a fabric 614 configured to cover the surgical helmet 620 and at least a portion of the head of the wearer. The surgical garment 612 may be configured as a hood, toga, or other similar medical garment, similar to either of the configurations of the surgical apparel system 10, 110 described above. The surgical garment 612 may further comprise a face shield 618, also referred to as a transparent face shield, and one or more attachment elements 658 positioned about the surgical garment 612. The attachment elements 658 may also be referred to as a second member or garment fastener. The attachment elements 658 may serve as an alignment element configured to removably couple the surgical garment 612 to the surgical helmet 620. Furthermore, the attachment elements 658 may be positioned proximate the outer perimeter of the face shield 618 such that the fabric 614 covers the attachment elements 658. This may serve to ensure the fabric 614 covers the attachment elements 658 to maintain the barrier provided by the surgical garment 612 between the wearer and the environment.

The attachment elements 658 may comprise a ferromagnetic material. In other words, the attachment element may comprise iron, nickel, cobalt, gadolinium, dysprosium, or alloys thereof, or combinations thereof. In certain configurations, it should be appreciated that the attachment elements may comprise a material, i.e., atoms, that is attracted to a magnetic field exhibited by the magnetic material positioned on the helmet. It is contemplated that the entirety of the attachment element 658 may consist of the ferromagnetic material in certain embodiments. It is also contemplated that the attachment element 658 comprises both ferromagnetic material and diamagnetic material. For example, the attachment elements 658 may comprise a diamagnetic material which has been coated with a ferromagnetic material. Alternatively, the attachment elements 658 may be formed from a ferromagnetic material as a core, and then coated with a plastic or similar non-magnetic coating configured to provide a sterile and/or wear-resistant surface. Other arrangements of the diamagnetic and magnetic material are contemplated for the attachment element 658. It should be appreciated that the surgical garment 612, and all components thereof, may be configured similarly and/or comprise the features of the surgical garment(s) 12, 112 described above.

The surgical garment 612 may also comprise a tab 655A, 655B. The tab 655A, 655B may be disposed on the wearer side or interior of the surgical garment 612. The tab 655A, 655B may comprise a pair of opposing edges 643A, 643B and define an opening 656A, 655B. As illustrated in FIG. 13A, the tab 655A may be formed as a portion of the face shield 618. The tab 655A may define at least a portion of the opening 656A, with a portion of the opening 656A also being defined by the face shield 618. It is also contemplated that the opening 656A may be entirely formed or defined within the tab 655A.

Alternatively, as illustrated in FIG. 13B, the tab 655B may be formed separate from the face shield 618. In this configuration, the tab 655B may be coupled directly to the interior surface of the fabric 14 of the surgical garment 612. The tab 655B may be formed from a plastic similar to the face shield 618 and may be coupled to the surgical garment 612 by an epoxy, glue, or similar adhesive. Alternatively, the tab 655B may be formed from a fabric similar to the fabric 614 of the surgical garment 612, wherein the tab 655B may be sewn or coupled to the surgical garment 612 by an adhesive. Furthermore, the opening 656B may be entirely defined by the tab 655B.

Referring again to FIGS. 13A, 13B, and 14, an exemplary configuration of the surgical apparel system 610 is described in detail. The system 610 may include a surgical garment 612 and surgical helmet 620. Similar to the systems 10, 110 described above, the configuration of the system 610 illustrated in FIGS. 13A, 13B, and 14 may comprise one or more peripheral devices 630, such as a ventilation assembly.

The ventilation assembly 630 illustrated in FIG. 14, is one example of a peripheral device 630 that may be incorporated into the surgical helmet 620 of the surgical apparel system 610. While the ventilation assembly 630 is shown as an integral component of the surgical helmet 620, it should be appreciated that each of the other peripheral devices 130 described above may be either an integral component of the surgical helmet 120, or may be removably coupled to the surgical helmet 620. The surgical helmet 620 illustrated in FIG. 14 comprises the ventilation assembly 630 positioned within the void of the housing 632. The ventilation assembly 630 may include a fan blade, impeller, propeller, fan wheel, or similar blade mechanism configured to induce air movement. The blade may be coupled to a motor configured to rotate the blade when energized by a power source. When the blade is actuated, the ventilation assembly 630 is configured to draw air into the void of the housing 632 through the intake opening in the top of the housing 632. The additional voids of the housing 632 may be connected to the void and serve as ducts for dispersing the air drawn into the void to the wearer.

Figure 15A:
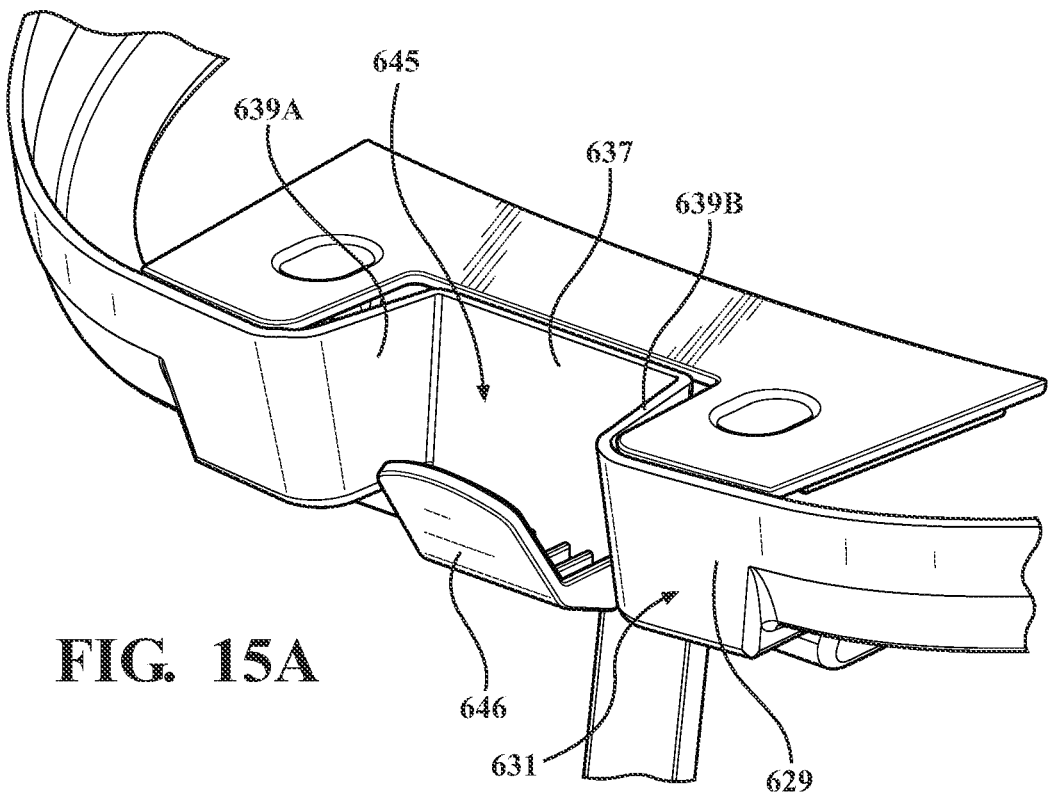
FIG. 15A is a close-up perspective view of the alignment channel of the helmet of FIG. 14.
Figure 15B:
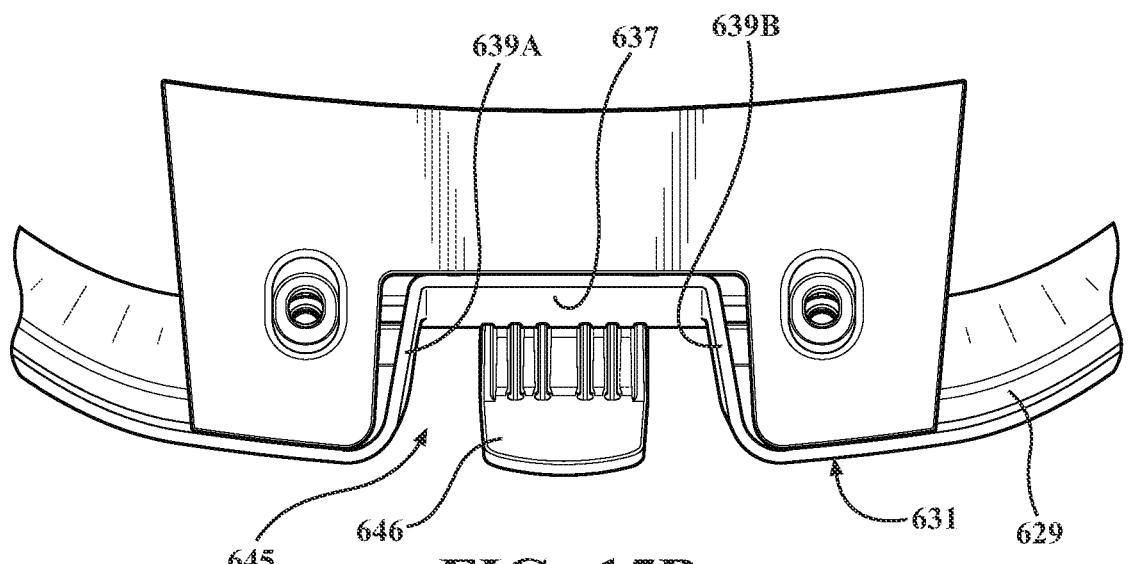
FIG. 15B is a close-up top view of the alignment channel of the helmet of FIG. 14.

Referring to FIGS. 14, 15A, and 15B, the surgical helmet 620 may comprise a top beam 629 positioned forward of the housing 632 of the surgical helmet 620 and configured to extend across the front of the surgical helmet 620. The top beam 629 may further comprise a recess. The recess of the top beam 629 may comprise a pair of laterally spaced-apart side walls 639A, 639B, and a proximal surface 637 that is positioned proximally from the distal surface 631 of the top beam 629. The side walls 639A, 639B, and the proximal surface 637 may define an alignment channel 645, wherein the alignment channel 645 is configured to receive a tab 655A, 655B disposed on the interior of the surgical garment 612 to align and/or orient the surgical garment 612 relative to the surgical helmet 620. As described above, the tab 655A may be integrally formed with and configured to extend from the face shield 618. Alternatively, the tab 655B may be formed independent of the face shield 618, wherein the tab 655B is configured to be coupled to the fabric 614 on the interior of the surgical garment 612. However, other configurations are contemplated. The spaced-apart side walls 639A, 639B of the alignment channel 645 should be spaced apart a distance greater than the width of the tab 655A, 655B to allow the tab 655A, 655B to be positioned between the spaced-apart side walls 639A, 639B.

The top beam 629 may further comprise a coupling feature 646 configured to removably engage the face shield 618 and/or surgical garment 612. The coupling feature 646 may comprise a protrusion, magnetic member, ferromagnetic member, hook and loop, or similar coupling mechanism configured to releasably engage the opening 656 in the tab 655A, 655B to align and/or couple the surgical garment 612 to the surgical helmet 620. For example, as illustrated in FIGS. 15A and 15B, the coupling feature 646 is realized as a protrusion 646 extending from the alignment channel 645 of the top beam 629. Here, the top beam 629 comprises the alignment channel 645 described above, and the coupling feature 646 may be disposed at least partially within the alignment channel 645, as illustrated in FIGS. 14, 15A, and 15B. The coupling feature 646 may be positioned within the alignment channel 645 such that the top of the upper most surface coupling feature 646 is arranged or otherwise positioned below the top of the top of the alignment channel 645 and/or the top surface of the top beam 629. The combination of the spaced-apart side walls 639A, 639B of the alignment channel 645 coupling feature 646 may serve to align and/or orient the face shield 618 and/or the surgical garment 612 relative to the surgical helmet 620. More specifically, the spaced-apart side walls 639A, 639B of the alignment channel 645 may serve to guide the tab 655A, 655B such that the opening 656 in the tab 655A, 655B is directed into engagement with the coupling feature 646 as the surgical garment 612 is placed over the surgical helmet 620.

The surgical helmet 620 may include a chin bar 624 that extends downwardly from the front portion of the surgical helmet 620. The chin bar 624 may comprise a first post 626A and a second post 626B. The first and second posts 626A, 626B may be coupled to the top beam 629, wherein the top beam 629 is configured to extend across the front of the surgical helmet 620. For example, as illustrated in FIG. 14, the first and second posts 626A, 626B may be connected to opposing ends of the top beam 129. The chin bar 624 may be constructed from a generally flexible or pliable material.

The chin bar 624 may further comprise a bottom beam 628 that may extend between the opposed free ends of the posts 626A, 626B. The chin bar 624 is formed so that the bottom beam 628 is located below and slightly forward of the chin of the person wearing the surgical helmet 620. The bottom beam 628 may be bowed outwardly from the free ends of posts 626A, 626B. The chin bar 624 may extend outwardly from the top beam 629 such that the chin bar 624 is positioned forward of and generally encircles the face of the wearer when the surgical helmet 620 is secured to the wearer's head. Collectively, the combination of the top beam 629, the posts 626A, 626B, and the bottom beam 628 may be referred to as the face frame, as they generally define an opening positioned in front of the wearer's face when the surgical helmet is positioned on top of the wearer's head.

A plurality of coupling members 648 may be mounted to or within the chin bar 624. The coupling members 648 comprise magnetic material and are configured to align and/or attach the face shield 618 of the surgical garment 612 to the surgical helmet 620. Each coupling member 648 may be positioned on the chin bar 624 proximate to the opposed posts 626A, 626B and/or adjacent opposing ends of the bottom beam 628. Alternatively, the coupling members 648 of the surgical helmet 620 could be arranged or otherwise configured in any suitable way to cooperate with the complementary attachment elements 658 of surgical garment 612 to releasably secure the surgical garment 612 to the surgical helmet 620. For example, as illustrated in FIG. 14, the coupling member 648 may be positioned on the chin bar 624 at opposing ends of the lower beam 628 proximate where each of the posts 626A, 626B connects to the lower beam 628. While the exemplary configuration of the surgical helmet 620 illustrated in FIG. 14 utilizes two coupling members 648, it is contemplated that the surgical helmet 620 may be configured such that the chin bar 624 comprises a single coupling member 648 or, in other configurations, three or more coupling members 648 may be spaced about the chin bar 624 and/or top beam 629. It is contemplated that other types of coupling members 648 may be used in place of and/or in addition to those comprising magnetic materials, such as with a hook and loop fasteners, snaps, coupling members comprising ferromagnetic material, or similar type fasteners. Other configurations are contemplated.

Figure 16A:
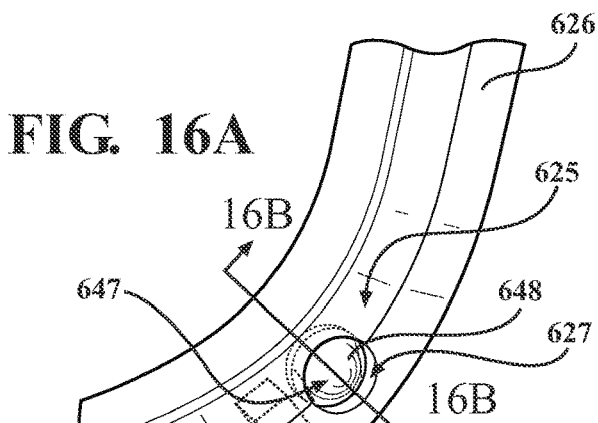
FIG. 16A is a perspective view of one of the coupling members in the chin bar of the helmet of FIG. 14, including the detector positioned adjacent the coupling member.
Figure 16B:
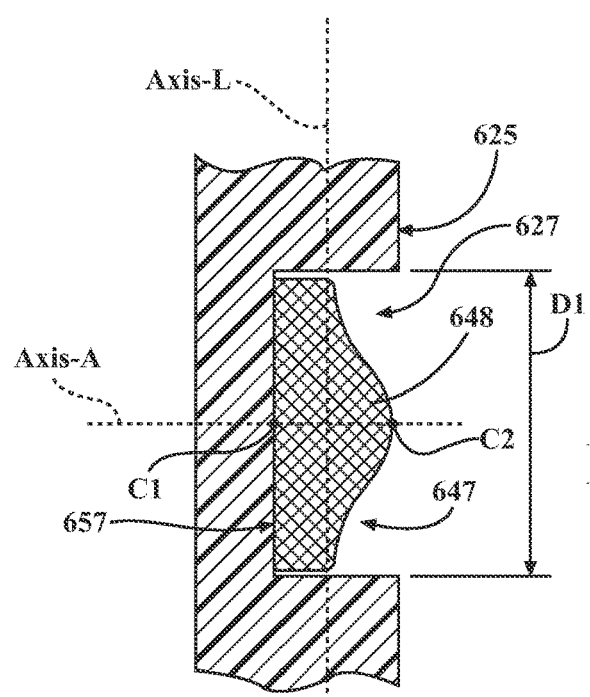
FIG. 16B is a sectional view of one of the coupling members of FIG. 16B.

Referring to FIGS. 16A and 16B, various views of an exemplary configuration of a coupling member 648 positioned within the chin bar 624 are illustrated. The coupling member 648 may comprise a distal surface 647. The chin bar 624 may comprise a recess 627 configured to receive the coupling feature 648. For example, as illustrated in FIGS. 16A and 16B, the coupling member 648 may be positioned within the recess of the chin bar 624, such that the distal surface 647 of the coupling member 648 is positioned proximally to a distal surface 625 of the chin bar 624.

The coupling member 648 may comprise one of a ferromagnetic material or a magnetic material. This may include the coupling member 648 being formed of or constructed from a ferromagnetic material or a magnetic material. It is also contemplated that only a portion of the coupling member 648 comprises a ferromagnetic material or a magnetic material. For example, the coupling member 648 may be injection-molded plastic and coated with a ferromagnetic material or magnetic material. Alternatively, the coupling member 648 may be formed from a ferromagnetic material or magnetic material, and then coated with a plastic or similar coating to provide a sterile and/or wear-resistant surface. It is also contemplated that a magnet may be "over-molded" with plastic material to define the coupling member 648. Generally, the coupling member 648 may comprise the other of the ferromagnetic material or magnetic material relative to the attachment element(s) 658 of the surgical garment 612 in order to create a magnetic attraction between the coupling member(s) 648 and the attachment element(s) 658 to couple the surgical garment 612 to the surgical helmet 620.

The surgical helmet 620 may further comprise a controller or processor (not illustrated), which may be disposed on or within the chin bar 624 or top beam 629 of the surgical helmet 620. Alternatively, the controller may be positioned at any suitable location within the surgical helmet 620. For example, the controller may be positioned in the bottom beam 628 of the chin bar 624. The controller may be in communication with the one or more detectors 670, such as a Hall-effect sensor, that is positioned within the chin bar 624 and adjacent to the coupling member 648. The detector 670 may be configured to detect a characteristic of the coupling member 648. For example, wherein the detector 670 is a Hall-effect sensor, the detector 670 may be configured to detect any changes to the magnetic field surrounding the coupling member 648. In operation, the detector 670 may be configured to detect a change in the magnetic field surrounding the coupling member 648 created by the presence or absence of an attachment element 658 of the surgical garment 612 being positioned adjacent the coupling member 648.

While FIGS. 16A and 16B illustrate only a portion of the chin bar 624 including a single coupling member 648, as discussed above, the chin bar 624 may comprise more than one coupling member 648. Similarly, the chin bar may comprise more than one detector 670. It is contemplated that the surgical helmet 620 may comprise a single detector 670 positioned adjacent to a single coupling member 648. It is also contemplated that in configurations of the surgical helmet 620 that include multiple coupling members 648, the surgical helmet 620 may comprise a single detector 670 positioned adjacent to one of the multiple coupling members 648. Alternatively, detectors 670 may be placed adjacent to two or more of the coupling members 648. Use of multiple detectors may provide redundancy in the event a detector 670 is damaged.

FIG. 16B illustrates a partial sectional view of the coupling member 648 disposed within a recess 627 of the chin bar 624. The recess 627 in the chin bar 624 may define a first dimension D1, such as a diameter. The coupling member 648 may generally be sized to fit within the dimension D1 of the aperture in the chin bar 624. Furthermore, the perimeter 653 of the distal surface 647 and the perimeter 651 of the proximal surface 657 of the coupling member 648 may define an Axis-A, that passes through center C1 of the proximal surface 657 and center C2 of the distal surface 647 of the coupling member 648. A transverse plane may be oriented to be parallel to the Axis-A and extending through the proximal surface 657 and the distal 647 surface of the coupling member 648 defining opposing lateral halves of the coupling member 648. In configurations where the coupling member 648 comprises a magnetic material, the transverse plane may define separation between the opposing poles of the magnetic material.

Furthermore, as can be seen in FIGS. 16A and 16B, the distal surface 647 of the coupling member 648 may comprise a generally curved shape. For example, the distal surface 647 may comprise a generally convex shaped surface. Alternatively, the distal surface 647 may comprise a generally protruded or polyaxial surface, such that the distal surface comprises a generally rounded surface extending outward from the center of the coupling member 648. While not illustrated in FIGS. 16A and 16B, it is contemplated that the distal surface 647 of the coupling member 648 may comprise a concave surface. Various exemplary configurations of a coupling member 648 included a concave or convex surface will be described in more detail below.

Figure 17A:
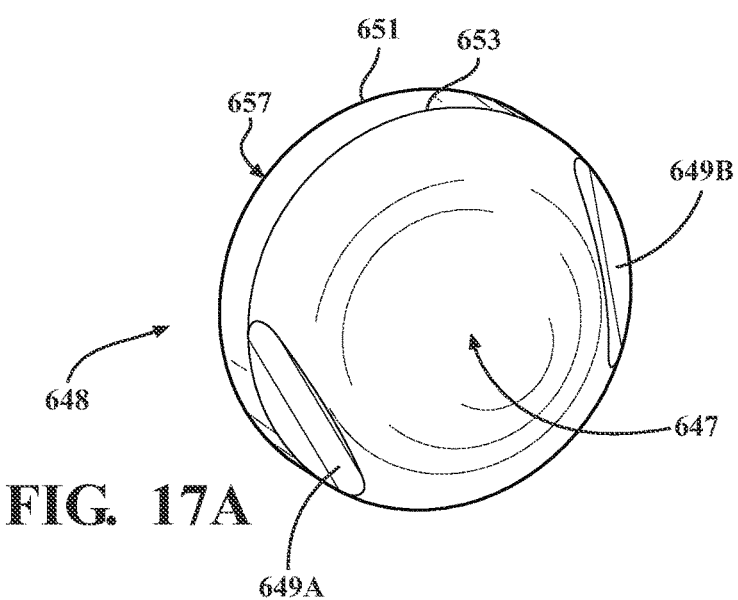
FIG. 17A is a perspective view of a first configuration of a coupling member of the helmet of FIG. 14.
Figure 17B:
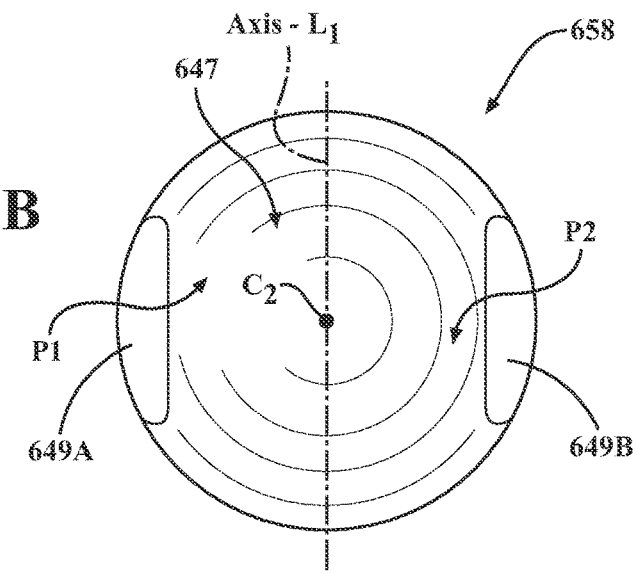
FIG. 17B is a top view of the first configuration of a coupling member of the helmet of FIG. 14.

Referring to FIGS. 17A and 17B, an exemplary configuration of the coupling member 648 is illustrated. The coupling member 648 may comprise a generally round cross-sectional shape with opposing proximal 657 and distal surfaces 647. As described above, the distal surface 647 may have a curved-shape. The coupling member 648 may also comprise one or more indents 649A, 649B on the distal surface 647. The indent(s) 649A, 649B may be configured as a groove, recess, aperture, cutout, or similar shape. The coupling member 648 may comprise a single indent or a pair of indents 649A, 649B, as illustrated in FIGS. 17A and 17B. It is also contemplated that the coupling member 648 may comprise more than two indents 649A, 649B. The indents 649A, 649B may serve as a structural and/or visual alignment feature for positioning the coupling member 648 relative to the chin bar 624 and/or the detector 670. For example, in configurations where the coupling member 648 comprises a magnetic material, the indents 649A, 649B or other indicator may provide a visual identifier as to the orientation and/or position of the magnetic poles of the coupling member 648. It will be appreciated that this configuration contributes to improved manufacturability in that the coupling member 648 can be readily and accurately position within the recess of the chin bar 624 so that the poles of coupling member 648 are properly oriented relative to the detector 670.

Referring to FIG. 17B, the coupling member may also define a lateral axis, Axis-L1, configured to intersect Axis-A of the coupling member 648. The lateral axis Axis-L1 may also be oriented to be generally perpendicular to Axis-A of the coupling member 648. For example, the lateral axis, Axis-L1, may be oriented in a generally horizontal direction to define opposing lateral halves of the coupling member 648. The coupling member 648 may have a first magnetic pole P1 and an opposing second magnetic pole P2 defined by opposing lateral halves of the coupling member 648 separated by lateral axis Axis-L1. For example, one lateral half of the coupling member 648 may define a volume representing the first magnetic pole P1 and the opposing lateral half of the coupling member 648 may define a volume representing the second magnetic pole P2.

Alternatively, it is contemplated that the respective magnetic poles P1, P2 of the magnetic material may be represented by individual points. The point defining each of the magnetic poles P1, P2 may be defined as the point within the respective lateral half of the coupling member 648 where the magnetic moment of the respective pole P1, P2 is strongest.

For example, the opposing magnetic poles P1, P2 of the magnetic material of the coupling member 648 may be defined as individual points within the opposing lateral halves of the coupling member 648. In this exemplary configuration, it is contemplated that the first magnetic pole P1 and the second magnetic pole P2 may each be positioned within their respective lateral half of the coupling member 648 such that the point defining each magnetic pole P1, P2 is closer to the perimeter of the coupling member than to a distal-most point (illustrated as C2 in FIG. 16B) of the distal surface 647. It is also contemplated that each of the respective magnetic poles P1, P2 may each be positioned within their respective lateral half of the coupling member 648 such that the point defining each magnetic pole P1, P2 is closer to the detector 670 than to the distal-most point C2 of the distal surface 647.

Referring to FIGS. 18A, 18B, 18C, and 18D, detailed views of an exemplary configuration of the face shield 618A for use with the surgical garment 612 is illustrated. Similar to the face shields 18, 118 described above, the face shield 618A may comprise a portion of the surgical garment 612 that allows the wearer to see through the barrier provided by the surgical garment 612. The face shield 618A is generally a sheet-like structure and may have a thickness of approximately 1 mm or less. The face shield 618A may be mounted and/or attached to an opening or cut-out formed in the surgical fabric 614 of the surgical garment 612. The surgical fabric 614 may be attached around the periphery or edge of the face shield 618A by sewing, snaps, hook and loop, adhesive, welding, or combinations thereof. The face shield 618A may be constructed from a transparent material, such as a polycarbonate. One such polycarbonate is sold under the trademark LEXAN™ by Sabic. The face shield 618A of the surgical garment 612 may also be tinted to protect the wearer's eyes from heightened exposure to bright lights. Furthermore, the face shield 618A may be flexible such that the face shield 618A may be curved to accommodate different head sizes, as will be described below.

The face shield 618A may further comprise the tab 655A described above, with regard to the surgical garment 612 of FIG. 13A. The tab 655A may extend from the top portion of the face shield 618A and may define at least a portion of the opening 656. The opening 656 may be generally rectangular-shaped. While not illustrated in the figures, it is further contemplated that the opening 656 may be configured in the shape of a circle, oval, square, or any similar polygonal shape. The opening 656 may also be generally centered between the opposing ends of the face shield 618A and serve as an alignment element configured to interact with the alignment channel 645 of the helmet 620 described above. Furthermore, the opening 656 may be positioned on the face shield 618A above the point of attachment for the surgical fabric 614 to the face shield 618A, so as to ensure the surgical fabric 614 covers the opening 656 to maintain the barrier provided by the surgical garment 612 between the wearer and the environment. While not illustrated in FIGS. 18A-18D, as previously discussed with reference to FIG. 13B, the tab 655B may be formed separate from the face shield 618B and coupled directly to the interior of the surgical garment 612. Aside from being formed separate from the face shield 618B, the tab 655B may still comprise all of the same or similar features of the tab 655A that is formed as part of the face shield 618A. The face shield 618A may further comprise one or more apertures 619 positioned in the bottom portion of the face shield 618A and be configured to couple the attachment elements 658A to the face shield 618A.

Figure 18A:
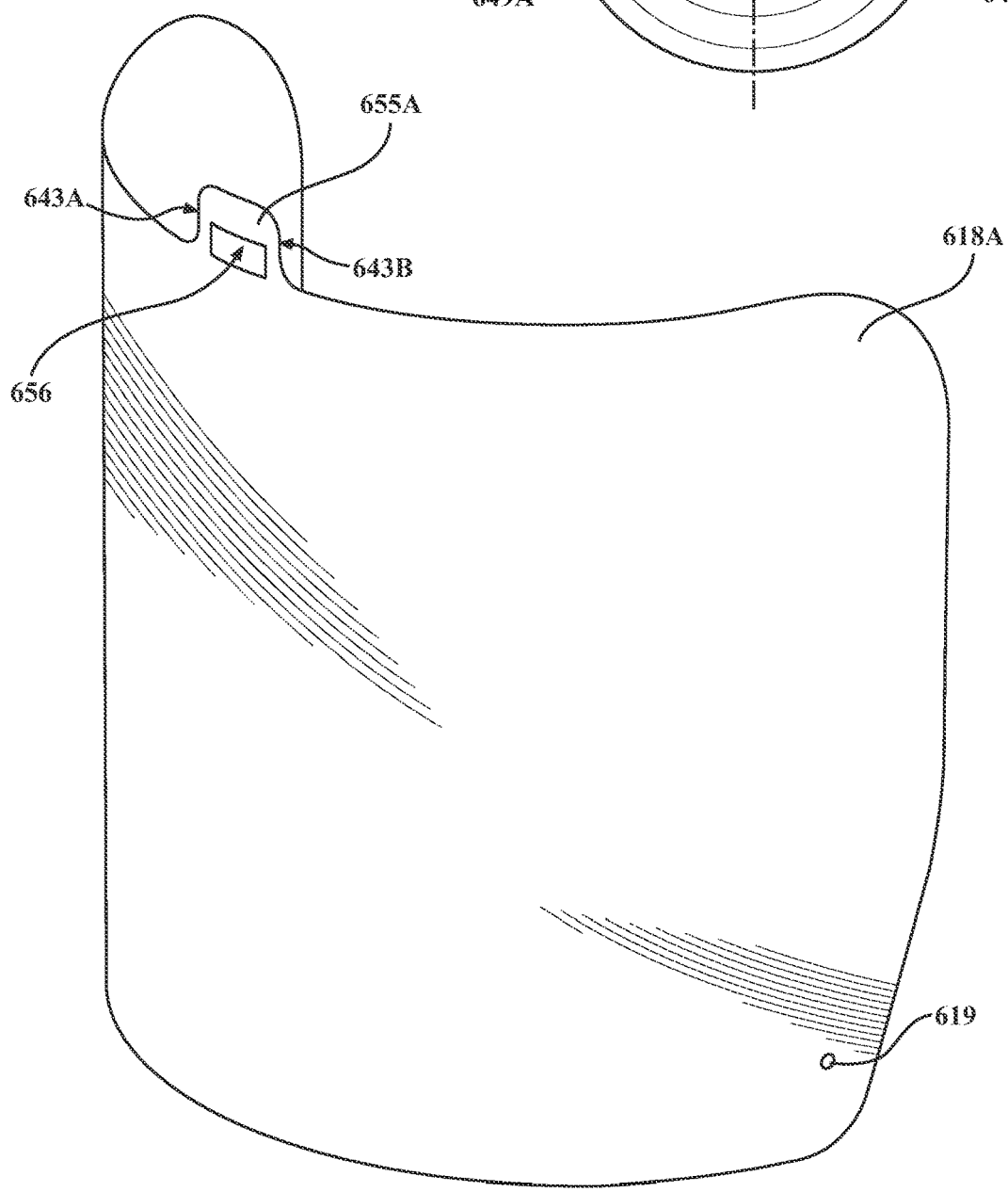
FIG. 18A is a perspective view of a front of the transparent face shield of the surgical apparel system of FIG. 16A including apertures for attaching attachment elements to the transparent face shield.
Figure 18B:
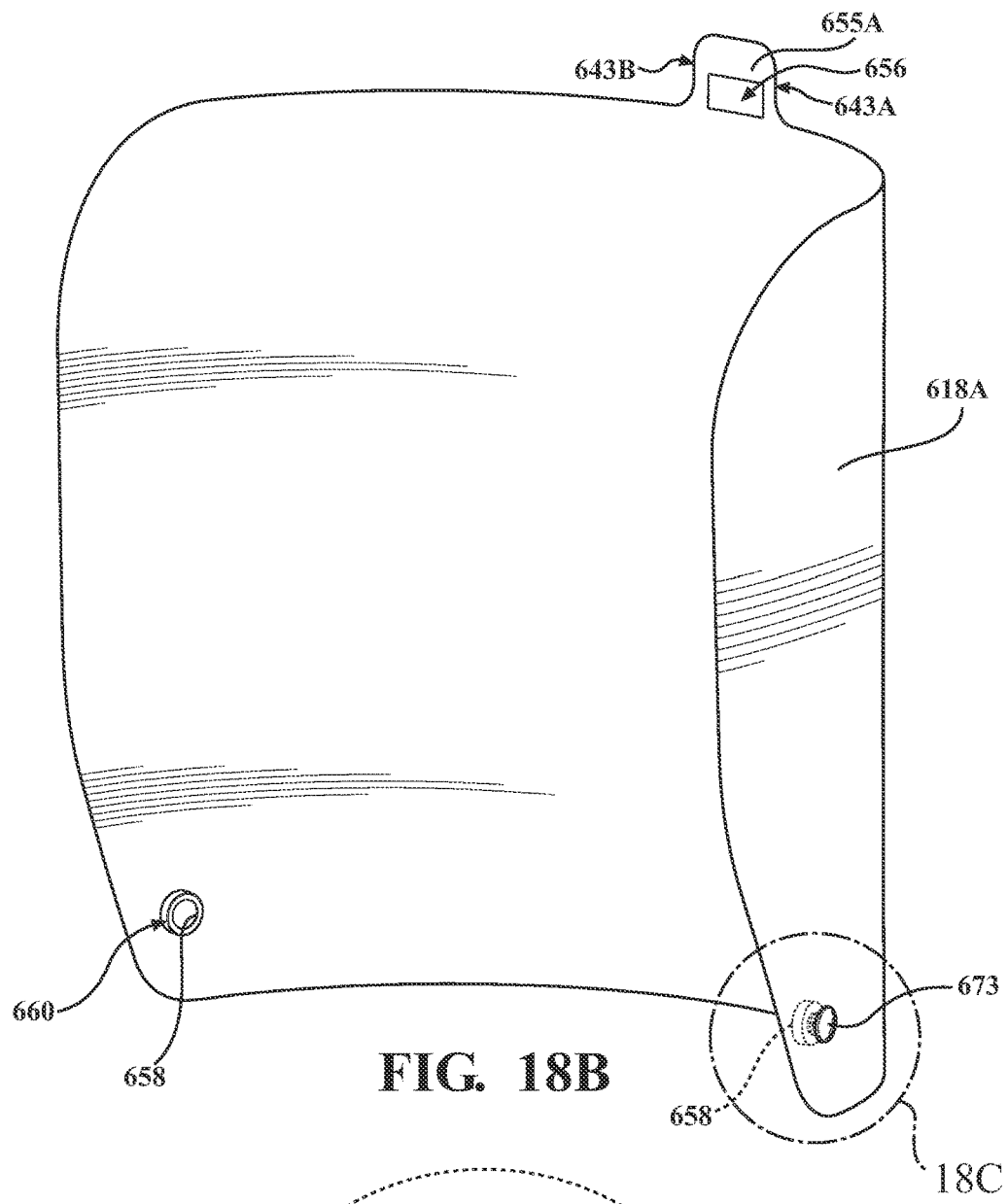
FIG. 18B is a perspective view of a rear of the transparent face shield of the surgical apparel system of FIG. 13A, including attachment members coupled to the transparent face shield.
Figure 18C:
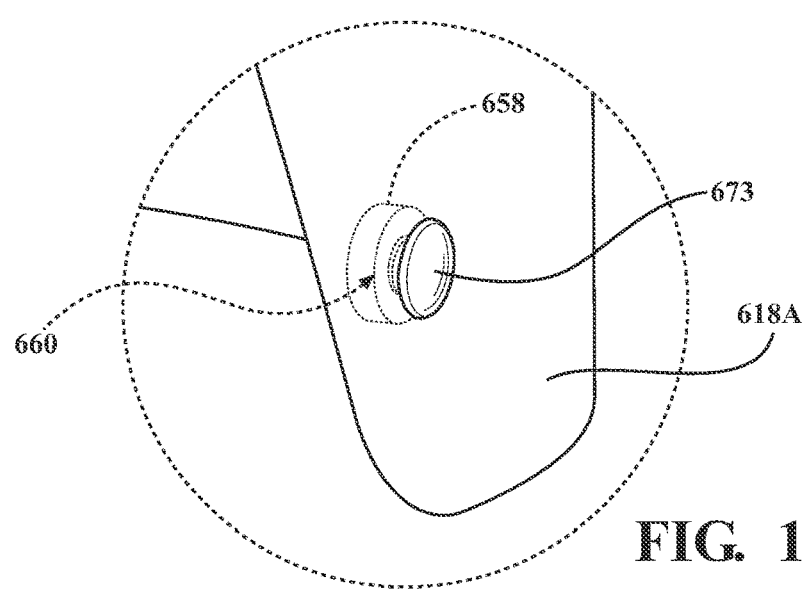
FIG. 18C is an enlarged view of one of the attachment members coupled to the transparent face shield as illustrated in FIG. 18B.
Figure 18D:
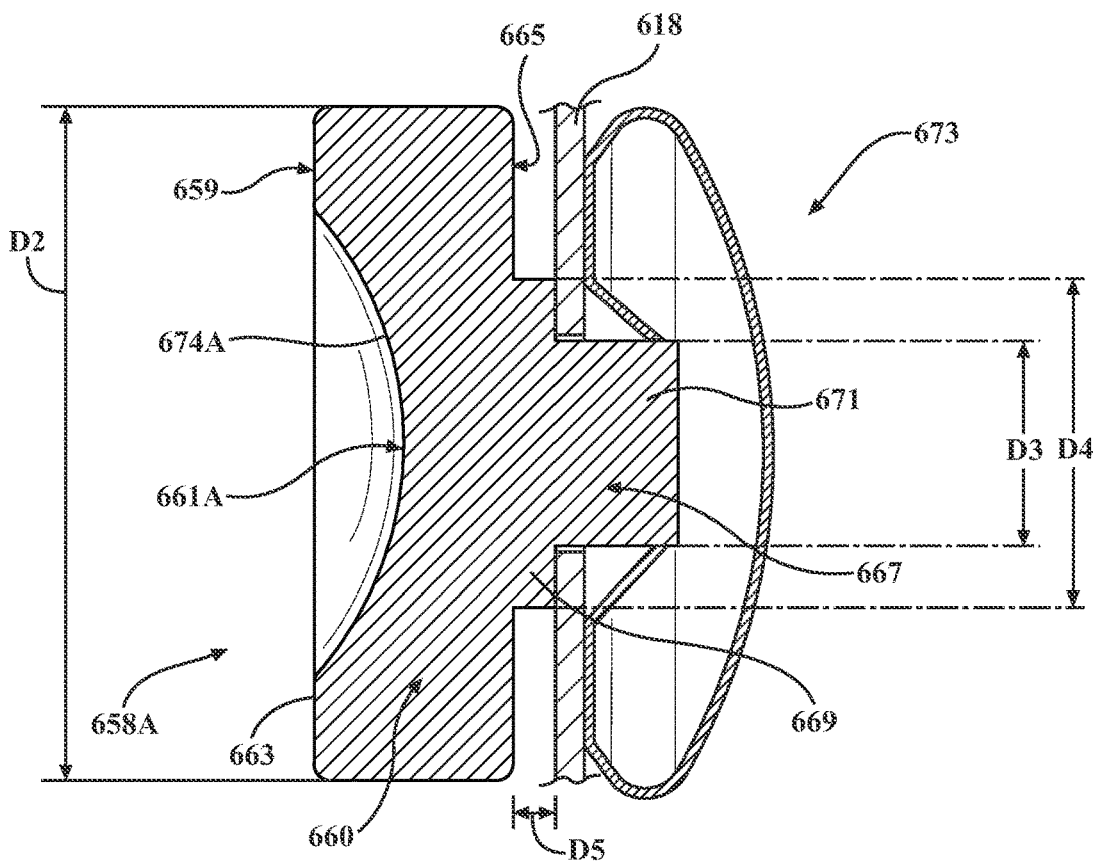
FIG. 18D is a partial sectional view of the first configuration of an attachment element of a medical garment coupled to the transparent face shield of the surgical apparel system of FIGS. 13A and 13B.

As illustrated in FIGS. 18B-18D, the attachment element 658A may comprise a head 660. The head 660 may define a second dimension D2, wherein the second dimension D2 is less the first dimension D1 of the aperture in the chin bar 624 (as illustrated in FIG. 16B), such that the head 660 is sized to be inserted within the aperture of the chin bar 624 when coupled to the coupling member 648. The head 660 of the attachment element 658A may also define a distal surface 665 and an opposing proximal surface 659. The head 660 may further define a recess 661A. The head 660 defines a recessed surface 674A that is positioned distally from the proximal surface 659 of the head 660. The head 660 may further comprise a rim 663 that may be at least partially defined by the proximal surface 659 of the head 660. The rim 663 may at least partially surround the recess 661A. The recess 661A may provide an increase in the surface area contact between the attachment element 658A and the coupling member 648 when coupled together. The increase in surface are contact can increase the strength and/or force of the magnetic bond between the attachment element 658A and the coupling member 648, required force to decouple the attachment element 658A and the coupling member 648. This can reduce accidental or unintended decoupling of the attachment element 658A and the coupling member 648 during use of the surgical garment 612 and surgical helmet 620. The size and/or shape of the recess 661A may also allow for the attachment element 658A and the coupling member 648 to interact at varying angles, which will be described in greater detail below.

A recess 661A may be defined as receding part, portion, or space, such as an indent, bay, or alcove. Generally, a recess 661A may refer to a void or absence of material. In the context of the attachment element 658A described above, the recess 661A may refer to a void or absence of material in the head 660. The size and shape of the void representing the recess 661A in the head 660 of the attachment element 658A may be defined by the recessed surface 674A. However, the recess 661A is not limited to being formed by a single component, such as the head 660 of the attachment element 658A. Any combination of components defining a void or absence of material may be considered a recess 661A. For example, in one configuration the void representing the recess 661A may be defined by a combination of the head 660 and post 667. In yet another configuration, the void representing the recess 661A may be defined by a combination of the head 660 and the face shield 618, as will be described below with respect to FIGS. 28A and 28B. Various exemplary configurations of the attachment member 658A and the recess 661A will be described in greater detail below.

In one exemplary configuration, the recess 661A may be formed in, and defined entirely by, the head 660 of the attachment element 658A. However, as described above, alternative configurations are contemplated. The recess 661A may removably receive at least a portion of the protruded surface 647 of the coupling member 648 to removably couple the surgical garment 612 to the surgical helmet 620. The recess 661A may be formed in a variety of shapes and sizes, which will be discussed in greater detailed below.

The attachment element 658A may further comprise a post 667 extending distally from the distal surface 665 of the attachment element 658A. The post 667 may comprise a proximal portion 669 and a distal portion 671, wherein the proximal portion 669 comprises a third dimension D3 and the distal portion 671 comprises a fourth dimension D4. The post 667 may be configured such that the third dimension D3 of the proximal portion 669 is larger than the fourth dimension D4 of the distal portion 671, creating a shoulder. The distal portion 671 of the post 667 should be configured to fit within the aperture 619 of the face shield 618A to facilitate coupling of the attachment element 658A to the face shield 618A.

In the configuration of the post 667 wherein the third dimension D3 of the proximal portion 669 is larger than the fourth dimension D4 of the distal portion 671, the shoulder created by the proximal portion 669 of the post 667 is intended to space the head 660 of the attachment element 658A from the face shield 618 at a distance D5. The shoulder may be utilized to space the attachment element 658A from the face shield 618 to allow the face shield 618 to flex relative the distal surface 665 of the attachment element 658A. This flexibility enables a more robust attachment between the attachment element 658A and the coupling member 648 in that the face shield 618 can flex without jarring the attachment element 658A loose from its position attached to the coupling member 648.

While the exemplary configuration of the attachment element 658A illustrated in FIG. 18D comprises a post 667 wherein the third dimension D3 of the proximal portion 669 is larger than the fourth dimension D4 of the distal portion 671, it is contemplated that the post 667 may comprise a single uniform dimension configured to fit within the aperture 619 of the face shield 618A.

Referring still to FIG. 18D, the attachment element 658A may be coupled to the face shield 618 by a retention feature 673. The retention feature 673 may take the form of a cap or similar fastener configured to engage the distal end of the post 667. For example, as illustrated in FIG. 18D, the post 667 may be inserted through the aperture 619 of the face shield and the retention feature 673 may be applied to the distal end of the post 667 to secure the attachment element 658A to the face shield 618.

Figure 19A:
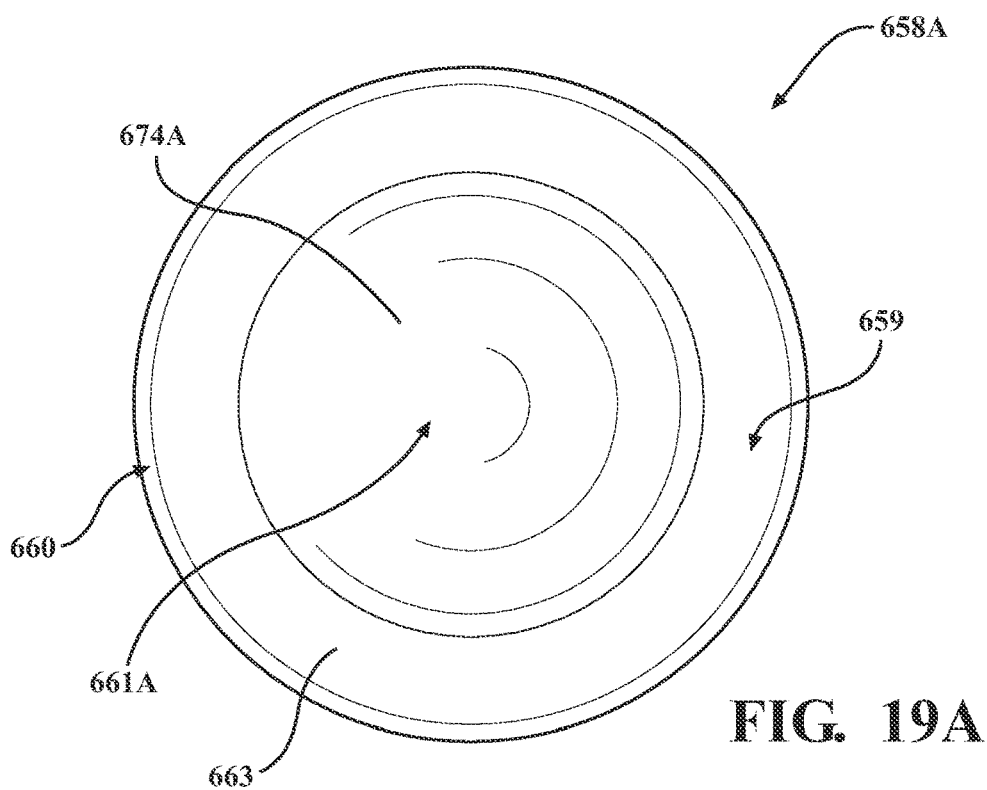
FIG. 19A is a front view of a first configuration of an attachment element of a surgical hood of the surgical apparel system of FIGS. 13A and 13B.
Figure 19B:
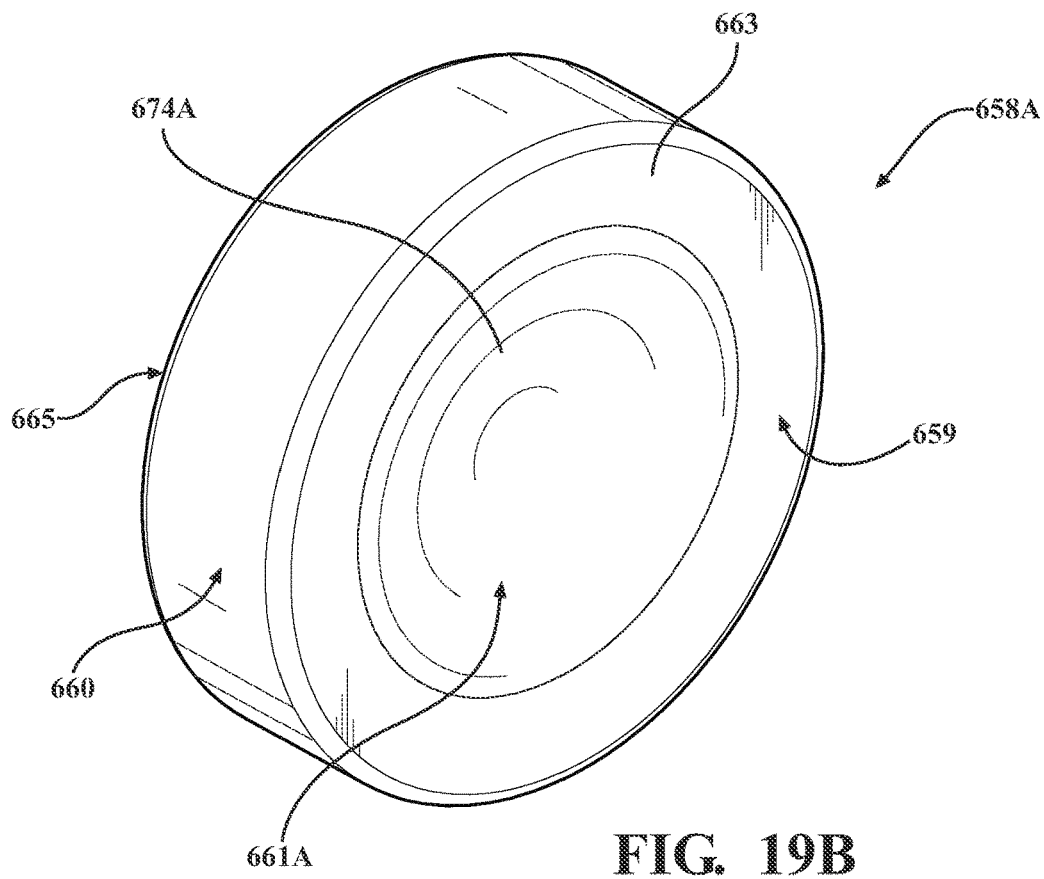
FIG. 19B is a front perspective view of the first configuration of an attachment element of a medical garment of the surgical apparel system of FIGS. 13A and 13B.
Figure 19C:
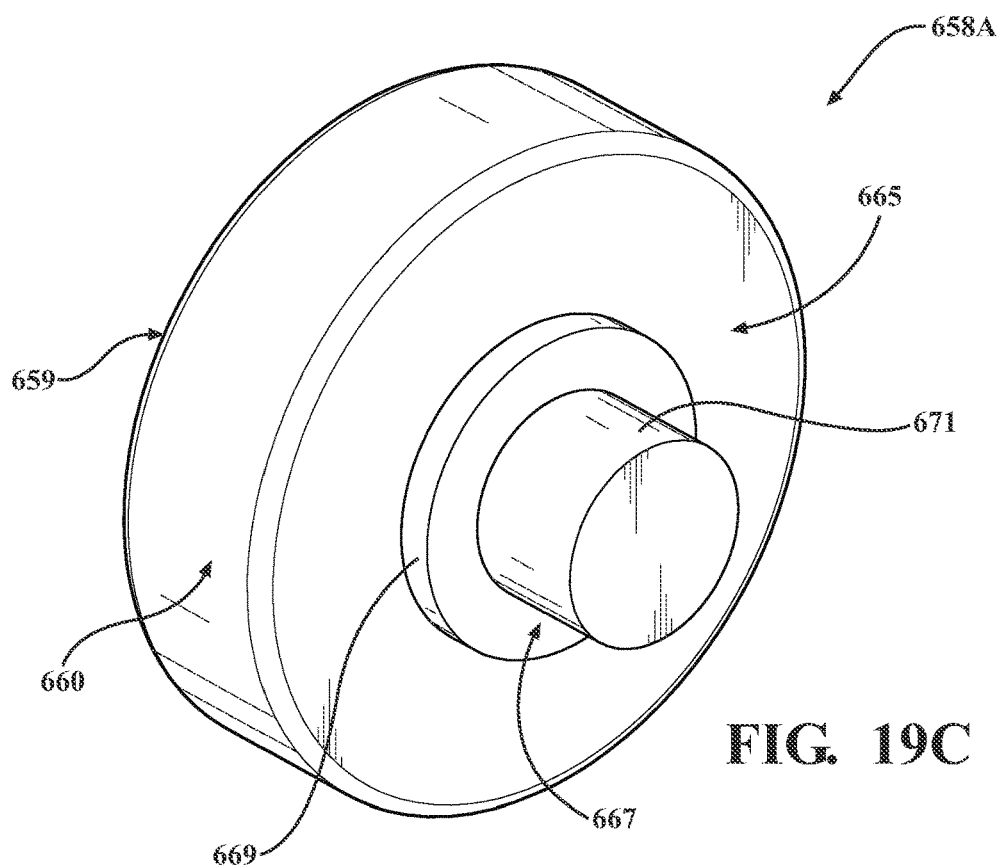
FIG. 19C is a rear perspective view of the first configuration of an attachment element of a medical garment of the surgical apparel system of FIGS. 13A and 13B.
Figure 20A:
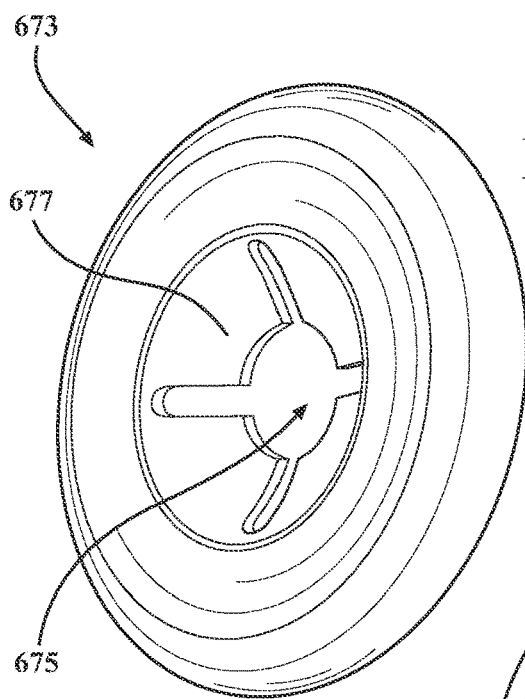
FIG. 20A is a rear perspective view of a retaining member for securing an attachment element to the transparent face shield of the surgical apparel system of FIGS. 13A and 13B.
Figure 20B:
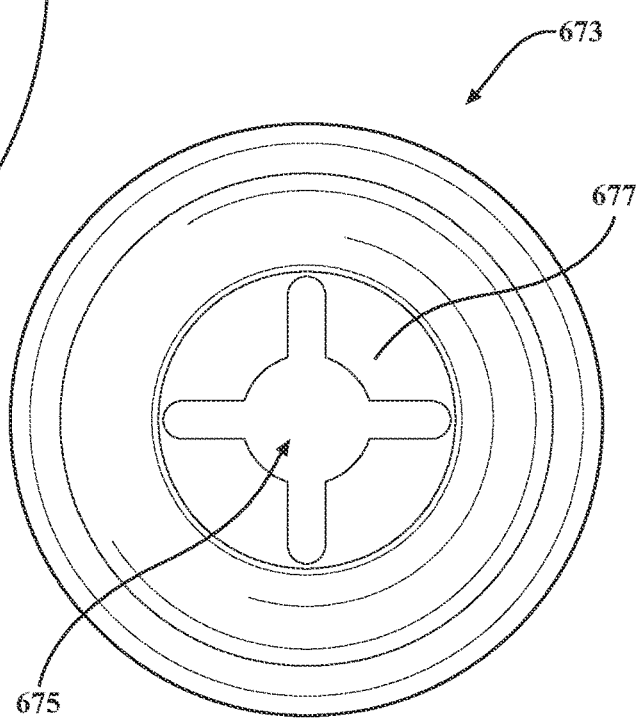
FIG. 20B is a rear view of the retaining member for securing an attachment element to the transparent face shield of the surgical apparel system of FIGS. 13A and 13B.
Figure 20C:
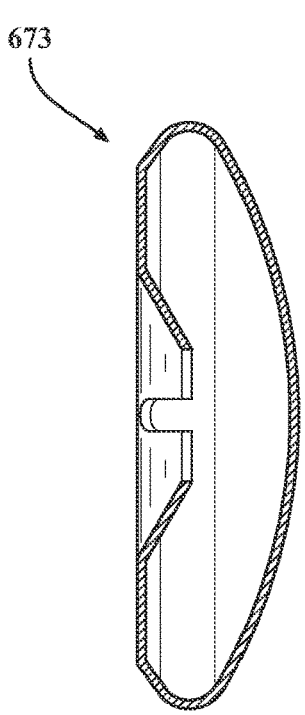
FIG. 20C is a sectional view of the retaining member for securing an attachment element to the transparent face shield of the surgical apparel system of FIGS. 13A and 13B.
Figure 20D:
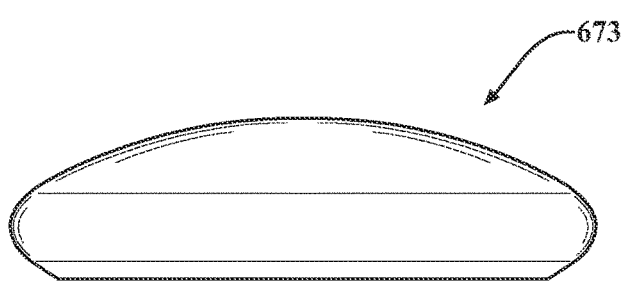
FIG. 20D is a side view of the retaining member for coupling an attachment element to the transparent face shield of the surgical apparel system of FIGS. 13A and 13B.

Referring to FIGS. 19A, 19B, and 19C, detailed views of another configuration of an attachment element 658A are illustrated. Similar to the attachment element 658 described above, the first configuration of the attachment element 658A comprises a head 660 having a distal surface 665 and an opposing proximal surface 659. The recess 661A of the attachment element 658A may comprise a generally concave shape, curving inward to define a void or absence of material in the head 660 of the attachment element 658A. The size and/or shape of the recess 661A may be defined by the recessed surface 674 of the head 660. Furthermore, the size and/or shape of the recess 661A may be defined relative to the size and/or shape of the protruded surface 647 of the coupling member 648. It is contemplated that the depth and/or radius of the recess 661A may be varied to allow the recess 661A to matingly receive the protruded surface 647 of the coupling member 648 when coupled together. For example, it is contemplated that the recess 661A defines a void space comprising a volume that is at least ten percent (10%) of the volume defined by the protruded surface 647 of the coupling member 648, to allow at least a portion of the protruded surface 647 to be disposed within the recess 661A of the attachment element 658A. However, it is contemplated that the recess 661A may define a void space comprising a volume that is at twenty-percent (20%), thirty-percent (30%), or more of the volume defined by the protruded surface 647.

In an exemplary configuration of the attachment element 658A, it is contemplated that the recess 661A may define a void space that allows for the protruded surface 647 to be positioned a certain distance within the recess 661A of the attachment element 658A. For example, the recess 661A may define a void space that allows the distal most point (illustrated as C2 in FIG. 16B) of the protruded surface 647 is positioned distally of the proximal surface 659 of the head 660. Specifically, the protruded surface 647 may be positioned within the recess 661A of the attachment element 658A such that the distal-most point (illustrated as C2 in FIG. 16B) of the protruded surface 647 is positioned distally at least one millimeter (1-mm) of the proximal surface 659 of the head 660. However, it is contemplated that the distal most point (illustrated as C2 in FIG. 16B) of the protruded surface 647 may be positioned distally two millimeters (2-mm), three millimeters (3-mm), four-millimeters (4-mm), or more relative to the proximal surface 659 of the head 660.

In another exemplary configuration of the attachment element 658A, the recess 661A may define a void space that allows for a volume of the protruded surface 647 to be positioned within the recess 661A of the attachment element 658A. For example, the recess 661A may define a void space that allows at least ten percent (10%) of the protruded surface 647 to be positioned distally of the proximal surface 659 of the head 660. However, it is contemplated that the protruded surface 647 may be positioned within the recess 661A of the attachment element 658A such that twenty-percent (20%), thirty-percent (30%), or more of the protruded surface 647 is positioned distally of the proximal surface 659 of the head 660. These various dimensions ensure there is a robust coupling of the surgical garment 612 to the surgical helmet 620, which resists lateral and axial forces, which would decouple the attachment element 658A from and coupling member 648. Additional exemplary configurations the recess 661A of the attachment element 658A will be described in greater detail below.

Referring to FIGS. 20A, 20B, 20C, and 20D, detailed views of an exemplary configuration of the retention feature 673 are illustrated. The retention feature 673 may comprise an aperture 675 that extends at least partially through the retention feature 673. The aperture 675 of the retention feature 673 may be defined by one or more tabs 677. The tabs 677 may be sized to define the aperture 675 such that the aperture 675 creates a friction fit with the distal portion 671 of the post 667 when inserted through the aperture 675 to couple the attachment element 658A to the face shield 618. For example, referring back to FIG. 18D, the distal portion 671 of the post 667 may be inserted through the aperture 619 in the face shield 618, and the retention feature 673 may be coupled to the attachment element 658A by inserting the distal portion 671 of the post 667 within the aperture 675 of the retention feature 673.

While not illustrated, it is contemplated that the attachment element 658A may also be coupled to the face shield 618 by inserting the post 667 through the aperture 619 in the face shield 618 and stamping the distal end of the post 667 that extends beyond the distal surface of the face shield 618A such that a flange is created on the opposite side of the face shield 618 from the head 660 of the attachment element 658A. This flange may abut a surface of the face shield 618 and act as the retaining feature 673 for the attachment element 658A.

Figure 28A:
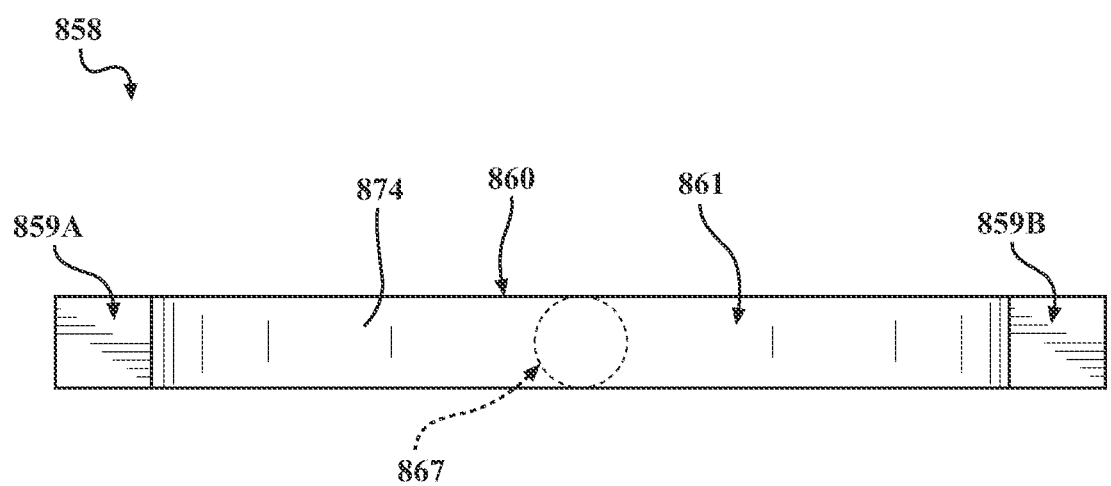
FIG. 28A is a front view of a seventh configuration of the attachment element for use with the medical garment of the surgical apparel system of FIGS. 13A and 13B.
Figure 28B:
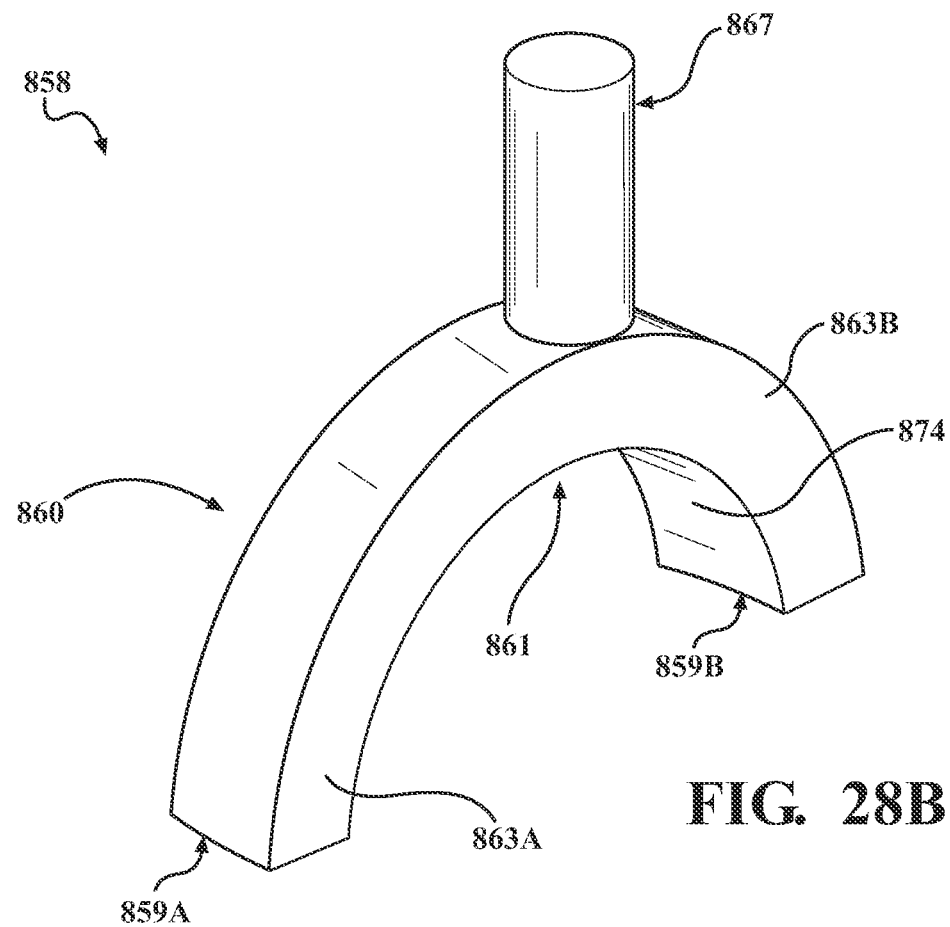
FIG. 28B is a front perspective view of the seventh configuration of the attachment element of FIG. 28A.

In configurations where the face shield 618 does not include an aperture, it is also contemplated that the attachment element 658A may be coupled to the face shield 618 via a glue, epoxy, sealant, or other similar adhesive. It is further contemplated that the attachment element 658A may be welded, or mechanically attached to the face shield 618 in another manner. An exemplary configuration is shown in FIGS. 28A and 28B, where the attachment element 1358 is secured to the fabric 614 or face shield 618 with adhesive.

Alternatively, the attachment element 658A may be coupled to the face shield 618 by inserting the post 667 through the aperture 619 in the face shield 618 and apply the adhesive to the post 667 on the distal side of the face shield 618 to secure the attachment element 658A to the face shield 618.

Figure 21A:
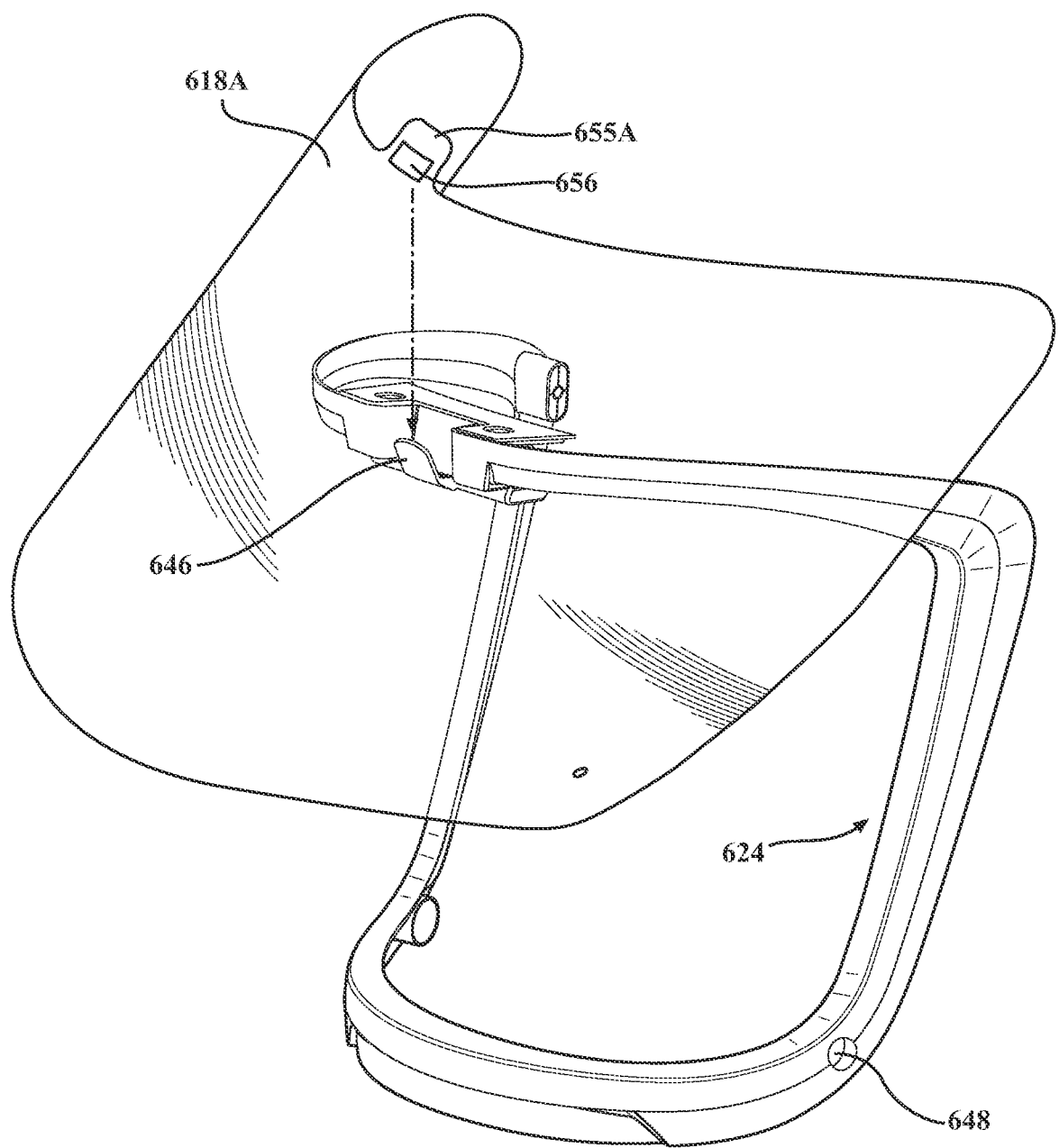
FIG. 21A is a perspective view of a face shield of the medical garment of FIG. 13A positioned relative to the chin bar and top beam of the surgical helmet prior to coupling the face shield to the surgical helmet.
Figure 21B:
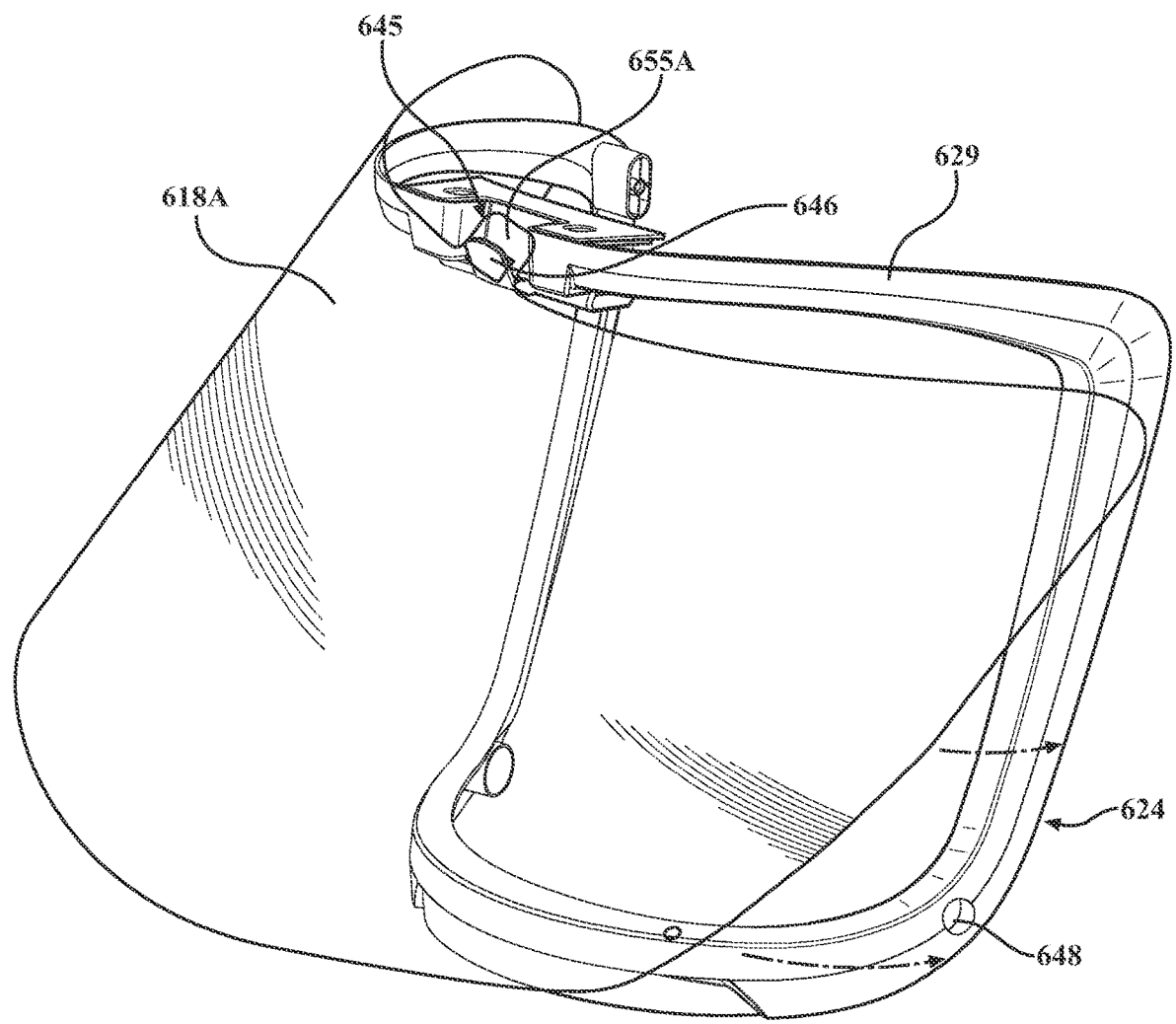
FIG. 21B is a perspective view of the face shield of the medical garment of FIG. 13A positioned relative to the chin bar and top beam of the surgical helmet as the face shield transitions to being coupled to the surgical helmet, including a tab positioned within an alignment channel of the top beam of the surgical helmet.

Referring to FIGS. 21A-21C, perspective views of various stages of coupling the face shield 618A, and by extension the surgical garment 612, to the surgical helmet 620 are illustrated. As described above, the surgical garment 612 may comprise a tab 655A, 655B defining an opening 656. The tab 655A may be formed as part of the face shield 618A, as illustrated in FIGS. 13A and 21A-21C. Alternatively, the tab 655B may be a separate component that is independently coupled to the surgical garment 612, as illustrated in FIG. 13B. The top beam 629 comprises the pair of laterally spaced-apart side walls 639A, 639B and the proximal surface 637 of the surgical helmet 620 that defines the alignment channel 645. The protrusion 646 may extend from the proximal surface 639. The face shield 618 comprises a plurality of attachment members 658A (not visible) secured to the periphery of the face shield 618 by the retaining feature 673.

To couple the surgical garment 612 to the surgical helmet 620 when the tab 655A is formed as part of the face shield 618A, the face shield 618A may be positioned with the opening 656 in the tab 655A above the alignment channel 645 and the protrusion 646 (see FIG. 21A). The tab 655A, and by extension the face shield 618A, may then be lowered onto the surgical helmet 620 such that at least a portion of the tab 655A is positioned within the alignment channel 645 between the pair of laterally spaced-apart side walls 639A, 639B. The tab 655A should be positioned within the alignment channel 645 such that the protrusion 646 is disposed within the opening 656 of the tab 655A (see FIG. 21B). The lower portion of the face shield 618A, that includes the attachment elements 658A, may then be manipulated to couple the attachment elements 658A to the complementary coupling members 648 positioned on the chin bar 624 (see FIGS. 21B and 21C). For example, once the tab 655A is positioned within the alignment channel 645 and the protrusion 646 is disposed within the opening 656 of the tab 655A, the face shield 618 may be pivoted about the protrusion 646 to position the attachment elements 658A adjacent to the complementary coupling members 648. This is one example of a method of coupling the surgical garment 612 to the surgical helmet.

Alternatively, when the tab 655B is formed independent of the face shield 618B (see the surgical garment 612 of FIG. 13B), the surgical garment 612 may be coupled to the surgical helmet 620 in a similar fashion as described above. The tab 655B, coupled to the wearer side of the surgical garment 612, may be positioned above the alignment channel 645 and the protrusion 646. The tab 655B, and by extension the surgical garment 612, may then be lowered onto the surgical helmet 620, such that at least a portion of the tab 655B is positioned within the alignment channel 645 between the pair of laterally spaced-apart side walls 639A, 639B. The tab 655B should be positioned within the alignment channel 645 such that the protrusion 646 is disposed within the opening 656 of the tab 655B. The lower portion of the face shield 618B, that includes the attachment elements 658A, may then be manipulated to couple the attachment elements 658A to the complementary coupling members 648 positioned on the chin bar 624.

Figure 22A:
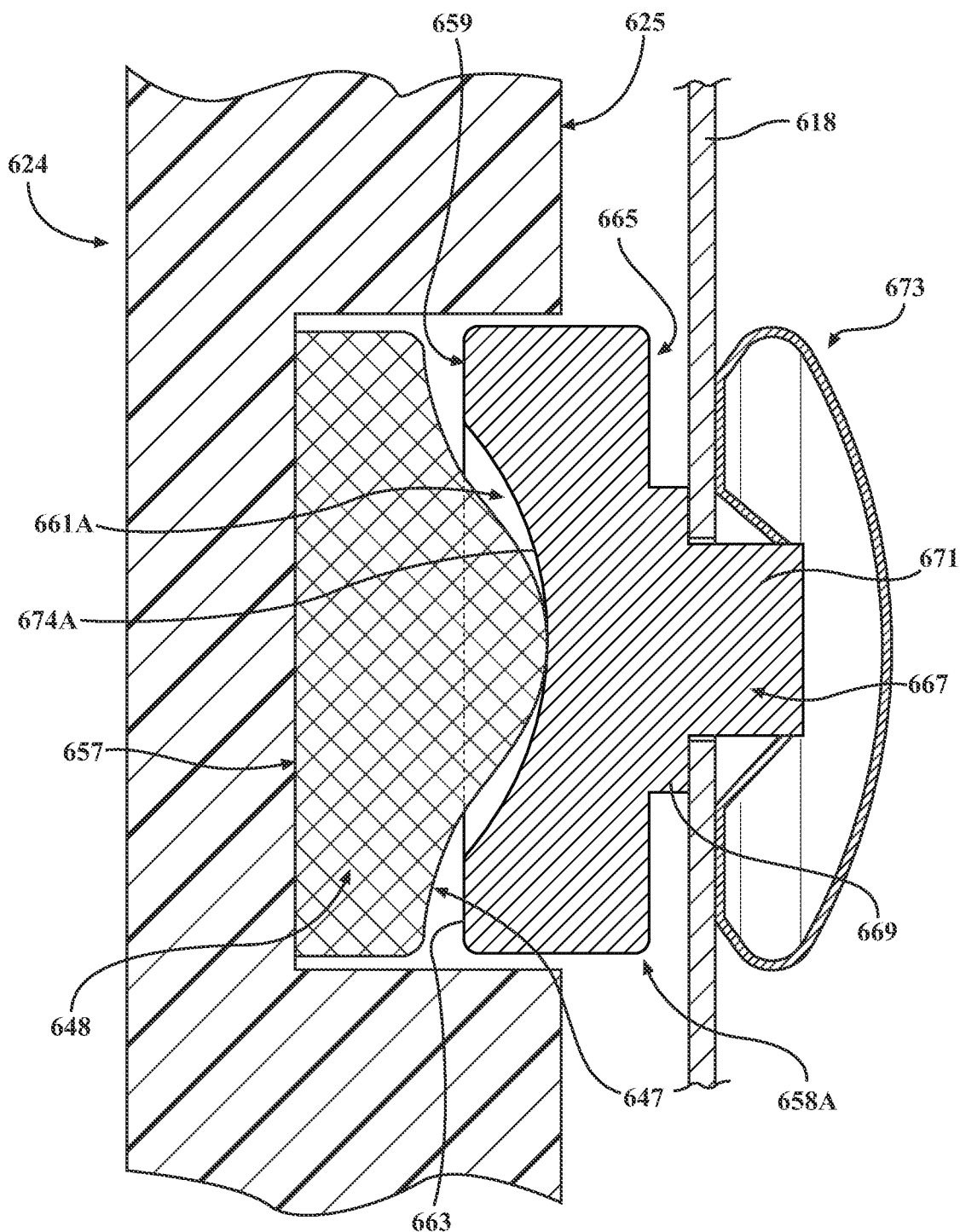
FIG. 22A is a partial sectional view of the first configuration of the attachment member of FIG. 18D coupled to the coupling member of FIGS. 13A-16C.

Referring to FIG. 22A, a partial sectional view of the attachment element 658A of the surgical garment 612 coupled to the coupling member 648 of the chin bar 624 is illustrated. The coupling member 648 is positioned in a recess of the chin bar 624. The coupling member 624 comprises the protruded surface 647, which is positioned proximally to the distal surface 625 of the chin bar 624.

The protruded surface 647 of the coupling member 648 may extend at least partially into the void defined by the recess 661A of the attachment element 658A. The complementary shapes of the protruded surface 647 of the coupling member 648 and the recessed surface 674A of the attachment element 658A may be configured to be in sliding contact when the surgical garment 612 is coupled to the surgical helmet 620. Alternatively, it is contemplated that there may be a void space or a gap between all or a portion of the protruded surface 647 and the recessed surface 674A. For example, the protruded surface 647 may comprise a sharp point having a small radius and the recessed surface 674A may comprise a concave shape having a larger radius relative to the radius of the protruded surface 647. In this configuration, the point or apex of the protruded surface 647 may contact a portion of the recessed surface 674A, while having a gap between other portions of the protruded surface 647 and the recessed surface 674A.

The complementary shapes of the protruded surface 647 of the coupling member 648 and the recess 661A of the attachment element 658A may allow the attachment element 658A to pivot about the coupling member 648 and remain coupled with the coupling member 648 at varying angles. This may allow for additional freedom of movement and/or positioning of the face shield 618 as it is manipulated or flexed to couple the attachment elements 658A to the corresponding coupling members 648, such as during removal of one or more film layers from the face shield 618. Furthermore, the complementary shapes of the protruded surface 647 of the coupling member 648 and the recess 661A of the attachment element 658A are designed to promote and/or maintain contact of the surgical garment 612 with the surgical helmet 620 during a medical procedure. By adding curvature to the coupling member 648 and/or the complementary recess 661A of the attachment element 658A of the surgical garment 612, forces are transferred into the physical materials making up the coupling member 648 and/or the attachment element 658A when the coupling member 648 and/or the attachment element 658A are mated and put in shear, thereby increasing the holding or retaining force. Additional holding force is provided by the curved and/or recessed surface(s) because these surfaces can pivot in a position where there is optimal magnetic holding force provided by the magnetic material in interacting with the ferromagnetic material. Therefore, by allowing the attachment element 658A to rotate relative to the coupling member 648, the force (moment arm) created by shear is dissipated. Additional holding force is provided because of the increased surface area that is in contact or close proximity, resulting from curved versus flat surfaces.

To couple the surgical garment 612 to the surgical helmet 620, in certain configurations, at least a portion of the head 660 of the attachment element 658A may be at least partially disposed within the recess 627 of the chin bar 624 in order for the recess 661 of the attachment element 648 to contact the protruded surface 647 of the coupling member 648. It is contemplated that the proximal surface 659 of the head 660 may be disposed within the recess 627 of the chin bar 624 such that the proximal surface 659 of the head 660 is positioned at least two millimeters (2-mm) proximally of the distal surface 625 of the chin bar 624. It is further contemplated that the proximal surface 659 of the head 660 may be positioned three millimeters (3-mm) or more proximally of the distal surface 625 of the chin bar 624. It is also contemplated that if the attachment element 658A is coupled to the coupling member 648 at an angle, as allowed for by the complementary surfaces 647, 674 of the respective attachment element 658A and the coupling member 648, the portion of the head 660 of the attachment element 658A disposed within the recess 627 of the chin bar 624 may defined as a percentage of the head 660 disposed within the recess 627. For example, at least ten percent (10%) of the volume of the head 660 of the attachment element 658A may be disposed within the recess 627 of the chin bar 624. Because the attachment element 658A is at least partially within the recess 627, the amount of force required to decouple the attachment element 658A from the coupling member 648 is greater. This is because the sidewall of the recess 627 in the chin bar 624 can provide additional resistance to decoupling of the coupling member 648 and the attachment element 658A. For example, the sidewall of the recess 627 in the chin bar 624 may prevent the attachment element 658A from sliding off the coupling member 648. This may be particularly true if a shear or lateral force is applied to the face shield 618. For example, when the face shield 618 comprises a plurality of removable layers for clearing debris from the face shield 618, the face shield 618, and by extension the attachment element 658A, may experience a shear or lateral force. The sidewalls of the recess 627 of the chin bar 624 may prevent any lateral movement of the attachment element 658A relative to the coupling member 648. This may be accomplished by configuring the dimension D1 of the recess 627 in the chin bar 624 to be at least slightly larger than the dimension D2 of the head 660 of the attachment element 658A. This can prevent the attachment element 658A from sliding laterally a sufficient distant that the head 660 of the attachment element 658A becomes decoupled from the coupling member 648.

As mentioned above, the coupling member 648 comprises one of a ferromagnetic material or a magnetic material and the attachment element 658A comprises the other of the ferromagnetic material or magnetic material, so that the coupling member 648 and the attachment element 658A may be magnetically attracted to one another. In the illustrated configurations, the coupling member 648 may comprise magnetic material, and hence a magnetic field may emanate from or otherwise be generated by the coupling member 648. When the coupling member 648 is coupled to the attachment element 658A, the magnetic field surrounding the component comprising the magnetic material will be altered when the component comprising the ferromagnetic material is placed adjacent to it.

The detector 670 positioned adjacent to the coupling member 648 may comprise a Hall-effect sensor configured to detect the change in the magnetic field, indicating the surgical garment 612 is coupled to the surgical helmet 620. For example, when the coupling member 648 comprises the magnetic material and the attachment element 658A comprises the ferromagnetic material, the detector 670 may detect a first configuration of the magnetic field surrounding the coupling member 648 when the attachment element 658A is separated from the coupling member 648. The detector 670 may then detect a second configuration of the magnetic field surrounding the coupling member 648 when the attachment element 658A is adjacent to the coupling member 648, indicating the surgical garment 612 is coupled to the surgical helmet 620. Alternatively, wherein the coupling member 648 comprises the ferromagnetic material and the attachment element 658A comprises the magnetic material, the detector 670 may detect the absence of the magnetic field surrounding the coupling member 648 when the attachment element 658A is separated from the coupling member 648. The detector 670 may then detect the presence of the magnetic field when the attachment element 658A is adjacent to the coupling member 648, indicating the surgical garment 612 is coupled to the surgical helmet 620. As described above, the controller may be configured to communicate operational commands to the detector 670 as well as be configured to receive a signal from the detector 670 related to a characteristic detected by the detector 670. The signal may be based on the presence of, absence of, and/or changes in the characteristic to be detected by the detector 670, which may be related to the presence or absence of the surgical garment 612 being coupled to the surgical helmet 620. The controller may also be connected to the one or more peripheral devices 630 of the surgical helmet 620, such as the ventilation assembly 630, wherein the controller is configured to communicate operational commands to and from the ventilation assembly 630, or other peripheral device 630 based on the signal received from the detector 670. For example, the controller may be configured to adjust the amount of power transmitted to the ventilation system 630 to control the speed of the fan blade.

Figure 22B:
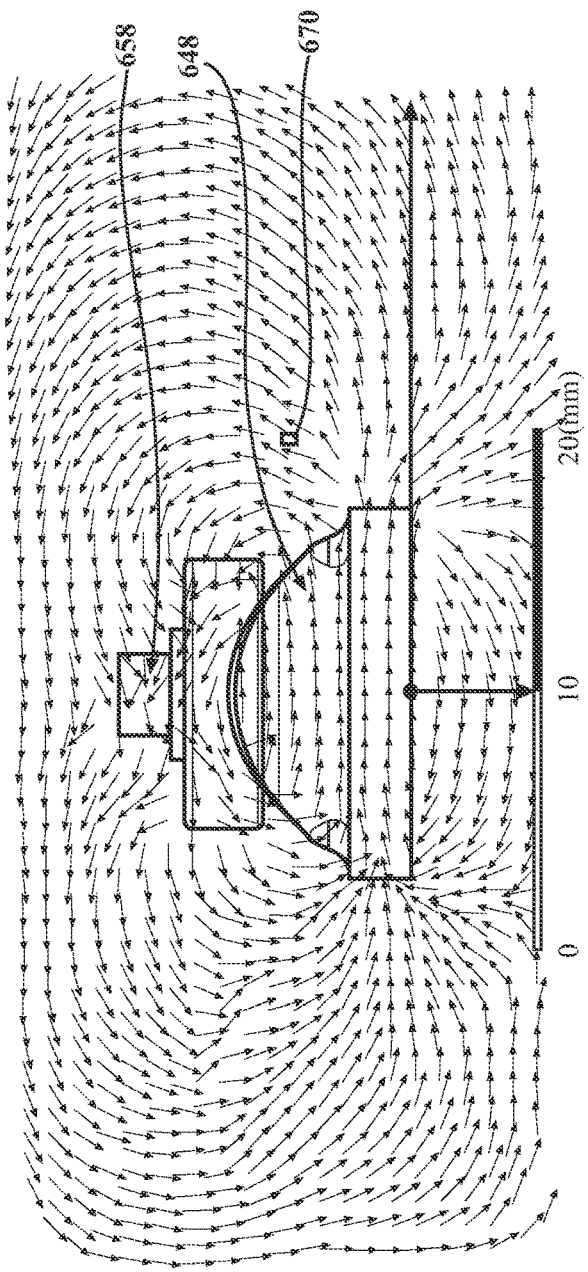
FIG. 22B is a schematic view of the magnetic field surrounding a coupling member of a surgical helmet relative to a detector when an attachment element is positioned adjacent the coupling member.
Figure 22B:
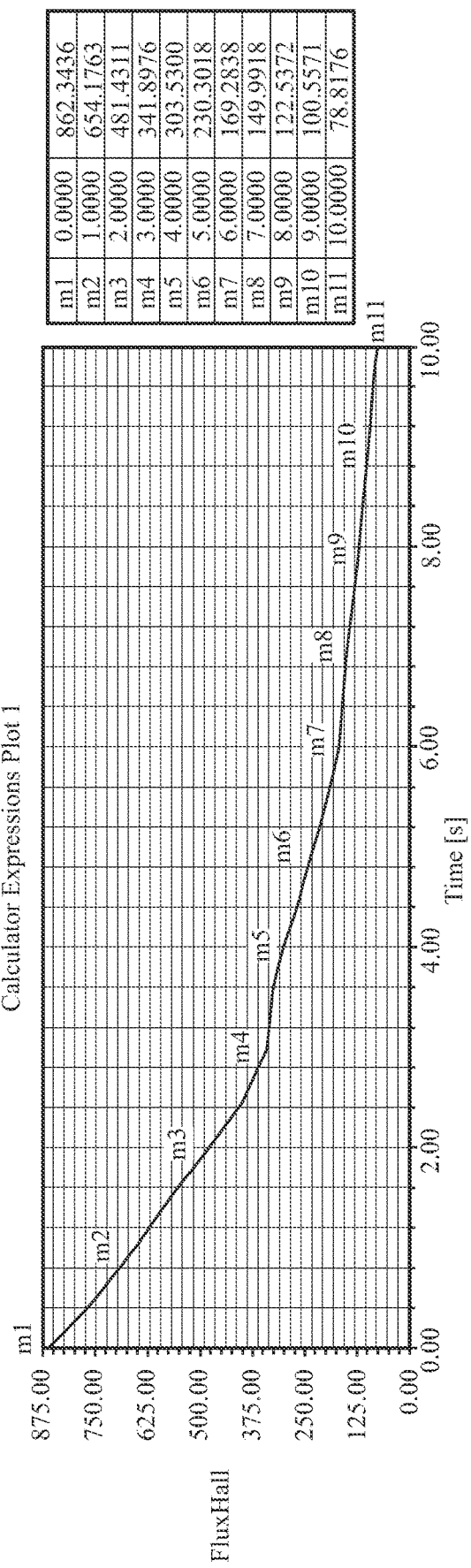

Referring to FIGS. 22B and 22C, a schematic of the magnetic field surrounding a coupling member 648 comprising a magnetic material is illustrated. FIG. 22B illustrates an exemplary magnetic field surrounding the coupling member 648 when the attachment element 658A is separated or absent from the coupling member 648. As described above, the detector 670 may detect a first configuration of the magnetic field. By contrast, FIG. 22C illustrates an exemplary magnetic field surrounding the coupling member 648 when the attachment element 658A is positioned adjacent the coupling member 648. As described above, the detector 670 may detect a second configuration of the magnetic field. Based on the magnetic field detected by the detector 670, the detector 670 may produce a signal indicating whether the surgical garment 612 is coupled to the surgical helmet 620.

Figure 23A:
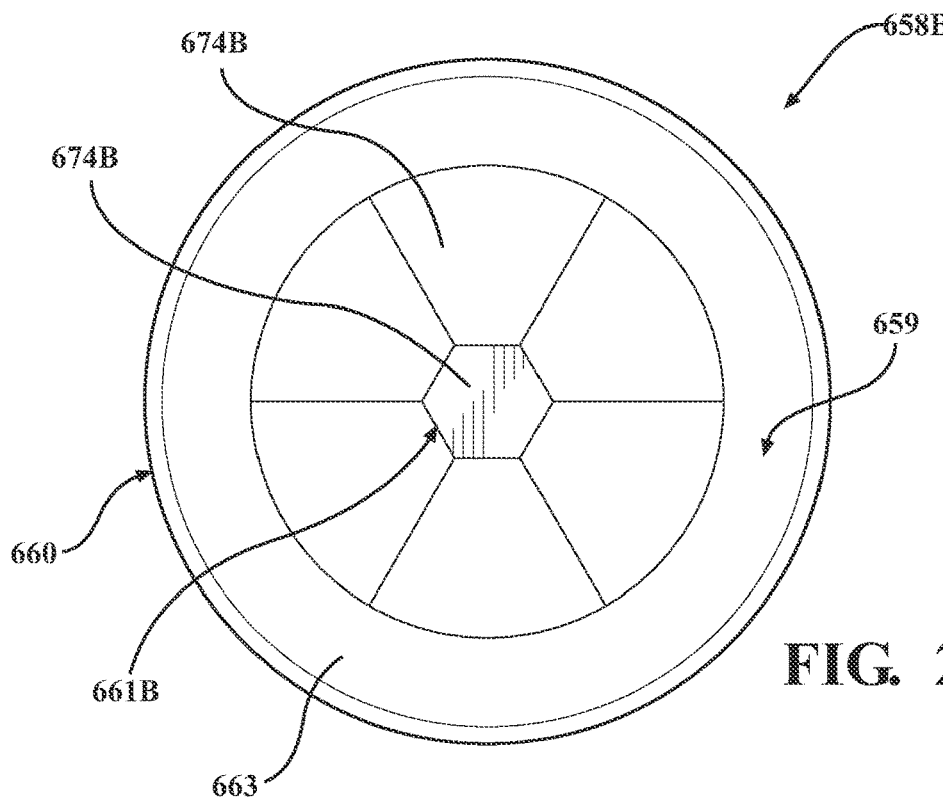
FIG. 23A is a front view of a second configuration of the attachment element for use with the medical garment of the surgical apparel system of FIGS. 13A and 13B.
Figure 23B:
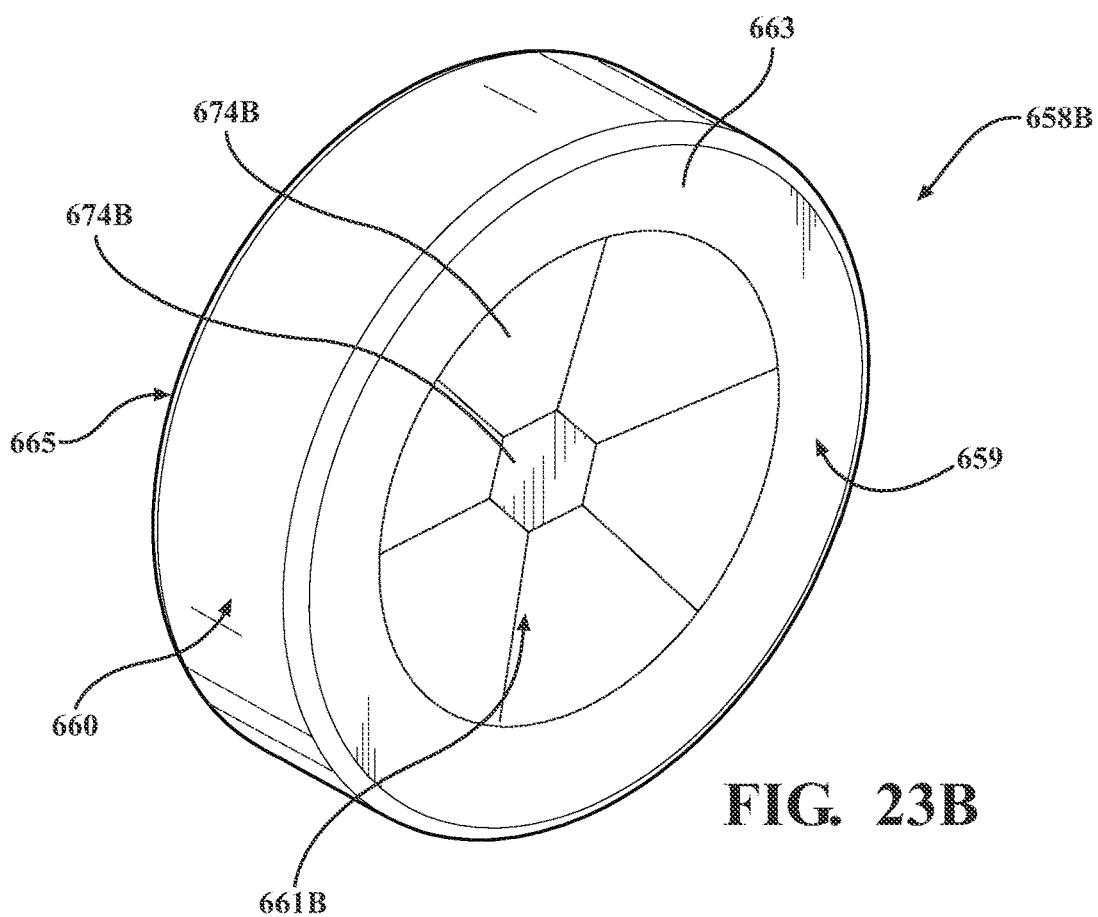
FIG. 23B is a front perspective view of the second configuration of the attachment element of FIG. 23A.

Referring to FIGS. 23A and 23B, detailed views of a second configuration of an attachment element 658B are illustrated. Similar to the attachment elements 658 described above, the second configuration of the attachment element 658B comprises a head 660 having a distal surface 665 and an opposing proximal surface 659. The head 660 may comprise a recessed surface 674B defining a recess 661b. The recessed surface 674B defining the recess 661B of the attachment element 658B may be formed such that the recessed surface 674B has a multi-faceted shape. The recessed surface 674B of the head 660 may comprise two or more faces that cooperate to define the recess 661B. It is contemplated that the number of faces of the multi-facetted shaped recess 661B may be varied to allow the recess 661B to matingly receive the protruded surface 647 of the coupling member 648 when coupled together.

Figure 24A:
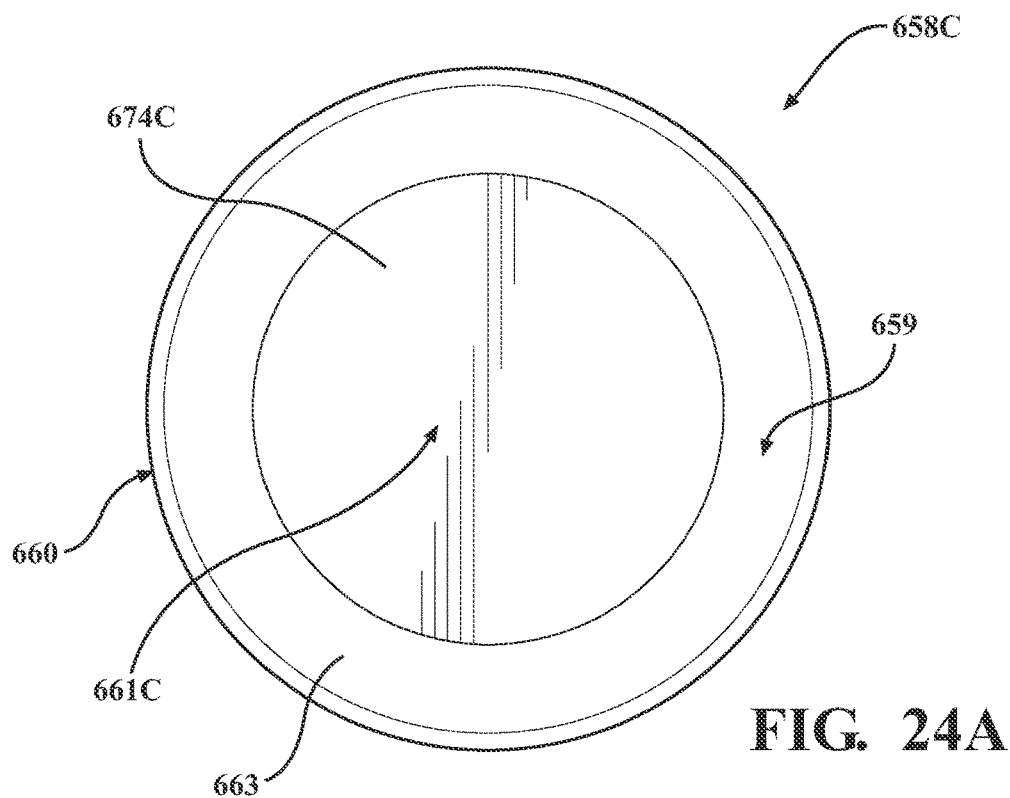
FIG. 24A is a front view of a third configuration of the attachment element for use with the medical garment of the surgical apparel system of FIGS. 13A and 13B.
Figure 24B:
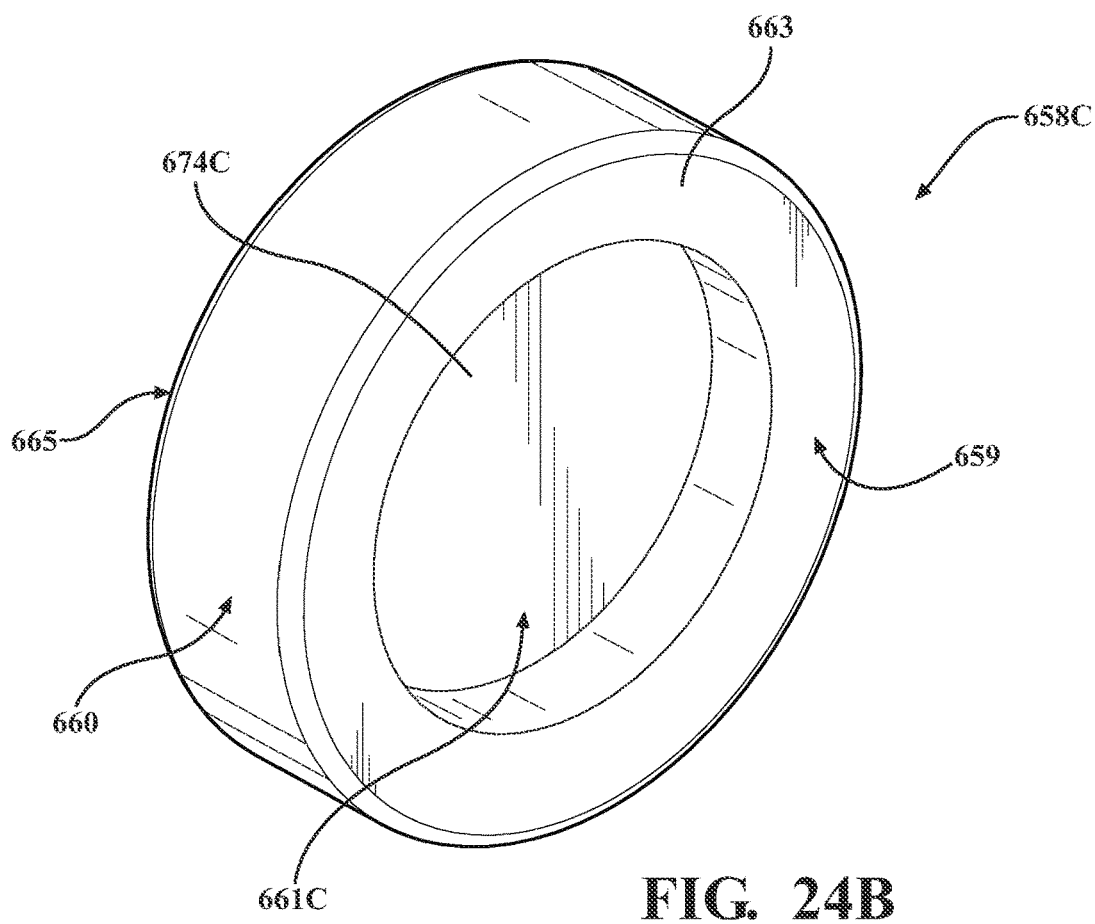
FIG. 24B is a front perspective view of the third configuration of the attachment element of FIG. 24A.

Referring to FIGS. 24A and 24B, detailed views of a third configuration of an attachment element 658C are illustrated. Similar to the attachment elements 658 described above, the third configuration of the attachment element 658C comprises a head 660 having a distal surface 665 and an opposing proximal surface 659. The head 660 may comprise a recessed surface 674C defining a recess 661C. The recess 661C of the attachment element 658C comprises a cylindrical shape. It is contemplated that the depth and/or diameter of the cylindrical-shaped recess 661C may be varied to allow the recess 661C to matingly receive the protruded surface 647 of the coupling member 648 when coupled together. While the surface 674C of the recess 661C illustrated in FIGS. 24A and 24B comprises a flat surface, it is contemplated that the recessed surface 674C defining the recess 661C may exhibit an arcuate shape.

Figure 25A:
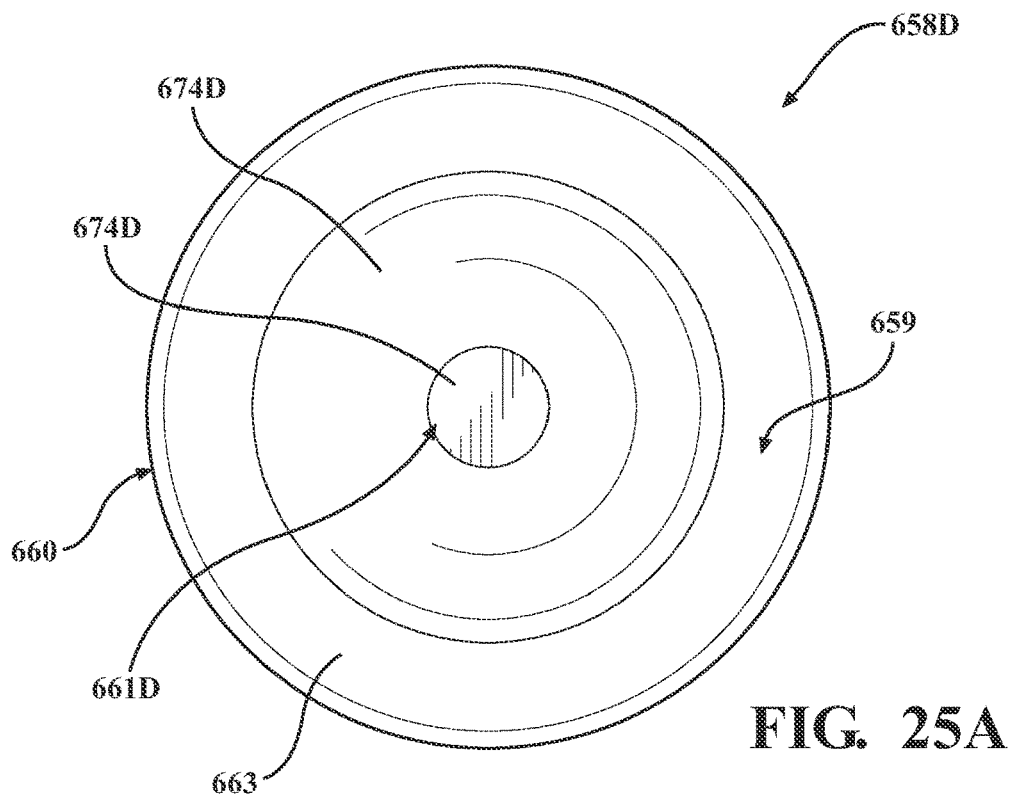
FIG. 25A is a front view of a fourth configuration of the attachment element for use with the medical garment of the surgical apparel system of FIGS. 13A and 13B.
Figure 25B:
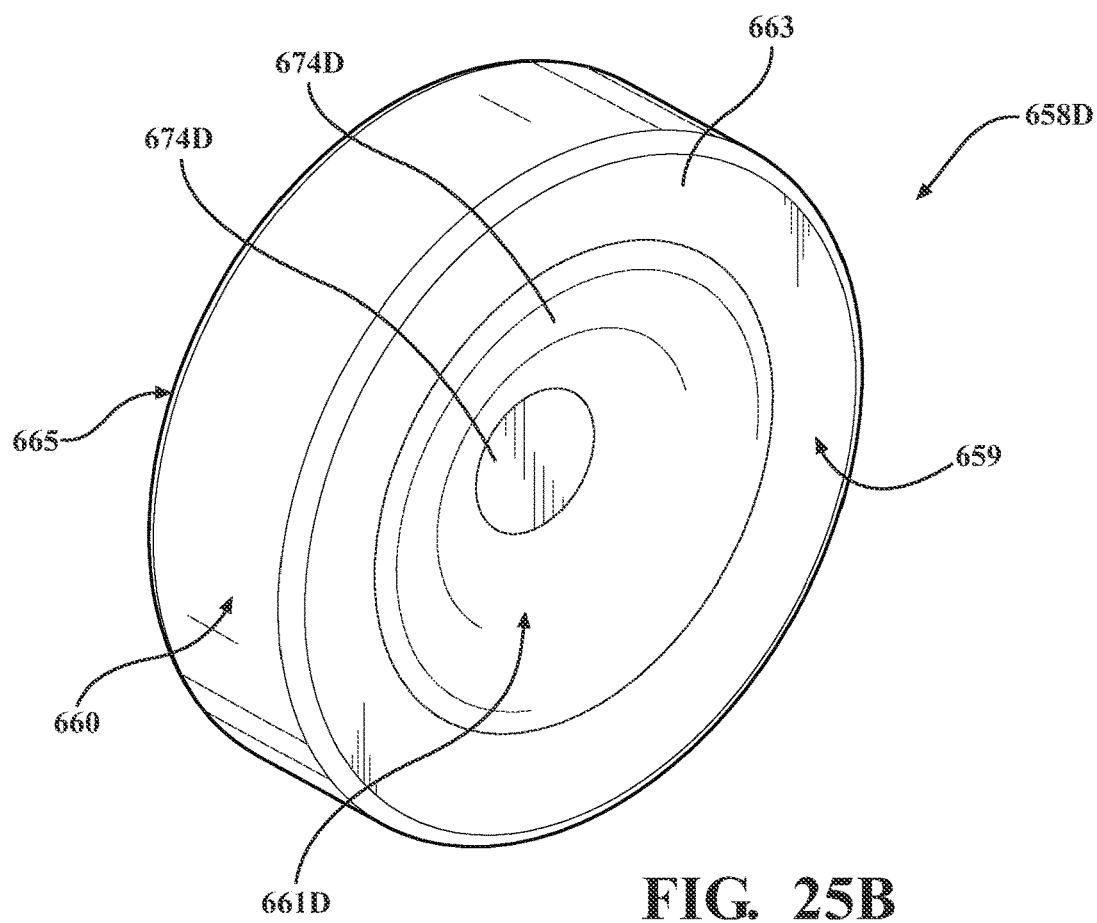
FIG. 25B is a front perspective view of the fourth configuration of the attachment element of FIG. 25A.

Referring to FIGS. 25A and 25B, detailed views of a fourth configuration of an attachment element 658D are illustrated. Similar to the attachment elements 658 described above, the fourth configuration of the attachment element 658D comprises a head 660 having a distal surface 665 and an opposing proximal surface 659. The head 660 may comprise a recessed surface 674D defining a recess 661D. The recess 661D of the attachment element 658D comprises a bowl-like shape including a flat surface. The flat surface may be positioned to be proximate the center and/or at the apex of the recess 661D. It is contemplated that the depth and/or radius of the curved portion of the bowl-like shaped recess 661D may be varied to allow the recess 661D to matingly receive the protruded surface 647 of the coupling member 648 when coupled together.

Figure 26A:
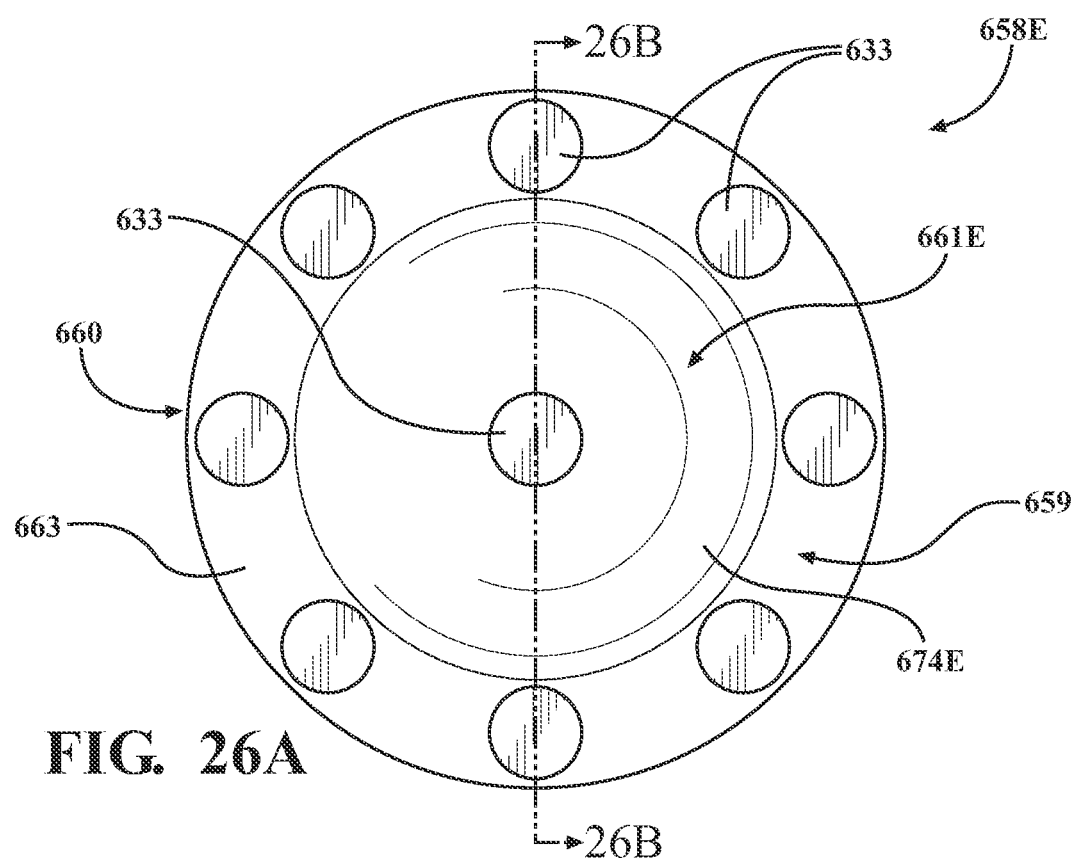
FIG. 26A is a front view of a fifth configuration of the attachment element for use with the medical garment of the surgical apparel system of FIGS. 13A and 13B, the attachment element including magnetic material inserts.
Figure 26B:
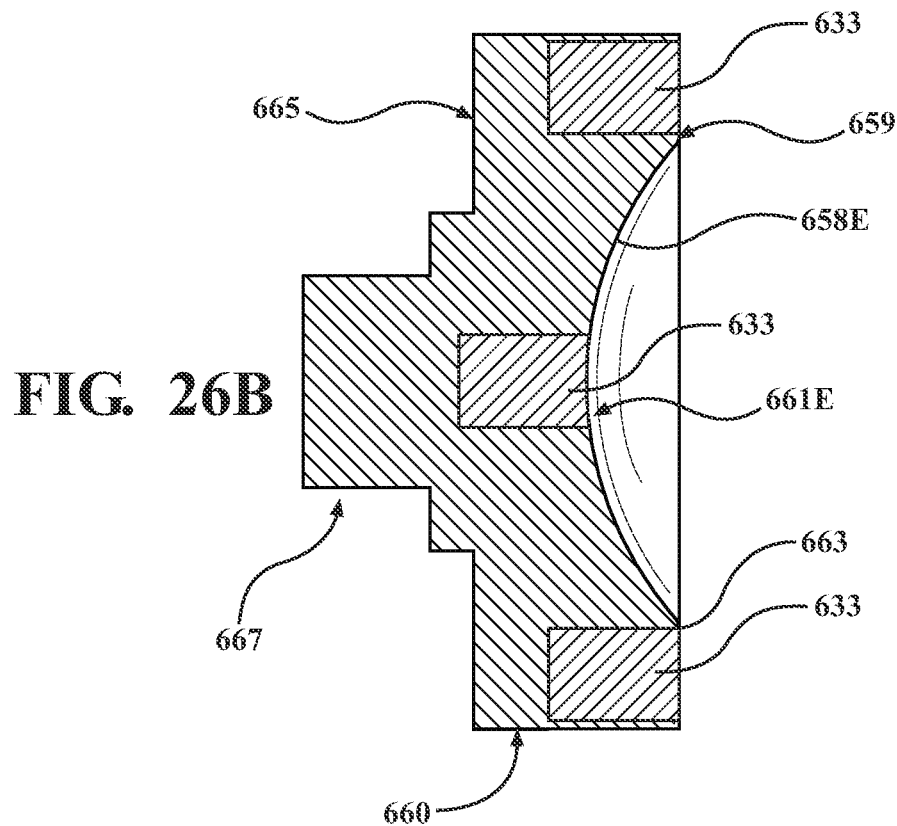
FIG. 26B is a sectional view of the fifth configuration of the attachment element of FIG. 26A.

Referring to FIGS. 26A and 26B, detailed views of a fifth configuration of an attachment element 658E are illustrated. Similar to the attachment element 658 described above, the fifth configuration of the attachment element 658E comprises a head 660 having a distal surface 665 and an opposing proximal surface 659. The head 660 may comprise a recessed surface 674E defining a recess 661E. The head 660 may also comprise a rim 663 at least partially surrounding the recess 661E. The recess 661E of the attachment element 658E may comprise a generally concave shape. The radius of the curvature and/or depth of the recess 661E illustrated in FIGS. 26A and 26B is not intended to be limiting. It is contemplated that the depth and/or radius of the recess 661E may be varied to allow the recess to matingly receive the protruded surface 647 of the coupling member when coupled together.

As described above, the attachment element 658 comprises both ferromagnetic material and diamagnetic material. At least a portion of the head 660 and/or the attachment element 658E may comprise a diamagnetic material, and the head 660 and/or the attachment element 658 may then be coated with a ferromagnetic material configured to interact with the coupling member 648 comprising a magnetic material. Alternatively, the head 660 of the attachment element 658E may comprise a diamagnetic material and further comprise ferromagnetic materials disposed within the diamagnetic material of the head 660. The fifth configuration of the attachment element 658E illustrated in FIGS. 26A and 26B is an example configuration of such an attachment element 658E. The attachment element 658E may further comprise a plurality of inserts 633 spaced about the rim 663 surrounding the recess 661E. The head 660 of the attachment element 658 may be formed of a diamagnetic material. The inserts 633 may then comprise a ferromagnetic material and be at least partially disposed within the head 660. The ferromagnetic material of the inserts 633 may be configured to interact with the coupling member 648 via magnetic attraction. The position and orientation of the inserts 633 illustrated in FIGS. 26A and 26B are only intended to be an exemplary configuration. It is contemplated that the number of inserts 633 may be increased or decreased as needed to create the necessary magnetic force of attraction between the coupling member 648 and the attachment element 658E. One or more inserts 633 may be positioned on or within the proximal surface 659 and/or or rim 663 of the head 660. Inserts 633 may also be positioned and/or at least partially disposed within the recessed surface 674E of the head 660 of the attachment element 658E. Furthermore, while the inserts 633 illustrated in FIGS. 26A and 26B are positioned in the proximal surface 659 and/or rim 663, as well as the recessed surface 674E of the head 660, it is contemplated that the inserts 633 may only be positioned in the proximal surface 659 and/or or rim 663, or only in the recessed surface 674E. Furthermore, while at least a portion of the inserts 633 are illustrated to form a portion of the proximal surface 659, rim 663, and/or recessed surface 674E, it is also contemplated that the inserts 633 may be positioned to be entirely disposed within and/or enclosed by the head 660. Alternatively, when the coupling member 648 comprises a ferromagnetic material, it is contemplated that the head 660 may comprise a diamagnetic material and the inserts 633 may comprise a magnetic material configured to interact with the coupling member 648 via magnetic attraction.

Figure 27A:
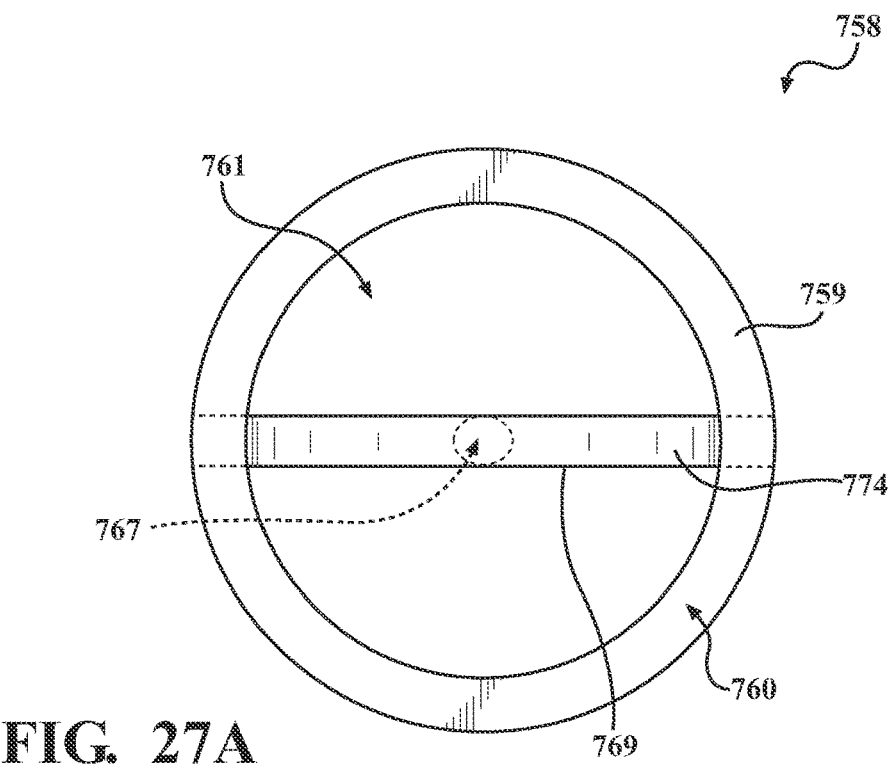
FIG. 27A is a front view of a sixth configuration of the attachment element for use with the medical garment of the surgical apparel system of FIGS. 13A and 13B.
Figure 27B:
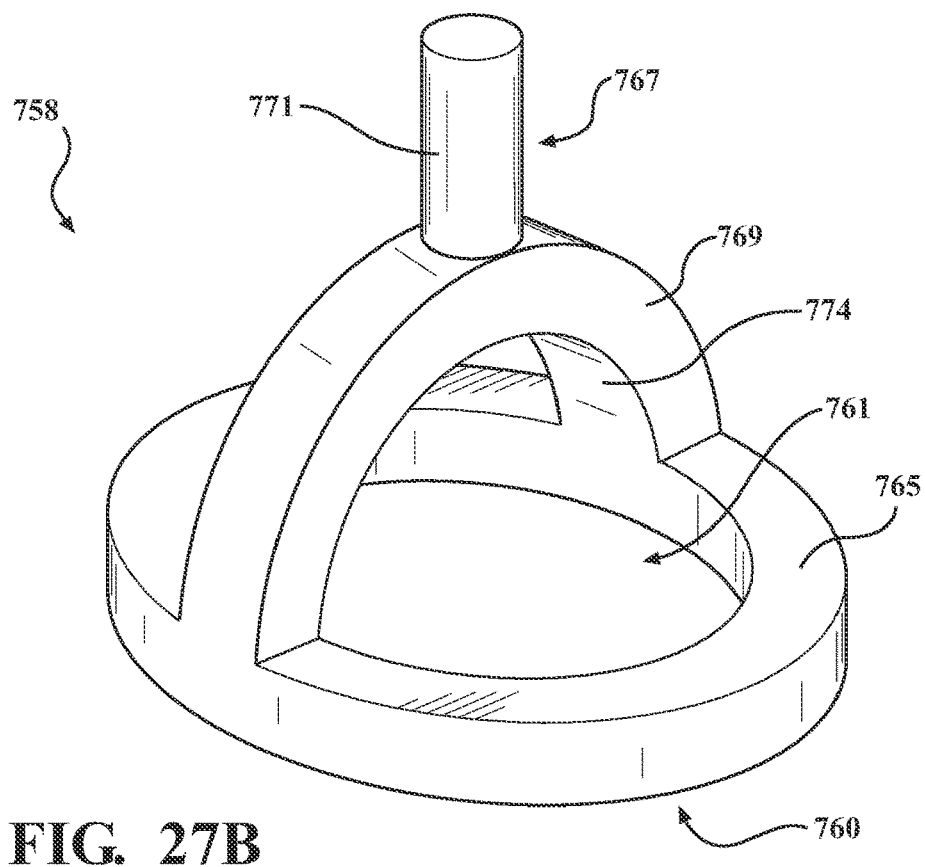
FIG. 27B is a front perspective view of the sixth configuration of the attachment element of FIG. 27A.

Referring to FIGS. 27A and 27B, detailed views of a sixth configuration of an attachment element 758 are illustrated. Similar to the attachment elements 658 described above, the fifth configuration of the attachment element 758 comprises a head 760 having a distal surface 765 and an opposing proximal surface 759. However, different from previously described attachment elements 658, the head 760 of the attachment element 758 may be configured in a ring, washer, or similar shape defining an aperture through the head 760. The attachment element 758 may further comprise a post 767 having a proximal portion 769. The proximal portion 769 may be coupled to the distal surface 765 of the head 760. The proximal portion 769 of the post 767 may comprise an arch-like, u-shape, or similar curved shape with opposing ends coupled to the distal surface 765 of the head 760. The combination of the head 760 and the proximal portion 769 of the post 767 may define a recess 761 of the attachment element 758 to receive the protruded surface 647 of the coupling member 648. It is contemplated that the depth and/or radius of the head 760 may be varied to allow the recess 761 to matingly receive the protruded surface 647 of the coupling member 648 when coupled together.

Referring to FIGS. 28A and 28B, detailed views of a seventh configuration of an attachment element 858 are illustrated. Similar to the attachment elements 658 described above, the sixth configuration of the attachment element 858 comprises a head 860 having a proximal surface 859A, 859B. However, different from previously described attachment elements 658, 758, the head 860 of the attachment element 858 may comprise an arch-like, u-shape, or similar curved shape with opposing ends terminating at the proximal surfaces 859A, 859B. The head 860 of the attachment element 858 may comprise two leg portions 863A, 863B defining a recess 861 of the attachment element 858 configured to receive the protruded surface 647 of the coupling member 648. Thus, the attachment element 858 may still define a recess 861 even if the attachment element 858 does not include surfaces that surround the recess 861 for 360 degrees. It is contemplated that the depth and/or radius of the leg portion 863A, 863B of the head 860 may be varied to allow the recess 861 to matingly receive the protruded surface 647 of the coupling member 648 when coupled together.

Figure 29A:
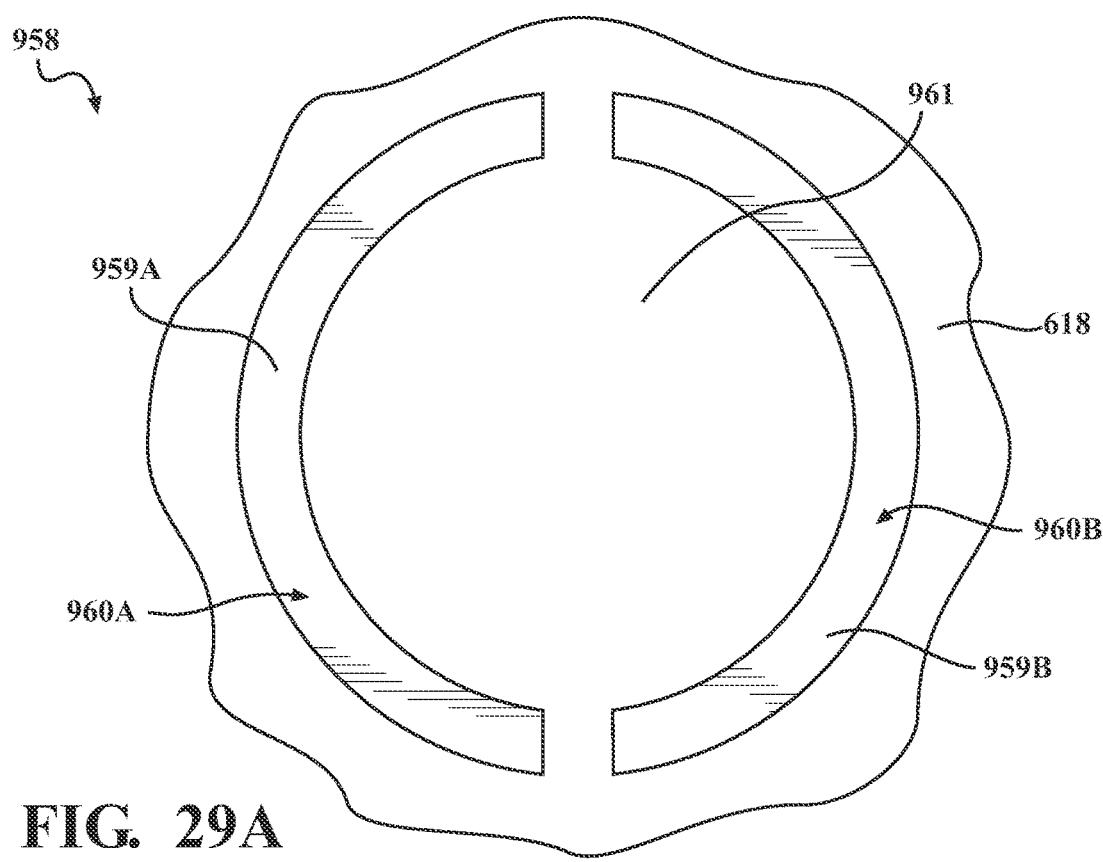
FIG. 29A is a front perspective view of an eighth configuration of the attachment element coupled to a portion of the face shield of the surgical apparel system of FIGS. 13A and 13B.
Figure 29B:
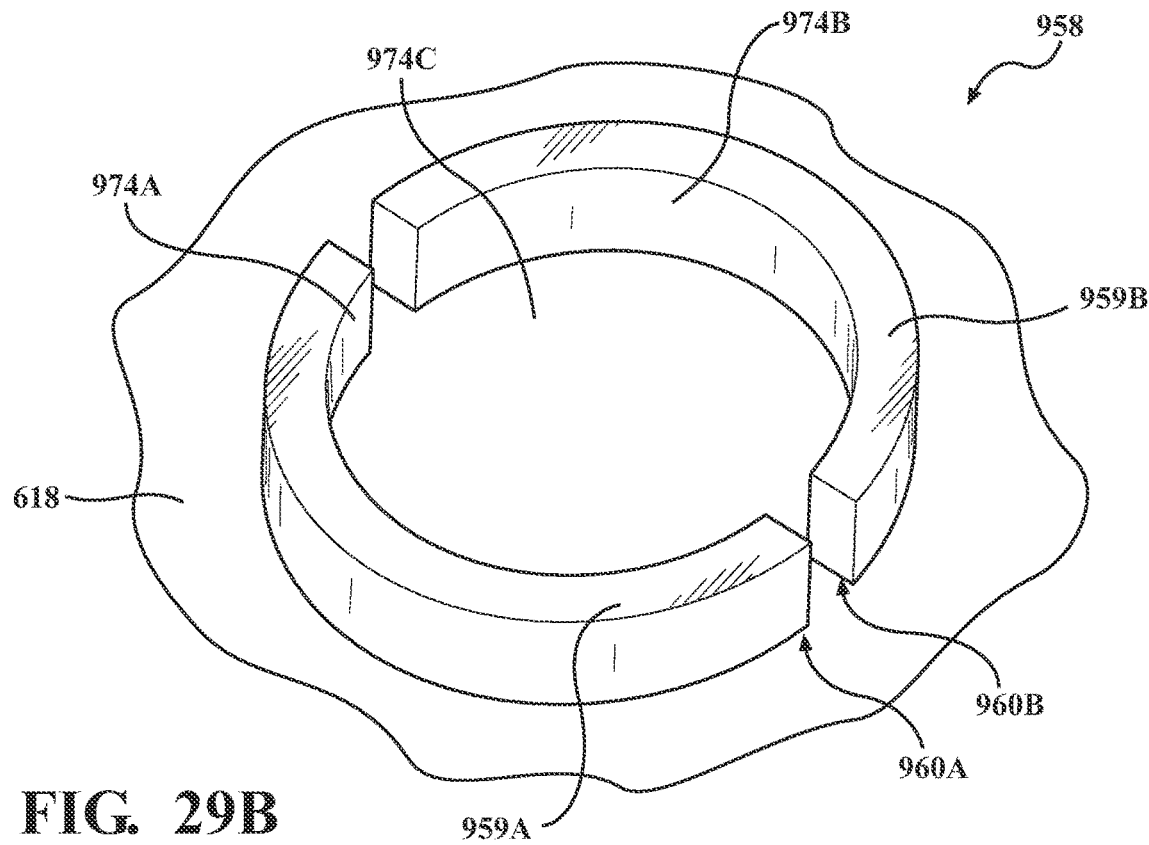
FIG. 29B is a front perspective view of the eighth configuration of the attachment element of FIG. 29A coupled to a portion of the face shield.

Referring to FIGS. 29A and 29B, detailed views of an eighth configuration of an attachment element 958 are illustrated. Similar to the attachment elements 658, 758, 858 described above, the seventh configuration of the attachment element 958 comprises a head 960A, 960B having a distal surface 965 and an opposing proximal surface 959. However, different from previously described attachment elements, the attachment element 958 may be configured without a post. The head 960A, 960B of the attachment element 958 may comprise two or more similar arcuate segments that at least partially define a ring or similar circular shape to define a recess 961 of the head 960. While the head 960A, 960B of the attachment element 958 in FIGS. 28A and 28B comprises two head portions 960A, 960B, it is contemplated that the head 960A, 960B may be configured as a solid ring or similar polygonal shape defining an aperture through the head 960A, 960B. Alternatively, it is also contemplated that the head 960A, 960B may be configured as more than two portions configured and/or arranged to define a ring or similar polygonal shape defining the recess 961 in combination with the face shield 618.

As the exemplary configuration of the attachment element 958 illustrated in FIGS. 29A and 29B does not comprise a post, each portion of the head 960A, 960B may be coupled directly to the face shield 618. For example, the distal surface 965A, 965B may be coupled directly to the face shield 618 using an epoxy, glue, sealant, or similar adhesive. However, it should be appreciated that it has been contemplated that each portion of the head 960A, 960B may comprise a post configured to couple each portion of the head 960A, 960B to the face shield 618 via corresponding apertures positioned to orient the portions of the head 960A, 960B in a similar configuration, as illustrated in FIGS. 29A and 29B.

In this configuration, the combination of the portions of the head 960A, 960B and the face shield 618 and/or surgical garment 612 may cooperate to define the recess 961 of the attachment element 958 configured to receive the protruded surface 647 of the coupling member 648. It is contemplated that the depth and/or radius of the portions of the head 960A, 960B of the attachment element 958 may be varied to allow the recess 961 to matingly receive the protruded surface 647 of the coupling member 648 when coupled together.

Figure 30:
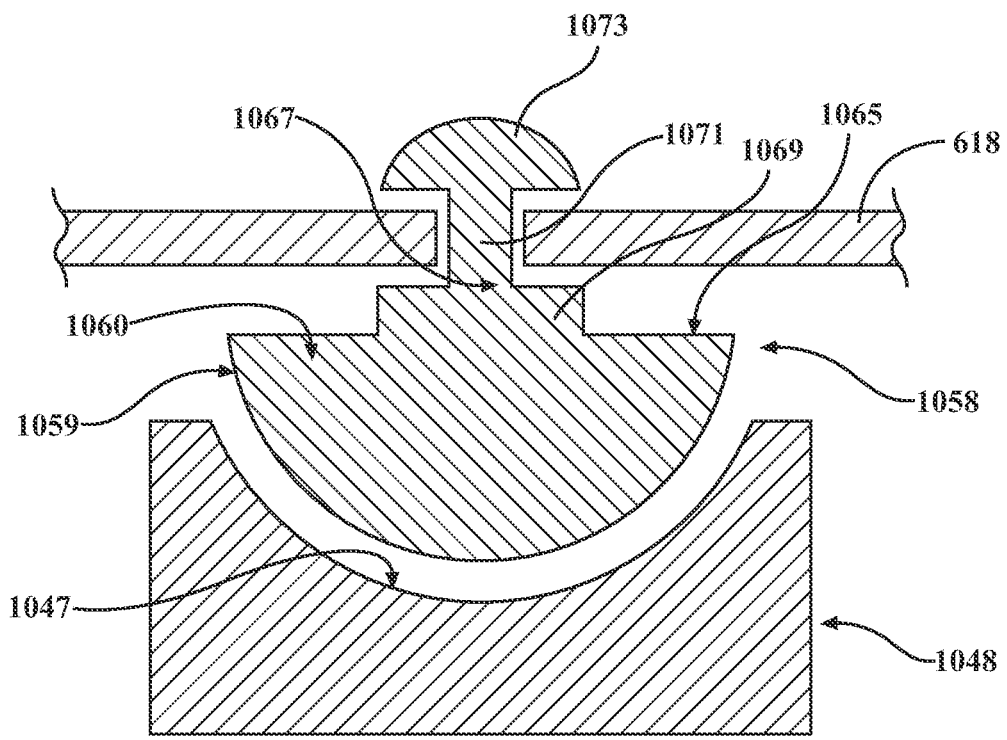
FIG. 30 is a schematic of a ninth configuration of an attachment element and coupling member for use with the medical garment of the surgical apparel system of FIGS. 13A and 13B.

Previously described configurations of the coupling member 648 and the attachment element 658, 758, 858, 958 have included a coupling member 648 with a protruded surface 647 and an attachment element 658, 758, 858, 958 with a recess 661, 761, 861, 961. However, the inverse relationship between the coupling member and attachment element is contemplated. Referring to FIG. 30, a partial schematic view of a ninth configuration of an attachment element 1058 coupled to a coupling member 1048 is illustrated. The attachment element 1058 may comprise a head 1060 including a proximal surface 1059 and an opposing distal surface 1065. The proximal surface 1059 may be configured to comprise a generally convex, hemispherical, or similar curved shape. The attachment element 1058 may also comprise a post 1067 extending distally from the distal surface 1065 of the head 1060. The post 1067 may comprise a proximal portion 1069 and a distal portion 1071. As described above, the proximal portion 1069 and the distal portion 1071 may comprise different dimension. For example, the post 1067 may be configured such that the proximal portion 1069 comprises a larger dimension than the distal portion 1071, creating a shoulder. At least the distal portion 1071 of the post 1067 should fit within the aperture 619 of the face shield 618 to couple the attachment element 1058 to the face shield 618. While the exemplary configuration of the attachment element 1058 illustrated in FIG. 30 comprises a post 1067 wherein the proximal portion 1069 comprises a larger dimension than the distal portion 1071, it is contemplated that the post 1067 may comprise a single uniform dimension configured to fit within the aperture 619 of the face shield 618. The distal portion of the post 1067 may further comprise a retention feature 1073 configured to couple the attachment element 1058 to the face shield 618. The retention feature 1073 may comprise a nut, cap, friction fit, or similar fastener. Alternatively, a distal end of the distal portion 1071 may be mushroomed over to define the retention feature 1073.

The coupling member 1048 may comprise a distal surface 1047, wherein the distal surface 1047 comprises a concave or similarly curved shape configured to define a recess 1061 to receive the proximal surface 1059 of the attachment element 1048.

Figure 31:
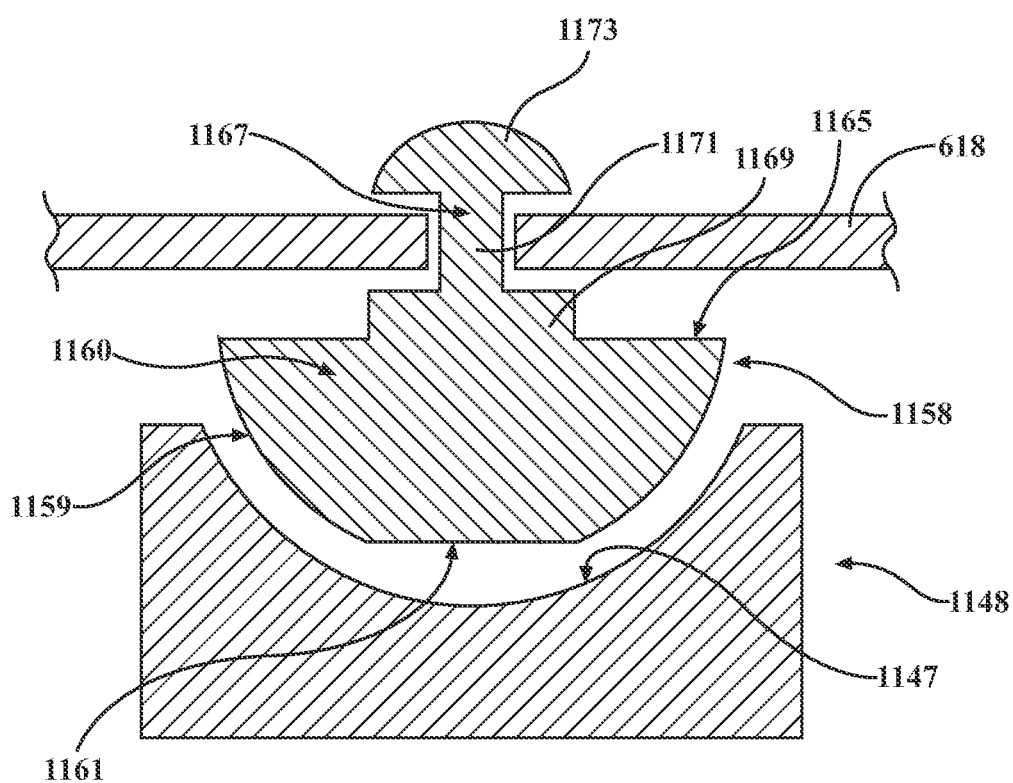
FIG. 31 is a schematic of a tenth configuration of an attachment element and coupling member for use with the medical garment of the surgical apparel system of FIGS. 13A and 13B.

Referring to FIG. 31, a partial schematic view of a tenth configuration of an attachment element 1158 coupled to a coupling member 1148 is illustrated. The attachment element 1158 may comprise a head 1160 including a proximal surface 1159 and an opposing distal surface 1165. The proximal surface 1159 may have a generally convex shape including a flat portion 1161. The proximal surface 1159 may be configured such that the flat portion 1161 is positioned proximate the apex of the convex-shaped proximal surface 1159. The attachment element 1158 may also comprise a post 1167 extending distally from the distal surface 1165 of the head 1160. The post may comprise a proximal portion 1169 and a distal portion 1171. As described above, the proximal portion 1169 and the distal portion 1171 may comprise different dimensions. For example, the post 1167 may be configured such that the proximal portion 1169 comprises a larger dimension than the distal portion 1171, creating a shoulder. At least the distal portion 1171 of the post 1167 should be configured to fit within the aperture 619 of the face shield 618 to couple the attachment element 1158 to the face shield 618. While the exemplary configuration of the attachment element 1158 illustrated in FIG. 31 comprises a post 1167 wherein the proximal portion 1169 comprises a larger dimension than the distal portion 1171, it is contemplated that the post 1167 may comprise a single uniform dimension configured to fit within the aperture 619 of the face shield 618. The distal portion of the post 1167 may further comprise a retention feature 1173 configured to couple the attachment element 1158 to the face shield 618. The retention feature 1173 may comprise a nut, cap, friction fit, or similar fastener. Alternatively, a distal end of the distal portion 1171 may be mushroomed over to define the retention feature 1173.

The coupling member 1148 may comprise a distal surface 1147, wherein the distal surface 1147 comprises a concave or similarly curved shape configured to define a recess 1161 to receive the proximal surface 1159 of the attachment element 1148.

Figure 32:
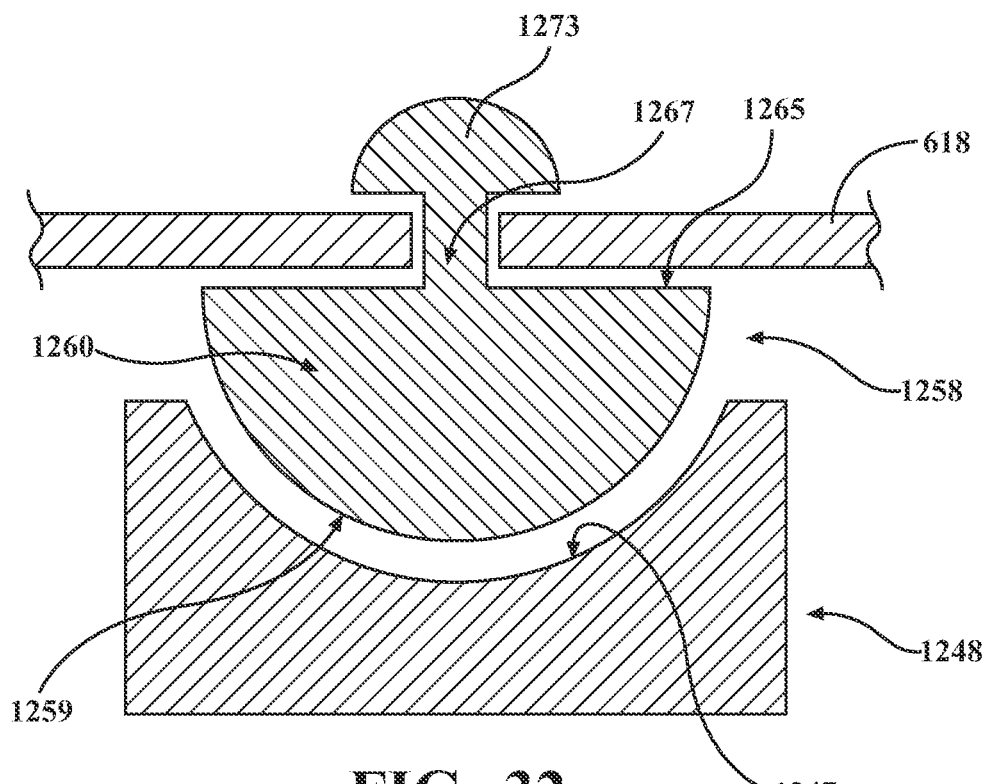
FIG. 32 is a schematic of an eleventh configuration of an attachment element and coupling member for use with the medical garment of the surgical apparel system of FIGS. 13A and 13B.

Referring to FIG. 32, a partial schematic view of an eleventh configuration of an attachment element 1258 coupled to a coupling member 1248 is illustrated. The attachment element 1258 may comprise a head 1260 including a proximal surface 1259 and an opposing distal surface 1265. The proximal surface 1259 may have a generally convex, hemispherical, or similar curved shape. The attachment element 1258 may also comprise a post 1267 extending distally from the distal surface 1265 of the head 1260. The exemplary configuration of the attachment element 1258 illustrated in FIG. 32 comprises a post 1267 including a single uniform dimension configured to fit within the aperture 619 of the face shield 618. However, as described above, the post 1267 may comprise a proximal portion and a distal portion, wherein the proximal portion may comprise a different dimension than the distal portion, creating a shoulder.

As described above, the distal portion of the post 1267 may further comprise a retention feature 1273 configured to couple the attachment element 1258 to the face shield 618. The retention feature 1273 may comprise a nut, cap, friction fit, or similar fastener. Alternatively, a distal end of the distal portion 1271 may be mushroomed over to define the retention feature 1273.

The coupling member 1248 may comprise a distal surface 1247, wherein the distal surface 1247 comprises a concave or similarly curved shape configured to define a recess to receive the proximal surface 1259 of the attachment element 1248.

Figure 33:
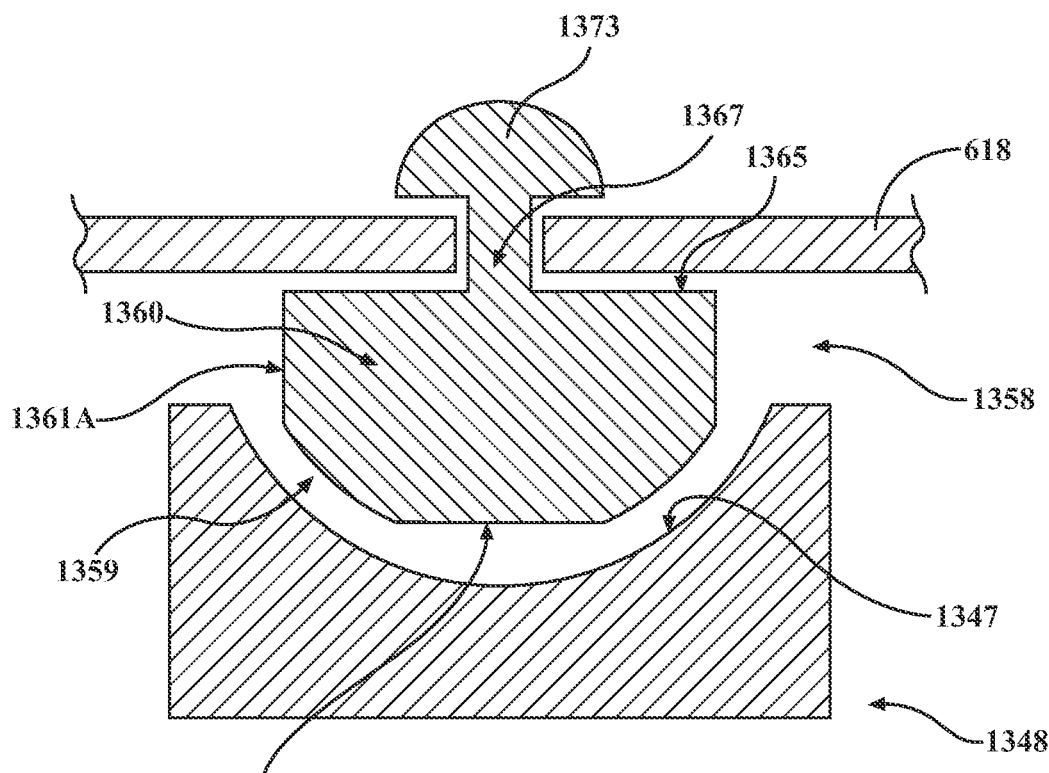
FIG. 33 is a schematic of a twelfth configuration of an attachment element and coupling member for use with the medical garment of the surgical apparel system of FIGS. 13A and 13B.

Referring to FIG. 33, a partial schematic view of a twelfth configuration of an attachment element 1358 coupled to a coupling member 1348 is illustrated. The attachment element 1358 may comprise a head 1360 including a proximal surface 1359 and an opposing distal surface 1365. The proximal surface 1359 may have a generally convex shape including a plurality of flat portions 1361A, 1361B. The proximal surface 1359 may be configured such that at least one of the flat portions 1361B is positioned proximate the apex of the convex-shaped proximal surface 1359. Another of the flat portions 1361A may be positioned at the perimeter of the head 1360 proximate the intersection of the proximal surface 1350 and the distal surface 1365. The attachment element 1358 may also comprise a post 1367 extending distally from the distal surface 1365 of the head 1360. The exemplary configuration of the attachment element 1358 illustrated in FIG. 33 comprises a post 1367 including a single uniform dimension configured to fit within the aperture 619 of the face shield 618. However, as described above, the post 1367 may comprise a proximal portion and a distal portion, wherein the proximal portion may comprise a different dimension than the distal portion, creating a shoulder. The distal portion of the post 1367 may further comprise a retention feature 1373 configured to couple the attachment element 1358 to the face shield 618. The retention feature 1373 may comprise a nut, cap, friction fit, or similar fastener. Alternatively, a distal end of the distal portion 1371 may be mushroomed over to define the retention feature 1373.

The coupling member 1348 may comprise a distal surface 1347, wherein the distal surface 1347 comprises a concave or similarly curved shape configured to define a recess 1361 to receive the proximal surface 1359 of the attachment element 1358.

In each of the various configurations illustrated in FIGS. 30-33, the attachment element 1058, 1158, 1258, 1358 comprises a proximal surface 1059, 1159, 1259, 1359 having a generally convex, hemispherical, or similar curved shape, and the complementary coupling member 1048, 1148, 1248, 1348 comprises a distal surface 1047, 1147, 1247, 1347, having a concave or similarly curved shape. Similar to configurations of the attachment elements and coupling member described above, the shapes of the attachment element 1058, 1158, 1258, 1358 and the coupling member 1048, 1148, 1248, 1348 of FIGS. 30-33 allow the attachment element 1058, 1158, 1258, 1358 to pivot or rotate relative to the coupling member 1048, 1148, 1248, 1348. This also allows the attachment element 1058, 1158, 1258, 1358 to couple to the coupling member 1048, 1148, 1248, 1348 at various angles without reducing the strength of the magnetic bond between the attachment element 1058, 1158, 1258, 1358 and the coupling member 1048, 1148, 1248, 1348. This can increase the amount of force required to decouple the attachment element 1058, 1158, 1258, 1358 from the coupling member 1048, 1148, 1248, 1348.

Method of Operating any of the Surgical Apparel Systems Described Above:

A method of operating a surgical apparel system 110 may comprise providing any configuration of the surgical apparel systems 110, 610 described above. For example, the method may comprise providing a surgical helmet 120, 620 configured to be worn on the head of an individual, and a surgical garment 112, 612 configured to be removably coupled to the surgical helmet 120, 620 to provide a microbial barrier between a medical environment and a wearer. The surgical helmet 120, 620 may comprise one or more peripheral device(s) 130, 630 configured to facilitate performance of the individual wearing the surgical helmet 120, 620 during a surgical procedure. The surgical helmet 120, 620 may also comprise a detector 170, 270, 370, 470, 570, 670 configured to detect the coupling of the surgical garment 112, 612 to the surgical helmet 120, 620 and to communicate a signal based, at least in part, on the presence or absence of the surgical garment 112, 612 being coupled to the surgical helmet 120, 620. A controller 180, 680 may also be coupled to the surgical helmet 120, 620 and configured to be in communication with the detector 170, 270, 370, 470, 570, 670 and/or the peripheral device(s) 130, 630. The system 110, 610 may also comprise, a portable energy source 182 removably interconnected with the surgical helmet 120, 620. The portable energy source 182 may be configured to be in communication with the controller 180.

The method may further comprise attaching or coupling the portable energy source 182 to the system 110, 610. For example, an energy source 182, such as a battery pack, may be coupled to a battery receiver of the surgical helmet 120, 620 or otherwise placed in electrical communication with the surgical helmet 120, 620.

Another step in the method may comprise detecting and/or determining whether the surgical garment 112, 612 is coupled to the surgical helmet 120, 620 utilizing the detector 170, 270, 370, 470, 570, 670. This may be accomplished using any of the various configurations of the detector 170, 270, 370, 470, 570, 670 described above, or other configurations not specifically described herein. For example, the presence or absence of the surgical garment 112 being coupled to the surgical helmet 120 may be accomplished using the first configuration of the detector 170, wherein the first member 154 is configured to selectively engage the toggle member 172 of the detector 170 based, at least in part, on the proximity of the attachment element 158 to the distal surface 147 of the coupling feature 146. Alternatively, the presence or absence of the surgical garment 112 being coupled to the surgical helmet 120 may be accomplished using the second configuration of the detector 270, wherein the first member 254 is configured to selectively move between the first region and the second region based, at least in part, on the proximity of the attachment element 158 to the distal surface 247 of the coupling feature 246. In yet another example, the presence or absence of the surgical garment 612 being coupled to the surgical helmet 620 may be accomplished using one of the combinations of the attachment elements and coupling members with the detector 670, wherein the detector 670 is configured to sense or detect a changing in the magnetic field surrounding the coupling members 648, 748, 848, 948, 1048 based on the proximity of attachment elements 658, 758, 858, 958, 1058, 1158, 1258, 1358 to the coupling members 648, 748, 848, 948, 1048.

The method may further comprise controlling an operational characteristic of the peripheral device(s) 130, 630 based, at least in part, on whether the detector 170, 270, 370, 470, 570, 670 indicates the surgical garment 112, 612 is coupled to the surgical helmet 120, 620. The controller 180 may be configured to selectively control one or more operational characteristic of the peripheral device(s) 130, 630. The controller 180 may be configured to control, e.g., allow, the transmission of power to and/or from the energy source 182 to the peripheral device(s) 130, 630. In other words, the controller 180 may control whether or not the peripheral device 130, 630 may activate. It may also include controlling a maximum and/or minimum operating speed of the peripheral device(s) 130, 630. For example, the controller 180 may be configured to prevent transmission of energy and/or limit the amount of energy (such as by limiting voltage) transferred to the peripheral device(s) 130, 630 until the detector 170, 270, 370, 470, 570, 670 has indicated the surgical garment 112, 612 is coupled to the surgical helmet 120, 620.

As described above, the surgical helmet 120, 620 of the system 110, 610 may further comprise a memory device 184 coupled to the surgical helmet 120, 620 and in communication with the controller 180. The memory device 184 may be configured to store data related to the operation of the peripheral device(s) 130, 630. The data on the memory device 184 may comprise current operational settings for the peripheral device(s), such as the fan speed, cooling intensity, and/or the light being on. The data on the memory device 184 may also include maximum and minimum operating conditions for each of the peripheral device(s) 130, 630 of the surgical helmet 120, 620.

As described above, the system 110, 610 may also comprise an energy sensor 186 in communication with the controller 180 and/or the energy source 182. The energy sensor 186 may be configured to detect a characteristic of energy source 182 and communicate an energy signal to the controller 180 based on the detected characteristic of the energy source 182. For example, the energy sensor 186 may be configured to communicate an energy signal to the controller 180 when the remaining power drops below a threshold value. The threshold value may be set by the controller 180, or may be set by the user. For example, the energy sensor 186 may be configured to communicate the energy signal to the controller 180 when the remaining power level drops below 15 percent (%).

The method may further comprise coupling the surgical garment 112, 612 to the surgical helmet 120, 620, such that the surgical garment 112, 612 is at least partially disposed over the surgical helmet 120, 620. The surgical garment 112, 612 may be coupled to the surgical helmet 120, 620 using any of the configuration of the attachment elements 158, 558, 658, 758, 858, 958, 1058, 1158, 1258, 1358, coupling members 148, 648, 748, 848, 948, 1048 and the coupling features 146, 246, 346, 446, 546 described above, or others not specifically described. This may include placing attachment elements 158, 558, 658, 758, 858, 958, 1058, 1158, 1258, 1358 of the surgical garment 112, 612 adjacent to the coupling members 148, 648, 748, 848, 948, 1048 and/or the coupling features 146, 246, 346, 446, 546 of the surgical helmet 120, 620.

Upon connecting the energy source 182 to the system 110, 610, the method may further comprise communicating the energy signal from the energy sensor 186 to the controller 180 indicating the characteristic of the energy source 182, such as the remaining power level of the energy source 182. The method may then comprise storing at least one user setting of the peripheral device(s) 130, 630 based upon the energy signal. For example, the controller 180 may be configured to store at least one user setting of the peripheral device(s) 130, 630 in based on the energy signal, such as at each occurrence of the energy signal indicating a drop of a 10 percent (%) increment of the remaining power level. Alternatively, the controller 180 may be configured to store at least one user setting of the peripheral device(s) 130, 630 when the energy signal indicates the remaining power level has dropped below a threshold value, such as dropping 15 percent (%) of power remaining. The controller 180 may be configured to store the current user settings of the peripheral device(s) 130, 630 on the memory device 184. More generally, this feature allows for the storage of the user settings of the peripheral device 130, 630 before the battery enters a low power state or is no longer operational.

The method may further comprise replacing the energy source 182 with a second energy source 182 while the surgical garment 112, 612 is coupled to the surgical helmet 120, 620. The controller 180 may be configured to provide a signal to the peripheral device 130 based on the user settings from the memory device 184 to the peripheral device(s) 130, 630, such as the most recently stored user settings, once the second energy source 182 is connected to the system 110, 610. The controller 180 may be further configured to restart the peripheral device(s) 130, 630 based on the most recently stored user settings following replacing the energy source 182. This may be contingent on the signal from the detector 170, 670 indicating that the surgical garment 112, 612 remained coupled to the surgical helmet 120, 620 while the energy source 182 was replaced, i.e., the controller did not receive a signal from the detector indicative of the garment being decoupled from the surgical helmet 120, 620 while either the first or second energy source was in communication with the controller. For example, if the user was operating a peripheral device 130, 630, such as the ventilation assembly at the third fan speed setting, the controller 180 may be configured to restart the ventilation assembly 130, 630 at the third fan speed setting once the second energy source 182 is connected. This configuration of the system may further comprise a capacitor or secondary back-up energy source in communication with the detector 170, 270, 370, 470, 570, 670, and configured to temporarily supply power to the detector 170, 270, 370, 470, 570, 670 while the energy source 182 is switched out. This will allow the detector 170, 270, 370, 470, 570, 670 to continue to detect the characteristic indicative of whether the surgical garment 112, 612 remains coupled to the surgical helmet 120, 620.

The method may also comprise deleting the user settings for the peripheral device(s) 130 stored on the memory device 184 when the detector 170, 270, 370, 470, 570, 670 indicates that the surgical garment 112, 612 is separated or absent from the surgical helmet 120, 620 and/or the energy source 182 or subsequent energy source 182 is disconnected from the system 110, 610. Once the surgical garment 112, 612 and the energy source 182 have both been removed from the surgical helmet 120, 620, the stored user settings related to operation of the peripheral device(s) 130, 630 may be cleared from the memory device 184, and the peripheral device(s) 130, 630 may be reset to their default settings.

In another exemplary configuration, the method may further comprise the steps of storing a user setting of the peripheral device(s) 130, 630 on the memory device 184 and separating the surgical garment 112, 612 from surgical helmet 120, 620 while the energy source 182 is in communication with the controller 180. The controller 180 may cease providing power to the peripheral devices 130, 630 if the detector 170, 270, 370, 470, 570, 670 determines that the surgical garment 112, 612 is separated from the surgical helmet 120, 620. Following removal of the first surgical garment 112, 612, a second surgical garment 112, 612 may be coupled to the surgical helmet 120, 620 while the energy source 182 remains in communication with the controller 180. The controller 180 may be configured to communicate the most recently stored user settings from the memory device 184 to the peripheral device(s) 130, 630 following coupling of the second surgical garment 112, 612 with the surgical helmet 120, 620. In doing so, the controller 180 may be configured to restart the peripheral device(s) 130, 630 based on the most recently stored settings prior to removal of the first surgical garment 112, 612.

The method may further comprise deleting the user settings of the peripheral device(s) 130, 630 that are stored on the memory device 184 when the detector 170, 270, 370, 470, 570, 670 indicates to the controller 180 that the surgical garment 112, 612 is separated from the surgical helmet 120, 620 and the energy source 182 is disconnected from the surgical helmet 120, 620. This may restore or reset the peripheral device(s) 130, 630 to their default settings.

In yet another exemplary configuration, the system may comprise a memory device 184 configured to store data related to one or more configurations of the surgical garment 112, 612. The method may comprise: identifying one of the plurality of configurations of the surgical garment 112, 612 that is coupled to the surgical helmet 120, 620 using the detector 170, 270, 370, 470, 570, 670, communicating the identified configuration of the surgical garment 112, 612 to the controller 180, and communicating a command related to at least one operational characteristic of the peripheral device(s) 130, 630 based, at least in part, on the identified configuration of the surgical garment 112, 612. For example, the controller 180 may be configured to control an operational characteristic of the peripheral device(s) 130, 630 based on the thickness or density of the fabric 114/116, 614/616 of the surgical garment 112, 612 that is coupled to the surgical helmet 120, 620. This may include increasing the speed of a peripheral device 130, 630, such as the ventilation assembly 130, 630, when a surgical garment 112, 612 comprising a denser filter fabric 116, 616 material is coupled to the surgical helmet 120, 620.

In another exemplary method of operating the system 110, 610, the method may comprise coupling the surgical garment 112, 612 to the surgical helmet 120, 620, such that the surgical garment 112, 612 is at least partially disposed over the surgical helmet 120, 620. The method may further comprise receiving the signal from the detector 170, 270, 370, 470, 570, 670 indicating the surgical garment 112, 612 is coupled to the surgical helmet 120, 620, and delaying transmission of power from the energy source 182 to the peripheral device(s) 130, 630 for a defined first period of time following receipt of the signal from the detector 170, 270, 370, 470, 570, 670. In other words, the controller 180 is configured to only transmit power to the peripheral device 130, 630 after the surgical garment 112, 612 has been coupled to the helmet 120, 620 and the first period of time has elapsed. The length of the first period may be adjusted based on a user preference or anticipated amount of time needed to accomplish a task prior to transmission of power to the peripheral device 130, 630. For example, the controller 180 may be configured to delay transmission of power from the energy source 182 to the peripheral device(s) 130, 630 for five seconds following the signal from the detector 170, 270, 370, 470, 570, 670 indicating the surgical garment 112, 612 is coupled to the surgical helmet 120, 612. This may allow the wearer additional time to get the surgical garment 112, 612 appropriately fitted and or adjusted prior to operation of the peripheral device 130, 630, such as the ventilation assembly, beginning. This may prevent circulation of microorganisms in the operating room before the appropriate sterile barrier is in place.

The method may also comprise separating the surgical garment 112, 612 from the surgical helmet 120, 620. The method may comprise receiving the signal from the detector 170, 270, 370, 470, 570, 670 indicating the surgical garment 112, 612 is separated from the surgical helmet 120, 620, and continuing transmission of power to said peripheral device(s) 130, 630 for a defined second period of time following receipt of the signal from the detector 170, 270, 370, 470, 570, 670. For example, the controller 180 may be configured to continue transmission of power from the energy source 182 to the peripheral device(s) 130, 630 for five seconds following the signal from the detector 170, 270, 370, 470, 570, 670 indicating the surgical garment 112, 612 is separated from the surgical helmet 120, 620. This may allow for operation of the peripheral device 130, 630, such as the ventilation assembly, to continue momentarily after removal of the surgical garment 112, 612 to clear any debris from the peripheral device 130, 630.

Figure 34:
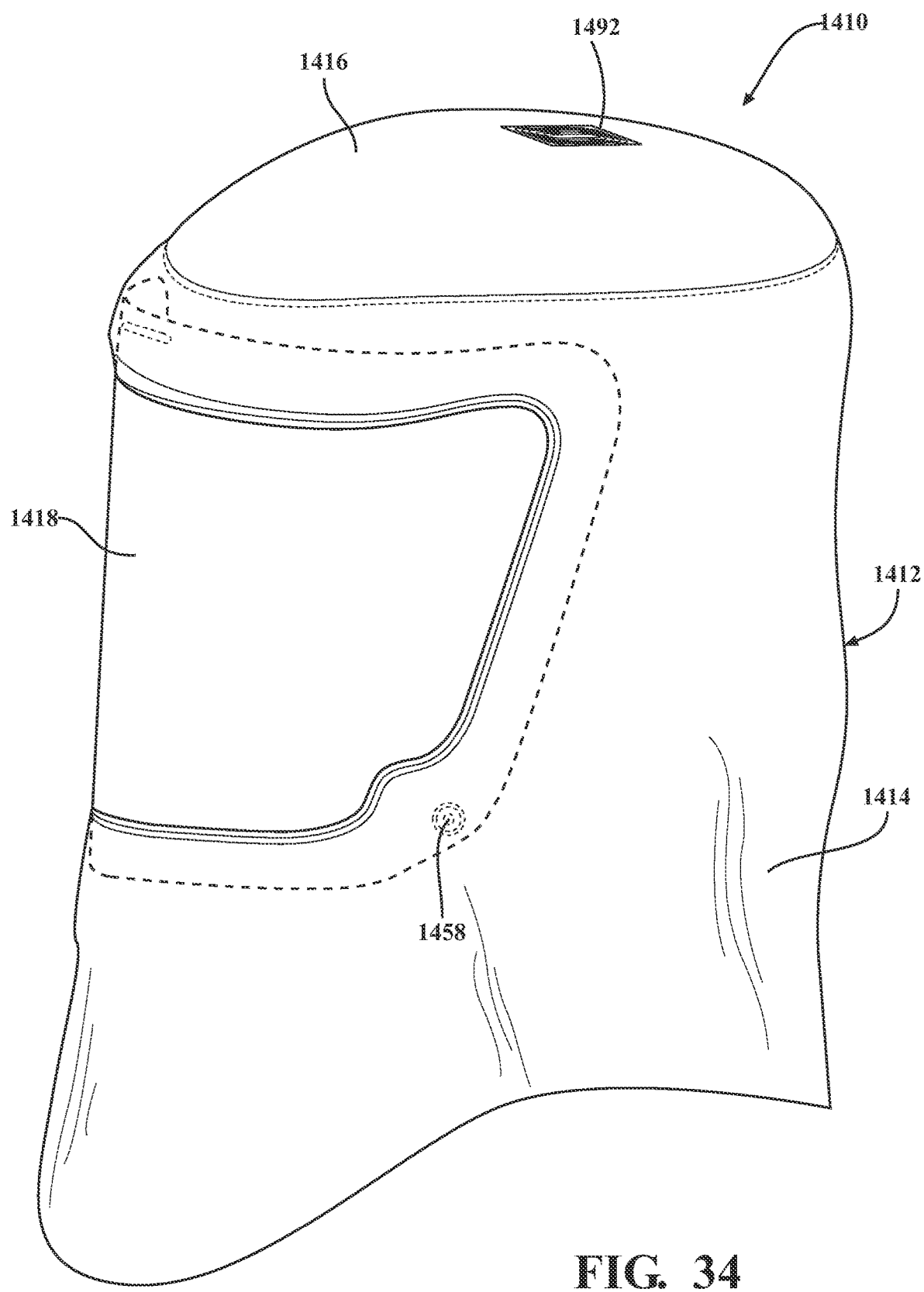
FIG. 34 is a perspective view of yet another exemplary configuration of a medical garment for use with a surgical helmet.
Figure 35:
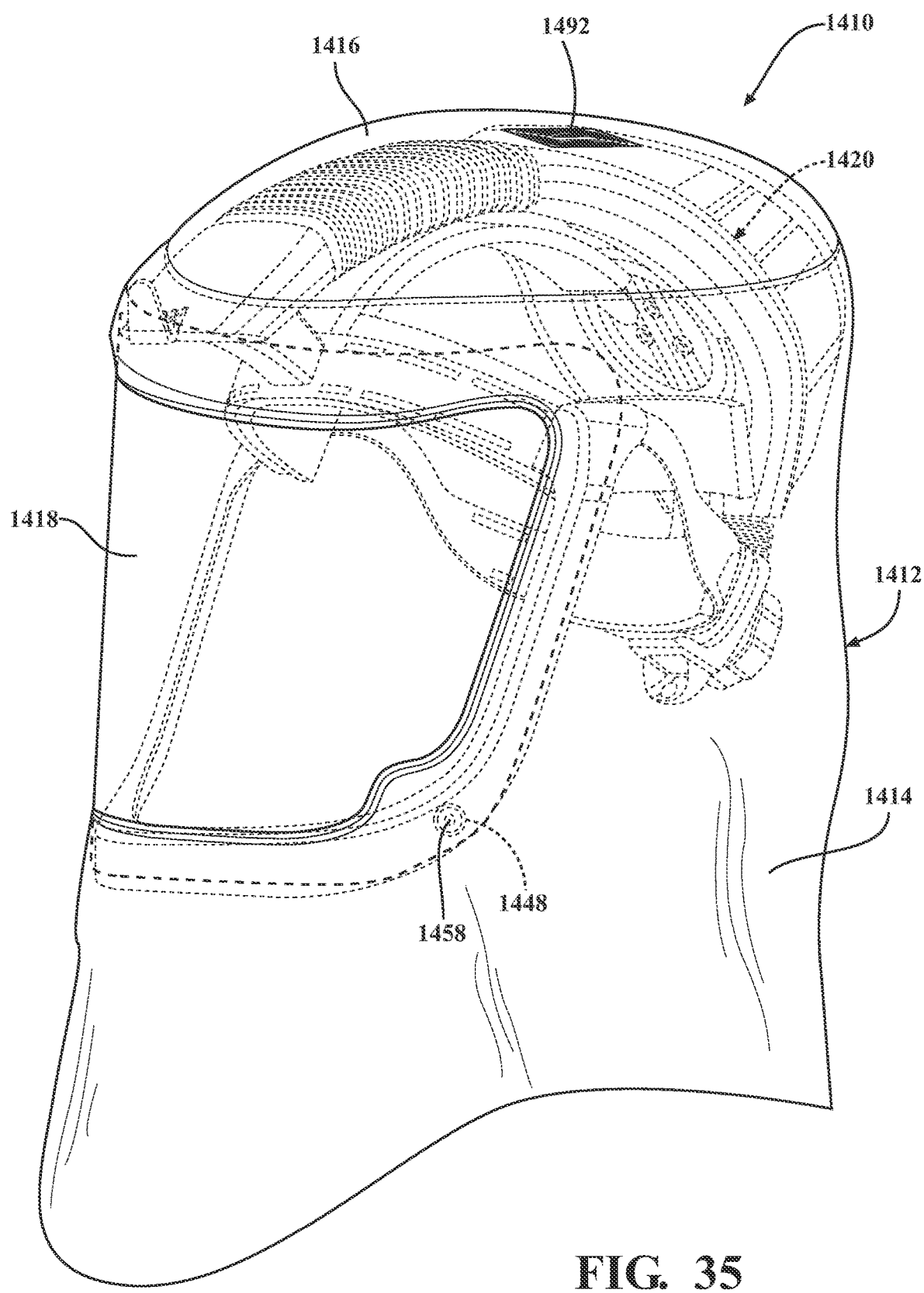
FIG. 35 is a perspective view of a fourth configuration of a surgical apparel system that includes the medical garment of FIG. 34 and a surgical helmet, with the surgical helmet shown in phantom.
Figure 36:
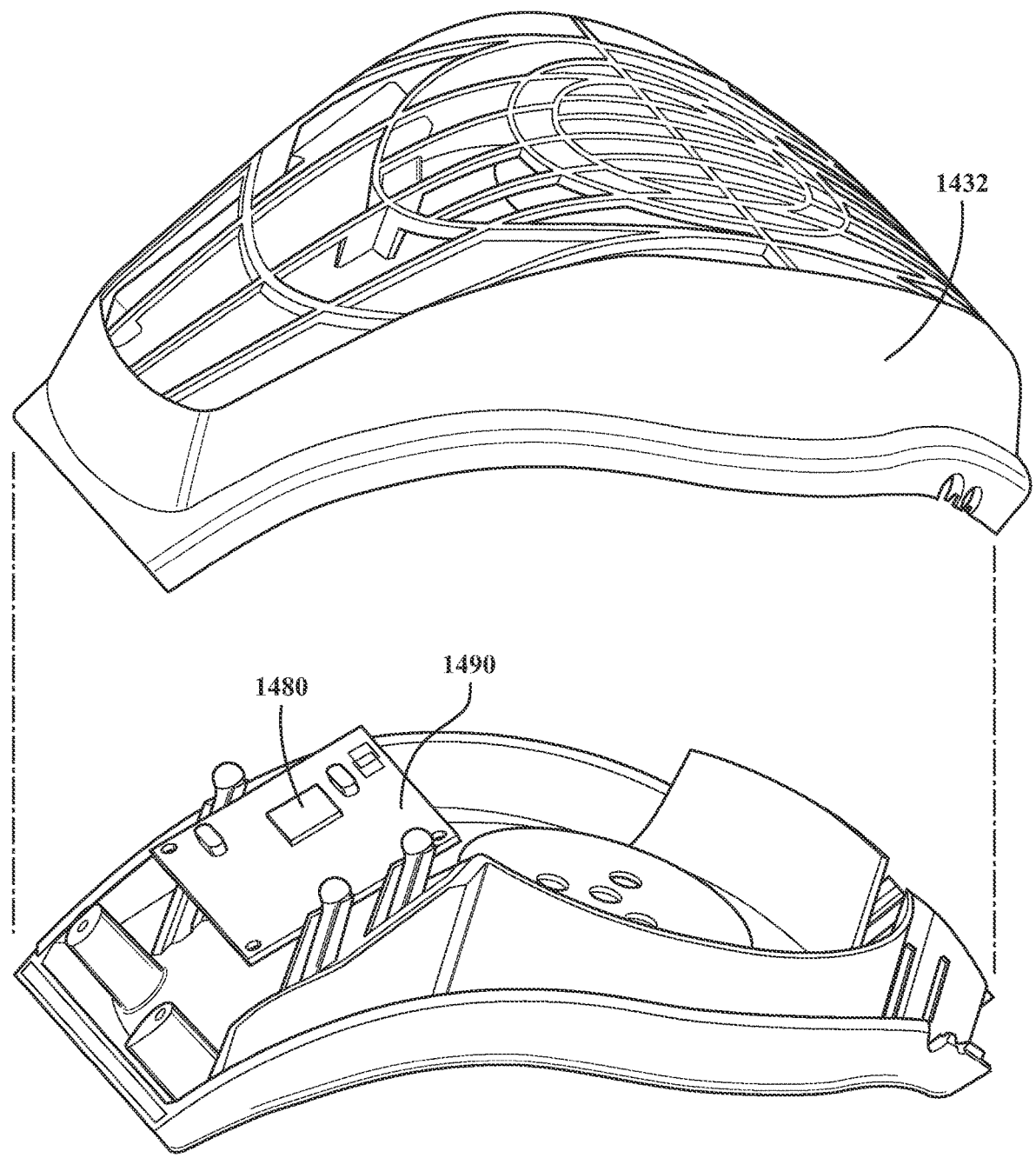
FIG. 36 is a partially exploded view of the surgical helmet of FIG. 35.

Additional features, components and/or sub-assemblies may be incorporated or combined with any of the surgical apparel systems 10, 110, 610 described above. A number of generic components for use with a surgical apparel system are illustrated in FIGS. 34, 35, and 36, and described below with regard to a generic system 1410. It should be understood that any of the components and/or features of the generic system 1410 described below may be incorporated and/or combined with the surgical apparel systems 10, 110, 610 described above.

The system 1410 may further comprise a transceiver 1490 that is coupled to the surgical helmet 1420 and in communication with the controller 1480. The controller 1480 may be operably coupled to the transceiver 1490 and configured to communicate data between the controller 1480 and the transceiver 1490.

The system 1410 may further comprise an electromagnetic tag 1492 attached to the surgical garment 1412 or medical garment. For example, the electromagnetic tag 1492 may comprise an RFID tag, or similar tag configured to contain identification information related to the particular surgical garment 1412. The electromagnetic tag 1492 may be positioned anywhere on the surgical garment 1412. For example, the electromagnetic tag 1492 may be attached to the filter fabric 1416 of the surgical garment 1412. Alternatively, the electromagnetic tag 1492 may be attached to the surgical fabric 1414 of the surgical garment 1412 or may be attached to the control housing of the surgical garment 1412. In one configuration, the tag 1492 may be attached to the surgical garment 1412 on the wearer side to reduce the likelihood of introducing a non-sterile or contaminated item on the environment side of the barrier defined by the surgical garment 1412. Alternatively, it is also contemplated that the tag 1492 may be attached to the surgical garment 1412 on the environment side of the barrier defined by the surgical garment 1412.

The electromagnetic tag 1492 may be configured to transmit or otherwise convey information to the transceiver 1490 coupled to the surgical helmet 1420, including information related to the particular surgical garment 1412. In one exemplary configuration, the electromagnetic tag 1492 may be configured to activate upon receipt of a signal, such as a request for transmission of data, from the transceiver 1490. Upon activation of the electromagnetic tag 1492, the electromagnetic tag 1492 may transmit a signal back to the transceiver 1490 comprising data related to the surgical garment 1412 associated with the electromagnetic tag 1492. In this configuration, the transceiver 1490 may be configured to actively broadcast a signal requesting the transmission of the data. The signal may be broadcast a defined distance from the transceiver 1490, and the electromagnetic tag 1492 may be configured to transmit a return signal including data related to the surgical garment 1412 when the electromagnetic tag 1492 is within the defined distance of the transceiver 1490. In an exemplary configuration, the electromagnetic tag 1492 may be positioned on the surgical garment 1412 such that when the surgical garment 1412 is attached to the surgical helmet 1420, the electromagnetic tag 1492 may be positioned in close proximity to the transceiver 1490. This arrangement may allow for the transmission of data from the electromagnetic tag 1492 to the transceiver 1490 when the surgical garment 1412 and surgical helmet 1420 are coupled to one another. For example, an exemplary arrangement of the electromagnetic tag 1492 and transceiver 1490 may comprise the electromagnetic tag 1492 being attached to the filter fabric 1416 and the transceiver 1490 being encased in the housing 1432 of the surgical helmet 1420.

As discussed above, the electromagnetic tag 1492 may be configured to store data and/or an identifier related to the surgical garment 1412, such as a serial number identifying the particular surgical garment 1412. The electromagnetic tag 1492 may also be configured to store information identifying the type of surgical garment 1412 associated with the electromagnetic tag 1492. The electromagnetic tag 1492 may also store data regarding operational parameters for the peripheral devices 1430 of the surgical helmet 1420 that are best suited for operation of the peripheral device 1430 based on the characteristics of the particular surgical garment 1412 attached to the surgical helmet 1420, such as the size of the surgical garment 1412, the type of fabric, whether the surgical garment 1412 is a hood or a toga, etc.

The transceiver 1490 of the helmet 1420 may be operably connected to the controller 1480, wherein the transceiver 1490 is configured to transmit data and/or information received from the electromagnetic tag 1492 to the controller 1480. As discussed above, the information received from the electromagnetic tag 1492 may be related to an identifier for the individual surgical garment 1412. The controller 1480, also being connected to the one or more peripheral devices 1430 of the surgical helmet 1420, may be configured to communicate operational commands to the peripheral device(s) 1430 based, at least in part, on the information received from the transceiver 1490 related to the surgical garment 1412. For example, the controller 1480 may be configured such that only after the surgical garment 1412 is mounted to a surgical helmet 1420, as confirmed by the transceiver 1490 identifying the electromagnetic tag 1492 of the surgical garment 1412, does the controller 1480 generate operational commands that result in the actuation of the peripheral devices 1430 of the surgical helmet 1420. In other words, the controller 1480 may be prevented from generating operational commands for and/or prevented from transmitting energy to one or more of the peripheral devices 1430 until the transceiver 1490 sends a signal corresponding to a suitable identifier read on the surgical garment 1412. Because the transceiver 1490 reads the electromagnetic tag 1492 once the surgical garment 1412 is placed in proximity to the surgical helmet 1420, this eliminates the disadvantages associated with providing a surgical apparel system 1410 with a ventilation assembly 1430 or other peripheral device 1430 that is actuated prior to the placement of the surgical garment 1412 on the surgical helmet 1420. As described above with regard to the functionality of the coupling features 146, 246, 346, 446, one disadvantage this eliminates is the generation of noise produced by the ventilation assembly 1430 when the ventilation assembly 1430 is not serving a useful purpose. A second disadvantage that may be eliminated by preventing the actuation of a peripheral device 1430 prior to mounting the surgical garment 1412 to the surgical helmet 1420, is the drawing down of the charge in the energy source 182 when actuation of the peripheral device 1430 is not needed.

In another exemplary configuration, a wearable surgical garment 1412, which may also be referred to as a medical garment, for use with a surgical helmet 1420, the surgical garment 1412 may further comprise an electromagnetic tag 1492 configured to store data related to the surgical garment 1412. The electromagnetic tag 1492 may be configured to exchange data with the transceiver 1490, which may also be referred to as an electromagnetic reader, of the surgical helmet 1420 when the electromagnetic tag 1492 and said transceiver 1490 are within a certain proximity to one another. The stored data on the electromagnetic tag 1492 related to the surgical garment 1412 may comprise an identifier specific to the surgical garment 1412. The operation of the peripheral device 1430 of the surgical helmet 1420 may be based, at least in part, on the stored identifier. The stored data on the electromagnetic tag 1492 related to said surgical garment 1412 may further comprise usage data indicating whether the surgical garment 1412 has been previously coupled to a surgical helmet 1420. The usage data may also indicate how many times the surgical garment 1412 has previously been coupled to a surgical helmet 1420. The stored data on the electromagnetic tag 1492 related to said surgical garment 1412 may further comprise authentication data indicating whether the surgical garment 1412 is compatible with said surgical helmet 1420. This authentication data may include the size of the surgical garment 1412, the type of garment, the manufacturer of the garment, and the like. The stored data related to the surgical garment 1412 may further comprise operational data including data utilized to generate operational commands for the peripheral device(s) 1430 of said surgical helmet 1420 based, at least in part, on said operational data. The operational data may include specific operation modes for the peripheral device(s) 1430 of the surgical helmet 1420 based on the characteristics of the surgical garment 1412. For example, the operational data stored on the electromagnetic tag 1492 related to the specific surgical garment 1412 may include minimum and maximum setting information for each of the peripheral device(s) 1430 based on the characteristics of the surgical garment 1412. The stored data related to the surgical garment 1412 may further comprise an identifier, wherein said identifier is utilized to identify and/or track the use of the surgical garment 1412. For example, the identifier may include a serial number specific to the surgical garment 1412, so the usage and location of the surgical garment 1412 may be tracked. The controller 1480 may prevent operation of the peripheral device(s) 1430 if the usage data related to the surgical garment 1412 indicates the usage of the specific surgical garment 1412 has exceeded a predetermined or threshold number of uses, such as a single use. Alternatively, the controller may be configured to allow a particular type of surgical garment 1412 to be worn a plurality of times, such as three uses, before the controller 1480 is configured to prevent the operation of the peripheral device(s) 1430.

In another exemplary configuration, a surgical apparel system 1410 may comprise a surgical helmet 1420 to be worn over the head of a wearer. The surgical helmet 1420 may comprise a peripheral device 1430 and a transceiver 1490. The system 1410 may further comprise a surgical garment 1412, which may also be referred to as a medical garment, comprising a surgical fabric 214/216 or shell configured to be at least partially disposed over said surgical helmet 1420 to provide a microbial barrier between a medical environment and a wearer. An electromagnetic tag 1492 may be coupled to the surgical garment 1412, wherein the electromagnetic tag 1492 may be configured to store an identifier related to the surgical garment 1412. An antenna may be operably coupled to the transceiver 1490 and configured to communicate with the electromagnetic tag 1492 to receive the identifier related to the surgical garment 1412. The surgical apparel system 1410 may further comprise a controller 1480 operably coupled to the peripheral device(s) 1430 and to the transceiver 1490. The controller 1480 may be configured to communicate operational commands to the peripheral device 1430 based, at least in part, on the identifier related to the surgical garment 1412. The electromagnetic tag 1492 may be configured to store and transmit usage data for the surgical garment 1412, and the controller 1480 may be configured to determine if the surgical garment 1412 has been previously worn with the surgical helmet 1420. The controller 1480 may be configured to prevent actuation of the peripheral device 1430 if the surgical garment 1412 has been previously worn based, at least in part, on the stored usage data. The electromagnetic tag 1492 may also be configured to store authentication data for the surgical garment 1412, and the controller 1480 may be configured to determine if the surgical garment 1412 is compatible with the surgical helmet 1420. The controller 1480 may be configured to prevent actuation of the peripheral device(s) 1430 if the surgical garment 1412 is not compatible with the surgical helmet 1420 based, at least in part, on the stored authentication data. When the identifier is related to the type of surgical garment 1412, the controller 1480 may be configured to determine an operating mode of (generate an operational command for) the peripheral device(s) 1430 based, at least in part, on the type of surgical garment 1412 attached to the surgical helmet 1420. For example, the controller 1480 may be configured to increase or decrease power output to the peripheral device 1430 based, at least in part, on the type of surgical garment 1412 attached to the surgical helmet 1420. In an exemplary configuration wherein the peripheral device 1430 is a ventilation assembly, the controller 1480 may be configured to increase the power output to said ventilation assembly when the type of surgical garment 1412 comprises a thicker fabric 1414/1416 and/or is a larger size (suggesting a larger volume of space under the surgical garment 1412).

The transceiver 1490 may also be coupled to the memory device 184 of the surgical helmet 1420. The memory device 184 may be configured to store the data received from the electromagnetic tag 1492 of the surgical garment 1412. The information stored on the memory device 184 may be utilized to identify when a previously worn surgical garment 1412 has been re-attached to the surgical helmet 1420. For example, a surgical garment 1412 may be attached to the surgical helmet 1420 by the wearer. The memory device 184 may be configured to store the data, such as a serial number, identifier, model number, garment characteristics, or similar information, received from the electromagnetic tag 1492 of the surgical garment 1412 for later use. The data stored in the memory device 184 may be utilized to prevent operation of the peripheral device(s) 1430 in the event a previously worn surgical garment 1412 is reattached to the surgical helmet 1420 at a later point in time. For example, in operation, when the surgical garment 1412 is attached to the surgical helmet 1420, and the transceiver 1490 receives data from the electromagnetic tag 1492 of the surgical garment 1412, the memory device 184 will store the data. The data may include a serial number or other identifying characteristic. If a wearer were to attempt to re-attach the same surgical garment 1412 to the surgical helmet 1420, when the transceiver 1490 receives the data from the electromagnetic tag 1492, the memory device 184 would already contain the same data. When the transceiver 1490 transfers the data from the memory device 184 to the controller 1480, the controller 1480 may be configured to recognize the second entry of data for the surgical garment 1412. Upon recognizing the second entry for the surgical garment 1412, the controller 1480 may be configured to prevent operation of the peripheral device 1430 until a new surgical garment 1412 is attached to the surgical helmet 1420.

It is possible for the energy or power source 182 for the system 1410 to run out during a medical procedure, which could result in a false positive identification of a re-used surgical garment 1412 when the system is restarted. For example, if the energy source 182, such as battery, for the system 1410 were to run out in the middle of the procedure, when a new battery is attached and a new signal is transmitted from the electromagnetic tag 1492 to the transceiver 1490, the memory 184 is likely to show that the attached surgical garment 1412 was previously used. As described above, in this scenario the controller 1480 may be configured to prevent the peripheral device 1430 from operating. In order to prevent non-operation of the peripheral device 1430 based on a false positive identification of the surgical garment 1412, the system 1410 may further comprise a capacitor operably coupled to the controller 1480 and configured to store energy. The controller 1480 may be configured to identify that if the capacitor is currently storing energy, the energy source 182 for the system 1410 was recently removed. Based on the identification that the energy source 182 was recently removed, the controller 1480 may be configured to allow for operation of the peripheral device 1430 even though the data from the memory device 184 suggests the surgical garment 1412 was previously worn. The controller 1480 may also be configured to allow for operation of the peripheral device(s) 1430 even though the data from the memory device 184 suggests the surgical garment 1412 was previously worn based on the amount of time between the first instance when the surgical garment 1412 was identified as being attached to the surgical helmet 1420, and the second instance when the surgical garment 1412 was identified as being attached to the surgical helmet 1420. For example, if the controller 1480 were to identify that the time between the first instance in which the surgical garment 1412 was attached and the second instance the surgical garment 1412 was attached was less than two hours, the controller 1480 may be configured to allow for operation of the peripheral device(s) 1430, whereas if the amount of time between the first and second instances was greater than two hours, the controller may prevent operation of the peripheral device 1430 with the worn surgical garment 1412. However, the amount of time may be configured as would be reasonably appropriate in the given industry based on the use of the surgical garment 1412, such as 1 hour, 24 hours, and the like.

Other configurations of the system 1410 may have different sub-assemblies for ensuring that only when the surgical garment 1412 is fitted to the surgical helmet 1420, the peripheral device(s) 1430, such as the ventilation assembly, may be actuated. For example, it should be understood that the surgical helmet 1420 may comprise additional and/or alternative garment detectors, in addition to the detectors 170, 270, 370, 470, 570, 670 described above. The garment detector may comprise a pressure sensor, a load sensor, or similar type of sensor configured to detect the attachment of the surgical garment 1412 to the surgical helmet 1420. For example, the chin bar 1424 may comprise a garment detector in the form of a pressure sensor configured to detect the attachment of the surgical garment 1412 to the surgical helmet 1420.

In another exemplary configuration of the system 1410, the system 1410 may be configured so that the controller 1480 may activate the peripheral device(s) 1430 for a predetermined period of time once an energy source 182 is attached to the surgical helmet 1420. This may allow the controller 1480 to complete a status check and confirm the peripheral device(s) 1430 are functioning properly. Once the controller 1480 has completed the status check, the controller 1480 may be configured to prevent any further actuation of the peripheral device(s) 1430 until the controller 1480 receives a signal from the garment detector indicating that the surgical garment 1412 has been attached to the surgical helmet 1420. Upon the controller 1480 receiving a signal from the garment detector indicating the surgical garment 1412 has been attached to the surgical helmet 1420, the controller 1480 may be configured to generate an operational command to allow the transmission of energy from the energy source 182 to the peripheral device(s) 1430.

For example, in operation, the wearer may place the surgical helmet 1420 including a peripheral device 1430, such as a ventilation assembly, on their head and attach an energy source 182 to the surgical helmet 1420. The controller 1480 may then actuate the ventilation assembly 1430 to confirm the ventilation assembly 1430 is working properly. The controller 1480 may then deactivate the ventilation assembly 1430. Next, the wearer may attach the surgical garment 1412 to the surgical helmet 1420. The attachment of the surgical garment 1412 to the surgical helmet 1420 may be detected by a pressure sensor, switch, or transceiver 1490 configured to detect the presence of an RFID tag 1492 or other electromagnetic tag on the surgical garment 1412, or similar detector as described above. The detector may then send a signal to the controller 1480 to confirm the surgical garment 1412 has been attached to the surgical helmet 1420. The controller 1480 may then actuate the ventilation assembly 1430.

In yet another configuration of the system 1410, the surgical garment 1412 and surgical helmet 1420 may each comprise complementary conductors. When the surgical garment 1412 is fitted to the surgical helmet 1420, a conductor integral with the surgical garment 1412 closes the connection between the surgical garment 1412 and the surgical helmet 1420. For example, the conductor of the surgical garment 1412 may be integrally formed with the face shield 1418 and the complementary conductor may be included in the chin bar 1424, such that the circuit becomes closed once the conductor of the face shield 1418 engages the conductor in the chin bar 1424. The conductors may further be in communication with the magnets/ferromagnetic elements of the attachment elements 1458 and/or the corresponding coupling members 1448 of the chin bar 1424. A garment detector may be configured to sense the closing of the circuit between the attachment elements 1458 of the face shield 1418 and surgical helmet 1420. In response to detecting this change in circuit state, the garment detector may generate a signal to the controller 1480 indicating that the circuit is in the closed state and ready for actuation. In certain configurations, the controller 1480 may only generate operational command signals that result in the actuation of the peripheral device(s) 1430 when this signal is received by the controller 1480.

It should be appreciated that in some configurations of the system 1410, the removal of the surgical garment 1412 from the surgical helmet 1420 may result in the reopening of the circuit between the attachment elements 1458 of the surgical garment 1412 and the surgical helmet 1420, respectively. The garment detector, in response to the detection of the reopening of this circuit may generate a signal indicating that the system 1410 is in the open state to the controller 1480. The controller 1480, in response to receiving the signal from the garment detector, may be configured to return the peripheral device(s) 1430 of the surgical helmet 1420 to the off state. Thus, a further feature of these configurations of the system 1410 is that, when the surgical garment 1412 is removed from the surgical helmet 1420 and use of the peripheral device(s) 1430, such as the ventilation assembly, is no longer required, the peripheral device(s) 1430 are automatically shut off or deactivated. Similar modes of operation are also contemplated with the other garment detector assemblies described above.

In some versions of the surgical apparel system 1410, based on whether or not the surgical garment 1412 is detected/fitted to the surgical helmet 1420 the controller 1480 may regulate whether or not other peripheral device(s) 1430 are actuated. Thus, the controller 1480 may inhibit the actuation of one or more of the light assembly, the communications unit or the cooling strip based on whether or not an appropriate surgical garment 1412 is fitted to the surgical helmet 1420.

The above are not directed to specific configurations of the surgical apparel system 10, 110, 610, 1410. It should be understood that the individual features of the different configurations of the system 10, 110, 610, 1410 may be combined to construct alternative configurations of the system 10, 110, 610, 1410.

Also, while the surgical apparel system 10, 110, 610, 1410 is generally intended to provide a barrier between the medical practitioner and the patient during a medical or surgical procedure, its use is not so limited. It is within the scope of this disclosure that the surgical apparel system 10, 110, 610, 1410 may be used in other endeavors in which it is desirable to provide a barrier between an individual and the surrounding environment. One alternative endeavor in which it may be so desirable to use the system 10, 110, 610, 1410 is one in which it is desirable to provide a barrier between the individual and hazardous material in the environment in which the individual is working.

Additional configurations of a surgical apparel system including a surgical garment for use with of a surgical helmet, the surgical garment comprising an attachment element for coupling the surgical garment to the surgical helmet. In describing the system, it should be understood that features and/or structures having the same reference number and/or the same last two digits may have the same features and/or functions as those of the helmets, garments, and/or systems described above.

Figure 37:
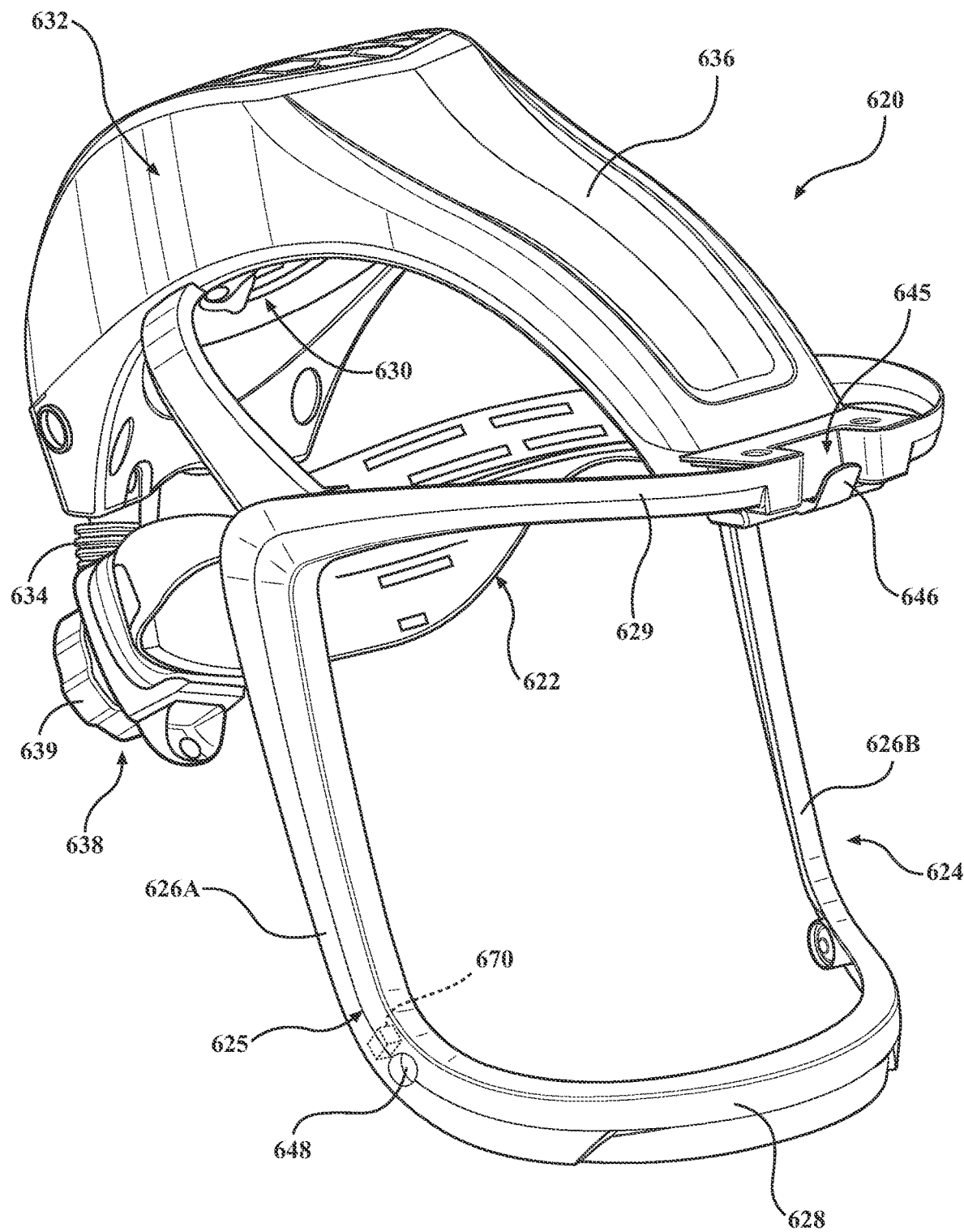
FIG. 37 is a perspective view of the surgical helmet for use with the surgical apparel system of FIGS. 13A and 13B, the helmet including an alignment channel and a chin bar.

Referring to FIG. 37, an exemplary configuration of a surgical helmet is illustrated, such as the surgical helmet of FIGS. 14-17B that is described above. The surgical helmet 620 may comprise a top beam 629 positioned forward of the housing 632 of the surgical helmet 620 and configured to extend across the front of the surgical helmet 620. The top beam 629 may further comprise a recess. The recess of the top beam 629 may comprise a pair of laterally spaced-apart side walls and a proximal surface that is positioned proximally from the distal surface of the top beam 629. The side walls and the proximal surface may define an alignment channel 645, wherein the alignment channel 645 is configured to receive a tab 655 disposed on the interior of the surgical garment 612 to align and/or orient the surgical garment 612 relative to the surgical helmet 620. As described above, the tab 655 may be integrally formed with and configured to extend from the face shield 618. Alternatively, the tab 655 may be formed independent of the face shield 618, wherein the tab 655 is configured to be coupled to the fabric 614 on the interior of the surgical garment 612. However, other configurations are contemplated. The spaced-apart side walls of the alignment channel 645 should be spaced apart a distance greater than the width of the tab 655 to allow the tab 655 to be positioned within the alignment channel 645.

The top beam 629 may further comprise a coupling feature 646 configured to removably engage the face shield 618 and/or surgical garment 612. The coupling feature 646 may comprise a protrusion, magnetic member, ferromagnetic member, hook and loop, or similar coupling mechanism configured to releasably engage the tab 655 to align and/or couple the surgical garment 612 to the surgical helmet 620. For example, the coupling feature 646 may be realized as a protrusion 646 extending from the alignment channel 645 of the top beam 629. Here, the top beam 629 comprises the alignment channel 645 as described above, and the coupling feature 646 may be disposed at least partially within the alignment channel 645. The coupling feature 646 may be positioned within the alignment channel 645 such that the top of the upper most surface coupling feature 646 is arranged or otherwise positioned below the top of the top of the alignment channel 645 and/or the top surface of the top beam 629. The combination of the spaced-apart side walls of the alignment channel 645 and the coupling feature 646 may serve to align and/or orient the face shield 618 and/or the surgical garment 612 relative to the surgical helmet 620. More specifically, the spaced-apart side walls of the alignment channel 645 may serve to guide the tab 655 such that the opening 656 in the tab 655 is directed into engagement with the coupling feature 646 as the surgical garment 612 is placed over the surgical helmet 620.

The surgical helmet 620 may include a chin bar 624 that extends downwardly from the front portion of the surgical helmet 620. The chin bar 624 may comprise a first post 626A and a second post 626B. The first and second posts 626A, 626B may be coupled to the top beam 629, wherein the top beam 629 is configured to extend across the front of the surgical helmet 620. For example, as illustrated in FIG. 37, the first and second posts 626A, 626B may be connected to opposing ends of the top beam 629. The chin bar 624 may be constructed from a generally flexible or pliable material.

The chin bar 624 may further comprise a bottom beam 628 that may extend between the opposed free ends of the posts 626A, 626B. The chin bar 624 is formed so that the bottom beam 628 is located below and slightly forward of the chin of the person wearing the surgical helmet 620. The bottom beam 628 may be bowed outwardly from the free ends of posts 626A, 626B. The chin bar 624 may extend outwardly from the top beam 629 such that the chin bar 624 is positioned forward of and generally encircles the face of the wearer when the surgical helmet 620 is secured to the wearer's head. Collectively, the combination of the top beam 629, the posts 626A, 626B, and the bottom beam 628 may be referred to as the face frame, as they generally define an opening positioned in front of the wearer's face when the surgical helmet 620 is positioned on top of the wearer's head.

A plurality of coupling members 648 may be mounted to or within the chin bar 624. The coupling members 648 comprise magnetic material and are configured to align and/or attach the face shield 618 of the surgical garment 612 to the surgical helmet 620. Each coupling member 648 may be positioned on the chin bar 624 proximate to the opposed posts 626A, 626B and/or adjacent opposing ends of the bottom beam 628. Alternatively, the coupling members 648 of the surgical helmet 620 could be arranged or otherwise configured in any suitable way to cooperate with the complementary attachment elements 658 of the surgical garment 612 to releasably secure the surgical garment 612 to the surgical helmet 620. For example, as illustrated in FIGS. 37 to 38B, the coupling member 648 may be positioned on the chin bar 624 at opposing ends of the lower beam 628 proximate where each of the posts 626A, 626B connects to the lower beam 628. While the exemplary configuration of the surgical helmet 620 illustrated in FIG. 37 utilizes two coupling members 648, it is contemplated that the surgical helmet 620 may be configured such that the chin bar 624 comprises a single coupling member 648 or, in other configurations, three or more coupling members 648 may be spaced about the chin bar 624 and/or top beam 629. It is contemplated that other types of coupling members 648 may be used in place of and/or in addition to those comprising magnetic materials, such as with a hook and loop fasteners, snaps, coupling members comprising ferromagnetic material, or similar type fasteners. Other configurations are contemplated.

Figure 38A:
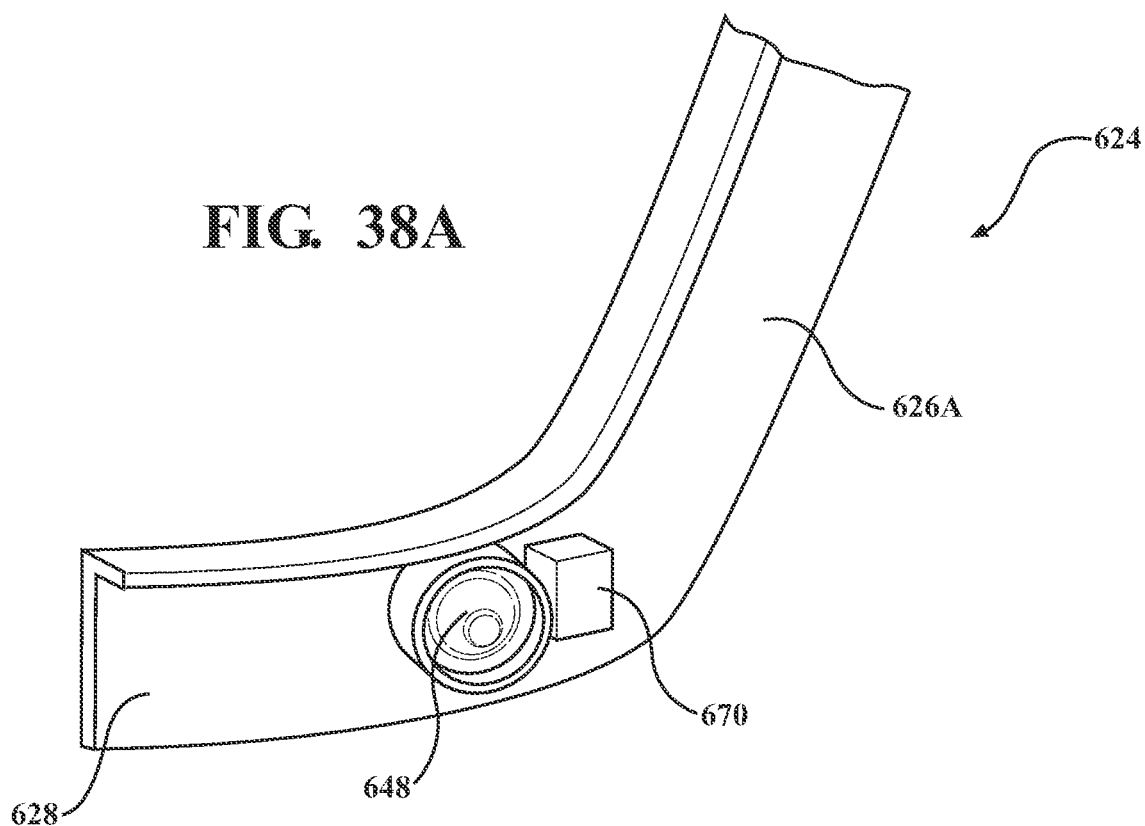
FIG. 38A is a partial section view of a portion of the chin bar of the surgical helmet of FIG. 37, the chin bar including an exemplary configuration of a coupling member and a detector positioned proximate the coupling member.
Figure 38B:
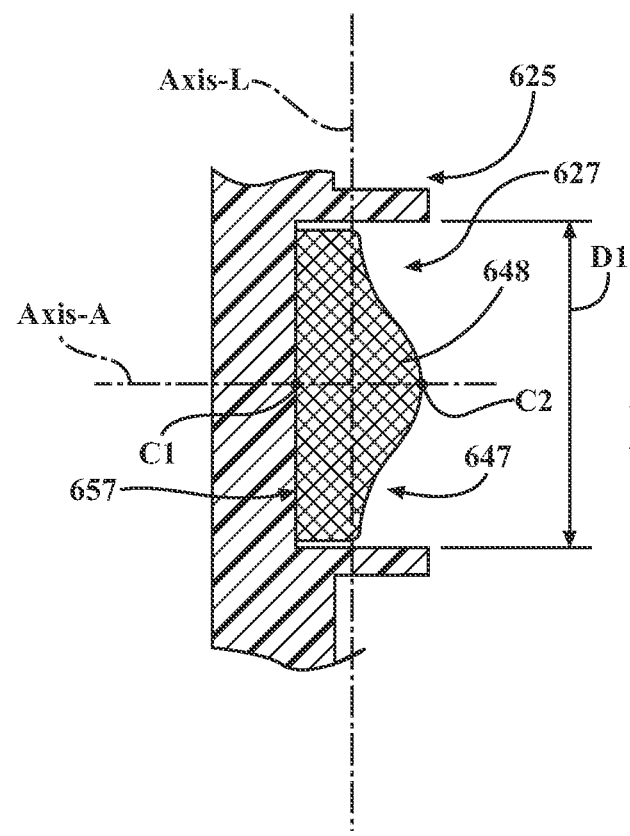
FIG. 38B is a sectional view of an exemplary configuration of the chin bar and the coupling member of FIG. 38A.

Referring to FIGS. 38A and 38B, an exemplary configuration of a coupling member 648 positioned within the chin bar 624 is illustrated. The coupling member 648 may comprise a distal surface 647. The chin bar 624 may comprise a recess 627 configured to receive the coupling feature 648. For example, as illustrated in FIGS. 38A and 38B, the coupling member 648 may be positioned within the recess of the chin bar 624, such that the distal surface 647 of the coupling member 648 is positioned proximally to a distal surface 625 of the chin bar 624.

The coupling member 648 may comprise one of a ferromagnetic material or a magnetic material. This may include the coupling member 648 being formed of or constructed from a ferromagnetic material or a magnetic material. It is also contemplated that only a portion of the coupling member 648 comprises a ferromagnetic material or a magnetic material. For example, the coupling member 648 may be injection-molded plastic and coated with a ferromagnetic material or magnetic material. Alternatively, the coupling member 648 may be formed from a ferromagnetic material or magnetic material, and then coated with a plastic or similar coating to provide a sterile and/or wear-resistant surface. It is also contemplated that a magnet may be "over-molded" with plastic material to define the coupling member 648. Generally, the coupling member 648 may comprise the other of the ferromagnetic material or magnetic material relative to one of the attachment element 658 of the surgical garment 612 in order to create a magnetic attraction between the coupling member 648 and the attachment element 658 to couple the surgical garment 612 to the surgical helmet 620.

The surgical helmet 620 may further comprise a controller or processor (not illustrated), which may be disposed on or within the chin bar 624 or top beam 629 of the surgical helmet 620. Alternatively, the controller may be positioned at any suitable location within the surgical helmet 620. For example, the controller may be positioned in the bottom beam 628 of the chin bar 624. The controller may be in communication with the one or more detectors 670, such as a Hall-effect sensor. The detector 670 may be that is positioned within the chin bar 624 and adjacent to the coupling member 648, as illustrated in FIGS. 37 and 38A. The detector 670 may be configured to detect a characteristic of the coupling member 648. For example, wherein the detector 670 is a Hall-effect sensor, the detector 670 may be configured to detect any changes to the magnetic field surrounding the coupling member 648. In operation, the detector 670 may be configured to detect a change in the magnetic field surrounding the coupling member 648 created by the presence or absence of an attachment element 658 of the surgical garment 612 being positioned adjacent the coupling member 648. For example, as illustrated in FIGS. 37 and 38A, the detector 670 may be positioned adjacent the coupling member 648 and lateral to the lower beam 628.

While FIGS. 38A and 38B illustrate only a portion of the chin bar 624 including a single coupling member 648, as discussed above, the chin bar 624 may comprise more than one coupling member 648. Similarly, the chin bar may comprise more than one detector 670. It is contemplated that the surgical helmet 620 may comprise a single detector 670 positioned adjacent to a single coupling member 648. It is also contemplated that in configurations of the surgical helmet 620 that include multiple coupling members 648, the surgical helmet 620 may comprise a single detector 670 positioned adjacent to one of the multiple coupling members 648. Alternatively, detectors 670 may be placed adjacent to two or more of the coupling members 648. Use of multiple detectors may provide redundancy in the event a detector 670 is damaged.

FIG. 38B illustrates a partial sectional view of the coupling member 648 disposed within a recess 627 of the chin bar 624. The recess 627 in the chin bar 624 may define a first dimension D1, such as a diameter. The coupling member 648 may generally be sized to fit within the dimension D1 of the aperture in the chin bar 624. Furthermore, the perimeter 653 of the distal surface 647 and the perimeter 651 of the proximal surface 657 of the coupling member 648 may define an Axis-A, that passes through center C1 of the proximal surface 657 and center C2 of the distal surface 647 of the coupling member 648. A transverse plane may be oriented to be parallel to the Axis-A and extending through the proximal surface 657 and the distal 647 surface of the coupling member 648 defining opposing lateral halves of the coupling member 648. In configurations where the coupling member 648 comprises a magnetic material, the transverse plane may define separation between the opposing poles of the magnetic material.

Furthermore, as can be seen in FIG. 38B, the distal surface 647 of the coupling member 648 may comprise a generally curved shape. For example, the distal surface 647 may comprise a generally convex shaped surface. Alternatively, the distal surface 647 may comprise a generally protruded or polyaxial surface, such that the distal surface comprises a generally rounded surface extending outward from the center of the coupling member 648. While not illustrated in FIG. 38B, it is contemplated that the distal surface 647 of the coupling member 648 may comprise a concave surface. Various exemplary configurations of a coupling member 648 included a concave or convex surface will be described in more detail below.

It is also contemplated that the coupling member 648 may comprise one or more indents. The indents may serve as a structural and/or visual alignment feature for positioning the coupling member 648 relative to the chin bar 624 and/or the detector 670. For example, in configurations where the coupling member 648 comprises a magnetic material, the indents or other indicator(s) may provide a visual identifier as to the orientation and/or position of the magnetic poles of the coupling member 648. It will be appreciated that this configuration contributes to improved manufacturability in that the coupling member 648 can be readily and accurately positioned within the recess of the chin bar 624 so that the poles of coupling member 648 are properly oriented relative to the detector 670.

Figure 39A:
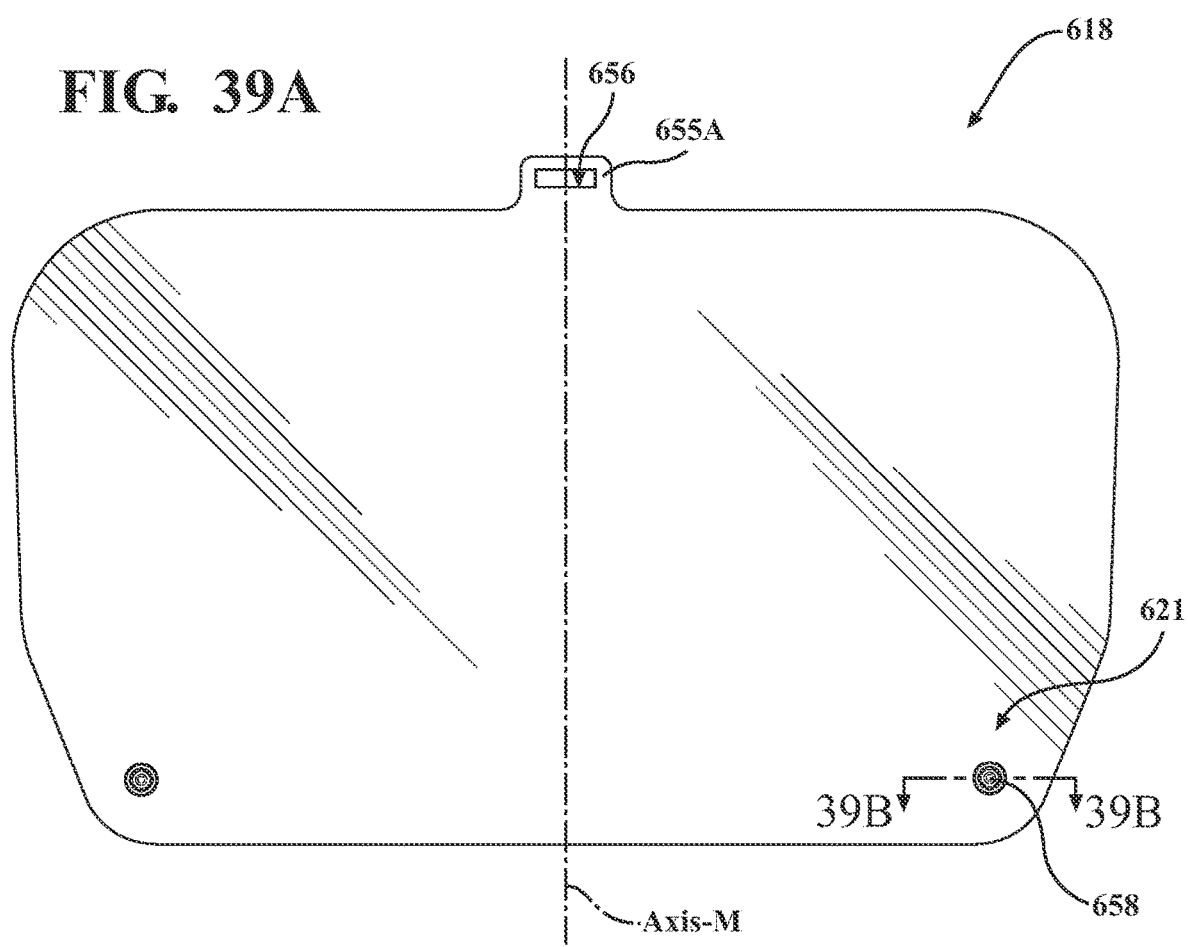
FIG. 39A is a rear view of a transparent face shield of a surgical garment of the surgical apparel system of FIG. 13A, including an attachment element coupled to the transparent face shield.
Figure 39B:
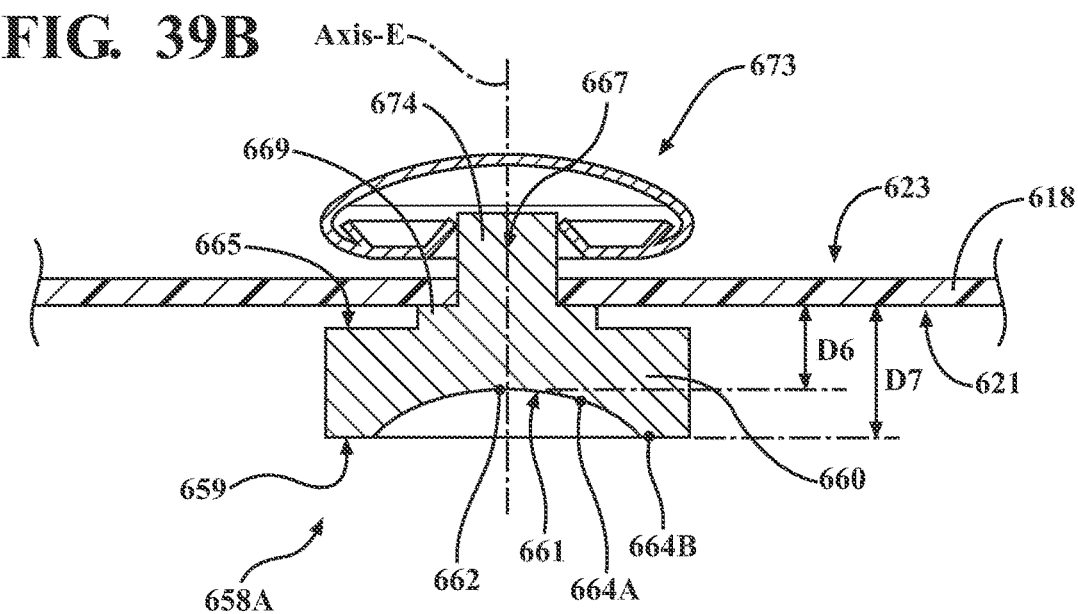
FIG. 39B is a partial sectional view of a configuration of an attachment element of a surgical garment coupled to the transparent face shield.

Referring to FIGS. 39A and 39B, an exemplary configuration of a transparent face shield 618 of a surgical garment described above is illustrated. The surgical garment 612 may also comprise a tab 655. The tab 655 may be disposed on the wearer side or interior of the surgical garment. The tab 655 may comprise a pair of opposing edges and define an opening 656. As illustrated in FIG. 39A, the tab 655 may be formed as a portion of the face shield 618. The tab 655 may define at least a portion of the opening 656, with a portion of the opening 656 also being defined by the face shield 618. It is also contemplated that the opening 656 may be entirely formed or defined within the tab 655. While not illustrated in the figures, it is also contemplated that the tab 655, including the opening 656, may be a separate component from the transparent face shield 618. The tab 655 may also be omitted in certain configurations of the transparent shield 618 and or surgical garment 612.

The surgical garment 612 may also comprise one or more attachment elements 658. The attachment elements 658 may also be referred to as a second member or garment fastener. The attachment element 658 may be coupled to the transparent face shield 618. The attachment elements 658 may serve as an alignment element configured to removably couple the surgical garment 612 to the surgical helmet 620. Furthermore, the attachment element 658 may be positioned proximate the outer perimeter of the transparent face shield 618 such that the fabric covers the attachment elements 658. This may serve to ensure the fabric covers the attachment elements 658 to maintain the barrier provided by the surgical garment 612 between the wearer and the environment. While not illustrated in the figures, it is also contemplated that the attachment elements 658 may be coupled to the surgical fabric 614 of the surgical garment 612 as opposed to being coupled to the transparent face shield 618. The attachment element 658 would still function in the same manner to removably couple the surgical garment 612 to the surgical helmet 620.

The attachment elements 658 may comprise a ferromagnetic material capable of creating a magnetic attraction and/or coupling with a magnetic material. For example, the attachment element 658 may be manufactured from AISI 1006 Low Carbon Steel including a material composition of approximately 99% iron. Alternatively, it is contemplated that attachment element 658 may be manufactured from other suitable materials, such as metal alloys including iron, nickel, cobalt, carbon, gadolinium, dysprosium, or alloys thereof, or combinations thereof. However, regardless of the specific alloy composition of the attachment element 658, the attachment element 658 should contain sufficient weight of at least one ferromagnetic material capable of creating a magnetic attraction with a magnetic material. For example, the alloy of the attachment element 658 may comprise a composition including at least 75% iron. More specifically, the attachment element 658 may comprise a composition including at least 85% iron. Even more specifically, the attachment element 658 may comprise a composition including at least 95% iron. Even more specifically, the attachment element 658 may comprise a composition including at least 98% or more iron.

In certain configurations, it should be appreciated that the attachment elements 658 may comprise a material, i.e., atoms, which are attracted to a magnetic field exhibited by the magnetic material positioned on the helmet 620. It is contemplated that the entirety of the attachment element 658 may consist of the ferromagnetic material in certain configurations. It is also contemplated that the attachment element 658 comprises both ferromagnetic material and diamagnetic material. For example, the attachment elements 658 may comprise a diamagnetic material which has been coated with a ferromagnetic material. Alternatively, the attachment elements 658 may be formed from a ferromagnetic material as a core, and then coated with a plastic or similar non-magnetic coating configured to provide a sterile and/or wear-resistant surface. Other arrangements of the diamagnetic and magnetic material are contemplated for the attachment element 658. It is also contemplated that the attachment element 658 may be formed from a magnetic material. As described above, the coupling member 648 of the surgical helmet 620 may comprise a magnetic material. When the attachment element 658 is formed from a magnetic material, the coupling member 648 may be formed from a ferromagnetic material capable of forming a magnetic attraction with the attachment element 658. Alternatively, it is also contemplated that both the coupling member 648 and the attachment element 658 are formed from a magnetic material. In this configuration, the coupling member 648 and the attachment element 658 may be oriented such that the polarity of each of the magnetic materials is inverted to allow the two magnetic materials to form a magnetic connection. In any of these configurations, the coupling member 648 and the attachment element 658, the placing of the attachment element 658 next to the coupling member 648 may be configured to trigger the detector 670, such as a hall effect sensors, as described above. It should be appreciated that the surgical garment 612, and all components thereof, may be configured similarly and/or comprise the features of the surgical garment(s) 12, 112, 612 described above.

As illustrated in FIG. 39B, the attachment element 658 may be coupled to the transparent face shield 618. The transparent face shield 618 comprising a first surface 621 and an opposing second surface 623. The first surface 621 being proximal to the user on the wearer side of the barrier created by the surgical garment 612 and the second surface 623 being distal to the user on the environment side of the barrier. The attachment element 658 may comprise a head 660. The head 660 may define a dimension, wherein the dimension of the head is less than the dimension of the recess 627 in the chin bar 624, such that the head 660 is sized to be inserted within the aperture of the chin bar 648 when coupled to the coupling member 648. The head 660 of the attachment element 658 may also define a distal surface 665 and an opposing proximal surface 659. The proximal surface 659 of the head 660 may further define a recess 661. A first point 662 may be positioned on the proximal surface 659 of the head 660. The first point 662 may be positioned at a center of the proximal surface 659. Alternatively, the first point 662 may be positioned at a location on the proximal surface 659 that in intersects with a first axis, Axis-E of the attachment element 658. The first axis, Axis-E, may also be the longitudinal axis of the attachment element 658. A second point 664A, 664B, may also be positioned on the proximal surface 659 of the head 660. As illustrated in FIG. 39B, the proximal surface 659 may comprise a plurality of second points 664A, 664B that are spaced about the proximal surface 659. Generally, the second point(s) 664A, 664B may be positioned on the proximal surface 659 such that they are spaced apart from the first point 662 on the proximal surface 659. For example, where the proximal surface 659 of the head 660 comprises a generally circular profile, the first point 662 may be positioned at the center of the proximal surface 659, and each of the one or more second point 664A, 664B may be radially spaced from the first point 662. Furthermore, the first point 662 may define a first distance D6 from the first surface 621 of the transparent face shield 618 and the second point(s) 664A, 664B may define a second distance D7 from the first surface 621 of the transparent face shield 618. The proximal surface 659 of the head 660 may be shaped such that the first distance D6 defined by the first point 662 is less than the second distance D7 defined by the second point(s) 664A, 664B defining a recess 661 in the proximal surface 659. For example, an exemplary configuration of the attachment element 658 may comprise the head 660 having a diameter of approximately ten (10) millimeters in diameter and approximately three (3) millimeters tall. The recess 661 may be generally centered on the proximal surface 659 of the head 660 and comprise a concave-shape. The recess 661 may have a diameter of approximately eight (8) millimeters and a depth of approximately one and a half (1.5) millimeters into the head 660. The shape of the proximal surface 659 may configured such that a portion of the proximal surface 659 of the head 660 including the second point(s) 664A, 664B may be at least partially disposed within the recess 627 of the chin bar 624 when the surgical garment 612 is coupled to the surgical helmet 620. For example, the portion of proximal surface 659 of the head 660 including the second point(s) 664A, 664B may positioned at least two millimeters (2-mm) proximally of the distal surface 625 of the chin bar 624 when the surgical garment 612 is coupled to the surgical helmet 620.

The head 660 of the attachment element 658 is formed from at least 50, 75, 85, or 90 wt. % of a metal alloy comprising at least 50%, 60, 70, 80, 90, 95, or 99 wt. % of a ferromagnetic material capable of being magnetically attracted to the coupling member 648 comprising a magnet. It is also contemplated that the head 660 of the attachment element 658 comprises at least 70, 80, or 90 wt. % of a ferritic or martensitic stainless steel or other steel capable of being attracted to a magnet and sufficient to retain the surgical garment 612 to the surgical helmet 620. It is further contemplated that the head 660 of the attachment element 658 comprises at least 0.5, 0.6, 0.7, 0.8, 0.9, 1, 1.2, 1.4, 1.5 or 1.8 g of a ferromagnetic material capable of being magnetically attracted to the coupling member 648 comprising a magnet. Example of suitable ferromagnetic materials may include iron, nickel, cobalt, carbon, gadolinium, dysprosium, or alloys thereof, or some combination thereof.

Figure 40:
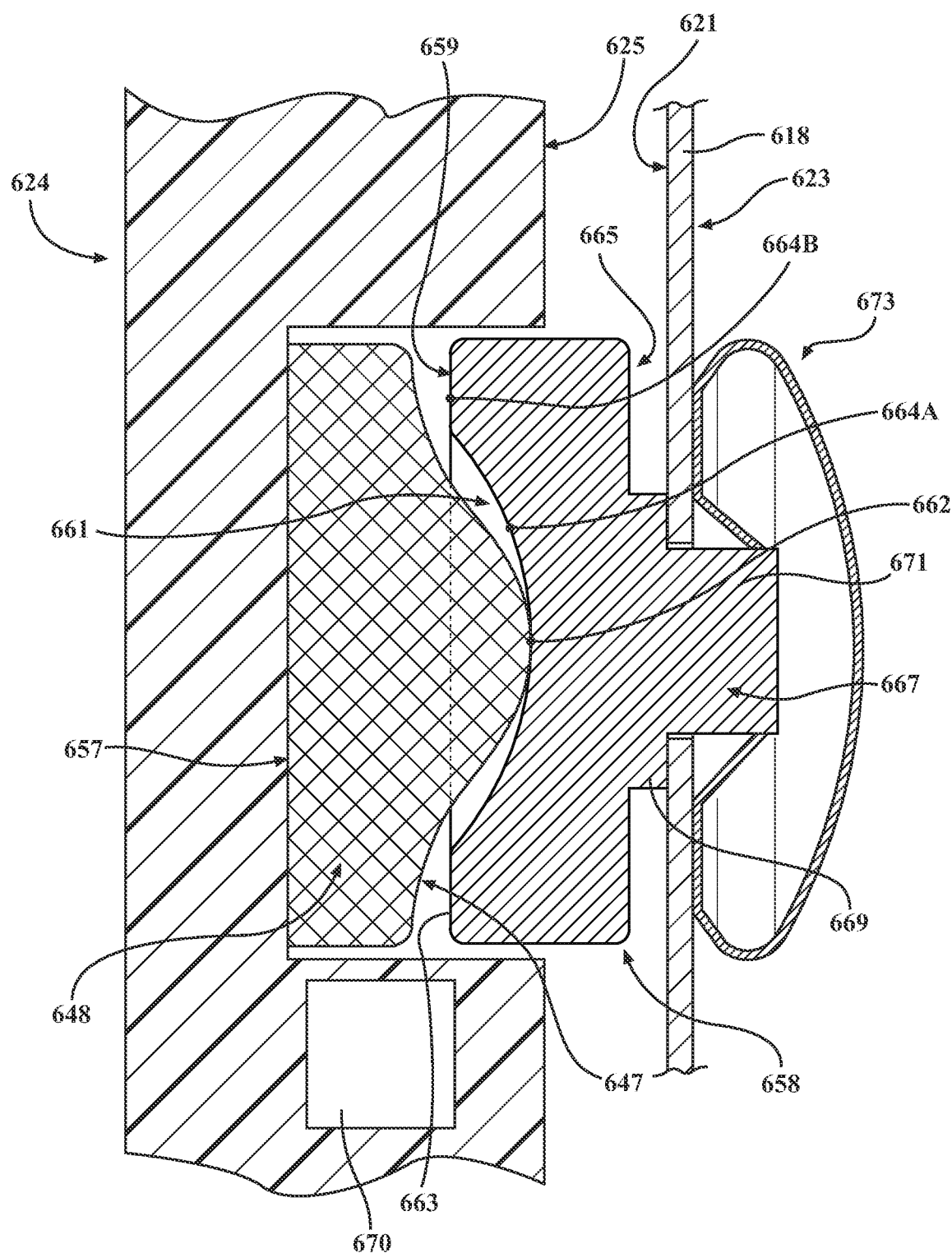
FIG. 40 is a partial sectional view of the attachment element of FIGS. 39A and 39B coupled to a surgical garment that is coupled to the coupling member of the surgical helmet of FIG. 37.

Referring to FIG. 40, the head 660 may further comprise a rim 663 that may be at least partially defined by the proximal surface 659 of the head 660. The rim 663 may at least partially surround the recess 661. The recess 661 may provide an increase in the surface area contact between the attachment element 658 and the coupling member 648 when coupled together. The increase in surface area contact can increase the strength and/or force of the magnetic bond between the attachment element 658 and the coupling member 648, which may increase the force required to decouple the attachment element 658 and the coupling member 648. This can reduce accidental or unintended decoupling of the attachment element 658 and the coupling member 648 during use of the surgical garment and surgical helmet 620. The size and/or shape of the recess 661 may also allow for the attachment element 658 and the coupling member 648 to interact at varying angles.

The recess 661 may be defined as a receding part, portion, or space, such as an indent, bay, or alcove. Generally, a recess 661 may refer to a void or absence of material. In the context of the attachment element 658 described above, the recess 661 may refer to a void or absence of material in the head 660. The size and shape of the void representing the recess 661 in the head 660 of the attachment element 658 may be defined by the proximal surface 659. However, the recess 661 is not limited to being formed by a single component, such as the head 660 of the attachment element 658. Any combination of components defining a void or absence of material may be considered a recess 661. For example, in one configuration the void representing the recess 661 may be defined by a combination of the head 660 and post 667. In yet another configuration, the void representing the recess 661 may be defined by a combination of the head 660 and the face shield 618. Various exemplary configurations of the proximal surface 659 of the attachment member 658, such as the recess 661 will be described in greater detail below.

The attachment element 658 may further comprise a post 667 extending distally from the distal surface 665 of the attachment element 658. The post 667 may comprise a proximal portion 669 and a distal portion 671. As described above, the proximal portion 669 of the post 667 may comprise a third dimension D3 and the distal portion 671 comprises a fourth dimension D4. The post 667 may be configured such that the third dimension D3 of the proximal portion 669 is larger than the fourth dimension D4 of the distal portion 671, creating a shoulder. The distal portion 671 of the post 667 should be configured to fit within an aperture 619 of the face shield 618 to facilitate coupling of the attachment element 658 to the face shield 618.

In the configuration of the post 667 wherein the third dimension D3 of the proximal portion 669 is larger than the fourth dimension D4 of the distal portion 671, the shoulder created by the proximal portion 669 of the post 667 is intended to space the head 660 of the attachment element 658 from the face shield 618. The shoulder may be utilized to space the head 660 from the face shield 618 to allow the face shield 618 to flex relative the distal surface 665 of the head 660. This flexibility enables a more robust attachment between the attachment element 658 and the coupling member 648 in that the face shield 618 can flex without jarring the attachment element 658 loose from its position attached to the coupling member 648. For example, an exemplary configuration of the post 667 may extend approximately three (3) millimeters from the distal surface 665 of the head 660. The distal portion 671 of the post 667 may comprise a diameter of approximately three (3) millimeters and a length of approximately two to two and a half (2-2.5) millimeters. The proximal portion 669 of the of the post 667 may comprise a diameter of approximately five (5) millimeters and a length of approximately half (0.5) a millimeter.

Referring to FIG. 39B, the attachment element 658 may be coupled to the face shield 618 by a retention feature 673. The retention feature 673 may take the form of a cap or similar fastener configured to engage the distal end of the post 667. For example, as illustrated in FIG. 39B, the post 667 may be inserted through the aperture 619 of the face shield and the retention feature 673 may be applied to the distal end of the post 667 to secure the attachment element 658 to the face shield 618. While not illustrated in the figures, it is contemplated that the attachment element 658 may be coupled to the transparent face shield 618 in other manners. For example, the post 667 and/or the head 660 of the attachment element 658 may be coupled to the transparent face shield 618 via an epoxy, glue, or similar type of adhesive. Alternatively, it is also contemplated that the post 667 may be shaped such that the distal portion 671 of the post 667 may be deformed or stamped after it the post 667 has been inserted through the aperture 619 in the transparent face shield 618 to secure the attachment element 658 to the transparent face shield 618.

Referring to FIG. 40, a partial sectional view of the attachment element 658 of the surgical garment coupled to the coupling member 648 of the chin bar 624 is illustrated. The coupling member 648 is positioned in a recess of the chin bar 624. The coupling member 648 comprises the protruded surface 647, which is positioned proximally to the distal surface 625 of the chin bar 624.

The protruded surface 647 of the coupling member 648 may extend at least partially into the recess 661 defined by the proximal surface 659 of the attachment element 658. The complementary shapes of the protruded surface 647 of the coupling member 648 and the proximal surface 659 of the attachment element 658 may be configured to be in sliding contact when the surgical garment 612 is coupled to the surgical helmet 620. Alternatively, it is contemplated that there may be a void space or a gap between all or a portion of the protruded surface 647 and the proximal surface 659. For example, the protruded surface 647 may comprise a sharp point having a small radius and the proximal surface 659 may comprise a concave shape having a larger radius relative to the radius of the protruded surface 647. In this configuration, the point or apex of the protruded surface 647 may contact a portion of the proximal surface 659, while having a gap between other portions of the protruded surface 647 and the proximal surface 659.

The complementary shapes of the protruded surface 647 of the coupling member 648 and the proximal surface 659 of the attachment element 658 may allow the attachment element 658 to pivot about the coupling member 648 and remain coupled with the coupling member 648 at varying angles. This may allow for additional freedom of movement and/or positioning of the face shield 618 as it is manipulated or flexed to couple the attachment elements 658 to the corresponding coupling members 648, such as during removal of one or more film layers from the face shield 618. Furthermore, the complementary shapes of the protruded surface 647 of the coupling member 648 and the proximal surface 659 of the attachment element 658 are designed to promote and/or maintain contact of the surgical garment 612 with the surgical helmet 620 during a medical procedure. By adding curvature to the coupling member 648 and/or the complementary proximal surface 659 of the attachment element 658 of the surgical garment 612, forces are transferred into the physical materials making up the coupling member 648 and/or the attachment element 658 when the coupling member 648 and/or the attachment element 658 are mated and put in shear, thereby increasing the holding or retaining force. Additional holding force is provided by the curved and/or recessed surface(s) because these surfaces can pivot in a position where there is optimal magnetic holding force provided by the magnetic material in interacting with the ferromagnetic material. Therefore, by allowing the attachment element 658 to rotate relative to the coupling member 648, the force (moment arm) created by shear is dissipated. Additional holding force is provided because of the increased surface area that is in contact or close proximity, resulting from curved versus flat surfaces.

To couple the surgical garment 612 to the surgical helmet 620, in certain configurations, at least a portion of the head 660 of the attachment element 658 may be at least partially disposed within the recess 627 of the chin bar 624 in order for the proximal surface 659 of the attachment element 648 to contact the protruded surface 647 of the coupling member 648. It is contemplated that a portion of the proximal surface 659 of the head 660 may be disposed within the recess 627 of the chin bar 624 such that the proximal surface 659 of the head 660 is positioned at least two millimeters (2-mm) proximally of the distal surface 625 of the chin bar 624. It is further contemplated that the proximal surface 659 of the head 660 may be positioned three millimeters (3-mm) or more proximally of the distal surface 625 of the chin bar 624. It is also contemplated that if the attachment element 658 is coupled to the coupling member 648 at an angle, as allowed for by the complementary surfaces 647, 659 of the respective attachment element 658 and the coupling member 648, the portion of the head 660 of the attachment element 658 disposed within the recess 627 of the chin bar 624 may defined as a percentage of the head 660 disposed within the recess 627. For example, at least ten percent (10%), 20, 30, 40, or 50% of the volume of the head 660 of the attachment element 658 may be disposed within the recess 627 of the chin bar 624. Furthermore, the coupling member 648 may be exposed in the chin bar 624 so that the coupling member 648 may be placed in contact with the attachment element 658.

As mentioned above, the coupling member 648 comprises one of a ferromagnetic material or a magnetic material and the attachment element 658 comprises the other of the ferromagnetic material or magnetic material, so that the coupling member 648 and the attachment element 658 may be magnetically attracted to one another. In the illustrated configurations, the coupling member 648 may comprise magnetic material, and hence a magnetic field may emanate from or otherwise be generated by the coupling member 648. When the coupling member 648 is coupled to the attachment element 658, the magnetic field surrounding the component comprising the magnetic material will be altered when the component comprising the ferromagnetic material is placed adjacent to it.

The detector 670, as illustrated in FIG. 40, may be positioned adjacent to the coupling member 648. The detector 670 may comprise a Hall-effect sensor configured to detect the change in the magnetic field, indicating the surgical garment 612 is coupled to the surgical helmet 620. For example, when the coupling member 648 comprises the magnetic material and the attachment element 658 comprises the ferromagnetic material, the detector 670 may detect a first level of the magnetic field surrounding the coupling member 648 when the attachment element 658 is separated from the coupling member 648. The detector 670 may then detect a second level of the magnetic field surrounding the coupling member 648 when the attachment element 658 is adjacent to the coupling member 648, indicating the surgical garment 612 is coupled to the surgical helmet 620. Alternatively, wherein the coupling member 648 comprises the ferromagnetic material and the attachment element 658 comprises the magnetic material, the detector 670 may detect the absence of the magnetic field surrounding the coupling member 648 when the attachment element 658 is separated from the coupling member 648. The detector 670 may then detect the presence of the magnetic field when the attachment element 658 is adjacent to the coupling member 648, indicating the surgical garment 612 is coupled to the surgical helmet 620. As described above, the controller may be configured to communicate operational commands to the detector 670 as well as be configured to receive a signal from the detector 670 related to a characteristic detected by the detector 670. The signal may be based on the presence of, absence of, and/or changes in the characteristic to be detected by the detector 670, which may be related to the presence or absence of the surgical garment 612 being coupled to the surgical helmet 620. The controller may also be connected to the one or more peripheral devices 630 of the surgical helmet 620, such as the ventilation assembly 630, wherein the controller is configured to communicate operational commands to and from the ventilation assembly 630, or other peripheral device 630 based on the signal received from the detector 670. For example, the controller may be configured to adjust the amount of power/voltage/current transmitted to the ventilation system 630 to control the speed of the fan blade.

Figure 41A:
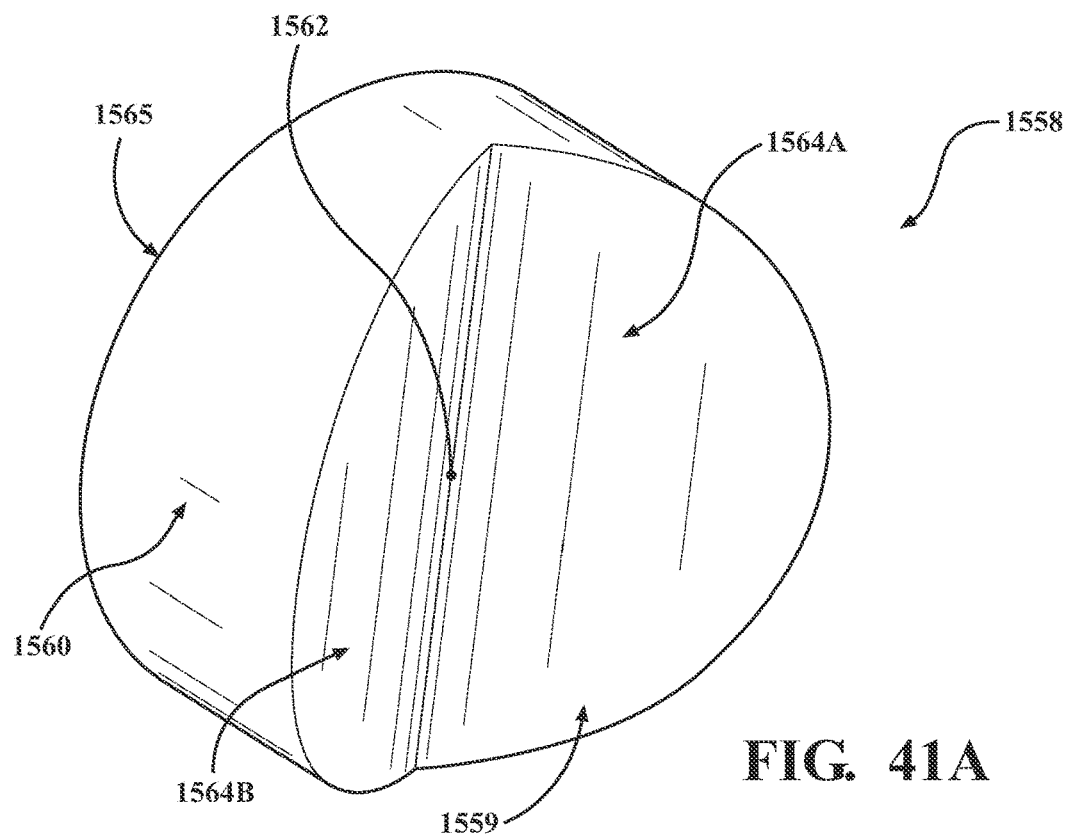
FIG. 41A is a front perspective view of a thirteenth configuration of the attachment element of the transparent face shield of FIGS. 39A and 39B.
Figure 41B:
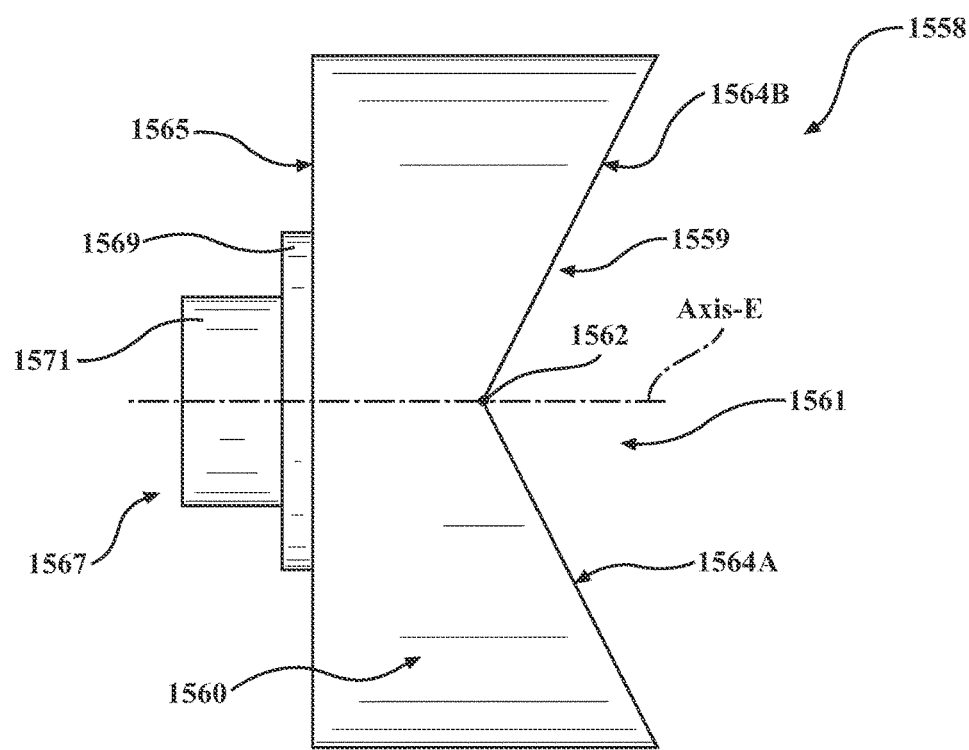
FIG. 41B is a side view of the thirteenth configuration of the attachment element of FIG. 41A.

The following are description of various alternative shapes and our configurations of the attachment element of the surgical garment assembly. It should be understood that any and all features, characteristics, and/or components of the system, assembly, and attachment element described above may also be applied to and/or incorporated into the various configurations of the attachment element described below. Referring to FIGS. 41A and 41B, a perspective view and a side view of a thirteenth configuration of an attachment element 1558 are illustrated. Similar to the attachment elements 658 described above, the thirteenth configuration of the attachment element 1558 comprises a head 1560 having a distal surface 1565 and an opposing proximal surface 1559. The head 1560 of the attachment element 1558 may comprise a generally cylindrical shape. The proximal surface 1559 of the head 1560 may comprise a first point 1562 defining a first distance D6 between the proximal surface 1559 and the first surface 621 of the transparent face shield 618. The proximal surface 1559 of the head 1560 may also comprise a second point 1564A, 1564B, defining a second distance D7 between the proximal surface 1559 and the first surface 621 of the transparent face shield 618. While not illustrated in the figures, it should be understood that first surface 621 of the transparent face shield 618 may be positioned distally of the distal surface 1565 of the head 1560. The proximal surface 1559 of the attachment element 1558 may be shaped such that the first distance D6 defined by the first point 1562 is less than the second distance D7 defined by the second point(s) 1564A, 1564B. For example, the attachment element 1558 may comprise a cylindrical head 1560 including a distal end and a proximal end. The proximal end may include a proximal surface 1559 having a first face angularly extending in a proximal direction from a medial plane of the cylindrical head to a first edge. The proximal surface 1559 may also have a second face angularly extending in the proximal direction from the medial plane of the cylindrical head to a second edge. The first point 1562 may be positioned on the proximal surface 1559 at the medial plane and the second point 1564A, 1564B may be positioned on the proximal surface 1559 at a point on at least one of the first and/or the second faces that angularly extend in the proximal direction. The first and the second faces of the proximal surface may generally define a recess 1561 in the head 1560 of the attachment element. It is contemplated that the depth and/or diameter of the cylindrical-shaped recess 1561 may be varied based on the angle of each of the first and second faces of the proximal surface 1559 to allow the proximal surface 1559 to matingly receive the protruded surface 647 of the coupling member 648 when coupled together. While the first and second faces of the proximal surface illustrated in FIGS. 41A and 41B comprises generally flat surfaces, it is contemplated that the proximal surface 1559 may define the recess 1561 to exhibit an arcuate shape.

Figure 42A:
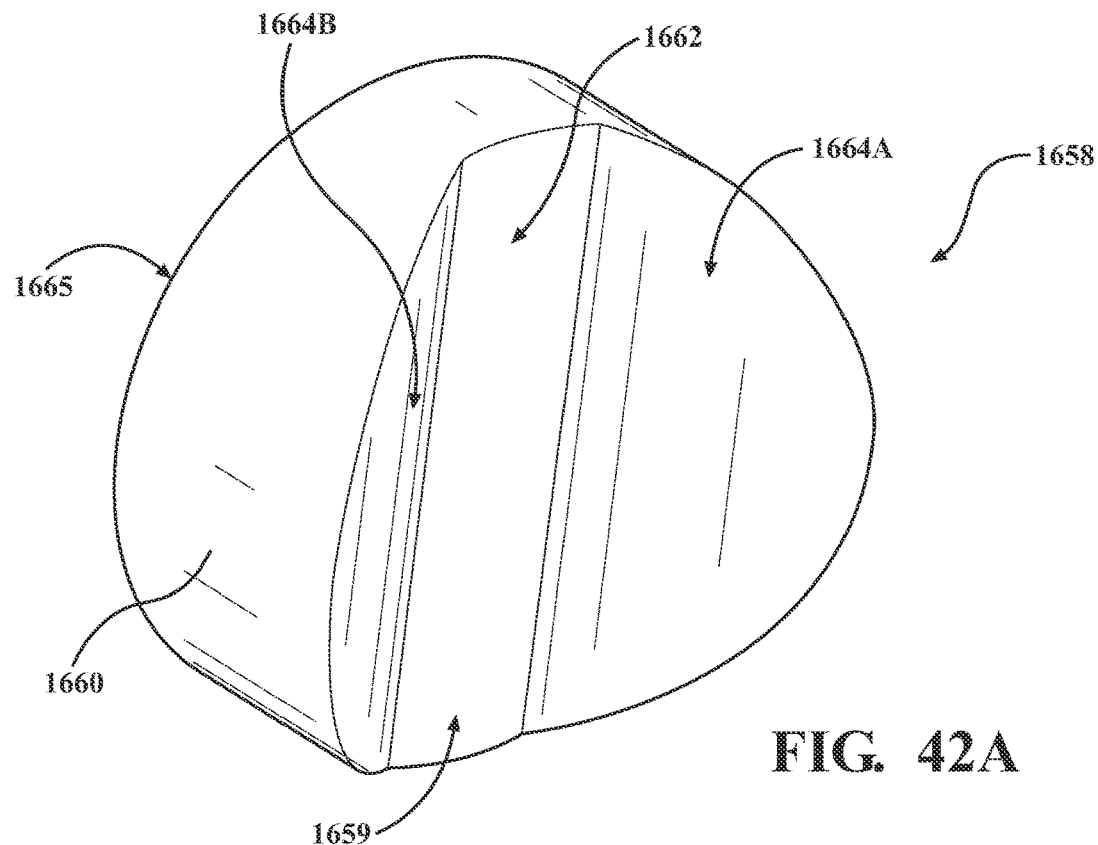
FIG. 42A is a front perspective view of a fourteenth configuration of the attachment element of the transparent face shield of FIGS. 39A and 39B.
Figure 42B:
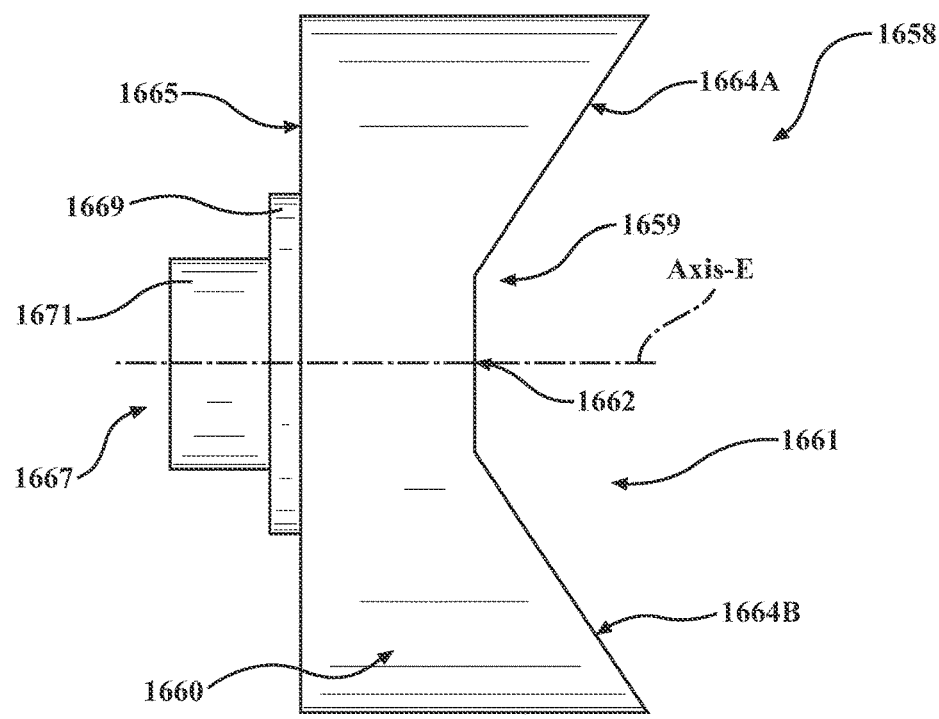
FIG. 42B is a side view of the fourteenth configuration of the attachment element of FIG. 42A.

Referring to FIGS. 42A and 42B, a perspective view and a side view of a fourteenth configuration of an attachment element 1658 are illustrated. Similar to the attachment elements 658 described above, the fourteenth configuration of the attachment element 1658 comprises a head 1660 having a distal surface 1665 and an opposing proximal surface 1659. The head 1660 of the attachment element 1658 may comprises a generally cylindrical shape. The proximal surface 1659 of the head 1660 may comprise a first surface 1662, wherein a point on the first surface 1662 may define a first distance D6 between the first surface 1662 and the first surface of the transparent face shield 618. The proximal surface 1659 of the head 1660 may also comprise a second surface 1664A, 1664B, wherein a point on the second surface 1664A, 1664B may define a second distance D7 between the second surface 1664A, 1664B and the first surface 621 of the transparent face shield 618. While not illustrated in the figures, it should be understood that first surface 621 of the transparent face shield 618 may be positioned distally of the distal surface 1665 of the head 1660. The proximal surface 1659 of the attachment element 1658 may be shaped such that the first distance D6 defined by the point on the first surface 1662 is less than the second distance D7 defined by the point on the second surface 1664A, 1664B. For example, the attachment element 1658 may comprises a cylindrical head including a distal end and a proximal end, the proximal end may define a proximal surface 1659 including a planar surface 1662 with a first side and a second side. The proximal surface may also include a first face 1664A angularly extending in a proximal direction from the first side of the planar surface 1662 to a first edge, and a second face 1664B angularly extending in the proximal direction from the second side of the planar surface 1662 to a second edge. The planar surface 1662 may be generally perpendicular to a longitudinal axis, Axis-E, of the attachment element 1658. The proximal surface 1659 may be shaped such that the first surface 1662 and the first and second face(s) 1664A, 1664B may generally define a recess 1661 in the head 1660 of the attachment element 1658. It is contemplated that the depth and/or diameter of the recess 1661 may be varied based on the angle of each of the first surface 1662 and the first and second faces 1664A, 1664B of the proximal surface 1659 to allow the proximal surface 1659 to matingly receive the protruded surface 647 of the coupling member 648 when coupled together. While the first surface 1662 and the first and second faces 1664A, 1664B of the proximal surfaces 1659 illustrated in FIGS. 42A and 42B comprises generally flat surfaces, it is contemplated that the proximal surface 1659 may define the recess 1661 to exhibit an arcuate shape.

Figure 43A:
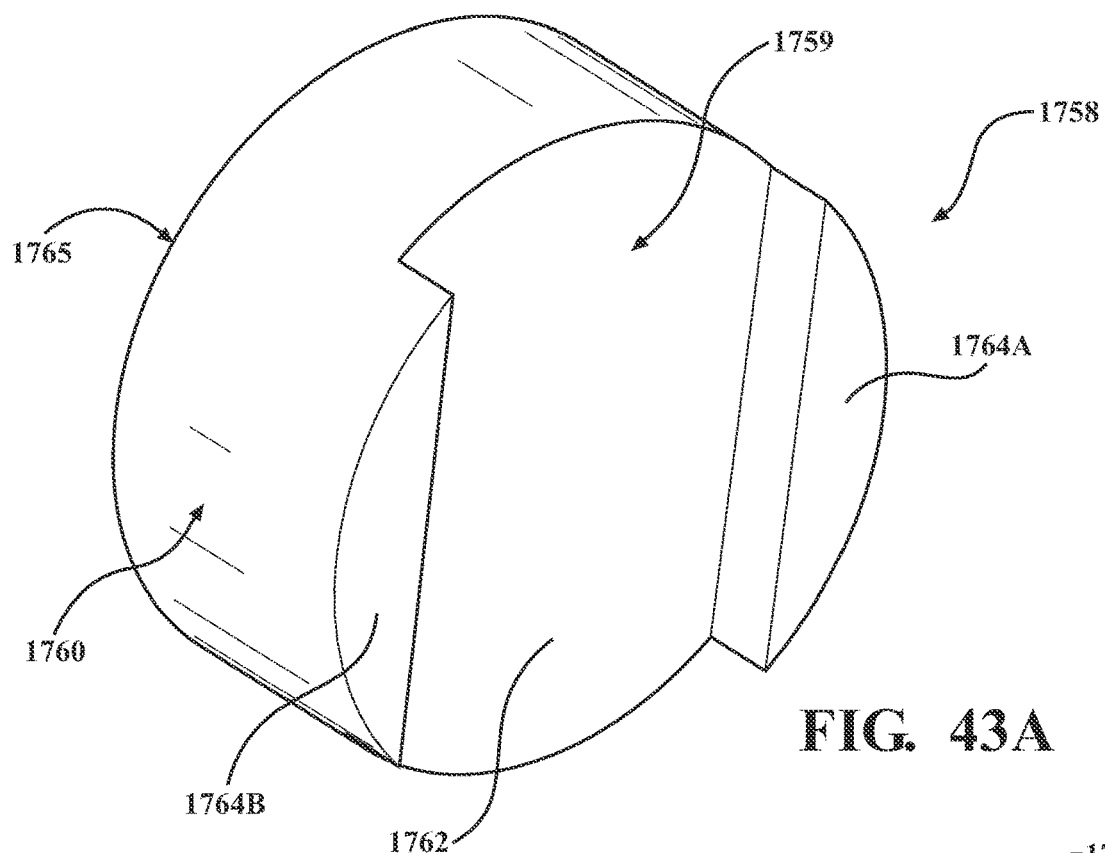
FIG. 43A is a front perspective view of a fifteenth configuration of the attachment element of the transparent face shield of FIGS. 39A and 39B.
Figure 43B:
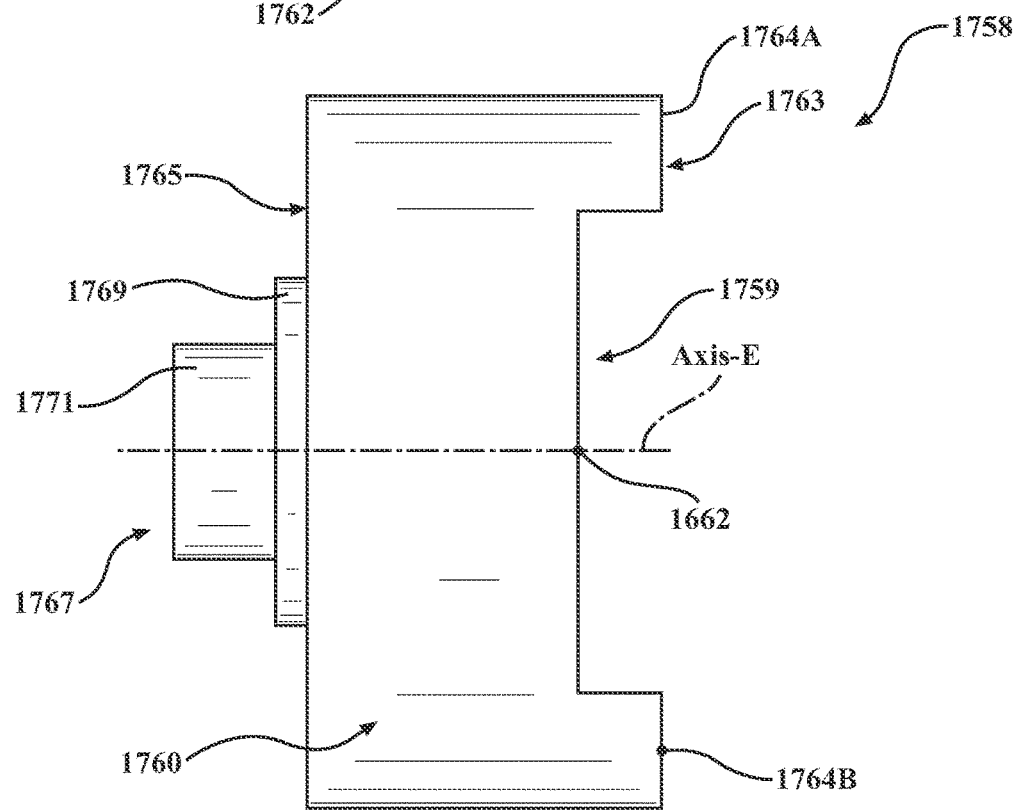
FIG. 43B is a side view of the fifteenth configuration of the attachment element of FIG. 43A.

Referring to FIGS. 43A and 43B, a perspective view and a side view of a fifteenth configuration of an attachment element 1758 are illustrated. Similar to the attachment elements 658 described above, the fifteenth configuration of the attachment element 1758 comprises a head 1760 having a distal surface 1765 and an opposing proximal surface 1759. The head 1760 of the attachment element 1758 may comprises a generally cylindrical shape. The proximal surface 1759 of the head 1760 may comprise a first surface 1762, wherein the first surface 1762 may be spaced a first distance D6 from the first surface of the transparent face shield 618. The proximal surface 1759 of the head 1760 may also comprise a second surface 1764A, 1764B, wherein the second surface 1764A, 1764B may be spaced a second distance D7 from the first surface of the transparent face shield 618. While not illustrated in the figures, it should be understood that first surface 621 of the transparent face shield 618 may be positioned distally of the distal surface 1765 of the head 1760. The proximal surface 1759 of the attachment element 1758 may be shaped such that the first distance D6 defined by the first surface 1762 is less than the second distance D7 defined by the second surface 1764A, 1764B. For example, the attachment element 1758 may comprise a cylindrical head 1760 including a distal end and a proximal end, the proximal end may define a proximal surface 1759 including a planar surface 1762 with a first side and a second side. The proximal surface 1759 may also include a first leg including a first face 1764A, the first face spaced proximally of the first side of the planar surface 1762, and a second leg including a second face 1764B, the second face 1764B spaced proximally from the second side of the planar surface 1762 to a second edge. The planar surface 1762 may be generally perpendicular to a longitudinal axis, Axis-E, of the attachment element 1758. The proximal surface 1759 may be shaped such that the first surface 1662 and the first and second face(s) 1764A, 1764B may generally define a recess 1761 in the head 1760 of the attachment element 1758. It is contemplated that the depth and/or diameter of the recess 1761 may be varied based on the angle of each of the first and second surfaces 1762, 1764A, 1764B of the proximal surface 1759 to allow the proximal surface 1759 to matingly receive the protruded surface 647 of the coupling member 648 when coupled together. While the first surface 1762 and the first and second faces 1764A, 1764B of the proximal surfaces 1759 illustrated in FIGS. 43A and 43B comprises generally flat surfaces, it is contemplated that the proximal surface 1759 may define the recess 1761 to exhibit an arcuate shape.

Figure 44A:
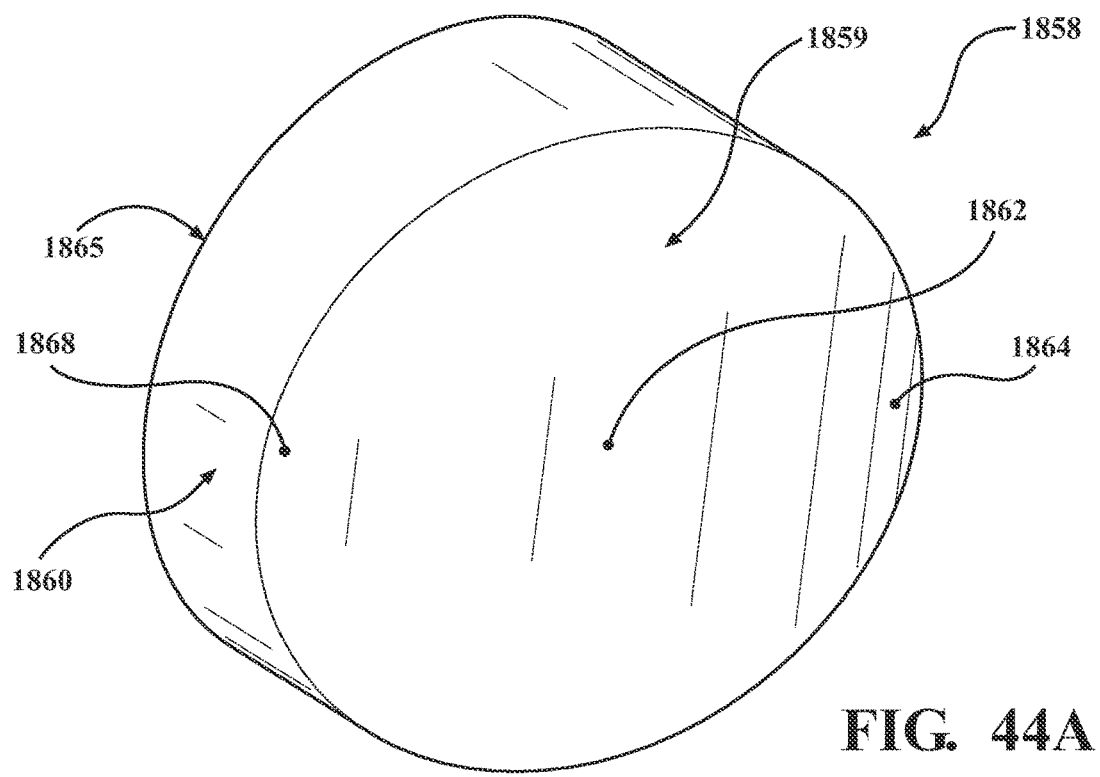
FIG. 44A is a front perspective view of a sixteenth configuration of the attachment element of the transparent face shield of FIGS. 39A and 39B.
Figure 44B:
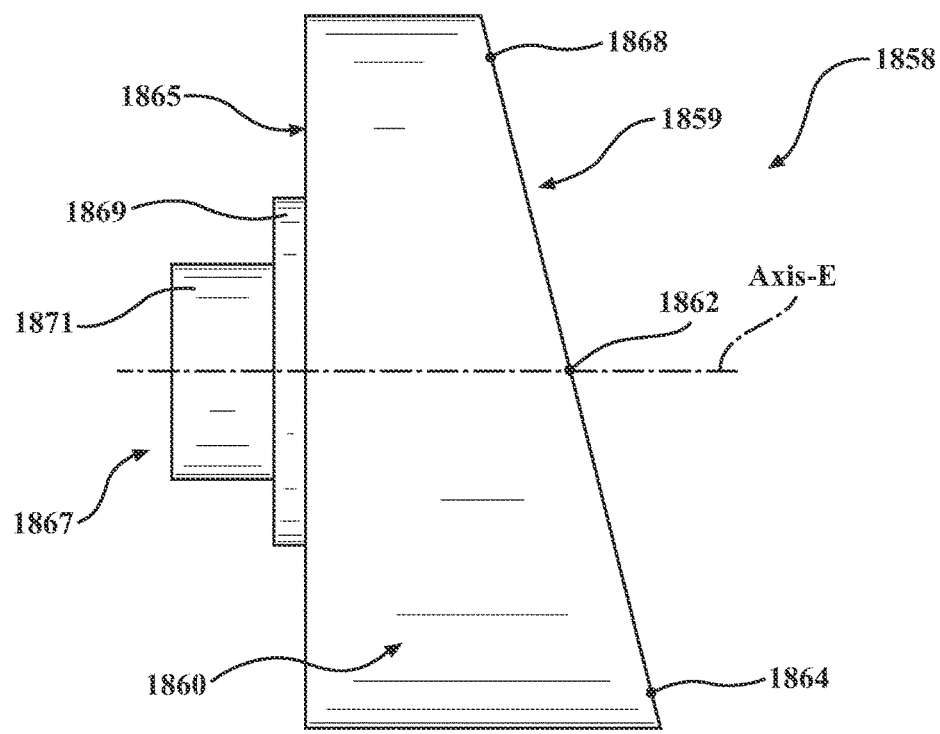
FIG. 44B is a side view of the sixteenth configuration of the attachment element of FIG. 44A.
Figure 44C:
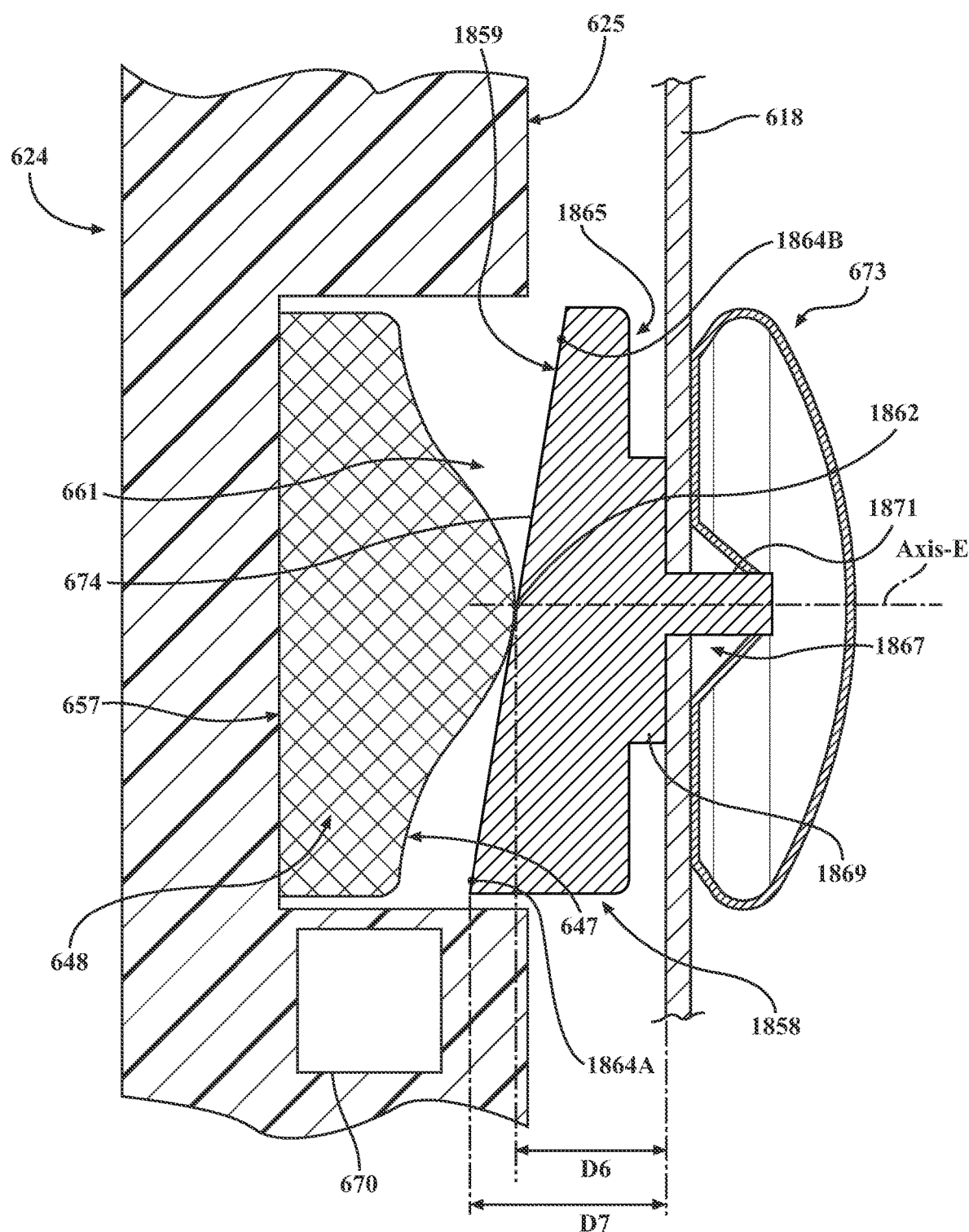
FIG. 44C is a partial sectional view of the sixteenth configuration of the attachment element of a surgical garment coupled to the coupling member of the surgical helmet of FIG. 37.

Referring to FIGS. 44A-44C, various views of a sixteenth configuration of an attachment element 1858 are illustrated. Similar to the attachment elements 658 described above, the sixteenth configuration of the attachment element 1858 comprises a head 1860 having a distal surface 1865 and an opposing proximal surface 1859. The head 1860 of the attachment element 1858 may comprises a generally cylindrical shape. The proximal surface 1859 of the head 1860 may comprise a first point 1862 defining a first distance D6 between the proximal surface 1859 and the first surface of the transparent face shield 618. The proximal surface 1859 of the head 1860 may also comprise a second point 1864A defining a second distance D7 between the proximal surface 1859 and the first surface of the transparent face shield 618. While not illustrated in the figures, it should be understood that first surface 621 of the transparent face shield 618 may be positioned distally of the distal surface 1865 of the head 1860. The proximal surface 1859 of the attachment element 1858 may be shaped such that the first distance D6 defined by the first point 1862 is less than the second distance D7 defined by the second point 1864A. For example, the attachment element 1858 may comprise a cylindrical head 1860 including a distal end with a distal surface 1865 and a proximal end with a proximal surface 1859. The proximal surface 1859 may be configured to angularly extend in a proximal direction from a first edge of the cylindrical body to a second edge of the cylindrical body. In yet another example, the proximal surface 1859 of the head 1860 may comprise a generally circular profile. The first point 1862 may be positioned at the center of the proximal surface 1859, and the second point 1864A may be radially spaced from the first point 1862. Furthermore, the first point 1862 may define a first distance D6 from the first surface 621 of the transparent face shield 618 and the second point 1864A may define a second distance D7 from the first surface 621 of the transparent face shield 618. The proximal surface 1859 of the head 1860 may be shaped such that the first distance D6 defined by the first point 1862 is less than the second distance D7 defined by the second point 1864A defining a sloped proximal surface 1859. It is contemplated that the slope and/or size of the proximal surface 1859 may be varied to allow the proximal surface 1859 to engage the protruded surface 647 of the coupling member 648 when coupled together. While the proximal surface 1859 illustrated in FIGS. 44A and 44B comprises a generally flat surface, it is contemplated that the proximal surface 1859 may exhibit an arcuate shape.

Referring to 44C, a partial sectional view of the attachment element 1858 of the surgical garment coupled to the coupling member 648 of the chin bar 624 is illustrated. The coupling member 648 is positioned in a recess of the chin bar 624. The coupling member 624 comprises the protruded surface 647, which is positioned proximally to the distal surface 625 of the chin bar 624.

The protruded surface 647 of the coupling member 648 may extend and be positioned adjacent a portion of the proximal surface 1859 of the attachment element 1858. The complementary shapes of the protruded surface 647 of the coupling member 648 and the proximal surface 1859 of the attachment element 1858 may be configured to be in sliding contact when the surgical garment is coupled to the surgical helmet 620. Alternatively, it is contemplated that there may be a void space or a gap between all or a portion of the protruded surface 647 and the proximal surface 1859. For example, the protruded surface 647 may comprise a sharp point having a small radius and the proximal surface 1859 may comprise a sloped profile. As described above, the proximal surface 1859 of the head 1860 may comprise a first point 1862 defining a first distance D6 between the proximal surface 1859 and the first surface of the transparent face shield 618. The proximal surface 1859 of the head 1860 may also comprise a second point 1864A, 1864B, defining a second distance D7 between the proximal surface 1859 and the first surface of the transparent face shield 618. The proximal surface 1859 of the attachment element 1858 may be shaped such that the first distance D6 defined by the first point 1862 is less than the second distance D7 defined by the second point(s) 1864A, 1864B. The attachment element 1858 may be oriented relative to the transparent face shield 618 such that the second point 1864A, which is spaced further from the first surface 621 of the transparent face shield 618 than the first point 1862, may be positioned proximate the detector 670 when coupled to the coupling member 648 of the surgical helmet 620. For example, wherein the detector 670 is positioned lateral to the coupling member 648 (as shown in FIG. 37), the attachment element 1858 may be oriented on the transparent face shield 618 such that the second point 1864A is positioned further from the midline, Axis-m, of the transparent face shield 618 than the first point 1862. This may allow the portion of the distal surface 1859 of the head 1860 that comprises the second point 1864A to be positioned nearer the detector 670, allow the detector to be triggered when the surgical garment 612 is coupled to the surgical helmet 620.

Figure 45A:
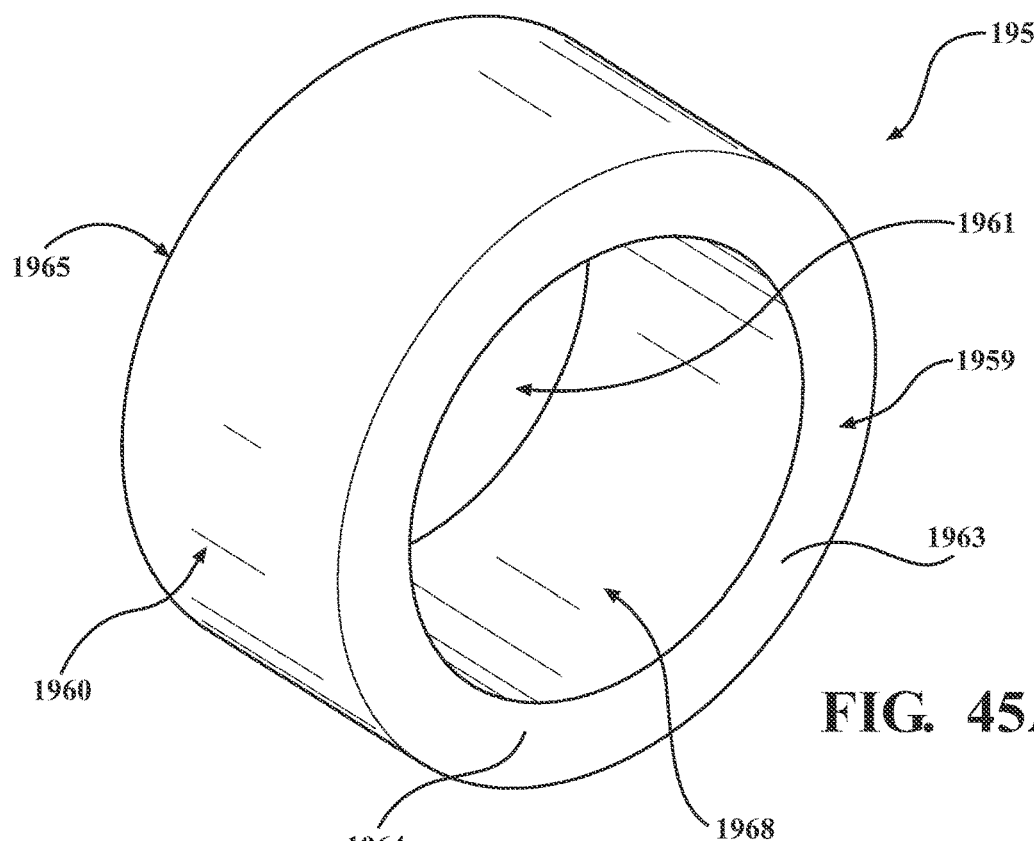
FIG. 45A is a front perspective view of a seventeenth configuration of the attachment element of the transparent face shield of FIGS. 39A and 39B.
Figure 45B:
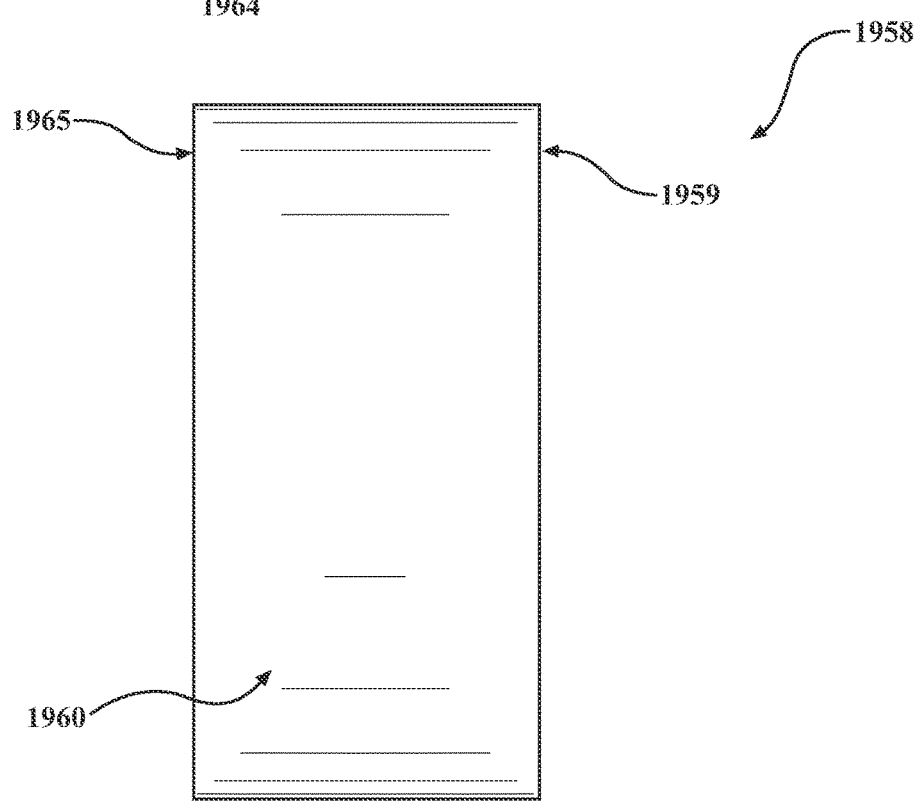
FIG. 45B is a side view of the seventeenth configuration of the attachment element of FIG. 45A.

Referring to FIGS. 45A and 45B, a perspective view and a side view of a seventeenth configuration of an attachment element 1958 are illustrated. Similar to the attachment elements 658 described above, the seventeenth configuration of the attachment element 1958 comprises a head 1960 having a distal surface 1965 and an opposing proximal surface 1959. The head 1960 of the attachment element 1958 may comprises a generally cylindrical shape. The proximal surface 1959 of the head 1960 may comprise an aperture 1968 extending along the longitudinal axis, Axis-E, of the head 1960. The head 1960, in combination with the first surface 621 of the transparent face shield 618, may be shaped to define a recess 1961 when coupled to the transparent shield 618. The proximal surface 1659 of the head 1960 may also comprise a rim 1963 encircling the aperture 1968. The recess 1961 defined by the combination of the head 1960 and the transparent face shield 618 may comprise a first point that is disposed within the aperture 1968 and positioned on the first surface 621 of the transparent face shield 618. A second point 1964 may be disposed on the proximal surface 1959 of the head 1960, such that the second point 1964 may be spaced proximally away from the first surface 621 of the face shield 618. For example, the second point 1964 may be on the rim 1963. With the first point 1962 being disposed on the first surface 621 of the transparent face shield 618, and the second point being on the rim 1963 of the attachment element 1958, the second point 1964 is further away from the first surface 621 of the transparent face shield 618 than the first point 1962 is. The attachment element 1958 in combination with the transparent face shield 618 may be shaped to generally define the recess 1961 in the head 1960 of the attachment element 1958. It is contemplated that the depth and/or diameter of the recess 1961 may be varied based on the size and shape of the aperture 1968 in the head 1960 to allow the proximal surface 1959 to matingly receive the protruded surface 647 of the coupling member 648 when coupled together.

Figure 46A:
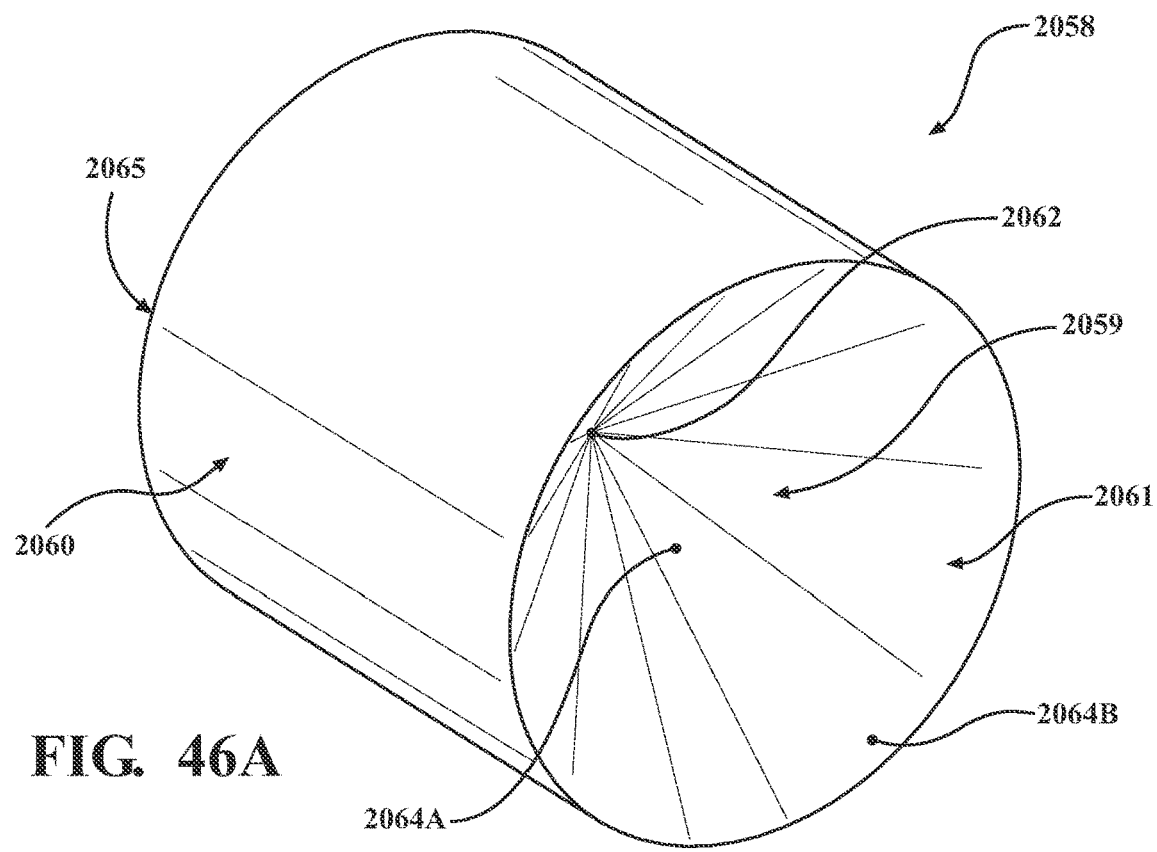
FIG. 46A is a front perspective view of an eighteenth configuration of the attachment element of the transparent face shield of FIGS. 39A and 39B.
Figure 46B:
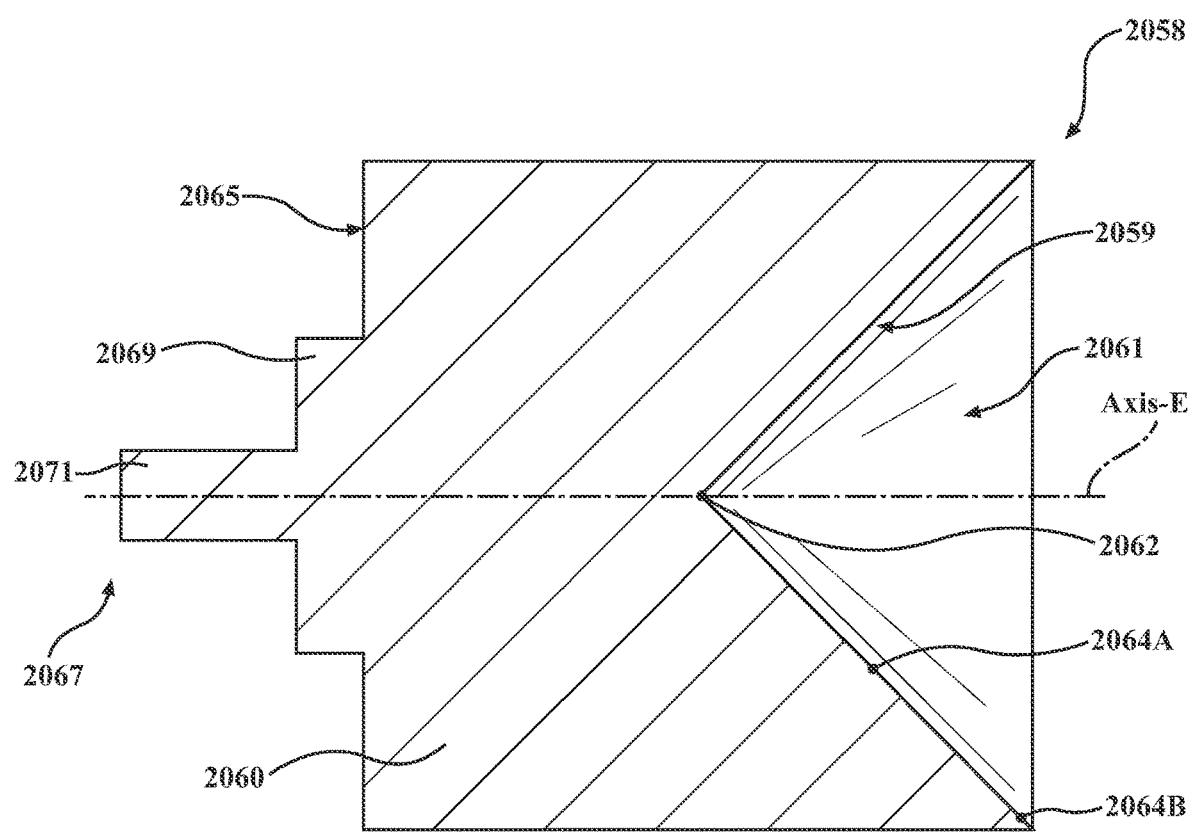
FIG. 46B is a side view of the eighteenth configuration of the attachment element of FIG. 46A.

Referring to FIGS. 46A and 46B, a perspective view and a sectioned side view of an eighteenth configuration of an attachment element 2058 are illustrated. Similar to the attachment elements 658 described above, the eighteenth configuration of the attachment element 2058 comprises a head 2060 having a distal surface 2065 and an opposing proximal surface 2059. The head 2060 of the attachment element 2058 may comprises a generally cylindrical shape. The proximal surface 2059 of the head 2060 may comprise a first point 2062 defining a first distance D6 between the proximal surface 2059 and the first surface 621 of the transparent face shield 618. The proximal surface 2059 of the head 2060 may also comprise a second point 2064A, 2064B, defining a second distance D7 between the proximal surface 2059 and the first surface 621 of the transparent face shield 618. While not illustrated in the figures, it should be understood that first surface 621 of the transparent face shield 618 may be positioned distally of the distal surface 2065 of the head 2060. The proximal surface 2059 of the attachment element 2058 may be shaped such that the first distance D6 defined by the first point 2062 is less than the second distance D7 defined by the second point(s) 2064A, 2064B. For example, the attachment element 2058 may comprise a cylindrical head 2060 including a distal end with a distal surface 2065 and a proximal end with a proximal surface 2059. The proximal surface 2059 may be may comprise a cone-shaped recess 2061. The first point 2062 may be positioned at the center or point of the cone-shaped recess 2061 of the proximal surface 2059, and each of the one or more second point(s) 2064A, 2064B may be radially spaced from the first point 2062. The proximal surface 2059 of the head 2060 may be shaped such that the first distance D6 defined by the first point 2062 is less than the second distance D7 defined by the second point(s) 2064A, 2064B defining a cone-shaped surface 659. It is contemplated that the slope and/or size of the cone-shaped recess 2061 of the proximal surface 2059 may be varied to allow the proximal surface 2059 to engage the protruded surface 647 of the coupling member 648 when coupled together. While the proximal surface 2059 illustrated in FIGS. 46A and 46B comprises a generally flat surface, it is contemplated that the proximal surface 2059 may exhibit an arcuate shape.

Figure 47A:
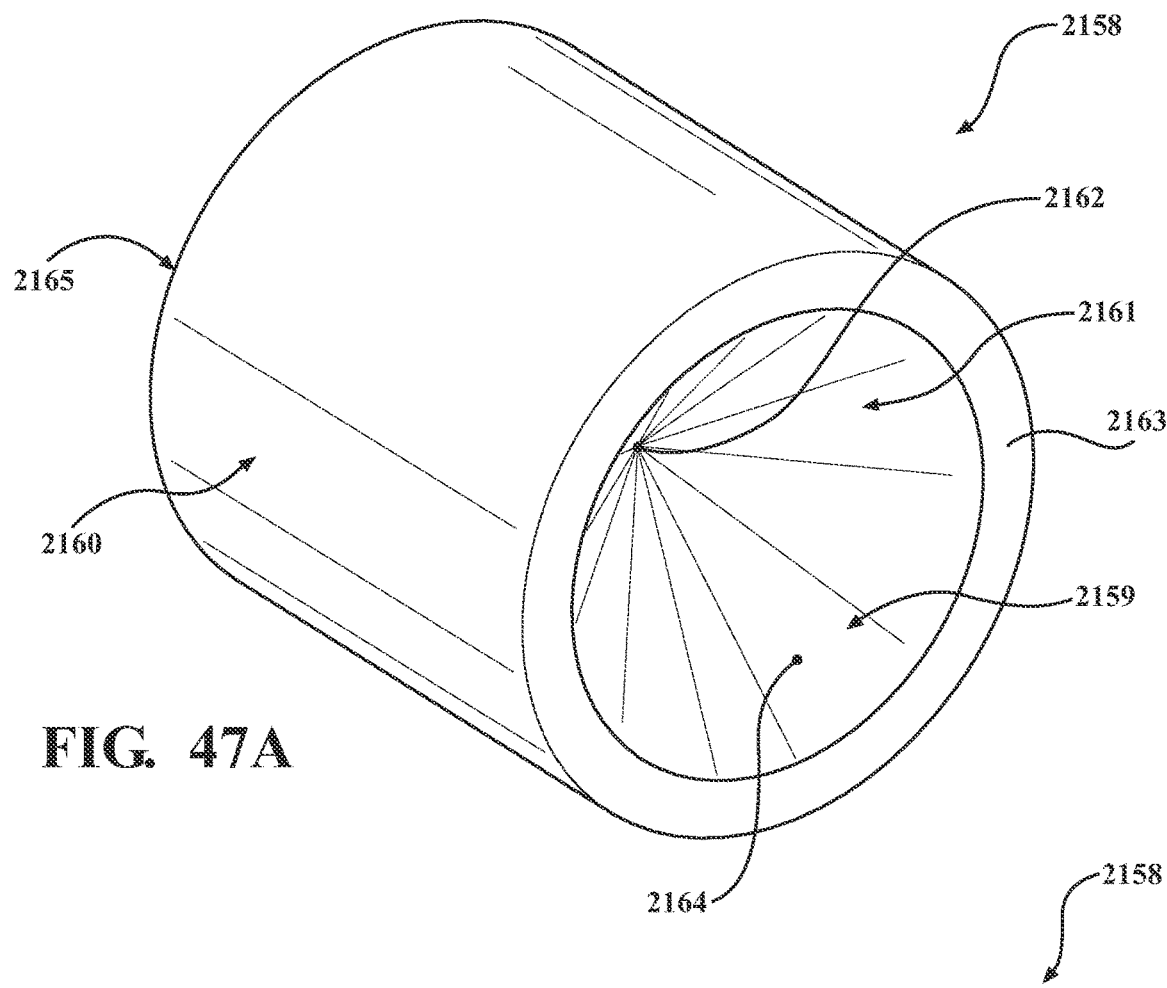
FIG. 47A is a front perspective view of a nineteenth configuration of the attachment element of the transparent face shield of FIGS. 39A and 39B.
Figure 47B:
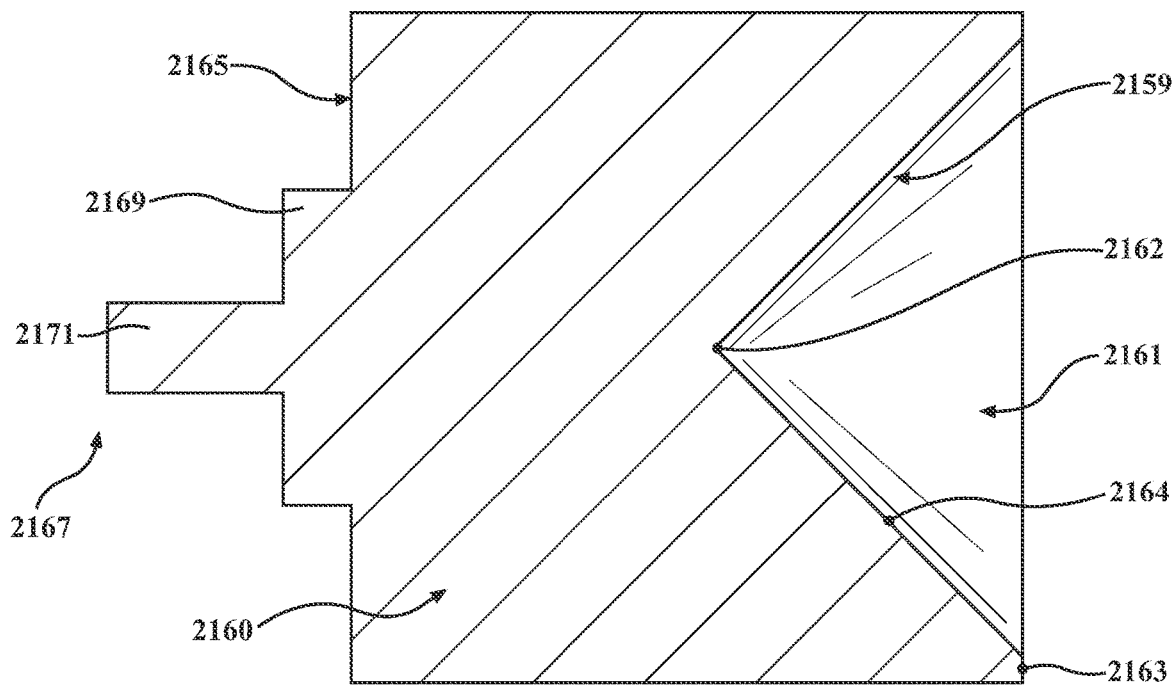
FIG. 47B is a side view of the nineteenth configuration of the attachment element of FIG. 47A.

Referring to FIGS. 47A and 47B, a perspective view and a sectioned side view of a nineteenth configuration of an attachment element 2158 are illustrated. Similar to the attachment elements 658 described above, the nineteenth configuration of the attachment element 2158 comprises a head 2160 having a distal surface 2165 and an opposing proximal surface 2159. The head 2160 of the attachment element 2158 may comprises a generally cylindrical shape. The proximal surface 2159 of the head 2160 may comprise a first point 2162 defining a first distance D6 between the proximal surface 2159 and the first surface 621 of the transparent face shield 618. The proximal surface 2159 of the head 2160 may also comprise a second point 2164, defining a second distance D7 between the proximal surface 2159 and the first surface 621 of the transparent face shield 618. While not illustrated in the figures, it should be understood that first surface 621 of the transparent face shield 618 may be positioned distally of the distal surface 2165 of the head 2160. The proximal surface 2159 of the attachment element 2158 may be shaped such that the first distance D6 defined by the first point 2162 is less than the second distance D7 defined by the second point(s) 2164. For example, the attachment element 2158 may comprise a cylindrical head 2160 including a distal end with a distal surface 2165 and a proximal end with a proximal surface 2159. The proximal surface 2159 may be may comprise a cone-shaped recess 2161. The proximal surface 2159 may also comprise a rim 2163 encircling the cone-shaped recess 2161. The rim 2163 may increase the amount and/or mass of ferromagnetic material at the periphery of the head 2160 near the proximal surface 2159. This may assist in triggering the detector 670 positioned adjacent the coupling member 648. The first point 2162 may be positioned at the center or point of the cone-shaped recess 2161 of the proximal surface 2159, and each of the one or more second point(s) 2164 may be radially spaced from the first point 2162. The proximal surface 2159 of the head 2160 may be shaped such that the first distance D6 defined by the first point 2162 is less than the second distance D7 defined by the second point(s) 2164, defining a cone-shaped proximal surface 2159. It is contemplated that the slope and/or size of the cone-shaped recess 2161 of the proximal surface 2159 may be varied to allow the proximal surface 2159 to engage the protruded surface 647 of the coupling member 648 when coupled together. While the proximal surface 2159 illustrated in FIGS. 47A and 47B comprises a generally flat surface, it is contemplated that the proximal surface 2159 may exhibit an arcuate shape.

Figure 48A:
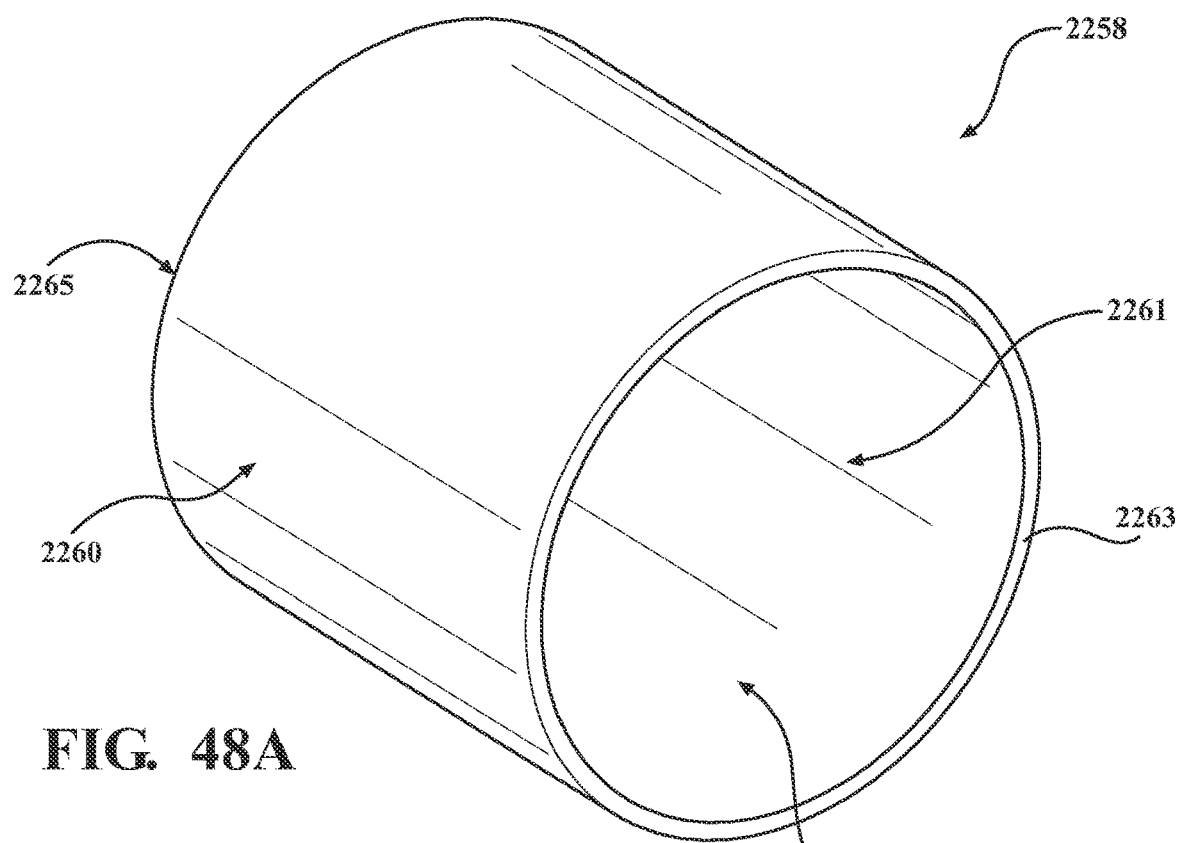
FIG. 48A is a front perspective view of a twentieth configuration of the attachment element of the transparent face shield of FIGS. 39A and 39B.
Figure 48B:
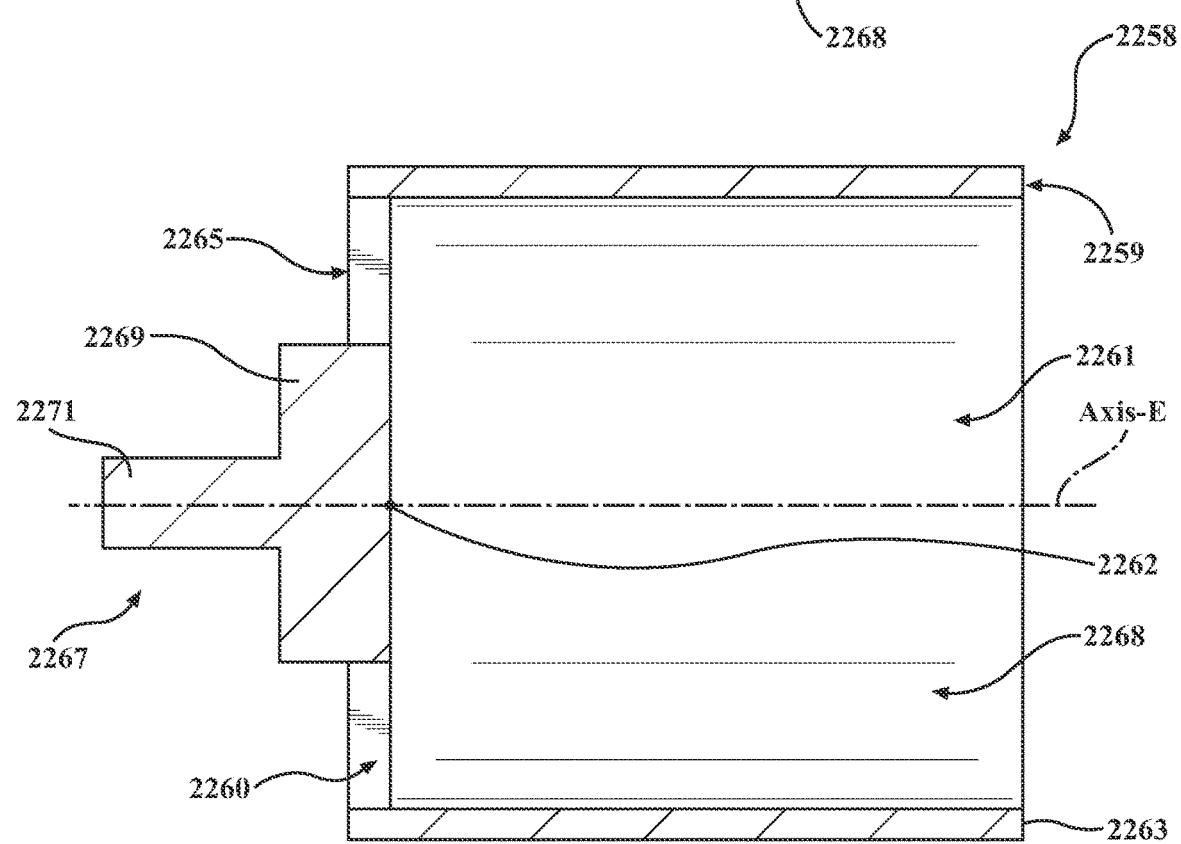
FIG. 48B is a side view of the twentieth configuration of the attachment element of FIG. 48A.

Referring to FIGS. 48A and 48B, a perspective view and a sectioned side view of a twentieth configuration of an attachment element 2258 are illustrated. Similar to the attachment elements 658 described above, the twentieth configuration of the attachment element 2258 comprises a head 2260 having a distal end 2265 and an opposing proximal end 2259. The head 2260 of the attachment element 2258 may comprise a generally cylindrical shape. For example, the attachment element 2258 may comprise a cylindrical head including a bore. The bore may extend along a longitudinal axis of the head 2260 between a closed distal end 2265 and an open proximal end 2259. The bore creating the open proximal end 2259 of the attachment element 2258 may be shaped to define a cylinder-shaped recess 2261 in the head 2260. The proximal end 2259 may also comprise a rim encircling the bore. It is contemplated that the slope and/or size of the cylinder-shaped recess 2261 of the proximal end 2259 may be varied to allow the proximal end 2259 to engage the protruded surface 647 of the coupling member 648 when coupled together. While the proximal end 2259 illustrated in FIGS. 48A and 48B comprises a generally flat surface, it is contemplated that the proximal surface 2259 may exhibit an arcuate shape.

Figure 49A:
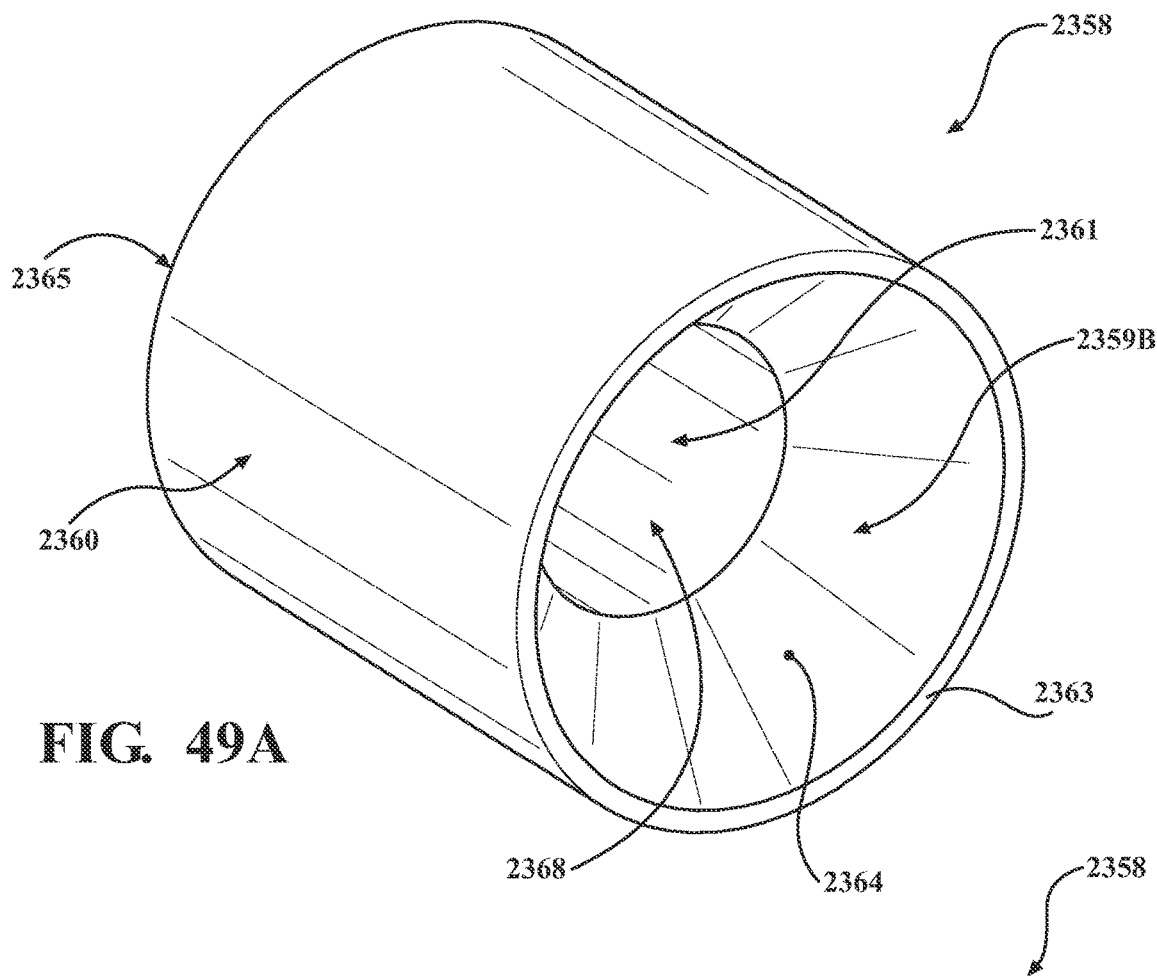
FIG. 49A is a front perspective view of a twenty-first configuration of the attachment element of the transparent face shield of FIGS. 39A and 39B.
Figure 49B:
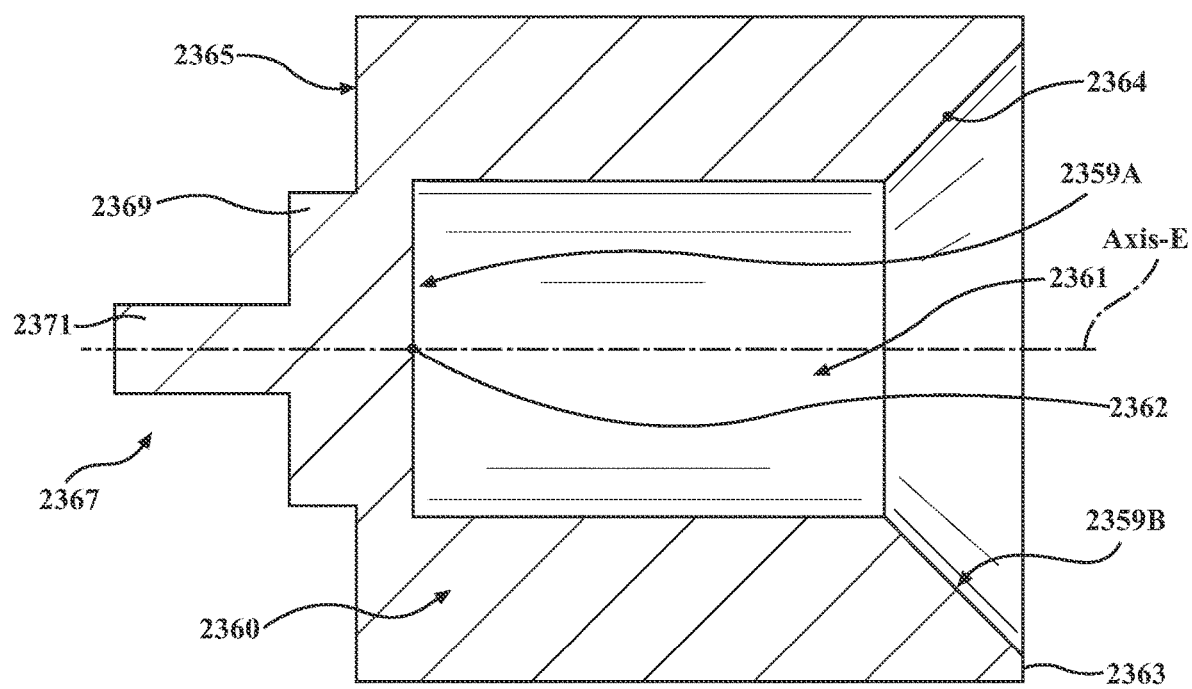
FIG. 49B is a side view of the a twenty-first configuration of the attachment element of FIG. 49A.

Referring to FIGS. 49A and 49B, a perspective view and a sectioned side view of a twenty-first configuration of an attachment element 2358 are illustrated. Similar to the attachment elements 658 described above, the twenty-first configuration of the attachment element 2358 comprises a head 2360 having a distal surface 2365 and an opposing proximal surface 2359. The head 2360 of the attachment element 2358 may comprises a generally cylindrical shape. For example, the attachment element 2358 may comprise a cylindrical head 2260 including a bore 2268. The bore 2268 may extend along a longitudinal axis, Axis-E, between a closed distal end and an open proximal end. The bore 2268 creating the open proximal end 2359 of the attachment element 2358 may be shaped to define a cylinder-shaped recess 2361 in the proximal surface 2359 of the head 2360. The bore 2268 may include a mouth encircling the open end of the bore 2268. The mouth may be configured to taper or slope circumferentially from the open proximal end towards the hollow passage defined by the bore 2268. The proximal end 2359 may also comprise a rim 2363 encircling the bore 2268 and/or the mouth of the bore 2268 to maintain a sufficient amount and/or mass of the ferromagnetic material of the head 2360 to trigger the detector 670 positioned adjacent the coupling member 648. It is contemplated that the slope and/or size of the taper of the mouth that defines a portion of the recess 2361 in the proximal end 2359 may be varied to allow the proximal surface 2359 to engage the protruded surface 647 of the coupling member 648 when coupled together. Referring to FIG. 50, the head 2360 may also comprise a first point 2362 on the proximal surface that defines a first distance D6 between the proximal surface 2359 and the first surface 621 of the transparent face shield 618. The head 2360 may also comprise a second point 2364 on the proximal surface 2359 that defines a second distance D7 between the proximal surface 2359 and the first surface 621 of the transparent face shield 618. For example, the first point 2362 on the proximal surface 2359 may be positioned at the distal most point of the bore 2368. The second point 2364 may positioned on the mouth and/or the rim 2363 of the proximal surface 2359. The proximal surface 2359 of the attachment element 2358 may be shaped such that the first distance D6 defined by the first point 2362 is less than the second distance D7 defined by the second point(s) 2364 forming the recess 2361. While not illustrated in the figures, it should be understood that first surface 621 of the transparent face shield 618 may be positioned distally of the distal surface 2365 of the head 2360. Furthermore, while the proximal surface 2359 illustrated in FIGS. 49A and 49B comprises a generally flat surface, it is contemplated that the proximal surface 2359 may exhibit an arcuate shape.

Referring to FIGS. 50A-50F, various views of a twenty-second and twenty-third configuration of an attachment element 2458, 2558 are illustrated. FIGS. 50A-50D include the twenty-second configuration of the attachment element 2458. The attachment element 2458 may be configured to couple to the transparent shield 618. The attachment element 2458 may comprise a head 2460. The head 2460 may define a dimension, wherein the dimension of the head is less than a dimension of the aperture in the chin bar 624, such that the head 2460 is sized to be inserted within the aperture of the chin bar 624 when coupled to the coupling member 648. The head 2460 of the attachment element 2458 may also define a distal surface 2465 and an opposing proximal surface 2459. A first point 2462 may be positioned on the proximal surface 2459 of the head 2460. The first point 2462 may be positioned at a center of the proximal surface 2459. Alternatively, the first point 2462 may be positioned at a location on the proximal surface 2459 that in intersects with a first axis, Axis-E, of the attachment element 2458. The first axis, Axis-E, may also be the longitudinal axis of the attachment element 2458. A second point 2464 may also be positioned on the proximal surface 2459 of the head 2460. Generally, the second point(s) 2464 may be positioned on the proximal surface 2459 such that it is spaced apart from the first point 2462 on the proximal surface 2459. For example, where the proximal surface 2459 of the head 2460 comprises a generally circular profile, the first point 2462 may be positioned at the center of the proximal surface 2459, and the second point 2464 may be radially spaced from the first point 2462.

The attachment element 2458 may further comprise a post 2467 extending distally from the distal surface 2465 of the attachment element 2458. The post 2467 may comprise a proximal portion 2469 and a distal portion 2471. As described above, the proximal portion 2469 of the post 2467 may comprise a third dimension D3 and the distal portion 2471 comprises a fourth dimension D4. The post 2467 may be configured such that the third dimension D3 of the proximal portion 2469 is larger than the fourth dimension D4 of the distal portion 2471, creating a shoulder. The distal portion 2471 of the post 2467 should be configured to fit within an aperture 619 of the face shield 618 to facilitate coupling of the attachment element 2458 to the face shield 618.

Figure 50A:
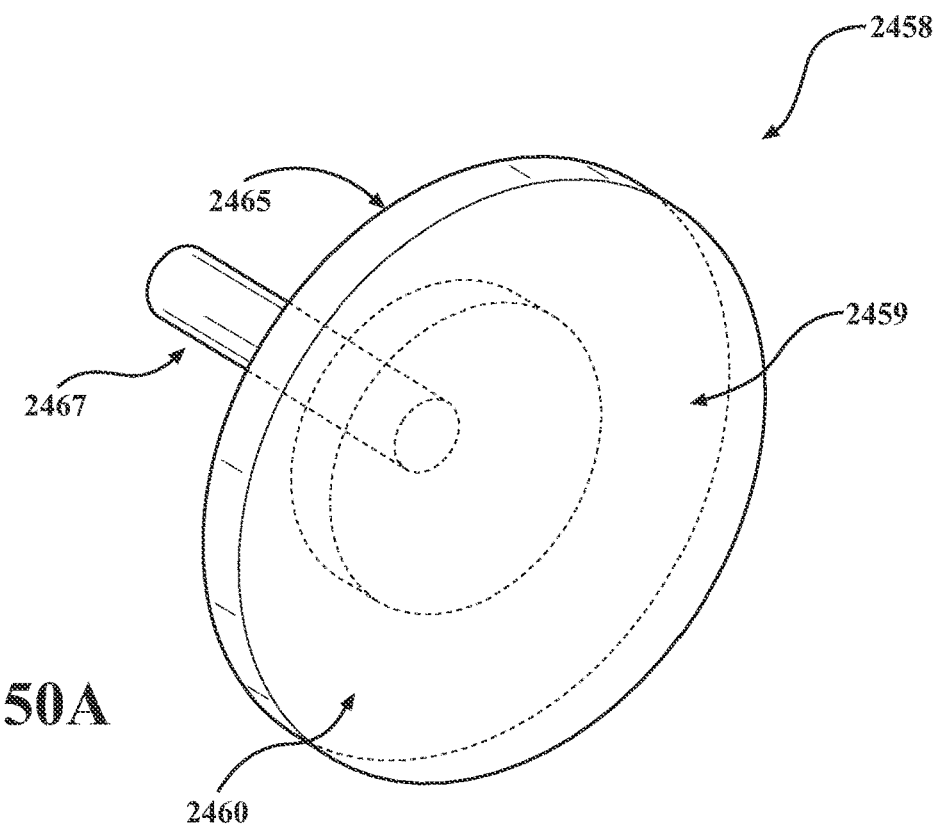
FIG. 50A is a front perspective view of a twenty-second configuration of the attachment element of the transparent face shield of FIGS. 39A and 39B.
Figure 50B:
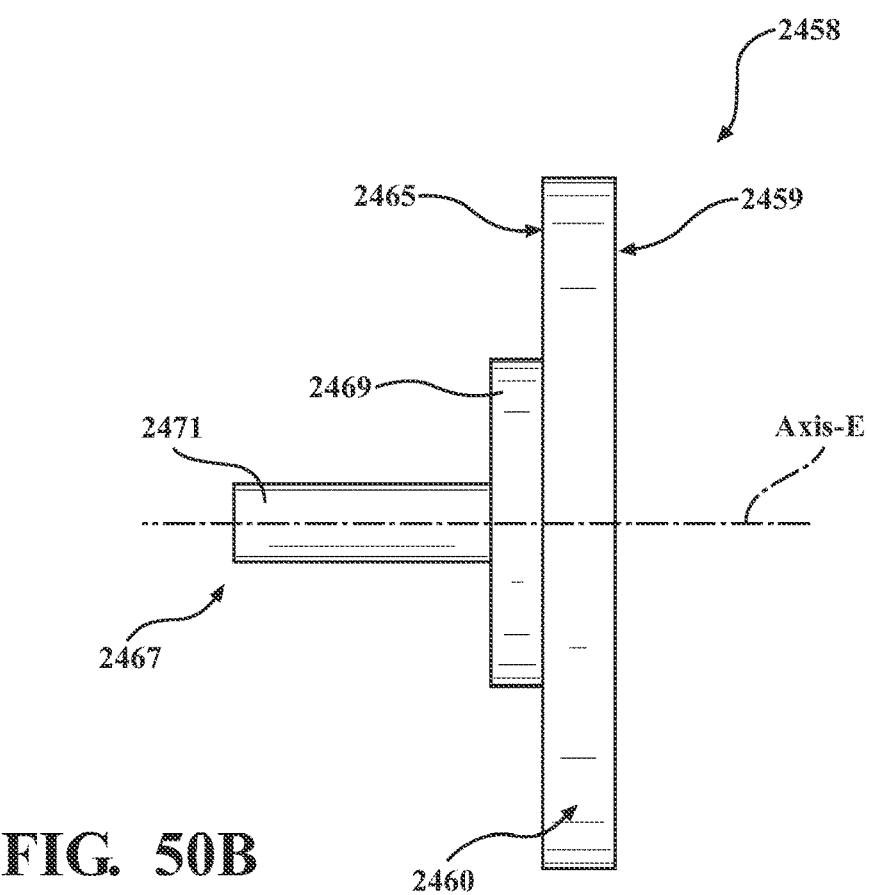
FIG. 50B is a side view of the twenty-second configuration of the attachment element of FIG. 50A.
Figure 50C:
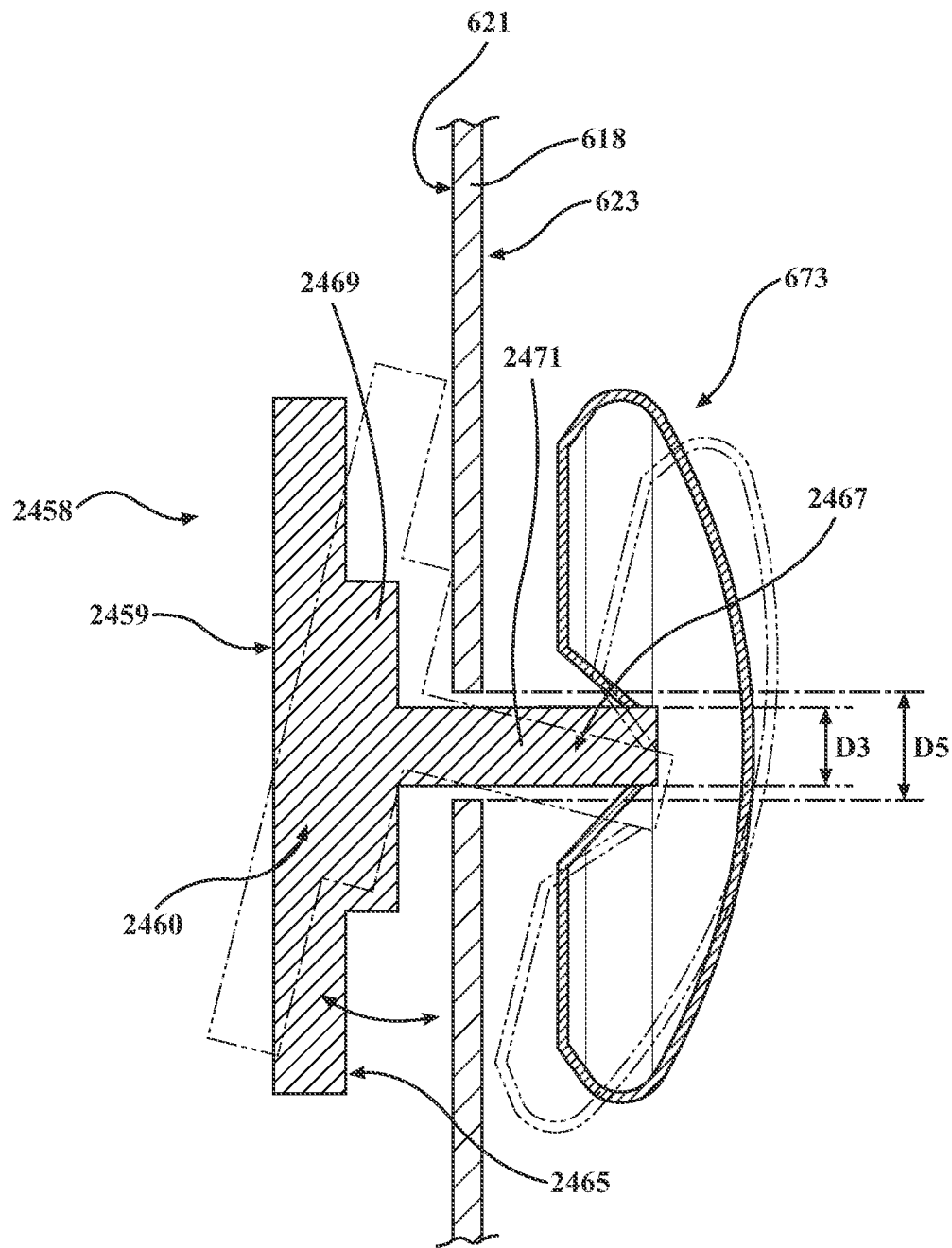
FIG. 50C is a partial sectional view of the twenty-second configuration of the attachment element of FIG. 50A coupled to the transparent face shield.
Figure 50D:
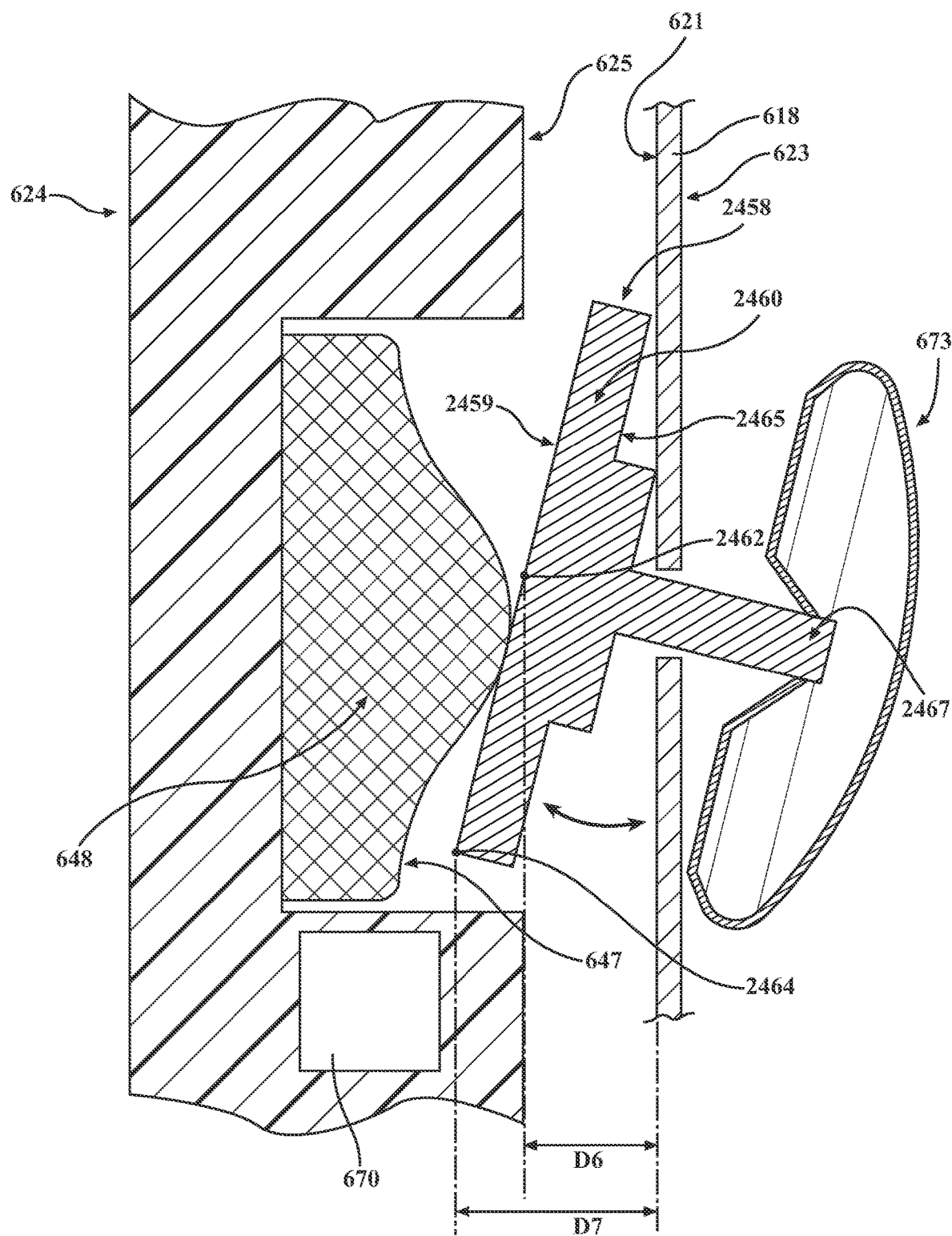
FIG. 50D is a partial sectional view of the twenty-second configuration of the attachment element of FIG. 50A coupled to the coupling member of the surgical helmet of FIG. 37.

The aperture 619 in the transparent face shield 618 and post 2467 extending from the distal surface 2465 of the head 2460 may be complementarily sized to allow the post 2467 to pivot within the aperture 619. For example, the distal portion 2471 of the post 2467 may comprise a dimension D3, such as a diameter, and aperture 619 may comprise a complementary dimension D5, such as a diameter. The dimension D3 of the post 2467 and the dimension D5 of the aperture 619 may be complementary sized such that the dimension D5 of the aperture 619 is larger than the dimension D3 of the post 2467. This may allow the attachment element 2458 to pivot relative to the transparent face shield 618 when coupled to the surgical helmet 620. However, the dimension D5 of the aperture 619 should be sized relative to the dimension D3 of the post 2467 such that the retention feature 673 may still couple the attachment element 2458 to the transparent face shield 618. For example, the couple member 648 may comprise a magnetic material and the coupling member 648 may be oriented such that the polarity of magnetic material is configured to pivot the attachment element 2458 relative to the transparent shield pulling a portion of the proximal surface 2459 of the head 2460 toward the detector 670. As illustrated in FIG. 50D, the proximal surface 2459 of attachment element 2458 may comprise a first point 2462 and a second point 2464. When the attachment element 2458 is placed adjacent the coupling member 648 of the surgical helmet 620, the attachment element 2458 may pivot relative to the transparent face shield 618 such that the first point 2462 may define a first distance D6 from the first surface 621 of the transparent face shield 618 and the second point(s) 2464 may define a second distance D7 from the first surface 621 of the transparent face shield 618. This may allow the second point 2464 on the proximal surface 2459 of the head 2460 to be positioned sufficiently close to the detector 670, such as a Hall Effect sensor, to trigger the detector 670.

Figure 50E:
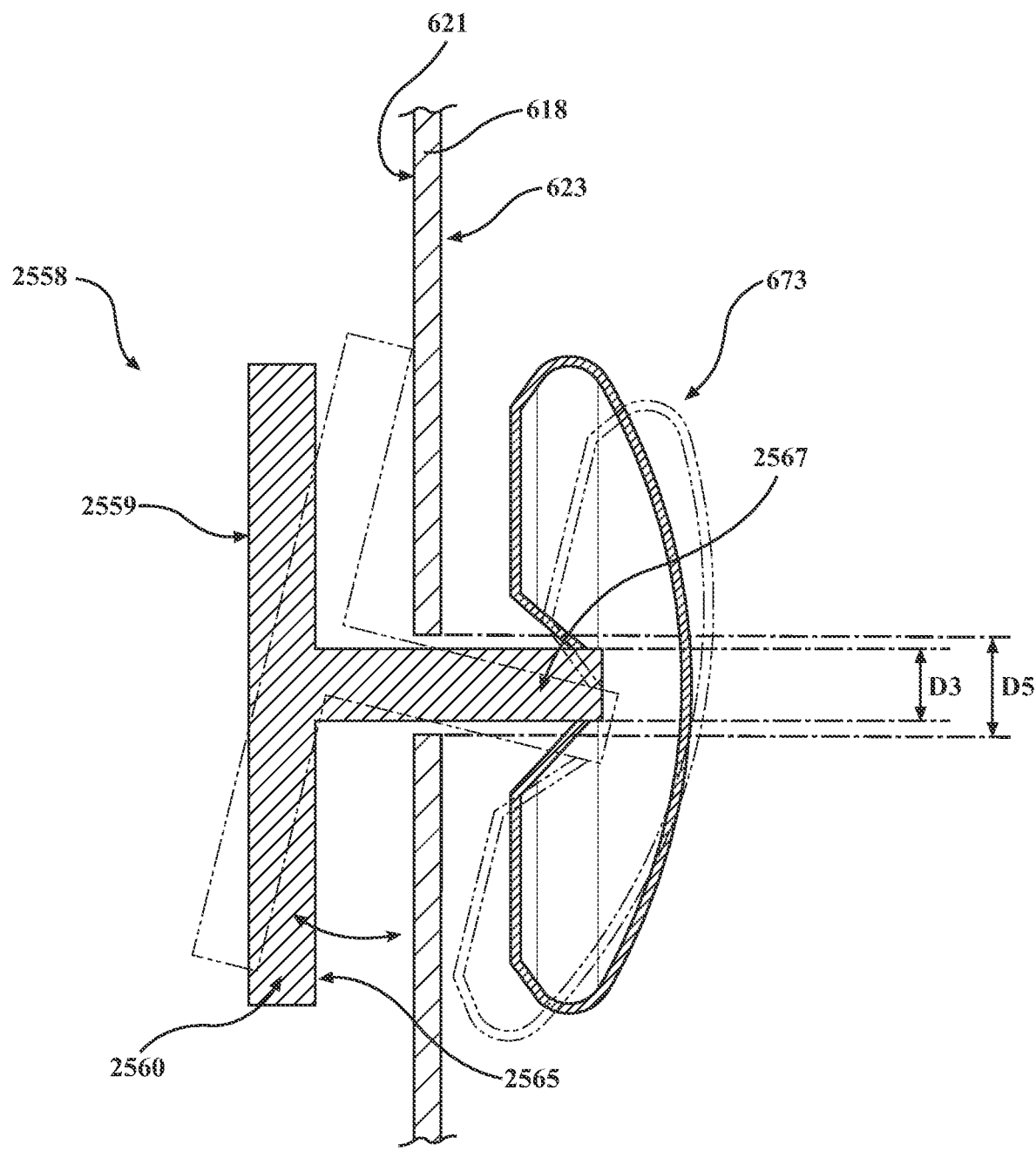
FIG. 50E is a partial sectional view of a twenty-third configuration of the attachment element of FIG. 50A coupled to the transparent face shield.
Figure 50F:
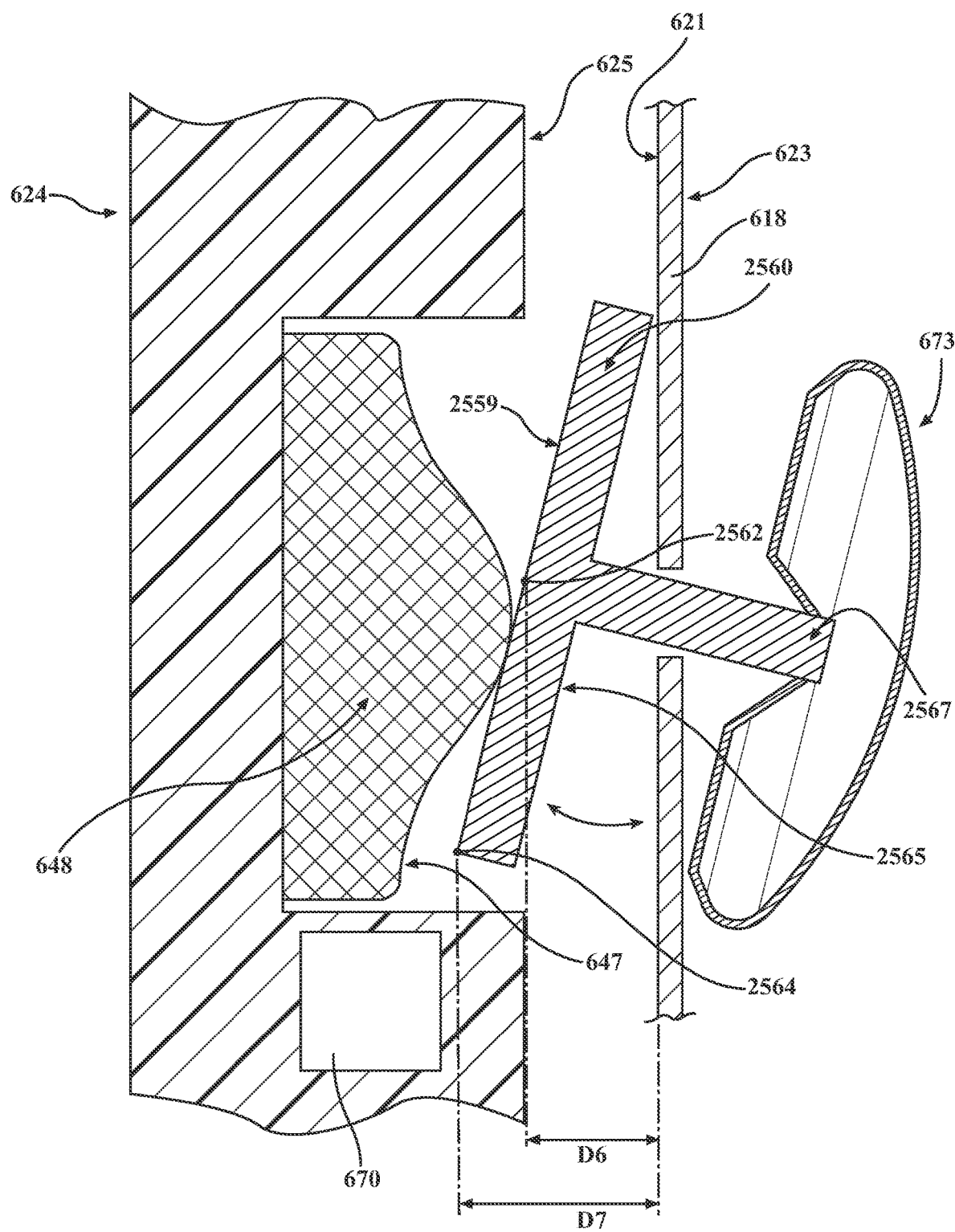
FIG. 50F is a partial sectional view of the twenty-third configuration of the attachment element of FIG. 50E coupled to the coupling member of the surgical helmet of FIG. 37.

Referring to FIGS. 50E-50F, partial sectional views of the twenty-third configuration of the attachment element 2558 are illustrated. Similar to the twenty-second configuration of the attachment element 2458, the twenty-third configuration of the attachment element 2558 may comprise a post 2567 extending distally from the distal surface 2565 of the attachment element 2558. However, the post 2567 may comprise a uniform size and/or diameter. As described above, the post 2567 may comprise a third dimension D3. The post 2567 may be configured to fit within an aperture 619 of the face shield 618 to facilitate coupling of the attachment element 2558 to the face shield 618.

The aperture 619 in the transparent face shield 618 and post 2567 extending from the distal surface 2565 of the head 2560 may be complementarily sized to allow the post 2567 to pivot within the aperture 619. For example, the post 2567 may comprise a dimension D3, such as a diameter, and aperture 619 may comprise a complementary dimension D5, such as a diameter. The dimension D3 of the post 2567 and the dimension D5 of the aperture 619 may be complementary sized such that the dimension D5 of the aperture 619 is larger than the dimension D3 of the post 2567. This may allow the attachment element 2558 to pivot relative to the transparent face shield 618 when coupled to the surgical helmet 620. However, the dimension D5 of the aperture 619 should be sized relative to the dimension D3 of the post 2567 such that the retention feature 673 may still couple the attachment element 2558 to the transparent face shield 618. For example, the couple member 648 may comprise a magnetic material and the coupling member 648 may be oriented such that the polarity of magnetic material is configured to pivot the attachment element 2558 relative to the transparent shield pulling a portion of the proximal surface 2559 of the head 2560 toward the detector 670. As illustrated in FIG. 50F, the proximal surface 2559 of attachment element 2558 may comprise a first point 2562 and a second point 2464. When the attachment element 2558 is placed adjacent the coupling member 648 of the surgical helmet 620, the attachment element 2558 may pivot relative to the transparent face shield 618 such that the first point 2562 may define a first distance D6 from the first surface 621 of the transparent face shield 618 and the second point(s) 2564 may define a second distance D7 from the first surface 621 of the transparent face shield 618. This may allow the second point 2564 on the proximal surface 2559 of the head 2560 to be positioned sufficiently close to the detector 670, such as a Hall Effect sensor, to trigger the detector 670.

Referring to FIGS. 51A-51D, various views of a twenty-fourth configuration of an attachment element 2658 are illustrated. The attachment element 2658 may be configured to couple to the transparent shield 618. The head 2660 may be sized to be inserted within the aperture of the chin bar 624 when coupled to the coupling member 648. The head 2660 of the attachment element 2658 may also define a distal surface 2665 and an opposing proximal surface 2659. The head 2660 made be shaped such that the proximal surface 2659 and the distal surface 2665 have a D-shaped profile when viewed from above. The proximal surface 2659 of the head 2660 may comprise a first surface 2662, wherein a point on the first surface 2662 may define a first distance D6 between the first surface 2662 and the first surface 621 of the transparent face shield 618. The proximal surface 2659 of the head 2660 may also comprise a second surface 2664, wherein a point on the second surface 2664 may define a second distance D7 between the second surface 2664 and the first surface 621 of the transparent face shield 618. While not illustrated in the figures, it should be understood that first surface 621 of the transparent face shield 618 may be positioned distally of the distal surface 2665 of the head 2660. The proximal surface 2659 of the attachment element 2658 may be shaped such that the first distance D6 defined by the point on the first surface 2662 is less than the second distance D7 defined by the point on the second surface 2664. For example, the attachment element 2658 may comprises a D-shaped head 2660 including a distal end and a proximal end, the proximal end may define a proximal surface 1659 including a planar surface 1662 with a first side and a second side. The proximal surface may also include a first face 1664A angularly extending in a proximal direction from the first side of the planar surface 1662 to a first edge. However, this is only one example an asymmetric shaped head 2660. Other asymmetric head configurations are contemplated. For example, any of the attachment elements described above may be bisected along the longitudinal axis, Axis-E, of the attachment element to define an asymmetric head shape.

Figure 51A:
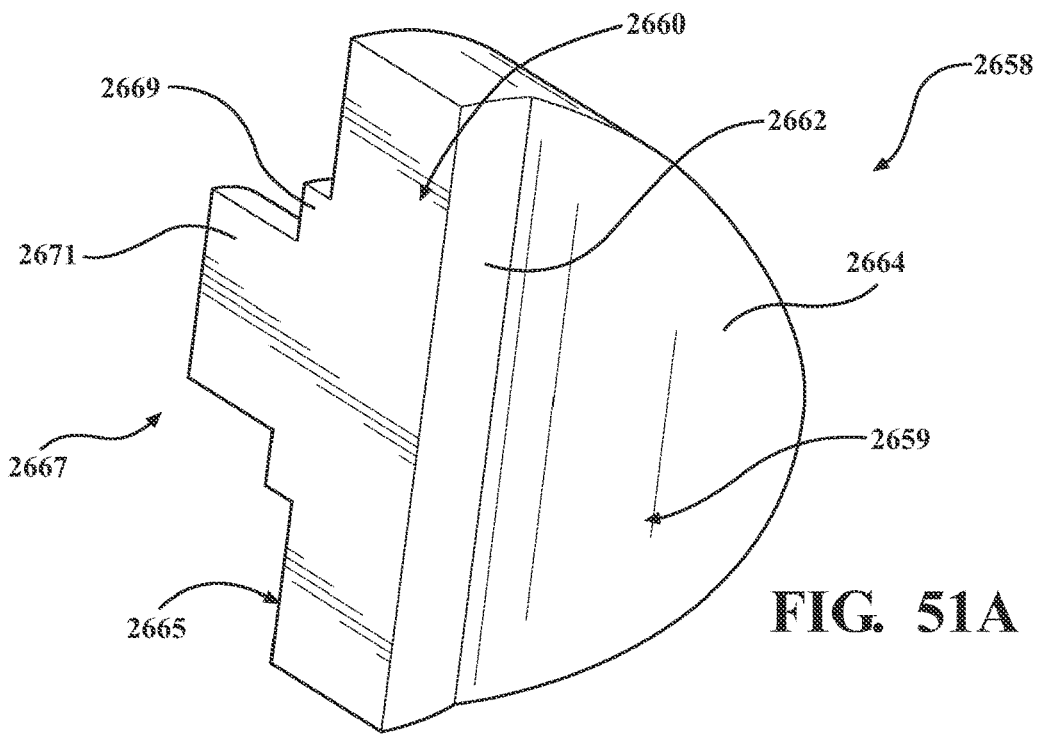
FIG. 51A is a front perspective view of a twenty-fourth configuration of the attachment element of the transparent face shield of FIGS. 39A and 39B.
Figure 51B:
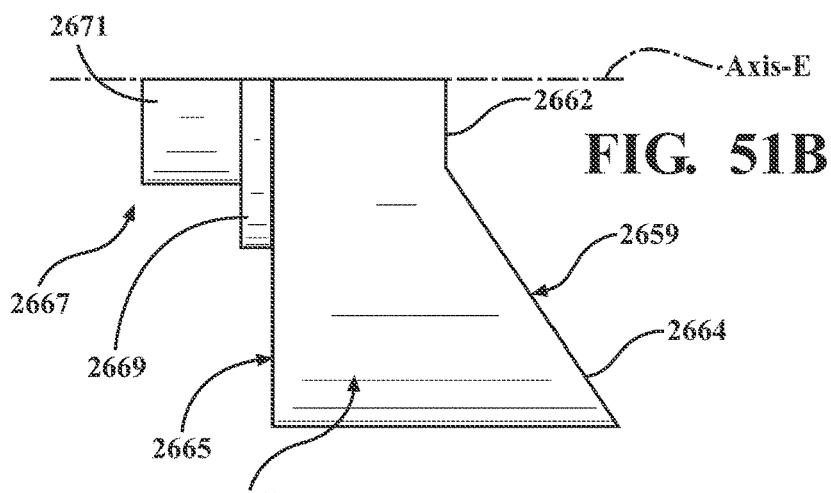
FIG. 51B is a side view of the twenty-fourth configuration of the attachment element of FIG. 51A.
Figure 51C:
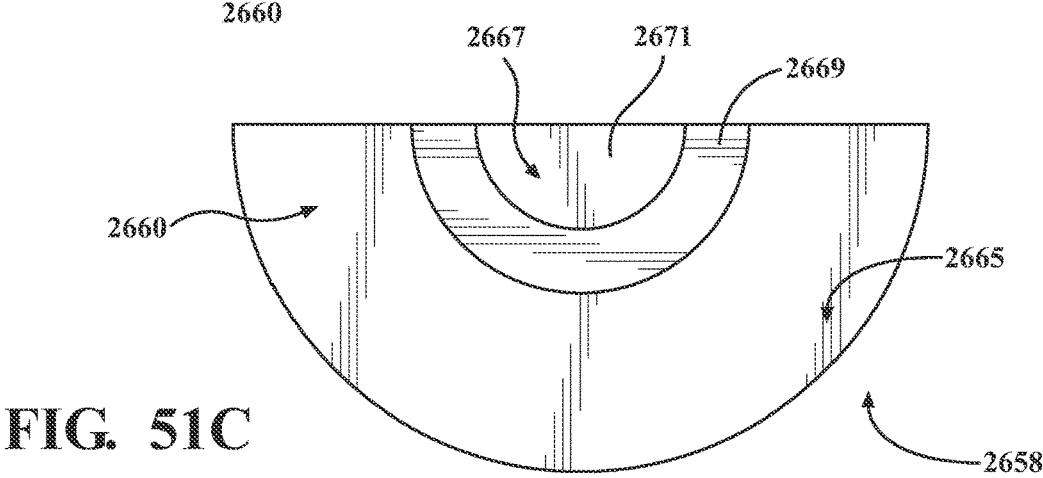
FIG. 51C is a bottom view of the twenty-fourth configuration of the attachment element of FIGS. 51A and 51B.

The attachment element 2658 may further comprise a post 2667 extending distally from the distal surface 2665 of the attachment element 2658. The post 2667 may comprise a D-shaped profile when viewed from the bottom, as seen in FIG. 51C. The post 2667 may comprise a proximal portion 2669 and a distal portion 2671. As described above, the proximal portion 2669 of the post 2667 may comprise a third dimension D3 and the distal portion 2671 comprises a fourth dimension D4. The post 2667 may be configured such that the third dimension D3 of the proximal portion 2669 is larger than the fourth dimension D4 of the distal portion 2671, creating a shoulder. The distal portion 2671 of the post 2667 should be configured to fit within an aperture 619 of the face shield 618 to facilitate coupling of the attachment element 2658 to the face shield 618.

The aperture 619 in the transparent face shield 618 and post 2667 extending from the distal surface 2665 of the head 2660 may be complementarily sized and shaped to allow the post 2667 to be at least partially disposed within the aperture 619. For example, the distal portion 2671 of the post 2667 may comprise a D-shaped profile and the transparent face shield 618 may comprise a complementary D-shaped aperture 619. The complementary D-shaped post 2667 and the aperture 619 may serve to prevent rotation of the attachment element 2658 relative to the transparent face shield 618, and by extension the coupling member 648 when the surgical garment 612 is coupled to the surgical helmet 620. This may serve to align the attachment element 2658 relative to the detector 670, such as when utilizing an attachment element 2658 with at least one asymmetric profile the requires the portion of the head 2660 including the second point and/or second surface 2664 to be appropriately oriented relative to the transparent face shield 618 in order to properly trigger the detector 670. For example, as illustrated in FIG. 51D, the post 2667 may serve to orient the second surface 2664 of the proximal surface 2659 such that the second surface 2664 is positioned proximate the detector 670 when the attachment element 2658 is magnetically coupled to the coupling member 648 of the surgical helmet 620. Based on the exemplary surgical helmet 620 of FIG. 37 wherein the detector 670 is positioned laterally relative to the coupling member 648, the post 2667 may be configured to orient the second surface 2664 away from the midline, Axis-M, of the transparent face shield 618 to position the second surface 2664 proximate the detector 670. This may allow the second surface 2664 on the proximal surface 2659 of the head 2660 to be positioned sufficiently close to the detector 670, such as a Hall Effect sensor, to trigger the detector 670. While not illustrated in the figures, it is contemplated that post 2667 may comprise other asymmetrical profiles to prevent the rotation of the attachment element 2658 within the aperture 619 of the transparent face shield 618. For example, the post 2667 may comprise a star, triangle, square, rectangle, or other similar polygonal shapes as a means of preventing the rotation of the attachment element 2658 within the aperture 619 of the transparent face shield 618.

Figure 52A:
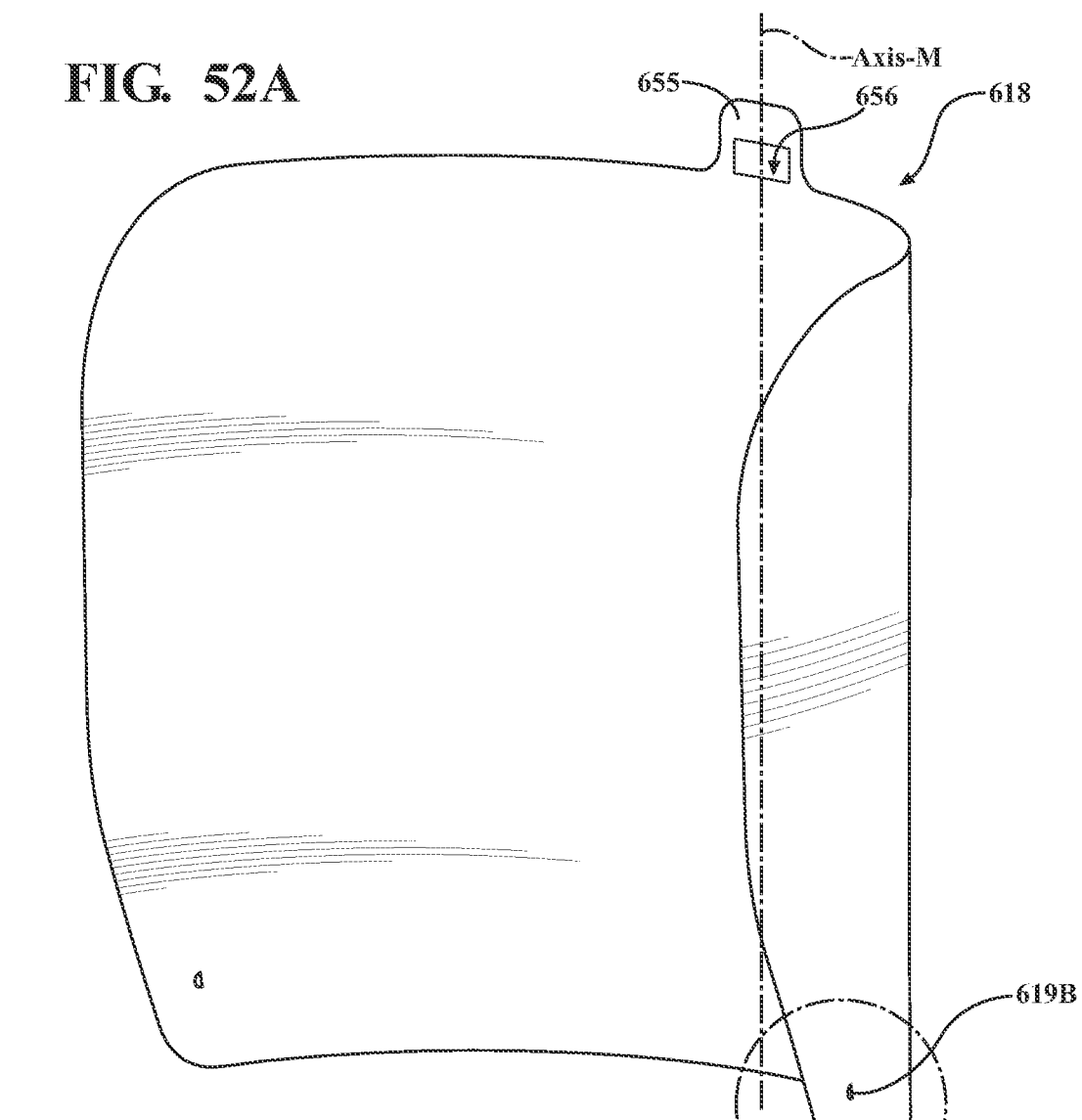
FIG. 52A is a perspective view of a configuration of a transparent shield of a surgical garment, the transparent shield including a shaped aperture for receiving an attachment element.
Figure 52B:
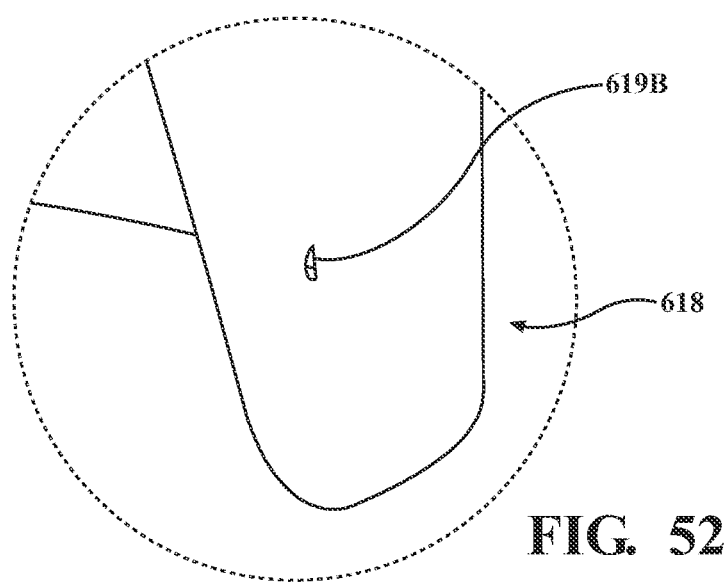
FIG. 52B is an enlarged perspective view of the shaped aperture of the transparent shield of FIG. 52A.

The asymmetric post 2667 illustrated and describe with regard to the attachment element 2658 of FIGS. 51A-51D may be applied to any of the attachment elements described above. Furthermore, it is also contemplated that any of the attachment elements described above may be configured without a post. An attachment element without a post may be coupled to the first surface of the transparent face shield 618 by an epoxy, glue, or other similar adhesive. The adhesive may be configured to provide a similar means of orienting the attachment element relative to the transparent face shield and/or preventing rotation of the attachment element relative to the transparent face shield Referring to FIGS. 52A and 52B, an exemplary configuration of a transparent face shield 618 including an asymmetric aperture 619B is illustrated. For example, the transparent face shield 618 may comprise an asymmetric aperture 619B comprising a D-shape corresponding to the exemplary D-shaped post 2667 of the attachment element described above. While not illustrated in the figures, it is contemplated that the asymmetric aperture 619B may comprise a star, triangle, square, rectangle, or other similar polygonal shape that is complementary to the post of the attachment element as a means of preventing the rotation of the attachment element within the aperture 619B of the transparent face shield 618.

It should be appreciated that different attachment members on the same surgical garment may vary in design from one another.

An adapter member may be configured to removably couple with one of the attachment elements described above. The adapter member may comprise a proximal surface and an opposing distal surface. The adapter member may comprise a first point on the proximal surface of the adapter member and a second point on the proximal surface of the adapter member similar to any of the various shapes and/or configurations of the proximal surface of the attachment elements of the surgical garment described above. The proximal surface of the adapter member may be complementarily shaped to engage a coupling member on a surgical helmet and capable of triggering the detector. The distal surface may comprise a complementary shaped configured to engage the proximal surface of an attachment element of a surgical garment. The second point on the proximal surface of the adapter member may be spaced apart from the first point on the proximal surface on the adapter member. The distal surface of said adapter member may be configured to removably engage the proximal surface of the first attachment element. The first point on the proximal surface of the adapter member may define a first distance from the first surface of the transparent face shield when the adapter member is coupled to the first attachment element. The second point on the proximal surface of the adapter member may define a second distance from the first surface of the transparent face shield when the adapter member is coupled to the first attachment element. The proximal surface of the adapter member may be shaped such that the first distance is less than the second distance from the first surface of the transparent face shield.

The adapter member may be formed from at least 50, 75, 85, or 90 wt. % of a metal alloy comprising at least 50%, 60, 70, 80, 90, 95, or 99 wt. % of a ferromagnetic material or magnetic material capable of being magnetically attracted to the coupling member and/or the attachment element comprising a magnet. It is also contemplated that the adapter member may comprise at least 70, 80, or 90 wt. % of a ferritic or martensitic stainless steel or other steel capable of being attracted to a magnet and sufficient to retain the surgical garment to the surgical helmet. It is further contemplated that the adapter member may comprise at least 0.5, 0.6, 0.7, 0.8, 0.9, 1, 1.2, 1.4, 1.5 or 1.8 g of a ferromagnetic material capable of being magnetically attracted to the coupling member and/or the attachment element comprising a magnet. Example of suitable ferromagnetic materials may include iron, nickel, cobalt, carbon, gadolinium, dysprosium, or alloys thereof, or some combination thereof.

Method of Reprocessing a Surgical Garment:

A method of reusing a feature of a surgical garment 612 may comprise obtaining a surgical garment 612 that has been used, the surgical garment 612 including a surgical fabric 614 defining an opening and a transparent face shield 618 disposed within the opening. The transparent face shield 618 may comprise an upper portion, a lower portion, a first surface 621 and an opposing second surface 623. The method may further comprise a first attachment element 658 secured to said lower portion of said transparent face shield 618, wherein the first attachment element 658 may comprise a ferromagnetic material and may define a coupling recess 661 on the wearer side of said surgical garment 612. The first attachment element 658 may be configured to removably engage the magnetic coupling member 648 on the helmet 620. The first attachment element 658 may further comprise a head 660 comprising a distal surface 665 and a proximal surface 659, and a post 667 extending distally from the distal surface 665 of the head 660. The coupling recess 661 may be formed in said proximal surface 659 of the head 660. The method may also comprise disengaging the first attachment element 658 from the transparent face shield 618. The method may further comprise discarding the surgical garment 612 and the transparent face shield 618. The method may also comprise cleaning and/or sterilizing the first attachment element 658. The method may also comprise coupling the cleaned or sterilized first attachment element 658 to a new surgical garment 612 having a new surgical fabric 614 and/or transparent face shield 618 such that, in subsequent use of the new surgical garment 612, the cleaned or sterilized first attachment element 658 may be utilized to couple the new surgical garment 612 to a helmet 620.

Method of Coupling a Surgical Garment to a Surgical Helmet Using an Adapter:

A method of coupling a surgical garment 612 including a first attachment element 658 to a surgical helmet 620 including a first coupling member 648 may comprise providing an adapter member. The adapter member may comprise a proximal surface and an opposing distal surface. The adapter member may also comprise a first point on the proximal surface of the adapter member and a second point on the proximal surface of the adapter member. The second point on the proximal surface of the adapter member may be spaced apart from the first point on the proximal surface of the adapter member. The first point on the proximal surface of the adapter member may define a first distance D6 from the first surface of the transparent face shield when the adapter member is coupled to the first attachment element. The second point on the proximal surface of the adapter member may define a second distance D7 from the first surface 621 of the transparent face shield when the adapter member is coupled to the first attachment element. The method may also comprise removably coupling the adapter member to the first coupling member of the surgical helmet. The method may further comprise removably coupling the adapter member to the first attachment element of the surgical garment.

Clauses Covering Additional Configurations of the System(s) Described Above:

I. A surgical apparel system comprising:

a surgical helmet to be worn over the head of a wearer, said surgical helmet comprising a helmet coupler, said helmet coupler comprising:

an enclosure comprising a distal surface, said enclosure defining a void space having a first region and a second region;

a mechanical switch at least partially disposed within said void space proximate said first region; and a first member movably disposed relative to said mechanical switch within said enclosure, said first member comprising one of a ferromagnetic material or a magnetic material;

a surgical garment configured to be at least partially disposed over said surgical helmet to provide a microbial barrier between a medical environment and a wearer, said surgical garment comprising a second member;

wherein said second member comprises the other of said ferromagnetic material or said magnetic material and is configured to releasably engage said distal surface of said helmet coupler; and wherein said first member is configured to selectively contact said mechanical switch based, at least in part, on the proximity of said second member relative to said distal surface of said enclosure.

II. The system of clause I, wherein said surgical helmet comprises a control housing that extends outwardly from said surgical helmet and is positioned generally forward of the face of the wearer of said surgical helmet, and said helmet coupler is at least partially disposed within said control housing.

III. The system of clause II, wherein said distal surface of said enclosure is configured to be recessed within said control housing.

IV. The system of clause I, wherein said first member of said helmet coupler is configured to selectively engage a toggle member that is operatively attached to said mechanical switch to move said toggle member between a first position and a second position;

wherein said toggle member is in said second position when said mechanical switch is engaged by said first member and said toggle member is in said first position when said first member abuts said distal surface of said enclosure.

V. The system of clause IV, wherein said surgical helmet comprises a ventilation assembly and a controller; and wherein said controller is in communication with said mechanical switch, and said controller is configured to control an operational characteristic of said ventilation assembly based, at least in part, on said position of said toggle member of said mechanical switch.

VI. The system of clause I, wherein said first member of said helmet coupler comprises said magnetic material and said second member comprises said ferromagnetic material; and wherein said first member and said second member are magnetically attracted to couple said surgical helmet to said surgical garment.

VII. The system of clause I, wherein said distal surface of said helmet coupler is configured to provide an alignment feature configured to align said second member of said surgical garment with said distal surface of said enclosure of said helmet coupler.

VIII. The system of clause VII, wherein said distal surface comprises a curved shape configured to define the alignment feature.

IX. The system of clause I, wherein the surgical garment further comprises a transparent face shield and a surgical fabric, and said transparent face shield is integrally formed with said surgical fabric.

X. The system of clause IX, wherein said second member is positioned about a perimeter of said transparent face shield and configured to define a curvature of said transparent face shield when coupled to said corresponding helmet coupler.

XI. The system of clause I, wherein said helmet coupler further comprises a third member positioned within said enclosure and proximate to said first region of said enclosure and adjacent to said mechanical switch, said third member comprising said ferromagnetic material or said magnetic material of said second member.

XII. The system of clause XI, wherein said third member is configured to manipulate position of said first member based, at least in part, on the proximity of said second member relative to said distal surface of said enclosure.

XIII The system of clause XII, wherein said first member of said helmet coupler comprises a magnet, said third member comprises a first ferromagnetic material, and said second member comprises a second ferromagnetic material;

wherein the magnetic mass of said second ferromagnetic material is greater than the magnetic mass of said first ferromagnetic material such that said magnet will be drawn distally away from said mechanical switch when said second member is positioned adjacent to said distal surface of said helmet coupler.

XIV. The system of clause XIII, wherein the magnetic mass of said second ferromagnetic material relative to the magnetic mass of said first ferromagnetic material comprises a ratio of 1.1 to 1 or greater.

XV. The system of clause XII, wherein said first member of said helmet coupler comprises a ferromagnetic material, said third member comprises a first magnet, and said second member comprises a second magnet;

wherein the magnetic field of said second magnet is greater than the magnetic field of said first magnet such that said ferromagnetic material will be drawn distally away from said mechanical switch when said second member is positioned adjacent to said distal surface of said helmet coupler.

XVI. The system of clause XV, wherein the magnetic field of said second magnet relative to the magnetic field of said first magnet comprises a ratio of 1.1 to 1 or greater.

XVII. A surgical apparel system comprising:
a head unit to be worn over the head of a wearer, said head unit comprising a first coupler, said first coupler comprising:
an enclosure comprising a distal surface, said enclosure defining a void space having a first region and a second region; and
a first member positioned within said enclosure and moveable between said first region and said second region;
a sensor positioned proximate said first region of said enclosure; and
a surgical garment configured to be at least partially disposed over said head unit to provide a microbial barrier between a medical environment and a wearer, said surgical garment comprising a second member;
wherein said first region is proximal to said sensor and said second region is distal to said sensor;
wherein said first member is configured to selectively move between said first region and said second region of said enclosure based, at least in part, on the proximity of said second member relative to said distal surface of said enclosure; and
wherein said sensor is configured to detect when said first member is in said first region and said second region.

XVIII. The surgical apparel system of clause XVII, further comprising a controller coupled to said sensor and configured to receive a signal from said sensor; and
wherein said controller is configured to control an operational characteristic of said head unit based on said signal from said sensor.

XIX. The surgical apparel system of clause XVII, wherein said second member is configured to releasably engage with said distal surface of said enclosure of said first coupler.

XX. The surgical apparel system of clause XVII, wherein said first member comprises a magnetic material and said sensor is a Hall Effect sensor.

XXI. A surgical helmet for use with a surgical garment having a second member and configured to be at least partially disposed over said surgical helmet, said surgical helmet comprising:
a helmet coupler, said helmet coupler comprising:
an enclosure comprising a distal surface, said enclosure defining a void space having a first region and a second region;
a mechanical switch at least partially disposed within said void space proximate said first region; and
a first member movably disposed relative to said mechanical switch within said enclosure, said first member comprising one of a ferromagnetic material or a magnetic material;
wherein the second member of the surgical garment comprises the other of said ferromagnetic material or said magnetic material and is configured to releasably engage said distal surface of said helmet coupler; and
wherein said first member is configured to selectively contact said mechanical switch based, at least in part, on the proximity of the second member relative to said distal surface of said enclosure.

XXII. The surgical helmet of clause XXI, wherein said surgical helmet further comprises a ventilation assembly and a controller, wherein said controller is in communication with said mechanical switch, and said controller is configured to receive a signal from said mechanical switch and to control an operational characteristic of said ventilation assembly based, at least in part, on said signal from said mechanical switch.

XXIII A surgical apparel system comprising:
a surgical helmet to be worn over the head of a wearer, said surgical helmet comprising a first member and a mechanical switch, wherein:
said first member comprises an aperture,
said first member comprises one of a ferromagnetic material or a magnetic material, and
said mechanical switch comprises a toggle member;
a surgical garment configured to be at least partially disposed over said surgical helmet to provide a microbial barrier between a medical environment and a wearer, said surgical garment comprising a second member comprising a protrusion configured to fit within said aperture;
wherein said second member comprises the other of said ferromagnetic material or said magnetic material;
wherein said first member and said second member are configured to be magnetically attracted to one another to releasably couple said surgical garment to said surgical helmet; and
wherein said protrusion of said second member is configured to engage said toggle member of said mechanical switch when said surgical garment is coupled to said surgical helmet.

XXIV. The surgical apparel system of clause XXIII, wherein said first member comprises said magnetic material; and
wherein said second member comprises said ferromagnetic material.

XXV. The surgical apparel system of clause XXIII, wherein said first member comprises said ferromagnetic material; and
wherein said second member comprises said magnetic material.

XXVI. The surgical apparel system of clause XXIII, wherein said aperture further comprises a bevel or a chamfer surrounding said aperture, said bevel or said chamfer configured to assist insertion of said protrusion into said aperture.

XXVII. The surgical apparel system of clause XXIII, wherein said first member comprises a distal surface;
wherein said second member comprises a base, said protrusion configured to project outward from said base; and
wherein said base is configured to abut said distal surface when said second member is coupled with said first member.

XXVIII. The surgical apparel system of clause XXIII, wherein the other of said ferromagnetic material or said magnetic material of said second member is coated in a plastic polymer.

XXIX. The surgical apparel system of clause XXIII, further comprising a controller in communication with said mechanical switch, said controller configured to receive a signal from said mechanical switch based on contact or lack of contact of said protrusion with said toggle member of said mechanical switch.

XXX. The surgical apparel system of clause XXIII, wherein said toggle member is at least partially disposed within said aperture of said first member.

XXXI. The surgical apparel system of clause XXX, wherein said toggle member is moveable between a first position and a second position.

XXXII. A surgical apparel system comprising:
a surgical helmet to be worn over the head of a wearer, said surgical helmet comprising a cylindrical first member and a sensor, wherein:
said cylindrical first member comprises a lateral surface and a distal surface, said distal surface comprising an aperture;
said cylindrical first member comprises one of a ferromagnetic material or a magnetic material; and
said aperture defining a first axis;
said cylindrical first member having a second axis perpendicular to said first axis; and
said sensor is positioned adjacent to said lateral surface of said cylindrical first member such that said sensor is generally aligned/parallel with said second axis of said cylindrical first member;
a surgical garment configured to be at least partially disposed over said surgical helmet to provide a microbial barrier between a medical environment and a wearer, said surgical garment comprising a second member comprising a protrusion configured to fit within said aperture;
wherein said second member comprises the other of said ferromagnetic material or said magnetic material;
wherein said cylindrical first member and said second member are configured to be magnetically attracted to one another to releasably couple said surgical garment to said surgical helmet; and
wherein said sensor is configured to detect a change in the magnetic field surrounding said cylindrical first member created by the presence or absence of said second member relative to said cylindrical first member.

XXXIII The surgical apparel system of clause XXXII, wherein said cylindrical first member comprises a magnet; and
wherein said second member comprises a ferromagnetic material.

XXXIV. The surgical apparel system of clause XXXII, wherein said cylindrical first member further comprises a bevel or a chamfer surrounding said aperture, said bevel or said chamfer configured to assist insertion of said protrusion in said aperture.

XXXV. The surgical apparel system of clause XXXII, further comprising a controller in communication with said sensor, said controller configured to receive a signal from said sensor based on the detection of the presences of said second member relative to said cylindrical first member.

XXXVI. The surgical apparel system of clause XXXII, wherein said sensor comprises a Hall Effect sensor configured to detect changes in the magnetic field surrounding said cylindrical first member based, at least in part, on the proximity of said second member relative to said cylindrical first member.

XXXVII. A surgical apparel system comprising:
a surgical helmet configured to be worn on a head of an individual;
a surgical garment configured to be at least partially disposed over said surgical helmet to provide a microbial barrier between a medical environment and a wearer, said surgical garment comprising a first member configured to removably couple said surgical garment to said surgical helmet;
wherein said surgical helmet comprises:
a peripheral device configured to facilitate performance of the individual wearing said surgical helmet during a surgical procedure;
a detector configured to detect the presence of said surgical garment being positioned adjacent to said surgical helmet and to produce a signal when said surgical garment is coupled to the surgical helmet; and
a controller in communication with said detector and said peripheral device, said controller configured to regulate an aspect of the operation of the peripheral device based, at least in part, on said signal from said detector.

XXXVIII. The surgical apparel system of clause XXXVII, wherein said surgical garment further comprises a transparent shield; and wherein said first member of said surgical garment is coupled to said transparent shield.

XXXIX. The surgical apparel system of clause XXXVIII, wherein said detector is a mechanical switch; and wherein said surgical helmet and said surgical garment are configured such that said transparent face shield abuts said mechanical switch when said surgical garment is positioned adjacent said surgical helmet.

XL. The surgical apparel system of clause XXXVII, wherein said controller is configured to store data/information in said memory related to the peripheral device when said signal from said detector indicates the presence of a power supply and absence of a surgical garment.

XLI. The surgical apparel system of clause XXXVII, further comprising a portable energy source removably coupled to said surgical helmet;

wherein said portable energy source is in communication with said controller; and wherein said controller is configured to control transmission of energy from said portable energy source to said peripheral device based, at least in part, on said signal from said detector.

XLII. The surgical apparel system of clause XLI, wherein said controller is configured to allow transmission of energy from said portable energy source to said peripheral device when said signal from said detector indicates said surgical garment is positioned adjacent said surgical helmet.

XLIII. The surgical apparel system of clause XXXVII, wherein said detector is configured to monitor the presence of a magnetic field.

XLIV. The surgical apparel system of clause XXXVII, wherein said peripheral device of said surgical helmet may comprise: a fan assembly, a light, a communication device, a cooling strip, or a video recorder.

XLV. A surgical apparel system comprising:

a surgical helmet configured to be worn on a head of an individual;

a surgical garment configured to be at least partially disposed over said surgical helmet to provide a microbial barrier between a medical environment and a wearer;

wherein said surgical helmet comprises:

a peripheral device configured to facilitate performance of the individual wearing said surgical helmet during a surgical procedure; and a detector configured to detect the presence of said surgical garment being positioned adjacent to said surgical helmet and to produce a signal when said surgical garment is coupled to the surgical helmet;

a controller in communication with said detector and said peripheral device, said controller configured to regulate an operational characteristic of said peripheral device based, at least in part, on said signal from said detector; and a portable energy source removably interconnected to said surgical helmet, said portable energy source in communication with said controller;

wherein said controller is configured to control transmission of energy from said portable energy source to said peripheral device based, at least in part, on said signal from said detector.

XLVI. The surgical apparel system of clause XLV, wherein said detector is configured to toggle between a first state and a second state;

wherein said detector is configured to be in said first state when said surgical garment is positioned adjacent said surgical helmet;

wherein said detector is configured to be in said second state when said surgical garment is separated from said surgical helmet; and wherein said detector is configured to produce said signal based, at least in part, on said controller being in said first state or said second state.

XLVII. The surgical apparel system of clause XLVI, wherein said controller is configured to delay transmission of power to said peripheral device for a defined first period of time once said controller receives said signal from said detector indicating said surgical garment is positioned adjacent said surgical helmet.

XLVIII. The surgical apparel system of clause XLVI, wherein said controller is configured to continue transmission of power to said peripheral device for a defined second period of time once said controller receives said signal from said detector indicating said surgical garment is separated from said surgical helmet.

XLIX. The surgical apparel system of clause XLVI, further comprising a memory device coupled to said surgical helmet and in communication with said controller, said memory device configured to store data related to the operation of said peripheral device.

L. The surgical apparel system of clause XLVI, further comprising an energy sensor in communication with said controller, said energy sensor configured to detect the power level of said portable energy source and an energy signal to said controller based on the power level of said portable energy source; and wherein said controller is configured to communicate data to said memory device for storage based on said energy signal from said energy sensor, said data related to a user setting for the peripheral device.

LI. The surgical apparel system of clause L, wherein said controller is configured to communicate data to said memory device for storage when said energy signal from said energy sensor indicates that the remaining power level of said portable energy source has reached a threshold value, said data related to said user setting of said peripheral device.

LII. The surgical apparel system of clause LI, wherein said memory device is configured to store said user setting of said peripheral device so long as said detector remains in said first state; and wherein said controller is configured to restart operation of said peripheral device based on stored said user settings upon replacement of said portable energy source.

LIII. The surgical apparel system of clause XLVI, wherein said memory device is configured to clear said data related to said user setting of said peripheral device when said detector toggles from said first state to said second state and said portable energy source is disconnected from said surgical helmet.

LIV. The surgical apparel system of clause XLVI, wherein said memory device is configured to store data related to a plurality of characteristics of said surgical garment;

wherein said detector is configured to identify one of a plurality of configurations of said surgical garment that is positioned adjacent said surgical helmet; and wherein said controller is configured to control at least one operational characteristic of said peripheral device based, at least in part, on the identified one of said plurality of configurations of said surgical garment.

LV. The surgical apparel system of clause XLV, wherein said detector comprises:

an enclosure comprising a distal surface, said enclosure defining a void space having a first region and a second region;

a mechanical switch at least partially disposed within said void space proximate said first region; and a first member movably disposed relative to said mechanical switch within said enclosure, said first member comprising one of a ferromagnetic material or a magnetic material;

wherein the surgical garment comprises a second member, said second member comprising the other of said ferromagnetic material or said magnetic material, and is configured to releasably engage said distal surface of said enclosure;

wherein said first member is configured to selectively contact said mechanical switch based, at least in part, on the proximity of said second member relative to said distal surface of said enclosure; and wherein said detector is configured to communicate said signal to said controller based, at least in part, on whether said first member is in contact with said mechanical switch.

LVI. The surgical apparel system of clause XLV, wherein said detector comprises:

an enclosure comprising a distal surface, said enclosure defining a void space having a first region and a second region;

a first member positioned within said enclosure and moveable between said first region and said second region; and a sensor positioned proximate said first region of said enclosure;

wherein the surgical garment comprises a second member configured to releasably engage said distal surface of said enclosure;

wherein said first region is proximal to said sensor and said second region is distal to said sensor;

wherein said first member is configured to selectively move between said first region and said second region of said enclosure based, at least in part, on the proximity of said second member relative to said distal surface of said enclosure;

wherein said sensor is configured to detect when said first member is in said first region and said second region; and wherein said detector is configured to communicate said signal to said controller based, at least in part, on whether said first member is positioned proximate said first region or proximate said second region.

LVII. A method of operating a surgical apparel system, said method comprising:

providing the surgical apparel system comprising:

a surgical helmet configured to be worn on a head of an individual;

a surgical garment configured to be removably coupled to the surgical helmet to provide a microbial barrier between a medical environment and a wearer;

wherein the surgical helmet comprises:

a peripheral device configured to facilitate performance of the individual wearing the surgical helmet during a surgical procedure;

a detector configured to detect the coupling of the surgical garment to the surgical helmet and to produce a signal based, at least in part, on the presence or absence of the surgical garment being coupled to the surgical helmet; and a controller in communication with the detector and the peripheral device;

a portable energy source removably interconnected with the surgical helmet, the portable energy source in communication with the controller; and coupling the portable energy source to the surgical helmet;

detecting whether the surgical garment is coupled to the surgical helmet utilizing the detector;

controlling an operational characteristic of the peripheral device based, at least in part, on whether the garment is coupled; and transmitting energy from the portable energy source to the peripheral device if the controller received the signal from the detector.

LVIII. The method of clause LVII, wherein the surgical helmet further comprises:

a memory device coupled to the surgical helmet and in communication with the controller, the memory device configured to store data related to the operation of the peripheral device; and an energy sensor in communication with the controller, the energy sensor configured to detect the remaining power level of the portable energy source and communicate an energy signal to the controller based on the remaining power level of the portable energy source.

LIX. The method of clause LVIII, further comprising coupling the surgical garment to the surgical helmet, such that the surgical garment is at least partially disposed over the surgical helmet.

LX. The method of clause LIX, further comprising:

communicating the energy signal from the energy sensor to the controller; and storing a user setting of the peripheral device when the energy signal from said energy sensor indicates that the remaining power level of the portable energy source has reached a threshold value.

LXI. The method of clause LX, further comprising:

storing the user setting of the peripheral device on the memory device;

replacing the portable energy source with a second portable energy source while the detector continues to communicate the signal to the controller indicating the surgical garment is coupled to the surgical helmet; and restarting the peripheral device based on the user setting stored on the memory device.

LXII. The method of clause LXI, further comprising deleting the user setting of the peripheral device stored on the memory device when the detector communicates the signal to the controller indicating the surgical garment is separated from the surgical helmet and the portable energy source is disconnected from the surgical helmet.

LXIII. The method of clause LIX, further comprising:

storing a user setting of the peripheral device on the memory device;

separating the surgical garment from the surgical helmet while the portable energy source is interconnected with the surgical helmet;

ceasing operation of the peripheral device upon receiving the signal from the detector indicating the surgical garment is separated from the surgical helmet;

coupling a second surgical garment to the surgical helmet while the portable energy source remains interconnected with the surgical helmet;

restarting the peripheral device based on the user setting stored on the memory device.

LXIV. The method of clause LXIII, further comprising deleting the user setting of the peripheral device stored on the memory device when the detector communicates the signal to the controller indicating the surgical garment is separated from the surgical helmet and the portable energy source is disconnected from the surgical helmet.

LXV. The method of clause LIX, wherein the memory device is configured to store data related to a plurality of configurations of the surgical garment; and
said method further comprises:
identifying one of the plurality of configurations of the surgical garment that is coupled to the surgical helmet using the detector;
communicating the identified configuration of the surgical garment to the controller; and
communicating a command related to at least one operational characteristic of the peripheral device based, at least in part, on the identified configuration of the surgical garment.

LXVI. The method of clause LVII, further comprising coupling the surgical garment to the surgical helmet, such that the surgical garment is at least partially disposed over the surgical helmet.

LXVII. The method of clause LXVI, further comprising:
receiving the signal from the detector indicating the surgical garment is coupled to the surgical helmet; and
delaying transmission of power from the portable energy source to the peripheral device for a defined first period of time following receipt of the signal from the detector.

LXVIII. The method of clause LXVI, further comprising separating the surgical garment from the surgical helmet, such that the surgical garment is not coupled to the surgical helmet.

LXIX. The method of clause LXVIII, further comprising:
receiving the signal from the detector indicating the surgical garment is separated from the surgical helmet; and
continuing transmission of power to said peripheral device for a defined second period of time following receipt of the signal from the detector.

LXX. A surgical apparel system comprising:
a helmet assembly comprising a headband with a control element for adjusting the size of headband, said helmet assembly configured to be worn by a user during a surgical procedure;
a surgical garment configured to define a microbial barrier between said helmet assembly and an environment, said surgical garment comprising:
a flexible shield member integral with said surgical garment;
an attachment member positioned proximate a top portion of said flexible shield member and configured to releasably couple said flexible shield member to said helmet assembly; and
wherein said attachment member is configured to operatively engage said helmet assembly which results in a curvature change of said top portion of said flexible shield member relative to the user's face when said control element of said headband is manipulated to minimize the distance between said flexible shield member and the user's face.

LXXI. The surgical apparel system of clause LXX, wherein said helmet assembly further comprises a ventilation system configured to circulate air in the space between said flexible shield member and the user's face.

LXXII. The surgical apparel system of clause LXX, wherein said attachment member comprises a first attachment member and a second attachment member;
wherein the flexible shield member comprises a centerline configured to bisect said flexible shield member to define a first region and a second region on opposing sides of said centerline;
wherein said first attachment member is positioned in said first region of said flexible shield member; and
wherein said second attachment member is positioned in said second region of said flexible shield member.

LXXIII. The surgical apparel system of clause LXXII, wherein said helmet assembly further comprises a chin bar that extends outwardly from said headband so that the chin bar extends around and forward of the face of the user wearing said helmet assembly.

LXXIV. The surgical apparel system of clause LXXIII, wherein said chin bar comprises at least two flexible members extending from opposite sides of said headband, each of said at least two flexible members comprising a first end configured to couple to said headband and an opposing second end; and
a beam configured to couple to and extend between said second end of each of said at least two flexible members so that said beam is positioned below and forward of the chin of the user wearing said helmet assembly.

LXXV. The surgical apparel system of clause LXXIV, wherein said at least two flexible members operatively engage said headband, such that when said control element of said headband is manipulated, said at least two flexible members are configured to flex based, at least in part, on the change in circumference of said headband.

LXXVI. The surgical apparel system of clause LXXIV, wherein said helmet assembly further comprises a first coupler and a second coupler, each of which is positioned proximate said first end of each of said at least two flexible members of said chin bar; and
wherein said first attachment member is configured to releasably engage said first coupler and said second attachment member is configured to releasably engage said second coupler.

LXXVII. The surgical apparel system of clause LXXVI, wherein said first coupler comprises one of a ferromagnetic material or a magnetic material; and
wherein said first attachment member comprises the other of said ferromagnetic material or said magnetic material LXXVIII. The surgical apparel system of clause LXX, wherein said attachment member comprises an elongate member configured to extend along said top portion of said flexible shield member.

LXXIX. A method of adjusting a surgical garment configured to be worn with a helmet assembly having a headband with a control member configured to adjust the size of the headband, said method comprising:
providing said surgical garment configured to be worn by a user during a surgical procedure, said surgical garment comprising:
a flexible shield member integral with the surgical garment;
an attachment member positioned proximate a top portion of the flexible shield member; and
wherein the attachment member is configured to operatively engage the helmet assembly to change curvature of the top portion of the flexible shield member relative to the user when the control element of the headband is manipulated to minimize the distance between the flexible shield member and the user's eyes; and
attaching the attachment member to the helmet assembly; and
manipulating the control member to adjust the circumference of the headband to change the curvature of the flexible shield member and minimize the distance between the flexible shield member and the user's eyes.

LXXX. The method of clause LXXIX, wherein the helmet assembly further comprises a ventilation system configured to circulate air in the space between the flexible shield member and the user's face; and manipulating the control member to change the curvature of the flexible shield member further comprises altering the circulation pattern of the air in the space between the flexible shield member and the user.

LXXXI. A surgical garment assembly for use with a surgical helmet worn by a user wherein said surgical helmet comprises an attachment feature and at least one coupling member, said surgical garment assembly configured to be at least partially disposed over the surgical helmet and configured to provide a microbial barrier between the user and a medical environment, said surgical garment assembly comprising:
  a surgical fabric defining an opening,
  a transparent face shield disposed within said opening, said transparent face shield comprising an upper portion, a lower portion, a first surface and an opposing second surface;
    a first aperture in said upper portion of said transparent face shield configured to removably engage the attachment feature of the surgical helmet to align said transparent face shield relative to the surgical helmet;
    a first attachment element, said first attachment element being secured to said lower portion of said transparent face shield;
    wherein said first attachment element comprises a retention feature, and said retention feature is closer to said second surface of said transparent face shield than said first surface;
    wherein said first attachment element comprises a magnetic material; and
    wherein said first attachment element defines a coupling recess on said wearer side of said microbial barrier configured to removably engage one of the at least one coupling members on the surgical helmet.

LXXXII. A surgical apparel system including a peripheral device, said surgical apparel system comprising:
  a surgical helmet to be worn over the head of a wearer, said surgical helmet comprising a face frame, said face frame comprising:
    a chin bar having a distal surface and defining a recess in said distal surface;
    a first coupling member disposed within said recess and having a distal surface positioned proximal to said distal surface of said chin bar, said first coupling member comprising one of a ferromagnetic material or a magnetic material;
  a surgical garment configured to be at least partially disposed over said surgical helmet to provide a microbial barrier between a medical environment and the wearer, said surgical garment comprising:
    a surgical fabric defining an opening configured to be positioned in front of the face of the wearer when at least partially disposed over said surgical helmet;
    a transparent face shield disposed within said opening of said surgical fabric, said transparent face shield comprising an upper portion, a lower portion, a first surface and an opposing second surface;
    a first attachment element coupled to said transparent face shield and comprising the other of the ferromagnetic material or the magnetic material, said first attachment element comprising a head having a proximal surface, said head configured to removably engage said first coupling member when said surgical garment is at least partially disposed over said surgical helmet; and
    wherein said proximal surface of said head is positioned proximal to said distal surface of said chin bar when said first attachment element engages said first coupling member.

LXXXIII. The surgical apparel system of clause LXXXII, wherein said surgical helmet further comprises a sensor disposed within said chin bar and positioned adjacent said first coupling member; and
  wherein said sensor is configured to detect when said surgical garment first attachment element is coupled to said surgical helmet by detecting the presence of said first attachment element adjacent to said first coupling member.

LXXXIV. The surgical apparel system of clause LXXXIII, wherein said first coupling member comprises a magnetic material and said first attachment element comprises a ferromagnetic material; and
  wherein said sensor is a Hall-Effect sensor configured to detect changes in the magnetic field surrounding said first coupling member based, at least in part, on the proximity of said first attachment element to said first coupling member.

LXXXV. The surgical apparel system of clause LXXXIII, wherein said first coupling member comprises a ferromagnetic material and said first attachment element comprises a magnetic material; and
  wherein said sensor is a Hall-Effect sensor configured to detect changes in the magnetic field surrounding said first coupling member based, at least in part, on the proximity of said first attachment element to said first coupling member LXXXVI. The surgical apparel system of clause LXXXII, wherein said first coupling member further comprises:
  a proximal surface opposite said distal surface; and
  a transverse plane extending through said proximal and distal surfaces of said first coupling member to define opposing lateral portions of said first coupling member;
  wherein said first coupling member comprises a magnetic material that is polarized across said transverse plane.

LXXXVII. The surgical apparel system of clause LXXXII, wherein said first coupling member further comprises:
  a proximal surface opposite said distal surface; and
  a transverse plane extending through said proximal and distal surfaces of said first coupling member to define opposing lateral portions of said first coupling member;
  wherein said first coupling member comprises a magnetic material that is polarized across said transverse plane such that one of said opposing lateral portions of said first coupling member comprises a first polarity and the other of said opposing lateral portions comprises a second polarity.

LXXXVIII. The surgical apparel system of clause LXXXVI or LXXXVII, wherein a periphery of each of said proximal surface and said distal surface defines a center axis of said first coupling member;
  wherein said transverse plane is configured to intersect said center axis of said first coupling member.

LXXXIX. The surgical apparel system of any of clauses LXXXVI-LXXXVIII, wherein said surgical helmet further comprises a sensor positioned on said transverse plane and adjacent to said first coupling member;
  wherein said sensor is configured to detect when said surgical garment first attachment element is coupled to said surgical helmet by detecting the presence of said first attachment element adjacent to said first coupling member.

XC. The surgical apparel system of clause LXXXII, wherein said proximal surface of said first attachment element defines a coupling recess on said wearer side of said microbial barrier and is configured to removably engage said first coupling member on said surgical helmet, said coupling recess shaped to resist decoupling of said surgical garment from the surgical helmet in response to a lateral force being applied to said transparent face shield.

XCI. The surgical apparel system of clause LXXXII, wherein said first attachment element further comprises a coupling recess formed in said proximal surface of said head and is configured to engage said first coupling member; and wherein said coupling recess of said first attachment element is positioned proximal to said distal surface of said chin bar when said first attachment element engages said first coupling member.

XCII. The surgical apparel system of clause XCI, wherein said coupling recess defines a coupling surface that opens toward said proximal surface of said head, said coupling surface having a concave shape.

XCIII. The surgical apparel system of clause LXXXII, wherein said transparent face shield further comprises a first aperture in said upper portion;

wherein said surgical helmet further comprises a top beam comprising an alignment channel; and wherein said top beam further comprises a protrusion at least partially disposed in said alignment channel, said protrusion configured to engage said first aperture in said upper portion of said face shield.

XCIV. The surgical apparel system of clause XCIII, wherein said transparent face shield further comprises a tab extending from said upper portion of said transparent face shield, said tab comprising opposing outer edges;

wherein said first aperture of said transparent face shield is at least partially disposed within said tab; and wherein said tab is configured to be at least partially disposed within said alignment channel when said first aperture engages said protrusion.

XCV. The surgical apparel system of clause LXXXII, wherein said head of said first attachment element further comprises a distal surface opposite said proximal surface and a post extending distally from said distal surface of said head.

XCVI. The surgical apparel system of clause XCV, wherein said post of said first attachment element further comprises a proximal portion and a distal portion;

wherein said proximal portion has a first dimension and said distal portion has a second dimension, said post configured such that said first dimension is greater than said second dimension;

wherein said transparent face shield further comprises a second aperture in said lower portion; and wherein said distal portion of said post of said first attachment element is at least partially disposed in said second aperture and said proximal portion abuts said transparent face shield to space said distal surface of said head from said first surface of said transparent face shield.

XCVII. The surgical apparel system of clause LXXXII, wherein said surgical helmet comprises a second coupling member disposed within a second recess in said distal surface of said chin bar and comprising the same material as said first coupling member;

wherein said surgical garment comprises a second attachment member comprising the same material as said first attachment member, said second attachment member coupled to said transparent face shield such that said first and second attachment members are coupled to opposing lateral sides of said transparent face shield; and wherein said second attachment member is configured to removably engage said second coupling member when said surgical garment is at least partially disposed over said surgical helmet.

XCVIII. A surgical apparel system to provide a microbial barrier between a medical environment and a wearer, said system comprising
a surgical helmet including at least two magnetic coupling members and a protrusion;
a surgical garment configured to be at least partially disposed over the surgical helmet, said surgical garment comprising an opening;
a transparent face shield disposed within said opening of said surgical garment, said transparent face shield comprising:
a first surface and an opposing second surface;
an upper portion and a lower portion;
a first aperture formed in said upper portion of said transparent face shield configured to removably engage said protrusion of said surgical helmet;
a first attachment element and a second attachment element, said first and second attachment elements being secured to said lower portion of said transparent face shield;
wherein each of said first and said second attachment elements comprises a ferromagnetic material;
wherein each of said first and said second attachment elements defines a respective coupling recess on said wearer side of said microbial barrier and is configured to removably engage the magnetic coupling members on said surgical helmet, said coupling recesses are shaped to resist decoupling of said surgical garment from said surgical helmet.

XCIX. The surgical apparel system of clause XCVIII, wherein said coupling recesses are shaped to resist decoupling of said surgical garment from said surgical helmet in response to a lateral force being applied to said transparent face shield.

C. A surgical apparel system including a peripheral device, said surgical apparel system comprising:
a surgical helmet to be worn over the head of a wearer, said surgical helmet comprising a face frame, said face frame comprising:
a top beam comprising a first member;
a chin bar extending from said top beam, said chin bar comprising a distal surface and defining a recess in said distal surface; and
a coupling member at least partially disposed within said recess in said chin bar, said coupling member comprising one of a ferromagnetic material or a magnetic material;
wherein said chin bar comprises a sensor; a surgical garment configured to be at least partially disposed over said surgical helmet to provide a microbial barrier between a medical environment and a wearer, said surgical garment comprising:
a surgical fabric comprising an opening;
a transparent face shield disposed within said opening of said surgical fabric, said transparent face shield having an upper portion and a lower portion; and
a first aperture in said upper portion of said transparent face shield configured to removably engage said first member of the surgical helmet to align said transparent face shield relative to the surgical helmet;
an attachment element comprising the other of the ferromagnetic material or the magnetic material, said attachment element configured to removably engage said coupling member to couple said surgical garment to said surgical helmet; and wherein said sensor is positioned and configured to detect when said attachment element is engaged with said coupling member and to transmit a signal related to operation of the peripheral device based on engagement of said attachment element with said coupling member.

CI. The surgical apparel system of clause C, further comprising a controller coupled to said sensor and configured to receive said signal from said sensor; and wherein said controller is configured to control an operational characteristic of said peripheral device based on said signal from said sensor.

CII. The surgical apparel system of clause CI, wherein said sensor is configured to toggle between a first state and a second state;

wherein said sensor is configured to be in said first state when said surgical garment is at least partially disposed over said surgical helmet and said attachment element is engaged with said coupling member;

wherein said sensor is configured to be in said second state when said surgical garment is separated from said surgical helmet and said attachment element is separated from said coupling member; and wherein said sensor is configured to produce said signal based, at least in part, on said sensor being in said first state or said second state.

CIII. The surgical apparel system of clause CII, wherein said controller is configured to delay transmission of power to said peripheral device for a defined first period of time once said controller receives said signal from said sensor indicating said surgical garment is at least partially disposed over said surgical helmet.

CIV. The surgical apparel system of clause CII, wherein said controller is configured to continue transmission of power to said peripheral device for a defined second period of time once said controller receives said signal from said sensor indicating said surgical garment is separated from said surgical helmet.

CV. The surgical apparel system of clause CII, further comprising a memory device coupled to said surgical helmet and in communication with said controller, said memory device configured to store data related to the operation of said peripheral device.

CVI. The surgical apparel system of clause CV, further comprising an energy sensor in communication with said controller, said energy sensor configured to detect the power level of said portable energy source and communicate an energy signal to said controller based on the power level of said portable energy source; and wherein said controller is configured to communicate data to said memory device for storage based on said energy signal from said energy sensor, said data related to a user setting for the peripheral device.

CVII. The surgical apparel system of clause CVI, wherein said controller is configured to communicate data to said memory device for storage when said energy signal from said energy sensor indicates that the remaining power level of said portable energy source has reached a threshold value, said data related to said user setting of said peripheral device.

CVIII. The surgical apparel system of clause CVII, wherein said memory device is configured to store said user setting of said peripheral device so long as said sensor remains in said first state; and wherein said controller is configured to restart operation of said peripheral device based on stored said user setting upon replacement of said portable energy source.

CIX. The surgical apparel system of clause CV, wherein said memory device is configured to clear said user setting of said peripheral device when said sensor toggles from said first state to said second state and said portable energy source is disconnected from said surgical helmet.

CX. The surgical apparel system of clause CV, wherein said memory device is configured to store data related to a plurality of characteristics of said surgical garment;

wherein said sensor is configured to identify one of a plurality of configurations of said surgical garment that is at least partially disposed over said surgical helmet; and wherein said controller is configured to control at least one operational characteristic of said peripheral device based, at least in part, on the identified one of said plurality of configurations of said surgical garment.

CXI. The surgical apparel system of clause C, wherein said coupling member comprises a magnetic material and said attachment element comprises a ferromagnetic material; and wherein said sensor is a Hall Effect sensor configured to detect changes in the magnetic field surrounding said coupling member based, at least in part, on the proximity of said attachment element relative to said coupling member.

CXII. The surgical apparel system of clause C, wherein said first coupling member further comprises:

a proximal surface opposite said distal surface;

a transverse plane extending through said proximal and distal surfaces of said first coupling member to define opposing lateral portions of said first coupling member;

wherein said first coupling member comprises a magnetic material that is polarized across said transverse plane.

CXIII The surgical apparel system of clause C, wherein said first coupling member further comprises:

a proximal surface opposite said distal surface;

a transverse plane extending through said proximal and distal surfaces of said first coupling member to define opposing lateral portions of said first coupling member;

wherein said first coupling member comprises a magnetic material that is polarized across said transverse plane such that one of said opposing lateral portions of said first coupling member comprises a first polarity and the other of said opposing lateral portions comprises a second polarity.

CXIV. The surgical apparel system of clauses CXII or CXIII, wherein a periphery of each of said proximal surface and said distal surface defines a center axis of said first coupling member;

wherein said transverse plane is configured to intersect said center axis of said first coupling member.

CXV. The surgical apparel system of any of clauses CXII-CXIV, wherein said surgical helmet further comprises a sensor positioned on said transverse plane and adjacent to said first coupling member;

wherein said sensor is configured to detect when said surgical garment first attachment element is coupled to said surgical helmet by detecting the presence of said first attachment element adjacent to said first coupling member.

CXVI. A surgical apparel system including a peripheral device, said surgical apparel system comprising:

a surgical helmet to be worn over the head of a wearer, said surgical helmet comprising a face frame, said face frame comprising:

a top beam extending across the width of said face frame, said top beam defining an alignment channel;

a protrusion disposed at least partially within said alignment channel;

a surgical garment assembly to be at least partially disposed over said surgical helmet to provide a microbial barrier between a medical environment and the wearer, said surgical garment assembly comprising:

a surgical fabric defining an opening configured to be positioned in front of the face of the wearer when at least partially disposed over said surgical helmet;

a transparent face shield disposed within said opening of said surgical fabric, said transparent face shield comprising an upper portion and a lower portion;

a tab extending from an outer perimeter of said upper portion of said transparent face shield;

wherein said tab at least partially defines a coupling aperture sized to at least partially receive said protrusion; and wherein said tab and said alignment channel are complementarily sized such that said tab can be positioned within said alignment channel and the coupling aperture can be slid over the protrusion.

CXVII. The surgical apparel system of clause CXVI, wherein said surgical helmet further comprises a chin bar extending from said top beam and configured to define a face frame, said chin bar comprising a distal surface and a recess in said distal surface;

a first coupling member disposed within said recess of said chin bar, said first coupling member comprising a distal surface and formed from a magnetic material; and wherein said transparent face shield further comprises a first attachment element comprising a proximal surface and formed from a ferromagnetic material, said first attachment member configured to removably couple with said first coupling member when said surgical garment is at least partially disposed over said surgical helmet.

CXVIII. The surgical apparel system of clause CXVII, wherein said proximal surface of said first attachment member is configured to engage said distal surface of said first coupling member when said surgical garment is at least partially disposed over said surgical helmet; and wherein said first coupling member is disposed within said recess of said chin bar such that said distal surface of said first coupling member is positioned proximal to said distal surface of said chin bar.

CXIX. The surgical apparel system of clause CXVIII, wherein said proximal surface of said first attachment member is configured to be positioned proximal to said distal surface of said chin bar when said surgical garment is at least partially disposed over said surgical helmet.

CXX. The surgical apparel system of any of the preceding clauses, wherein at least one of said coupling members comprises a protruded surface; and wherein said attachment element comprises a reciprocal recessed surface on said wearer side of said microbial barrier that is configured to removably engage said protruded surface of said coupling member on said surgical helmet when said surgical garment is at least partially disposed over said surgical helmet.

CXXI. A method of attaching a surgical garment to a surgical helmet, the surgical helmet comprising a top beam, the top beam defining an alignment channel and a first member at least partially disposed within the alignment channel, a chin bar defining a first attachment recess, and a second attachment recess, with the chin bar including a first magnet at least partially disposed within said first attachment recess and a second magnet at least partially disposed within said second attachment recess, said method comprising:

providing a surgical garment including a transparent face shield, the face shield comprising a first aperture at least partially disposed within a tab extending from a top portion of the transparent face shield, and a first attachment element and a second attachment element coupled to a bottom portion of the transparent face shield, each of the first and second attachment elements having a recessed surface, the surgical garment being inside-out;

positioning the surgical garment such that the tab of the transparent face shield is at least partially within the alignment channel;

arranging the surgical garment such that the first member of the surgical helmet extends through the first aperture; and manipulating the surgical garment about an interface between the first aperture of the face shield and the first member to position the transparent face shield in front of the wearer's face.

CXXII. The method of clause CXXI, further comprising the step of positioning the transparent face shield such that the first ferromagnetic attachment element is at least partially within the first attachment recess and the second ferromagnetic attachment element is at least partially within the second attachment recess so that the first and second ferromagnetic attachment element are attracted to the first and second magnet after the step of manipulating.

CXXIII The method of clause CXXI, wherein the surgical garment is provided in a sterile package; and wherein said method further comprises opening the package and removing at least a portion of the surgical garment from the package prior to the step of positioning the surgical garment such that the tab of the transparent face shield is at least partially within the alignment channel.

CXXIV. A surgical garment to provide a microbial barrier between a medical environment and a wearer, said surgical garment configured to be disposed over a surgical helmet including at least two magnetic coupling members, said surgical garment comprising:

a first material configured to be at least partially disposed over the surgical helmet, said first material comprising an opening;

a transparent face shield disposed within said opening of said first material, said transparent face shield comprising:

a first surface and an opposing second surface; and an upper portion and a lower portion;

a first attachment element and a second attachment element, said first and second attachment elements being secured to said transparent face shield;

wherein at least one of said first and second attachment elements comprises a ferromagnetic material; and wherein at least one of said first and second attachment elements defines a respective coupling recess on said wearer side of said microbial barrier and is configured to removably engage the magnetic coupling members on the surgical helmet.

CXXV. The surgical garment of clause CXXIV, wherein each of said attachment elements and the magnetic coupling members comprises a complementary polyaxial surface that allow said attachment element to slidably engage the respective magnetic coupling member.

CXXVI. A surgical garment to provide a microbial barrier between a medical environment and a wearer, said surgical garment configured to be disposed over a surgical helmet including a magnetic coupling member, said surgical garment comprising:

a means of coupling said surgical garment to the magnetic coupling member of the surgical helmet;

wherein the magnetic coupling member comprises a convex shaped surface.

CXXVII. The surgical garment of clause CXXVI, wherein said surgical garment comprises a first attachment element;

wherein said first attachment element comprises a ferromagnetic material; and wherein said first attachment element defines a coupling recess on said wearer side of said microbial barrier that is configured to removably engage the magnetic coupling member on the surgical helmet.

CXXVIII. A surgical garment to provide a microbial barrier between a medical environment and a wearer, said surgical garment configured to be disposed over a surgical helmet including a protrusion at least partially disposed within an alignment channel, and a chin bar, wherein the chin bar includes at least two magnetic coupling members, said surgical garment comprising:

a first material configured to be at least partially disposed over the surgical helmet, said first material comprising an opening;

a transparent face shield disposed within said opening of said first material, said transparent face shield comprising:
  a first surface and an opposing second surface;
  an upper portion and a lower portion; and
  a first aperture in said transparent face shield configured to removably engage the protrusion of the surgical helmet to align said first material relative to the surgical helmet;

a first attachment element and a second attachment element, said first and second attachment elements being secured to said lower portion of said transparent face shield on opposing lateral sides of said first aperture;
  wherein each of said first and second attachment elements comprises a retention feature;
  wherein at least one of said first and second attachment elements at least partially comprises a ferromagnetic material; and
  wherein at least one of said first and second attachment elements defines a respective coupling recess on said wearer side of said microbial barrier, and each of said first and second attachment elements is configured to removably engage one of the magnetic coupling members on the surgical helmet.

CXXIX. The surgical garment of clause CXXVIII, wherein each of said attachment elements further comprises a head comprising a distal surface and a proximal surface, said distal surface being closer to said first surface of said transparent face shield than said second surface; and wherein said coupling recess is formed in said proximal surface of said head.

CXXX. The surgical garment of clause CXXIX, wherein said coupling recess defines a coupling surface that opens toward said proximal surface of said head, said coupling surface having a concave shape configured to resist decoupling of said first and second attachment elements from the at least two magnetic coupling members of the surgical helmet.

CXXXI. The surgical garment of clause CXXIX, wherein said coupling recess defines a coupling surface that opens toward said proximal surface of said head, said coupling surface being multi-faceted and configured to resist decoupling of said first and second attachment elements from the at least two magnetic coupling members of the surgical helmet.

CXXXII. The surgical garment of clause CXXIX, wherein said coupling recess defines a coupling surface that opens toward said proximal surface of said head, said coupling surface having a generally hemispherical shape configured to resist decoupling of said first and second attachment elements from the at least two magnetic coupling members of the surgical helmet.

CXXXIII. The surgical garment of clause CXXIX, wherein said coupling recess defines a coupling surface that opens toward said proximal surface of said head, said coupling surface being generally bowl-shaped and configured to resist decoupling of said first and said second attachment elements from the at least two magnetic coupling members of the surgical helmet.

CXXXIV. The surgical garment of clause CXXIX, wherein said coupling recess is substantially arcuate in at least one dimension and configured to resist decoupling of said first and second attachment elements from the at least two magnetic coupling members of the surgical helmet.

CXXXV. The surgical garment of clause CXXIX, wherein said head further comprises a rim that annularly surrounds said coupling recess on said proximal surface.

CXXXVI. The surgical garment of clause CXXIX, wherein said head of each of said first and second attachment elements further comprises a post extending distally from said distal surface of said head.

CXXXVII. The surgical garment of clause CXXXVI, wherein said transparent face shield further comprises a second aperture and a third aperture, each of said second and third apertures positioned in said lower portion of said transparent face shield; and wherein said post of said first attachment element is at least partially disposed in said second aperture and said post of said second attachment element is at least partially disposed in said third aperture.

CXXXVIII. The surgical garment of clause CXXXVI, wherein said post of said first attachment element further comprises a proximal portion and a distal portion;

wherein said proximal portion has a first dimension and said distal portion has a second dimension, said post configured such that said first dimension is greater than said second dimension; and wherein said distal portion of said post of said first attachment element is at least partially disposed in said second aperture and said proximal portion abuts said transparent face shield to space said distal surface of said head from said first surface of said transparent face shield.

CXXXIX. The surgical garment of clause CXXXVIII, further comprising a transparent layer removably coupled to said transparent face shield on said environment side of said microbial barrier; and wherein said transparent layer is configured to be removed from said transparent face shield to remove any debris accumulated on said transparent layer that may obstruct the wearer's view through said transparent face shield.

CXL. The surgical garment of clause CXXXVII, further comprising a retaining member, said retaining member at least partially receives said post of said attachment element and abuts said second surface of said transparent face shield to define said retention feature.

CXLI. The surgical garment of clause CXXVIII, wherein said surgical garment assembly is in the form of a toga.

CXLII. The surgical garment of clause CXXVIII, wherein said transparent face shield further comprises a first axis extending from said upper portion to said lower portion and bisects said transparent face shield, and said first and second attachment elements are symmetrically spaced relative to said first axis of said transparent face shield.

CXLIII. The surgical garment of clause CXXVIII, wherein said transparent face shield further comprises a perimeter section that is covered by said surgical garment.

CXLIV. The surgical garment of clause CXLIII, wherein said first and second attachment elements are coupled to said perimeter section of said transparent face shield.

CXLV. The surgical garment of clause CXXVIII, wherein said retention features are closer to said second surface of said transparent face shield than said first surface.

CXLVI. The surgical garment of clause CXXVIII, wherein said coupling recess of at least one of said first and second attachment elements is defined by a combination of at least one of said first or second attachment elements and said first surface of said transparent face shield.

CXLVII. A surgical garment to provide a microbial barrier between a medical environment and a wearer, said surgical garment configured to be disposed over a surgical helmet including at least two magnetic coupling members, said surgical garment comprising:
a first material configured to be at least partially disposed over the surgical helmet, said first material comprising an opening;
a transparent face shield disposed within said opening of said first material, said transparent face shield comprising:
a first surface and an opposing second surface; and
an upper portion and a lower portion;
a first coupler disposed on the wearer side of said first material to removably engage the surgical helmet; and
a first attachment element and a second attachment element, said first and second attachment elements being secured to said lower portion of said transparent face shield;
wherein each of said first and second attachment elements comprises a retention feature;
wherein at least one of said first and second attachment elements comprises a ferromagnetic material; and
wherein at least one of said first and second attachment elements defines a respective coupling recess on said wearer side of said microbial barrier and is configured to removably engage the magnetic coupling members on the surgical helmet.

CXLVIII. The surgical garment of clause CXLVII, wherein each of said attachment elements further comprises a head having a distal surface and a proximal surface; and
wherein said coupling recess is formed in said proximal surface of said head.

CXLIX. The surgical garment of clause CXLVIII, wherein said coupling recess defines a coupling surface that opens toward said proximal surface of said head, said coupling surface having a concave shape configured to resist decoupling of said first and second attachment elements from the at least two magnetic coupling members of the surgical helmet.

CL. The surgical garment of clause CXLVIII, wherein said head of said first attachment element further comprises a post extending distally from said distal surface of said head.

CLI. The surgical garment assembly of clause CL, wherein said transparent face shield further comprises a second aperture, said second aperture positioned in said lower portion of said transparent face shield; and
wherein said post of said first attachment element is at least partially disposed in said second aperture.

CLII. The surgical garment of clause CL, wherein said post of said first attachment element further comprises a proximal portion and a distal portion;

wherein said proximal portion comprises a first dimension and said distal portion comprises a second dimension, said post configured such that said first dimension is greater than said second dimension; and
wherein said distal portion of said post is at least partially disposed in said second aperture and said proximal portion abuts said first surface of said transparent face shield to space said distal surface of said head from said first surface of said transparent face shield.

CLIII. The surgical garment of clause CXLVII, wherein said retention features are closer to said second surface of said transparent face shield than said first surface.

CLIV. The surgical garment of clause CXLVII, wherein said coupling recess of at least one of said first and second attachment elements is defined by a combination of at least one of said first or second attachment elements and said first surface of said transparent face shield.

CLV. A surgical garment to provide a microbial barrier between a medical environment and a wearer, said surgical garment configured to be disposed over a surgical helmet that includes at least two magnetic coupling members, said surgical garment comprising:
a first material configured to be at least partially disposed over the surgical helmet, said first material comprising an opening;
a transparent face shield disposed within said opening of said first material, said transparent face shield comprising an upper portion and a lower portion;
a first coupler to removably engage the surgical helmet; and
a first attachment element and a second attachment element, said first and second attachment elements being secured to said lower portion of said transparent face shield;
wherein each of said first and second attachment elements comprises a head comprising a distal surface and a proximal surface, and a post extending from said distal surface;
wherein said post comprises a distal portion and a proximal portion, said proximal portion abutting said distal surface of said head;
wherein said proximal portion comprises a first dimension and said second portion comprises a second dimension, said first dimension being greater than said second dimension; and
wherein said head of each of said first and second attachment elements comprises a ferromagnetic material and said proximal surface of each of said heads is configured to removably engage one of the magnetic coupling members on the surgical helmet.

CLVI. A surgical garment to provide a microbial barrier between a medical environment and a wearer, said surgical garment configured to be disposed over a surgical helmet including a magnetic coupling member, said surgical garment comprising:
a first material configured to be at least partially disposed over the surgical helmet, said first material comprising an opening;
a transparent face shield disposed within said opening of said first material, said transparent face shield comprising:
a first surface and an opposing second surface; and
an upper portion and a lower portion;
a first coupler disposed on the wearer side of said first material that is configured to removably engage the surgical helmet; and
a first attachment element secured to said lower portion of said transparent face shield;
wherein said first attachment element comprises a ferromagnetic material; and wherein said first attachment element defines a coupling recess on said wearer side of said microbial barrier that is configured to removably engage the magnetic coupling member on the surgical helmet.

CLVII. The surgical garment of clause CLVI, wherein said first attachment element comprises a retention feature configured to secure said first attachment element to said transparent face shield; and wherein said retention feature is closer to said second surface of said transparent face shield than said first surface.

CLVIII. A medical garment configured to provide a barrier between an environment and a wearer, said medical garment intended for use with a helmet that includes a protrusion at least partially disposed within an alignment channel, and a chin bar, wherein the chin bar includes a magnetic coupling member, said medical garment comprising:

a shell configured to be at least partially disposed over the helmet, said shell comprising an opening;

a transparent face shield disposed within said opening of said shell, said transparent face shield comprising an upper portion and a lower portion;

a tab on the wearer side of said shell, said tab having opposing outer edges for aligning said shell relative to the helmet via the alignment channel of the helmet;

a first aperture formed in said tab and configured to removably engage the protrusion of the helmet to align said shell relative to the helmet; and a first attachment element secured to said lower portion of said transparent face shield;

wherein said first attachment element comprises a ferromagnetic material;

wherein said first attachment element defines a coupling recess on the wearer side of said barrier and is configured to removably engage the magnetic coupling member on the helmet.

CLIX. The medical garment of clause CLVIII, wherein said attachment element further comprises:

a head comprising a distal surface and a proximal surface; and a post extending distally from said distal surface of said head; and wherein said coupling recess is formed in said proximal surface of said head.

CLX. The medical garment of claim CLIX, wherein said coupling recess defines a coupling surface that opens to said proximal surface of said head, said coupling surface having a concave shape configured to resist decoupling of said first attachment element from the magnetic coupling member of the helmet.

CLXI. The medical garment of clause CLIX, wherein said coupling recess is substantially arcuate in at least one dimension.

CLXII. The medical garment of clause CLIX, wherein the coupling recess of the first attachment element provides a means for attaching said medical garment to the magnetic coupling member having a convex surface.

CLXIII The medical garment of clause CLIX, wherein said transparent face shield further comprises a second aperture, said second aperture positioned in said lower portion of said transparent face shield; and wherein said post of said first attachment element is at least partially disposed in said second aperture.

CLXIV. The medical garment of clause CLXIII, wherein each of said first and second attachment elements comprises a retention feature, and said retention featured coupled to a distal end of said post.

CLXV. The medical garment of clause CLVIII, wherein said tab is configured to extend from said upper portion of said transparent face shield.

CLXVI. The medical garment of clause CLVIII, wherein said tab is formed such that said opposing outer edges are generally parallel to one another.

CLXVII. The medical garment of clause CLVIII, wherein said first attachment element is secured to said transparent face shield with an adhesive.

CLXVIII. A medical garment to provide a barrier between an environment and a wearer, said medical garment intended for use with a helmet including a protrusion at least partially disposed within an alignment channel, and a chin bar, wherein the chin bar includes at least two magnetic coupling members, said medical garment comprising:

a shell configured to be at least partially disposed over the helmet, said shell comprising an opening;

a transparent face shield disposed within said opening of said shell, said transparent face shield comprising:

a first surface and an opposing second surface; and an upper portion and a lower portion;

a tab on said wearer side of said shell, said tab having outer edges for aligning said shell relative to the helmet via the alignment channel of the helmet;

a first aperture at least partially formed in said tab and configured to removably engage the protrusion of the helmet to align said shell relative to the helmet; and a first attachment element and a second attachment element, said first and second attachment elements being secured to said lower portion of said transparent face shield on opposing lateral sides of said first aperture;

wherein each of said first and second attachment elements comprises a retention feature, and said retention features are closer to said second surface of said transparent face shield than said first surface;

wherein said first and second attachment elements each comprises a ferromagnetic material; and wherein at least one of said first and second attachment elements defines a respective coupling recess on said wearer side of said barrier, and said first and second attachment elements are each configured to removably engage one of the magnetic coupling members on the helmet.

CLXIX. The medical garment of clause CLXVIII, wherein each of said attachment elements further comprises a head comprising a distal surface and a proximal surface, said distal surface being closer to said first surface of said transparent face shield than said second surface; and wherein said coupling recess is formed in said proximal surface of said head of at least one of said first and second attachment elements.

CLXX. The medical garment of clause CLXVIII, wherein said retention features are closer to said second surface of said transparent face shield than said first surface.

CLXXI. The medical garment of clause CLXVIII, wherein said coupling recess of at least one of said first and second attachment elements is defined by a combination of at least one of said first or second attachment elements and said first surface of said transparent face shield.

CLXXII. The medical garment of clause CLXVIII, wherein said tab extends from said upper portion of said transparent face shield.

CLXXIII The medical garment of clause CLXVIII, wherein each of said first and second attachment elements further comprises:

a head comprising a distal surface and a proximal surface; and a post extending distally from said distal surface of said head; and wherein said coupling recess is formed in said proximal surface of said head of both of said first attachment element and said second attachment element.

CLXXIV. The medical garment of clause CLXXIII, wherein said retention featured is coupled to a distal end of said post to secure each of said first and second attachment elements to said transparent face shield.

CLXXV. A medical garment configured to provide a barrier between an environment and a wearer, said medical garment intended for use with a helmet that includes a protrusion at least partially disposed within an alignment channel, and a chin bar, wherein the chin bar includes at least two magnetic coupling members, said medical garment comprising:

a shell configured to be at least partially disposed over the helmet, said shell comprising an opening;

a transparent face shield disposed within said opening of said shell, said transparent face shield comprising an upper portion, a lower portion, a first surface and an opposing second surface;

a tab extending from said upper portion of said transparent face shield, said tab having outer edges for aligning said shell relative to the helmet via the alignment channel of the helmet;

a first aperture at least partially formed in said tab and configured to removably engage the protrusion of the helmet to align said shell relative to the helmet; and a first attachment element and a second attachment element, said first and second attachment elements being secured to said lower portion of said transparent face shield on opposing lateral sides of said first aperture;

wherein said first and second attachment elements each comprises a ferromagnetic material;

wherein at least one of said first and second attachment elements defines coupling recess on the wearer side of said barrier that is configured to removably engage one of the magnetic coupling members on the helmet.

CLXXVI. The medical garment of clause CLXXV, wherein each of said first and second attachment elements further comprises:

a head comprising a distal surface and a proximal surface; and a post extending distally from said distal surface of said head; and wherein said coupling recess is formed in said proximal surface of said head of at least one of said first attachment element and said second attachment element.

CLXXVII. The medical garment of clause CLXXVI, wherein each of said first and second attachment elements comprises a retention feature coupled to a distal end of said post, and said retention features are closer to said second surface of said transparent face shield than said first surface.

CLXXVIII. A medical garment configured to provide a barrier between an environment and a wearer, said medical garment intended for use with a helmet that includes a protrusion at least partially disposed within an alignment channel, and a chin bar, wherein the chin bar includes a magnetic coupling member, said medical garment comprising:

a shell configured to be at least partially disposed over the helmet, said shell comprising an opening;

a transparent face shield disposed within said opening of said shell, said transparent face shield comprising an upper portion, a lower portion, a first surface and an opposing second surface;

a tab extending from said upper portion of said transparent face shield, said tab having outer edges for aligning said shell relative to the helmet via the alignment channel of the helmet;

a first aperture at least partially formed in said tab and configured to removably engage the protrusion of the helmet to align said shell relative to the helmet; and a first attachment element, said first attachment element being secured to said lower portion of said transparent face shield;

wherein said first attachment element comprises a ferromagnetic material;

wherein said first attachment element defines a coupling recess on the wearer side of said barrier and is configured to removably engage the magnetic coupling member on the helmet.

CLXXIX. The medical garment of clause CLXXVIII, wherein said attachment element further comprises:

a head comprising a distal surface and a proximal surface; and a post extending distally from said distal surface of said head; and wherein said coupling recess is formed in said proximal surface of said head.

CLXXX. The medical garment of clause CLXXIX, wherein said first attachment element comprises a retention feature coupled to a distal end of said post, and said retention features are closer to said second surface of said transparent face shield than said first surface.

CLXXXI. A surgical garment assembly for use with a surgical helmet comprising a magnetic coupling member disposed in a recess and a hall-effect sensor spaced from the coupling member, said surgical garment assembly configured to be at least partially disposed over the surgical helmet to provide a microbial barrier between a user and a medical environment, said surgical garment assembly comprising:

a surgical fabric defining an opening;

a transparent face shield disposed within said opening, said transparent face shield comprising an upper portion, a lower portion, a first surface and an opposing second surface;

a first attachment element coupled to said lower portion of said transparent face shield, said first attachment element comprising:

a ferromagnetic material;

said first attachment element defining a proximal surface facing away from said transparent face shield, said proximal surface including a first point that lies on a longitudinal axis of said first attachment element and that defines a first distance from said first surface of said transparent face shield;

said proximal surface including a second point that defines a second distance from said first surface of said transparent face shield, wherein said second point on said proximal surface is spaced apart from said first point on said proximal surface;

wherein said proximal surface is shaped such that said first distance is less than said second distance; and wherein said first attachment element is configured to removably engage the coupling member on the surgical helmet and trigger the hall-effect sensor when said first attachment element is coupled to the coupling member.

CLXXXII. The surgical garment assembly of claim CLXXXI, wherein said first point of said proximal surface is positioned at a position on said proximal surface that is nearest the first surface of the transparent face shield relative to the second point.

CLXXXIII The surgical garment assembly of claim CLXXXI or CLXXXII, further comprising a tab disposed on said surgical fabric on a user side of the microbial barrier, said tab defining a first aperture configured to removably engage an attachment feature of the surgical helmet to align said transparent face shield relative to the surgical helmet.

CLXXXIV. The surgical garment assembly of claim CLXXXI, wherein said transparent face shield further defines a first aperture in said upper portion of said transparent face shield configured to removably engage an attachment feature of the surgical helmet to align said transparent face shield relative to the surgical helmet.

CLXXXV. The surgical garment assembly of any of clauses CLXXXI-CLXXXIV, wherein said first attachment element further comprises a head that defines said proximal surface, and a distal surface opposite said proximal surface, and a post extending distally from said distal surface of said head.

CLXXXVI. The surgical garment assembly of claim CLXXXV, wherein said post of said first attachment element further comprises a proximal portion and a distal portion; and
wherein said proximal portion has a first dimension and said distal portion has a second dimension, said post configured such that said first dimension is greater than said second dimension.

CLXXXVII. The surgical garment assembly of claim CLXXXVI, wherein said transparent face shield further comprises a second aperture in said lower portion; and
wherein said distal portion of said post of said first attachment element is at least partially disposed in said second aperture, and said proximal portion of said post abuts said transparent face shield to space said distal surface of said first attachment element from said first surface of said transparent face shield.

CLXXXVIII. The surgical garment assembly of claim CLXXXVI, wherein said first attachment element comprises a retention feature coupled to said distal portion of said post, and said retention feature is closer to said second surface of said transparent face shield than to said first surface.

CLXXXIX. The surgical garment assembly of any of clauses CLXXXV-CLXXXVIII, wherein said head of said attachment element comprises metal alloy comprising at least 50% of a ferromagnetic material capable of being magnetically attracted to the coupling member comprising a magnet.

CXC. The surgical garment assembly of any of clauses CLXXXV-CLXXXVIII, wherein said head of said attachment element comprises metal alloy comprising at least 90% of a ferromagnetic material capable of being magnetically attracted to the coupling member comprising a magnet.

CXCI. The surgical garment assembly of any of clauses CLXXXV-CLXXXVIII, wherein said head of said attachment element comprises metal alloy comprising at least half a gram (0.5 g) of a ferromagnetic material capable of being magnetically attracted to the coupling member comprising a magnet.

CXCII. The surgical garment assembly of any of clauses CLXXXV-CLXXXVIII, wherein said head of said attachment element comprises metal alloy comprising at least 95% of a ferromagnetic material capable of being magnetically attracted to the coupling member comprising a magnet.

CXCIII. The surgical garment assembly of any of clauses CLXXX-CLXXXVIII, wherein said head of said attachment element comprises metal alloy comprising at least 98% of a ferromagnetic material capable of being magnetically attracted to the coupling member comprising a magnet.

CXCIV. The surgical garment assembly of any of clauses CLXXXV-CLXXXVIII, wherein said head of said attachment element is formed of metal alloy comprising at least 95% wt. % of a ferromagnetic material capable of being magnetically attracted to the coupling member comprising a magnet.

CXCV. The surgical garment assembly of any of clauses CLXXXIX-CXCIV, wherein said ferromagnetic material is a material chosen from iron, cobalt, and nickel.

CXCVI. The surgical garment assembly of any of clauses CLXXXV-CLXXXVIII, wherein an outer perimeter of said proximal surface is radially spaced from a center of said proximal surface.

CXCVII. The surgical garment assembly of claim CXCVI, wherein said distal surface defines an outer perimeter and a center; and
said center of said proximal surface and said center of said distal surface defining a first axis.

CXCVIII. The surgical garment assembly of claim CXCVII, further comprising a second axis orthogonal to said first axis and positioned to bisect said proximal surface to define a first portion and a second portion;
a first protrusion extending distally from said first portion proximate said outer perimeter of said proximal surface;
a second protrusion extending distally from said second portion proximate said outer perimeter of said proximal surface;
wherein said first protrusion and said second protrusion cooperate to define a recess in said proximal surface; and
wherein said first attachment element is oriented such that at least one of said first protrusion or said second protrusion is positioned proximate the hall-effect sensor when said surgical garment assembly is at least partially disposed over the surgical helmet.

CXCIX. The surgical garment assembly of any of clauses CLXXXI-CXCVIII, wherein a portion of said proximal surface of said first attachment element is configured to be at least partially disposed in the recess of the surgical helmet when said surgical garment assembly is at least partially disposed over the surgical helmet.

CC. The surgical garment assembly of any of clauses CLXXXI-CXCVIII, wherein a portion of said proximal surface that defines said second point is configured to be at least partially disposed in the recess of the surgical helmet when said surgical garment assembly is at least partially disposed over the surgical helmet.

CCI. A surgical garment assembly for use with a surgical helmet comprising a coupling member disposed in a recess and a hall-effect sensor spaced apart from the coupling member, said surgical garment assembly configured to be at least partially disposed over the surgical helmet and configured to provide a microbial barrier between a user and a medical environment, said surgical garment assembly comprising:
a surgical fabric defining an opening;
a transparent face shield disposed within said opening, said transparent face shield comprising an upper portion, a lower portion, a first surface and an opposing second surface;

a first attachment element coupled to said lower portion of said transparent face shield, said first attachment element defining a proximal surface facing away from said transparent face shield;

a first axis of said first attachment element intersecting said proximal surface;

wherein said proximal surface is shaped such that a first point on said proximal surface that lies on said first axis defines a first distance from said first surface of said transparent face shield and such that a second point on said proximal surface defines a second distance from said first surface of said transparent face shield;

wherein said second point on said proximal surface is spaced apart from said first point on said proximal surface, and said first distance is less than said second distance;

wherein said first attachment element comprises a ferromagnetic material; and wherein said first attachment element is configured to removably engage the coupling member on the surgical helmet.

CCII. The surgical garment assembly of claim CCI, wherein said first point of said proximal surface is positioned at a position on said proximal surface that is nearest the first surface of the transparent face shield relative to the second point.

CCIII. The surgical garment assembly of claim CCI or CCII, further comprising a tab disposed on said surgical fabric on a user side of the microbial barrier, said tab defining a first aperture configured to removably engage an attachment feature of the surgical helmet to align said transparent face shield relative to the surgical helmet.

CCIV. The surgical garment assembly of claim CCI, wherein said transparent face shield further defines a first aperture in said upper portion of said transparent face shield configured to removably engage an attachment feature of the surgical helmet to align said transparent face shield relative to the surgical helmet.

CCV. The surgical garment assembly of any of clauses CCI-CCIV, wherein said first attachment element further comprises a head that defines said proximal surface and a distal surface opposite said proximal surface.

CCVI. The surgical garment assembly of claim CCV, wherein said head of said attachment element comprises metal alloy comprising at least 50% of a ferromagnetic material capable of being magnetically attracted to the coupling member comprising a magnet.

CCVII. The surgical garment assembly of claim CCV, wherein said head of said attachment element comprises metal alloy comprising at least 90% of a ferromagnetic material capable of being magnetically attracted to the coupling member comprising a magnet.

CCVIII. The surgical garment assembly of claim CCV, wherein said head of said attachment element comprises metal alloy comprising at least half a gram (0.5 g) of a ferromagnetic material capable of being magnetically attracted to the coupling member comprising a magnet.

CCIX. The surgical garment assembly of claim CCV, wherein said head of said attachment element comprises metal alloy comprising at least 95% of a ferromagnetic material capable of being magnetically attracted to the coupling member comprising a magnet.

CCX. The surgical garment assembly of claim CCV, wherein said head of said attachment element comprises metal alloy comprising at least 98% of a ferromagnetic material capable of being magnetically attracted to the coupling member comprising a magnet.

CCXI. The surgical garment assembly of claim CCV, wherein said head of said attachment element is formed of metal alloy comprising at least 95% wt. % of a ferromagnetic material capable of being magnetically attracted to the coupling member comprising a magnet.

CCXII. The surgical garment assembly of any of clauses CCVI-CCXI, wherein said ferromagnetic material is a material chosen from iron, cobalt, and nickel.

CCXIII The surgical garment assembly of claim CCXV, further comprising a post extending distally from said distal surface of said head CCXIV. The surgical garment assembly of claim CCXIII, wherein said post of said first attachment element further comprises a proximal portion and a distal portion; and wherein said proximal portion has a first dimension and said distal portion has a second dimension, said post configured such that said first dimension is greater than said second dimension.

CCXV. The surgical garment assembly of claim CCXIV, wherein said transparent face shield further defines a second aperture in said lower portion; and wherein said distal portion of said post of said first attachment element is at least partially disposed in said second aperture, and said proximal portion abuts said transparent face shield to space said distal surface of said first attachment element from said first surface of said transparent face shield.

CCXVI. The surgical garment assembly of claim CCXIV or CCXV, wherein said first attachment element comprises a retention feature coupled to said distal portion of said post, and said retention feature is closer to said second surface of said transparent face shield than said first surface.

CCXVII. The surgical garment assembly of any of clauses CCV, wherein an outer perimeter of said proximal surface is radially spaced from a center of said proximal surface.

CCXVIII. The surgical garment assembly of any of clauses CCXVII, wherein said distal surface defines an outer perimeter and a center; and said center of said proximal surface and said center of said distal surface defining a first axis.

CCXIX. The surgical garment assembly of claim CCXVIII, further comprising a second axis orthogonal to said first axis and positioned to bisect said proximal surface to define a first portion and a second portion;

a first protrusion extending distally from said first portion proximate said outer perimeter of said proximal surface;

a second protrusion extending distally from said second portion proximate said outer perimeter of said proximal surface;

wherein said first protrusion and said second protrusion cooperate to define a recess in said proximal surface; and wherein said first attachment element is oriented such that at least one of said first protrusion or said second protrusion is positioned proximate the detector hall-effect sensor when said surgical garment assembly is at least partially disposed over the surgical helmet.

CCXX. The surgical garment assembly of any of clauses CCI-CCXIX, wherein a portion of said proximal surface of said first attachment element is configured to be at least partially disposed in the recess of the surgical helmet when said surgical garment assembly is at least partially disposed over the surgical helmet.

CCXXI. The surgical garment assembly of any of clauses CCI-CCXIX, wherein a portion of said proximal surface that defines said second point is configured to be at least partially disposed in the recess of the surgical helmet when said surgical garment assembly is at least partially disposed over the surgical helmet.

CCXXII. A surgical garment assembly for use with a surgical helmet, said surgical garment comprising a coupling member disposed in a recess and a hall-effect sensor spaced apart from the coupling member, said surgical garment assembly configured to be at least partially disposed over the surgical helmet and configured to provide a microbial barrier between a user and a medical environment, said surgical garment assembly comprising:
  a surgical fabric defining an opening;
  a transparent face shield disposed within said opening, said transparent face shield comprising an upper portion, a lower portion, a first surface and an opposing second surface;
  a first attachment element coupled to said lower portion of said transparent face shield, said first attachment element defining a proximal surface facing away from said transparent face shield;
  wherein said proximal surface is shaped such that a first point on said proximal surface defines a first distance from said first surface of said transparent face shield and such that a second point on said proximal surface defines a second distance from said first surface of said transparent face shield;
  wherein said second point on said proximal surface is spaced apart from said first point on said proximal surface, and said first distance is less than said second distance;
  wherein said first attachment element comprises a ferromagnetic material; and
  wherein said first attachment element is configured to removably engage the coupling member on the surgical helmet.

CCXXIII The surgical garment assembly of any of clauses CCXXII, wherein said first attachment element further comprises a head that defines said proximal surface and a distal surface opposite said proximal surface.

CCXXIV. The surgical garment assembly of claim CCXXIII, wherein said head of said attachment element comprises metal alloy comprising at least 50% of a ferromagnetic material capable of being magnetically attracted to the coupling member comprising a magnet.

CCXXV. The surgical garment assembly of claim CCXXIII, wherein said head of said attachment element comprises metal alloy comprising at least 90% of a ferromagnetic material capable of being magnetically attracted to the coupling member comprising a magnet.

CCXXVI. The surgical garment assembly of claim CCXXIII, wherein said head of said attachment element comprises metal alloy comprising at least half a gram (0.5 g) of a ferromagnetic material capable of being magnetically attracted to the coupling member comprising a magnet.

CCXXVII. The surgical garment assembly of claim CCXXIII, wherein said head of said attachment element comprises metal alloy comprising at least 95% of a ferromagnetic material capable of being magnetically attracted to the coupling member comprising a magnet.

CCXXVIII. The surgical garment assembly of claim CCXXIII, wherein said head of said attachment element comprises metal alloy comprising at least 98% of a ferromagnetic material capable of being magnetically attracted to the coupling member comprising a magnet.

CCXXIX. The surgical garment assembly of claim CCXXIII, wherein said head of said attachment element is formed of metal alloy comprising at least 95% wt. % of a ferromagnetic material capable of being magnetically attracted to the coupling member comprising a magnet.

CCXXX. The surgical garment assembly of any of clauses CCXXIV-CCXXIX, wherein said ferromagnetic material is a material chosen from iron, cobalt, and nickel.

CCXXXI. The surgical garment assembly of claim CCXXIII, further comprising a post extending distally from said distal surface of said head CCXXXII. A surgical garment assembly for use with a surgical helmet comprising a coupling member disposed in a recess and a detector spaced from the coupling member, said surgical garment assembly configured to be at least partially disposed over the surgical helmet and configured to provide a microbial barrier between a user and a medical environment, said surgical garment assembly comprising:
  a surgical fabric defining an opening;
  a transparent face shield disposed within said opening, said transparent face shield comprising an upper portion, a lower portion, a first surface and an opposing second surface;
  a first attachment element comprising a head, said head defining a proximal surface facing away from said transparent face shield;
  wherein said proximal surface is shaped such that a first portion of said proximal surface extends a first distance from said first surface of said transparent face shield, and a second portion of said proximal surface extends a second distance from said first surface of said transparent face shield;
  wherein said first distance is less than said second distance; and
  wherein said first attachment element is configured to removably engage the coupling member on the surgical helmet.

CCXXXIII The surgical garment assembly of claim CCXXXII, wherein said head of said attachment element comprises metal alloy comprising at least 50% of a ferromagnetic material capable of being magnetically attracted to the coupling member comprising a magnet.

CCXXXIV. The surgical garment assembly of claim CCXXXII, wherein said head of said attachment element comprises metal alloy comprising at least 90% of a ferromagnetic material capable of being magnetically attracted to the coupling member comprising a magnet.

CCXXXV. The surgical garment assembly of claim CCXXXII, wherein said head of said attachment element comprises metal alloy comprising at least half a gram (0.5 g) of a ferromagnetic material capable of being magnetically attracted to the coupling member comprising a magnet.

CCXXXVI. The surgical garment assembly of claim CCXXXII, wherein said head of said attachment element comprises metal alloy comprising at least 95% of a ferromagnetic material capable of being magnetically attracted to the coupling member comprising a magnet.

CCXXXVII. The surgical garment assembly of claim CCXXXII, wherein said head of said attachment element comprises metal alloy comprising at least 98% of a ferromagnetic material capable of being magnetically attracted to the coupling member comprising a magnet.

CCXXXVIII. The surgical garment assembly of claim CCXXXII, wherein said head of said attachment element is formed of metal alloy comprising at least 95% wt. % of a ferromagnetic material capable of being magnetically attracted to the coupling member comprising a magnet.

CCXXXIX. The surgical garment assembly of any of clauses CCXXXIII-CCXXXVIII, wherein said ferromagnetic material is a material chosen from iron, cobalt, and nickel.

CCXL. A surgical garment assembly for use with a surgical helmet comprising a coupling member disposed in a recess and a detector spaced from the coupling member, said surgical garment assembly configured to be at least partially disposed over the surgical helmet and configured to provide a microbial barrier between a user and a medical environment, said surgical garment assembly comprising:

a surgical fabric defining an opening;
a transparent face shield disposed within said opening, said transparent face shield comprising a first surface and an opposing second surface, and being bisected by a midline;
a first attachment element coupled to said transparent face shield, said first attachment element comprising:
a head defining a proximal surface;
a first point on said proximal surface that lies on an axis of said first attachment element and defines a first distance from said first surface of said transparent face shield;
a second point on said proximal surface that defines a second distance from said first surface of said transparent face shield;
wherein said second point on said proximal surface is spaced apart from said first point on said proximal surface;
wherein said proximal surface is shaped such that said first distance is less than the second distance;
wherein said first attachment element is oriented such that said second point on said proximal surface is positioned farther away from said midline of said transparent face shield than said first point on said proximal surface.

CCXLI. The surgical garment assembly of claim CCXL, wherein said head of said attachment element comprises metal alloy comprising at least 50% of a ferromagnetic material capable of being magnetically attracted to the coupling member comprising a magnet.

CCXLII. The surgical garment assembly of claim CCXL, wherein said head of said attachment element comprises metal alloy comprising at least 90% of a ferromagnetic material capable of being magnetically attracted to the coupling member comprising a magnet.

CCXLIII. The surgical garment assembly of claim CCXL, wherein said head of said attachment element comprises metal alloy comprising at least half a gram (0.5 g) of a ferromagnetic material capable of being magnetically attracted to the coupling member comprising a magnet.

CCXLIV. The surgical garment assembly of claim CCXL, wherein said head of said attachment element comprises metal alloy comprising at least 95% of a ferromagnetic material capable of being magnetically attracted to the coupling member comprising a magnet.

CCXLV. The surgical garment assembly of claim CCXL, wherein said head of said attachment element comprises metal alloy comprising at least 98% of a ferromagnetic material capable of being magnetically attracted to the coupling member comprising a magnet.

CCXLVI. The surgical garment assembly of claim CCXL, wherein said head of said attachment element is formed of metal alloy comprising at least 95% wt. % of a ferromagnetic material capable of being magnetically attracted to the coupling member comprising a magnet.

CCXLVII. The surgical garment assembly of any of clauses CCXLI-CCXLVI, wherein said ferromagnetic material is a material chosen from iron, cobalt, and nickel.

CCXLVIII. A surgical garment assembly for use with a surgical helmet comprising a coupling member disposed in a recess and a detector spaced from the coupling member, said surgical garment assembly configured to be at least partially disposed over the surgical helmet and configured to provide a microbial barrier between a user and a medical environment, said surgical garment assembly comprising:

a surgical fabric defining an opening;
a transparent face shield disposed within said opening, said transparent face shield comprising a first surface and an opposing second surface, and being bisected by a midline; and
a first attachment element coupled to said transparent face shield, said first attachment element comprising:
a head defining a proximal surface and an opposing distal surface;
a first point on said proximal surface that defines a first distance from said first surface of said transparent face shield;
a second point on said proximal surface that defines a second distance from said first surface of said transparent face shield;
wherein said second point on said proximal surface is spaced apart from said first point on said proximal surface;
wherein said proximal surface is shaped such that said first distance is less than the second distance;
wherein said transparent face shield and said first attachment element comprise complementary features configured to prevent said first attachment element from rotating relative to said transparent face shield; and
wherein said first attachment element is oriented such that said second point on said proximal surface is positioned farther away from said midline of said transparent face shield than said first point on said proximal surface.

CCXLIX. The surgical garment assembly of claim CCXLVIII, wherein said complementary features of said transparent face shield and said first attachment element comprise:
an aperture in a lower portion of said transparent face shield extending between said first surface and said second surface, said aperture having a first shape; and
a post extending from said distal surface of said head, said post having a complementary shape to said first shape configured to prevent said post from rotating within said aperture.

CCL. The surgical garment assembly of claim CCXLVIII, wherein said head of said attachment element comprises metal alloy comprising at least 50% of a ferromagnetic material capable of being magnetically attracted to the coupling member comprising a magnet.

CCLI. The surgical garment assembly of claim CCXLVIII, wherein said head of said attachment element comprises metal alloy comprising at least 90% of a ferromagnetic material capable of being magnetically attracted to the coupling member comprising a magnet.

CCLII. The surgical garment assembly of claim CCXLVIII, wherein said head of said attachment element comprises metal alloy comprising at least half a gram (0.5 g) of a ferromagnetic material capable of being magnetically attracted to the coupling member comprising a magnet.

CCLIII. The surgical garment assembly of claim CCXLVIII, wherein said head of said attachment element comprises metal alloy comprising at least 95% of a ferromagnetic material capable of being magnetically attracted to the coupling member comprising a magnet.

CCLIV. The surgical garment assembly of claim CCXLVIII, wherein said head of said attachment element comprises metal alloy comprising at least 98% of a ferromagnetic material capable of being magnetically attracted to the coupling member comprising a magnet.

CCLV. The surgical garment assembly of claim CCXLVIII, wherein said head of said attachment element is formed of metal alloy comprising at least 95% wt. % of a ferromagnetic material capable of being magnetically attracted to the coupling member comprising a magnet.

CCLVI. The surgical garment assembly of any of clauses CCL-CCLV, wherein said ferromagnetic material is a material chosen from iron, cobalt, and nickel.

CCLVII. A surgical garment assembly for use with a surgical helmet comprising a coupling member disposed in a recess and a detector spaced from the coupling member, said surgical garment assembly configured to be at least partially disposed over the surgical helmet and configured to provide a microbial barrier between a user and a medical environment, said surgical garment assembly comprising:
  a surgical fabric defining an opening;
  a transparent face shield disposed within said opening, said transparent face shield comprising a first surface and an opposing second surface, and being bisected by a midline;
  a first attachment element coupled to said transparent face shield, said first attachment element comprising:
  a head defining a proximal surface and an opposing distal surface;
  said surgical garment assembly comprising a means to prevent the rotation of the first attachment element relative to said transparent face shield;
  a first point on said proximal surface that defines a first distance from said first surface of said transparent face shield;
  a second point on said proximal surface that defines a second distance from said first surface of said transparent face shield;
  wherein said second point on said proximal surface is spaced apart from said first point on said proximal surface;
  wherein said proximal surface is shaped such that said first distance is less than the second distance;
  wherein said first attachment element is oriented such that said second point on said proximal surface is positioned farther away from said midline of said transparent face shield than said first point on said proximal surface.

CCLVIII. The surgical garment assembly of claim CCLVII, wherein said means to prevent the rotation of the first attachment element relative to said transparent face shield comprises:
  an aperture that extends between said first surface and said second surface; and
  a post extending distally from said distal surface of said head, said post at least partially disposed within said aperture;
  wherein said post and said aperture comprise complementary features that prevent the rotation of said post within said aperture.

CCLIX. The surgical garment assembly of claim CCLVII, wherein said head of said attachment element comprises metal alloy comprising at least 50% of a ferromagnetic material capable of being magnetically attracted to the coupling member comprising a magnet.

CCLX. The surgical garment assembly of claim CCLVII, wherein said head of said attachment element comprises metal alloy comprising at least 90% of a ferromagnetic material capable of being magnetically attracted to the coupling member comprising a magnet.

CCLXI. The surgical garment assembly of claim CCLVII, wherein said head of said attachment element comprises metal alloy comprising at least half a gram (0.5 g) of a ferromagnetic material capable of being magnetically attracted to the coupling member comprising a magnet.

CCLXII. The surgical garment assembly of claim CCLVII, wherein said head of said attachment element comprises metal alloy comprising at least 95% of a ferromagnetic material capable of being magnetically attracted to the coupling member comprising a magnet.

CCLXIII The surgical garment assembly of claim CCLVII, wherein said head of said attachment element comprises metal alloy comprising at least 98% of a ferromagnetic material capable of being magnetically attracted to the coupling member comprising a magnet.

CCLXIV. The surgical garment assembly of claim CCLVII, wherein said head of said attachment element is formed of metal alloy comprising at least 95% wt. % of a ferromagnetic material capable of being magnetically attracted to the coupling member comprising a magnet.

CCLXV. The surgical garment assembly of any of clauses CCLIX-CCLXIV, wherein said ferromagnetic material is a material chosen from iron, cobalt, and nickel.

CCLXVI. A method of making a surgical garment assembly for use with a surgical helmet, said method comprising:
  providing a fabric suitable to provide a microbial barrier, the fabric defining an opening, and the fabric shaped to encompass at least a portion of a wearer's head, the fabric defining an environment side and a wearer side;
  providing a transparent face shield including an upper portion and an opposing lower portion;
  forming a recess in a proximal surface of a head of an attachment element, wherein the head of the attachment element comprises at least 90 wt. % of a ferromagnetic material;
  attaching the attachment element to the transparent face shield; and
  coupling the transparent face shield to the fabric such that the proximal surface of the head of the attachment element is positioned on the wearer side of the fabric.

CCLXVII. A method of reusing a feature of a surgical garment, comprising:
  obtaining a surgical garment that has been used, the used surgical garment including:
  a surgical fabric defining an opening;
  a transparent face shield disposed within the opening, the transparent face shield comprising an upper portion, a lower portion, a first surface and an opposing second surface;
  a first attachment element secured to the lower portion of the transparent face shield;
  wherein the first attachment element defines a coupling recess on a wearer side of the surgical garment and is configured to removably engage a magnetic coupling member on a helmet, wherein the first attachment element further comprises:
  a head comprising a distal surface and a proximal surface, wherein the first attachment element comprises at least 95 wt. % of a ferromagnetic material; and
  a post extending distally from the distal surface of the head;
  wherein the coupling recess is formed in the proximal surface of the head; and
  disengaging the used first attachment element from the used transparent face shield;
  discarding the used surgical garment and the used transparent face shield;
  cleaning and/or sterilizing the used first attachment element; and
  coupling the cleaned or sterilized first attachment element to a new surgical garment having a new face shield such that, in subsequent use of the new surgical garment, the cleaned or sterilized first attachment element may be utilized to couple the new surgical garment to a helmet.

CCLXVIII. A surgical garment assembly for use with a surgical helmet comprising a coupling member, said surgical garment assembly comprising:
   a surgical fabric defining an opening;
   a transparent face shield disposed within said opening, said transparent face shield comprising a first surface and an opposing second surface;
   a first attachment element coupled to said transparent face shield, said first attachment element defining a proximal surface;
   an adapter member configured to removably couple with said first attachment element, said adapter member comprising:
      a proximal surface and an opposing distal surface;
      a first point on said proximal surface of said adapter member;
      a second point on said proximal surface of said adapter member;
      wherein said second point on said proximal surface of said adapter member is spaced apart from said first point on said proximal surface of said adapter member; and
      wherein said distal surface of said adapter member is configured to removably engage said proximal surface of said first attachment element;
      wherein said first point on said proximal surface of said adapter member defines a first distance from said first surface of said transparent face shield when said adapter member is coupled to said first attachment element;
      wherein said second point on said proximal surface of said adapter member defines a second distance from said first surface of said transparent face shield when said adapter member is coupled to said first attachment element;
      wherein said proximal surface of said adapter member is shaped such that said first distance is less than the second distance from said first surface of said transparent face shield.

CCLXIX. The surgical garment assembly of claim 88, wherein said first attachment element comprises a magnetic material and said adapter member comprises a ferromagnetic material.

CCLXX. A method of coupling a surgical garment including a first attachment element to a surgical helmet including a coupling member, said method comprising:
   providing an adapter member comprising:
      a proximal surface and an opposing distal surface;
      a first point on the proximal surface of the adapter member;
      a second point on the proximal surface of the adapter member;
      wherein the second point on the proximal surface of the adapter member is spaced apart from the first point on the proximal surface of the adapter member; and
      wherein the first point on the proximal surface of the adapter member defines a first distance from the first surface of a transparent face shield when the adapter member is coupled to the first attachment element;
      wherein the second point on the proximal surface of the adapter member defines a second distance from the first surface of the transparent face shield when the adapter member is coupled to the first attachment element; and
   removably coupling the adapter member to the first coupling member of the surgical helmet; and
   removably coupling the adapter member to the first attachment element of the surgical garment.

CCLXXI. The method of claim CCLXX, wherein each of the first attachment element and the first coupling member comprises a magnetic material, and the adapter member comprises a ferromagnetic material.

CCLXXII. The surgical garment assembly of claim CCLXX, wherein said adapter member comprises metal alloy comprising at least 50% of a ferromagnetic material capable of being magnetically attracted to the coupling member comprising a magnet.

CCLXXIII The surgical garment assembly of claim CCLXX, wherein said adapter member comprises metal alloy comprising at least 90% of a ferromagnetic material capable of being magnetically attracted to the coupling member comprising a magnet.

CCLXXIV. The surgical garment assembly of claim CCLXX, wherein adapter member comprises metal alloy comprising at least half a gram (0.5 g) of a ferromagnetic material capable of being magnetically attracted to the coupling member comprising a magnet.

CCLXXV. The surgical garment assembly of claim CCLXX, wherein said adapter member comprises metal alloy comprising at least 95% of a ferromagnetic material capable of being magnetically attracted to the coupling member comprising a magnet.

CCLXXVI. The surgical garment assembly of claim CCLXX, wherein said adapter member comprises metal alloy comprising at least 98% of a ferromagnetic material capable of being magnetically attracted to the coupling member comprising a magnet.

CCLXXVII. The surgical garment assembly of claim CCLXX, wherein said adapter member is formed of metal alloy comprising at least 95% wt. % of a ferromagnetic material capable of being magnetically attracted to the coupling member comprising a magnet.

CCLXXVIII. The surgical garment assembly of any of clauses CCLXXII-CCLXXVII, wherein said ferromagnetic material is a material chosen from iron, cobalt, and nickel.

CCLXXIX. A surgical garment assembly for use with a surgical helmet comprising a coupling member disposed in a recess and a hall-effect sensor spaced from the coupling member, said surgical garment assembly configured to be at least partially disposed over the surgical helmet to provide a microbial barrier between a user and a medical environment, said surgical garment assembly comprising:
   a surgical fabric defining an opening;
   a transparent face shield disposed within said opening, said transparent face shield comprising an upper portion, a lower portion, a first surface and an opposing second surface;
   a first attachment element coupled to said lower portion of said transparent face shield, said first attachment element comprising:
      a head including a distal end and an opposing proximal end;
      wherein the proximal end defines a proximal surface facing away from said transparent face shield, said proximal surface including:
         a first portion angularly extending in a proximal direction from a medial plane of the head to a first edge; and
         a second portion angularly extending in the proximal direction from the medial plane of the head to a second edge;
      wherein said head comprises a ferromagnetic material; and
      wherein said first attachment element is configured to removably engage the coupling member on the surgical helmet and trigger the hall-effect sensor when said first attachment element is coupled to the coupling member.

CCLXXX. A surgical garment assembly for use with a surgical helmet comprising a magnetic coupling member disposed in a recess and a hall-effect sensor spaced from the coupling member, said surgical garment assembly configured to be at least partially disposed over the surgical helmet to provide a microbial barrier between a user and a medical environment, said surgical garment assembly comprising:

a surgical fabric defining an opening;

a transparent face shield disposed within said opening, said transparent face shield comprising an upper portion, a lower portion, a first surface and an opposing second surface;

a first attachment element coupled to said lower portion of said transparent face shield, said first attachment element comprising:

a head including a distal end and an opposing proximal end;

wherein said proximal end defines a proximal surface facing away from said transparent face shield, said proximal surface including:

a planar surface with a first side and a second side;

a first face angularly extending in a proximal direction from said first side of said planar surface to a first edge;

a second face angularly extending in said proximal direction from said second side of said planar surface to a second edge;

wherein said planar surface is perpendicular to a longitudinal axis;

wherein said head comprises a ferromagnetic material; and wherein said first attachment element is configured to removably engage the coupling member on the surgical helmet and trigger the hall-effect sensor when said first attachment element is coupled to the coupling member.

CCLXXXI. A surgical garment assembly for use with a surgical helmet comprising a magnetic coupling member disposed in a recess and a hall-effect sensor spaced from the coupling member, said surgical garment assembly configured to be at least partially disposed over the surgical helmet to provide a microbial barrier between a user and a medical environment, said surgical garment assembly comprising:

a surgical fabric defining an opening;

a transparent face shield disposed within said opening, said transparent face shield comprising an upper portion, a lower portion, a first surface and an opposing second surface;

a first attachment element coupled to said lower portion of said transparent face shield, said first attachment element comprising:

a head including a distal end with a distal surface and a proximal end with a proximal surface;

wherein said proximal surface angularly extends in a proximal direction from a first edge of said head to a second edge of said head; and wherein said first attachment element is configured to removably engage the coupling member on the surgical helmet and trigger the hall-effect sensor when said first attachment element is coupled to the coupling member.

CCLXXXII. A surgical garment assembly for use with a surgical helmet comprising a magnetic coupling member disposed in a recess and a hall-effect sensor spaced from the coupling member, said surgical garment assembly configured to be at least partially disposed over the surgical helmet to provide a microbial barrier between a user and a medical environment, said surgical garment assembly comprising:

a surgical fabric defining an opening;

a transparent face shield disposed within said opening, said transparent face shield comprising an upper portion, a lower portion, a first surface and an opposing second surface;

a first attachment element coupled to said lower portion of said transparent face shield, said first attachment element comprising:

a head defining a bore, said bore extending along a longitudinal axis between a distal end and a proximal end;

wherein said head comprises a ferromagnetic material; and wherein said first attachment element is configured to removably engage the coupling member on the surgical helmet and trigger the hall-effect sensor when said first attachment element is coupled to the coupling member.

CCLXXXIII A surgical garment assembly for use with a surgical helmet comprising a magnetic coupling member disposed in a recess and a hall-effect sensor spaced from the coupling member, said surgical garment assembly configured to be at least partially disposed over the surgical helmet to provide a microbial barrier between a user and a medical environment, said surgical garment assembly comprising:

a surgical fabric defining an opening;

a transparent face shield disposed within said opening, said transparent face shield comprising an upper portion, a lower portion, a first surface and an opposing second surface;

a first attachment element coupled to said lower portion of said transparent face shield, said first attachment element comprising:

a head defining a bore, said bore extending along a longitudinal axis between a closed distal end and an open proximal end;

wherein said bore includes a mouth, said mouth tapers from said open proximal end towards a center of said bore;

wherein said head comprises a ferromagnetic material; and wherein said first attachment element is configured to removably engage the coupling member on the surgical helmet and trigger the hall-effect sensor when said first attachment element is coupled to the coupling member.

CCLXXXIV. The surgical garment assembly of any of clauses CCLXXIX-CCLXXXIII, wherein said head of said attachment element comprises metal alloy comprising at least 50% of a ferromagnetic material capable of being magnetically attracted to the coupling member comprising a magnet.

CCLXXXV. The surgical garment assembly of any of clauses CCLXXIX-CCLXXXIII, wherein said head of said attachment element comprises metal alloy comprising at least 90% of a ferromagnetic material capable of being magnetically attracted to the coupling member comprising a magnet.

CCLXXXVI. The surgical garment assembly of any of clauses CCLXXIX-CCLXXXIII, wherein said head of said attachment element comprises metal alloy comprising at least half a gram (0.5 g) of a ferromagnetic material capable of being magnetically attracted to the coupling member comprising a magnet.

CCLXXXVII. The surgical garment assembly of any of clauses CCLXXIX-CCLXXXIII, wherein said head of said attachment element comprises metal alloy comprising at least 95% of a ferromagnetic material capable of being magnetically attracted to the coupling member comprising a magnet.

CCLXXXVIII. The surgical garment assembly of any of clauses CCLXXIX-CCLXXXIII, wherein said head of said attachment element comprises metal alloy comprising at least 98% of a ferromagnetic material capable of being magnetically attracted to the coupling member comprising a magnet.

CCLXXXIX. The surgical garment assembly of any of clauses CCLXXIX-CCLXXXIII, wherein said head of said attachment element is formed of metal alloy comprising at least 95% wt. % of a ferromagnetic material capable of being magnetically attracted to the coupling member comprising a magnet.

CCXC. The surgical garment assembly of any of clauses CCLXXXIV-CCLXXXIX, wherein said ferromagnetic material is a material chosen from iron, cobalt, and nickel.

CCXCI. The surgical garment assembly of any of clauses CCLXXI-CCLXXXIII, wherein said head is cylindrically shaped.

CCXCII. A surgical garment assembly for use with a surgical helmet comprising a magnetic coupling member disposed in a recess and a hall-effect sensor spaced from the coupling member, said surgical garment assembly configured to be at least partially disposed over the surgical helmet to provide a microbial barrier between a user and a medical environment, said surgical garment assembly comprising:
 a surgical fabric defining an opening;
 a transparent face shield disposed within said opening, said transparent face shield comprising an upper portion, a lower portion, a first surface and an opposing second surface;
 a first attachment element coupled to said surgical fabric, said first attachment element comprising:
 a ferromagnetic or magnetic material;
 said first attachment element defining a proximal surface facing away from said fabric, said proximal surface including a first point that defines a first distance from a surface of said surgical fabric;
 said proximal surface including a second point that defines a second distance from said surface of said surgical fabric, wherein said second point on said proximal surface is spaced apart from said first point on said proximal surface;
 wherein said proximal surface is shaped such that said first distance is less than said second distance; and
 wherein said first attachment element is configured to removably engage the coupling member on the surgical helmet and trigger the hall-effect sensor when said first attachment element is coupled to the coupling member.

CCXCIII. A surgical garment assembly for use with a surgical helmet comprising a magnetic coupling member disposed in a recess and a hall-effect sensor spaced from the coupling member, said surgical garment assembly configured to be at least partially disposed over the surgical helmet to provide a microbial barrier between a user and a medical environment, said surgical garment assembly comprising:
 a surgical fabric defining an opening;
 a transparent face shield disposed within said opening, said transparent face shield comprising an upper portion, a lower portion, a first surface and an opposing second surface;
 a first attachment element coupled to said surgical fabric, said first attachment element comprising:
 a ferromagnetic or magnetic material;
 said first attachment element having any of the shapes described through the drawings and specification, including FIGS. 18, 19, 23, 24, 25, 26, 27, 28, 29, 41, 42, 43, 44, 45, 46, 47, 48, 49, 50, 51;
 wherein said first attachment element is configured to removably engage the coupling member on the surgical helmet and trigger the hall-effect sensor when said first attachment element is coupled to the coupling member.

CCXCIV. A method of attaching a surgical garment to a surgical helmet, the surgical helmet comprising a chin bar defining a first attachment recess, with the chin bar including a first magnet at least partially disposed within said first attachment recess, said method comprising:
 providing a surgical garment including a transparent face shield and a surgical fabric, and a first attachment element coupled to the transparent face shield or the fabric, the surgical garment being inside-out, the first attachment element comprising a ferromagnetic material or a magnetic material, the first attachment element optionally having any of the shapes or features described through the drawings and specification, including FIGS. 18, 19, 23, 24, 25, 26, 27, 28, 29, 41, 42, 43, 44, 45, 46, 47, 48, 49, 50, 51 or have a flat cylindrical shape;
 positioning the surgical garment such that the first attachment element is at least partially within the first attachment recess sufficient to trigger a hall-effect sensor in the surgical helmet; and
 manipulating the surgical garment to position the transparent face shield in front of the wearer's face.

CCXCV. A surgical garment assembly for use with a surgical helmet comprising a magnetic coupling member disposed in a recess and a hall-effect sensor spaced from the coupling member, said surgical garment assembly configured to be at least partially disposed over the surgical helmet to provide a microbial barrier between a user and a medical environment, said surgical garment assembly comprising:
 a surgical fabric defining an opening;
 a transparent face shield disposed within said opening, said transparent face shield comprising an upper portion, a lower portion, a first surface and an opposing second surface;
 a first attachment element coupled to said surgical fabric or the transparent face shield, said first attachment element comprising:
 a magnetic material;
 said first attachment element having any of the shapes or features described through the drawings and specification, including FIGS. 18, 19, 23, 24, 25, 26, 27, 28, 29, 41, 42, 43, 44, 45, 46, 47, 48, 49, 50, 51;
 wherein said first attachment element is configured to removably engage the coupling member on the surgical helmet and trigger the hall-effect sensor when said first attachment element is coupled to the coupling member.

Several configurations have been discussed in the foregoing description. However, the configurations discussed herein are not intended to be exhaustive or limit the system 10, 110, 610, 1410 to any particular form. The terminology which has been used is intended to be in the nature of words of description rather than of limitation. Many modifications and variations are possible in light of the above teachings and the system may be practiced otherwise than as specifically described. Furthermore, it should be understood that elements described in the various configurations including reference numbers in increments of 100 may comprise similar features.

What is claimed is:
1. A surgical garment configured to provide a barrier defining an environment side and a wearer side of the surgical garment, the surgical garment intended for use with a helmet, the surgical garment comprising:

a shell formed from a fabric, the shell defining an opening;

a transparent face shield disposed within the opening of the shell, the transparent face shield having a first surface and a second surface;

a first attachment element and a second attachment element, each of the first attachment element and the second attachment element are coupled to the transparent face shield and at least one of the first attachment element or the second attachment element comprises:

a head comprising a distal surface and a proximal surface; and a coupling recess defined in the proximal surface of the head; and wherein the first attachment element or the second attachment element is coupled to the transparent face shield such that the distal surface of the head is closer to the first surface of the transparent face shield than the second surface.

2. The surgical garment of claim 1, wherein the transparent face shield comprises an upper portion and a lower portion; and wherein the first attachment element is coupled to the upper portion of the transparent face shield and the second attachment element is coupled to the lower portion of the transparent face shield.

3. The surgical garment of claim 1, wherein the transparent face shield further defines an aperture; and at least one of the first attachment element or the second attachment element comprises a post extending distally from the distal surface of the head;

wherein the post of the first attachment element or the second attachment element is at least partially disposed in the aperture.

4. The surgical garment of claim 3, wherein at least one of the first attachment element or the second attachment element comprises a retention feature, and the retention featured coupled to the post to couple the first attachment element or the second attachment element to the transparent face shield.

5. The surgical garment of claim 4, wherein the retention feature is positioned closer to the second surface of the transparent face shield than the first surface when the retention feature is coupled to the post of the first attachment feature or the second attachment element.

6. The surgical garment of claim 1, wherein the coupling recess of the first attachment element provides a means for coupling the first attachment element to a convex surface.

7. The surgical garment of claim 1, wherein the coupling recess defines a coupling surface that opens to the proximal surface of the head, the coupling surface having a concave shape.

8. The surgical garment of claim 1, wherein at least one of the first attachment element or the second attachment element comprises a ferromagnetic material.

9. The surgical garment of claim 1, wherein at least one of the first attachment element or the second attachment element comprises a metallic material.

10. The surgical garment of claim 1, wherein the transparent face shield further comprising a tab defining an aperture;

wherein the transparent face shield comprises an upper portion and a lower portion, and the tab extends from the upper portion of the transparent face shield.

11. A surgical garment to provide a microbial barrier between a medical environment and a wearer, the surgical garment comprising:

a first material defining a hood with an opening;

a transparent face shield disposed within the opening of the hood, the transparent face shield comprising:

a first surface and an opposing second surface; and a first attachment element coupled to the transparent face shield, the first attachment element comprising:

a head having a distal surface and a proximal surface, and defining a coupling recess;

wherein the first attachment element is coupled to the transparent face shield such that the distal surface of the head is closer to the first surface of the transparent face shield than the second surface; and wherein the coupling recess is defined in the proximal surface of the head of the first attachment element.

12. The surgical garment of claim 11, wherein the first attachment element is coupled to an upper portion of the transparent shield.

13. The surgical garment of claim 12, further comprising a second attachment element coupled to a lower portion of the transparent face shield.

14. The surgical garment of claim 11, wherein the first attachment element further comprises a post extending distally from the distal surface of the head.

15. The surgical garment of claim 14, wherein the first attachment element comprises a retention feature, and the retention feature coupled to the post to couple the first attachment element to the transparent face shield.

16. The surgical garment of claim 15, wherein the retention feature is positioned closer to the second surface of the transparent face shield than the first surface when the retention feature is coupled to the post of the first attachment feature.

17. The surgical garment of claim 11, wherein the transparent face shield further defines an aperture; and wherein at least one of the first and the second attachment elements further comprises a post that is at least partially disposed in the aperture.

18. The surgical garment of claim 11, wherein the first attachment element comprises a ferromagnetic material.

19. The surgical garment of claim 11, wherein the first attachment element comprises a metallic material.

20. A surgical garment configured to provide a barrier defining an environment side and a wearer side of the surgical garment, the surgical garment comprising:

a shell formed from a fabric, the shell defining an opening;

a transparent face shield disposed within the opening of the shell; and a first attachment element coupled to the transparent face shield, the first attachment element comprising:

a head having a proximal surface and a distal surface, the proximal surface defining a coupling recess; and a post extending distally from the distal surface of the head;

wherein the transparent face shield further defines an aperture; and wherein the post is at least partially disposed in the aperture.

21. The surgical garment of claim 20, wherein the transparent face shield comprises an upper portion and a lower portion; and wherein the first attachment element is coupled to the upper portion of the transparent face shield.

* * * * *